(12) United States Patent
Suh et al.

(10) Patent No.: US 12,133,459 B2
(45) Date of Patent: Oct. 29, 2024

(54) HETEROCYCLIC COMPOUND AND ORGANIC LIGHT EMITTING DEVICE COMPRISING SAME

(71) Applicant: LG CHEM, LTD., Seoul (KR)

(72) Inventors: Sang Duk Suh, Daejeon (KR); Dong Hoon Lee, Daejeon (KR); Boon Jae Jang, Daejeon (KR); Min Woo Jung, Daejeon (KR); Jungha Lee, Daejeon (KR); Su Jin Han, Daejeon (KR); Seulchan Park, Daejeon (KR); Sunghyun Hwang, Daejeon (KR)

(73) Assignee: LG CHEM, LTD., Seoul (KR)

( * ) Notice: Subject to any disclaimer, the term of this patent is extended or adjusted under 35 U.S.C. 154(b) by 714 days.

(21) Appl. No.: 17/282,678

(22) PCT Filed: Jan. 13, 2020

(86) PCT No.: PCT/KR2020/000610
§ 371 (c)(1),
(2) Date: Apr. 2, 2021

(87) PCT Pub. No.: WO2020/149596
PCT Pub. Date: Jul. 23, 2020

(65) Prior Publication Data
US 2021/0351360 A1     Nov. 11, 2021

(30) Foreign Application Priority Data

Jan. 15, 2019  (KR) .................. 10-2019-0005246
Jan. 9, 2020   (KR) .................. 10-2020-0003325

(51) Int. Cl.
*H10K 85/60*   (2023.01)
*C07D 491/048* (2006.01)
(Continued)

(52) U.S. Cl.
CPC ....... *H10K 85/654* (2023.02); *C07D 491/048* (2013.01); *C07D 495/04* (2013.01);
(Continued)

(58) Field of Classification Search
None
See application file for complete search history.

(56) References Cited

U.S. PATENT DOCUMENTS

2014/0346483 A1   11/2014  Yu et al.
2014/0357866 A1   12/2014  Kim et al.
(Continued)

FOREIGN PATENT DOCUMENTS

JP   5238025 B2   4/2013
JP   5357150 B2   12/2013
(Continued)

OTHER PUBLICATIONS

English translation (Year: 2018).*

*Primary Examiner* — Jeffrey D Washville
(74) *Attorney, Agent, or Firm* — Bryan Cave Leighton Paisner LLP

(57) ABSTRACT

A heterocyclic compound represented by Chemical Formula 1 and an organic light emitting device comprising the same, and the heterocyclic compound used as a material of an organic material layer of the organic light emitting device (Continued)

and providing improved properties of efficiency, driving voltage and lifetime characteristics of the organic light emitting device.

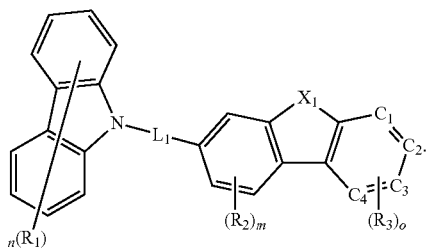

[Chemical Formula 1]

13 Claims, 1 Drawing Sheet

(51) Int. Cl.
*C07D 495/04* (2006.01)
*H10K 50/11* (2023.01)
(52) U.S. Cl.
CPC ....... *H10K 85/657* (2023.02); *H10K 85/6572* (2023.02); *H10K 85/6574* (2023.02); *H10K 50/11* (2023.02)

(56) References Cited

U.S. PATENT DOCUMENTS

| | | |
|---|---|---|
| 2015/0115205 A1 | 4/2015 | Kang et al. |
| 2015/0218441 A1 | 8/2015 | Cho et al. |
| 2017/0062718 A1 | 3/2017 | Numata et al. |
| 2017/0141323 A1 | 5/2017 | Miyazaki et al. |
| 2018/0261791 A1 | 9/2018 | Yoo et al. |
| 2021/0074929 A1* | 3/2021 | Kim ................ H10K 50/12 |
| 2021/0143340 A1 | 5/2021 | Ogawa et al. |

FOREIGN PATENT DOCUMENTS

| | | |
|---|---|---|
| JP | 5666907 B2 | 2/2015 |
| JP | 2015-534547 A | 12/2015 |
| KR | 10-2013-0053846 A | 5/2013 |
| KR | 10-2013-0061371 A | 6/2013 |
| KR | 10-2013-0073537 A | 7/2013 |
| KR | 10-2013-0127563 A | 11/2013 |
| KR | 10-2014-0032823 A | 3/2014 |
| KR | 10-2015-0034333 A | 4/2015 |
| KR | 10-2017-0025990 A | 3/2017 |
| KR | 10-2017-0056951 A | 5/2017 |
| KR | 10-2017-0139443 A | 12/2017 |
| KR | 10-2018-0008279 A | 1/2018 |
| KR | 10-2018-0104258 A | 9/2018 |
| KR | 10-2018-0136377 A | 12/2018 |
| KR | 10-2019-0064251 A | 6/2019 |
| WO | 2003-012890 A2 | 2/2003 |
| WO | 2013-179645 A1 | 12/2013 |
| WO | 2018198844 A1 | 11/2018 |

* cited by examiner

[FIG. 1]
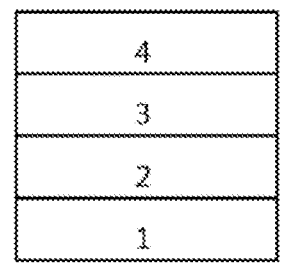
[FIG. 2]
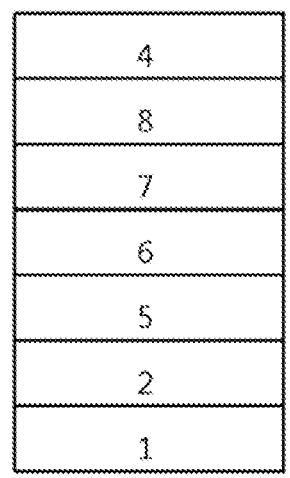

HETEROCYCLIC COMPOUND AND ORGANIC LIGHT EMITTING DEVICE COMPRISING SAME

CROSS-REFERENCE TO RELATED APPLICATION(S)

This application claims is a National Stage Application of International Application No. PCT/KR2020/000610 filed on Jan. 13, 2020, which claims priority to and benefit of Korean Patent Application No. 10-2019-0005246 filed on Jan. 15, 2019 and Korean Patent Application No. 10-2020-0003325 filed on Jan. 9, 2020, the disclosures of which are incorporated herein by reference in their entirety.

FIELD OF DISCLOSURE

The present disclosure relates to a novel compound and an organic light emitting device using the same.

BACKGROUND

In general, an organic light emitting phenomenon refers to a phenomenon where electric energy is converted into light energy by using an organic material. The organic light emitting device using the organic light emitting phenomenon has characteristics such as a wide viewing angle, an excellent contrast, a fast response time, an excellent luminance, driving voltage and response speed, and thus many studies have proceeded.

The organic light emitting device generally has a structure which comprises an anode, a cathode, and an organic material layer interposed between the anode and the cathode. The organic material layer frequently has a multilayered structure that comprises different materials in order to enhance efficiency and stability of the organic light emitting device, and for example, the organic material layer may be formed of a hole injection layer, a hole transport layer, a light emitting layer, an electron transport layer, an electron injection layer and the like. In the structure of the organic light emitting device, if a voltage is applied between two electrodes, the holes are injected from an anode into the organic material layer and the electrons are injected from the cathode into the organic material layer, and when the injected holes and electrons meet each other, an exciton is formed, and light is emitted when the exciton falls to a ground state again.

There is a continuing need for the development of new materials for the organic materials used in the organic light emitting devices as described above.

RELATED ARTS (Patent Literature 0001) Korean Unexamined Patent Publication No. 10-2013-073537

SUMMARY

It is an object of the present disclosure to provide a novel compound and an organic light emitting device comprising the same.

In an aspect of the present disclosure, there is provided a compound represented by the following Chemical Formula 1:

[Chemical Formula 1]

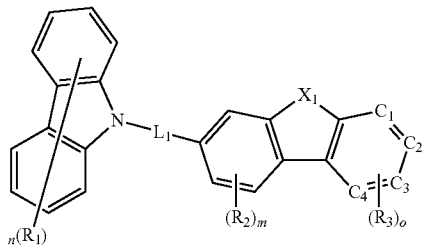

[Chemical Formula 2]

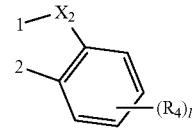

in the Chemical Formula 1, two adjacent carbons of $C_1$ to $C_4$ are respectively connected to 1 and 2 of Chemical Formula 2, where $C_1$ and $C_2$ are not connected to 2 and 1 of Chemical Formula 2 respectively, and $C_4$ and $C_3$ are not connected to 1 and 2 of Chemical Formula 2 respectively, $L_1$ is independently a direct bond; or a substituted or unsubstituted $C_{6-60}$ arylene, $R_1$ is hydrogen; deuterium; a substituted or unsubstituted $C_{1-60}$ alkyl; a substituted or unsubstituted $C_{6-60}$ aryl; or a substituted or unsubstituted $C_{5-60}$ heteroaryl containing at least one heteroatom selected from the group consisting of N, O and S, or is fused with an adjacent ring to form a benzene ring, $R_2$ to $R_4$ are each independently hydrogen; deuterium; a substituted or unsubstituted $C_{1-60}$ alkyl; a substituted or unsubstituted $C_{6-60}$ aryl; or a substituted or unsubstituted $C_{5-60}$ heteroaryl containing at least one heteroatom selected from the group consisting of N, O and S, n is an integer of 0 to 8, m and o are each independently an integer of 0 to 3, l is an integer of 0 to 4, $X_1$ is NR' and $X_2$ is O or S, or $X_1$ is O or S and $X_2$ is NR', R' is

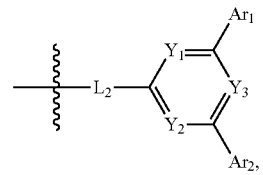

$L_2$ is a direct bond; or a substituted or unsubstituted $C_{6-60}$ arylene, $Y_1$, $Y_2$ and $Y_3$ are each independently CH; or N, and at least two of $Y_1$, $Y_2$ and $Y_3$ are N, and $Ar_1$ and $Ar_2$ are each independently a substituted or unsubstituted $C_{6-60}$ aryl; or a substituted or unsubstituted $C_{5-60}$ heteroaryl containing at least one heteroatom selected from the group consisting of N, O and S.

In another aspect of the present disclosure, there is provided an organic light emitting device comprising: a first electrode; a second electrode that is provided opposite to the first electrode; and one or more organic material layers that are provided between the first electrode and the second electrode, wherein at least one layer of the organic material layers includes the above-mentioned compound of the present disclosure.

Advantageous Effects

The above-mentioned compound represented by Chemical Formula 1 can be used as a material of an organic material layer of an organic light emitting device, and can improve the efficiency, achieve low driving voltage and/or improve lifetime characteristics in the organic light emitting device. In particular, the above-mentioned compound represented by Chemical Formula 1 can be used as a material of a light emitting layer.

DESCRIPTION OF DRAWINGS

FIG. 1 depicts an example of an organic light emitting device comprising a substrate 1, an anode 2, a light emitting layer 3 and a cathode 4.

FIG. 2 depicts an example of an organic light emitting device comprising a substrate 1, an anode 2, a hole injection layer 5, a hole transport layer 6, a light emitting layer 7, an electron transport layer 8 and a cathode 4.

DETAILED DESCRIPTION

Hereinafter, embodiments of the present disclosure will be described in more detail to facilitate understanding of the invention.

As used herein, the notation

means a bond linked to another substituent group.

As used herein, the term "substituted or unsubstituted" means being unsubstituted or substituted with one or more substituents selected from the group consisting of deuterium; a halogen group; a nitrile group; a nitro group; a hydroxy group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a heterocyclic group containing at least one of N, O and S atoms, or being unsubstituted or substituted with a substituent to which two or more substituents of the above-exemplified substituents are connected. For example, "a substituent in which two or more substituents are connected" may be a biphenyl group. Namely, a biphenyl group may be an aryl group, or it may be interpreted as a substituent in which two phenyl groups are connected.

In the present disclosure, the carbon number of a carbonyl group is not particularly limited, but is preferably 1 to 40. Specifically, the carbonyl group may be a compound having the following structural formulas, but is not limited thereto.

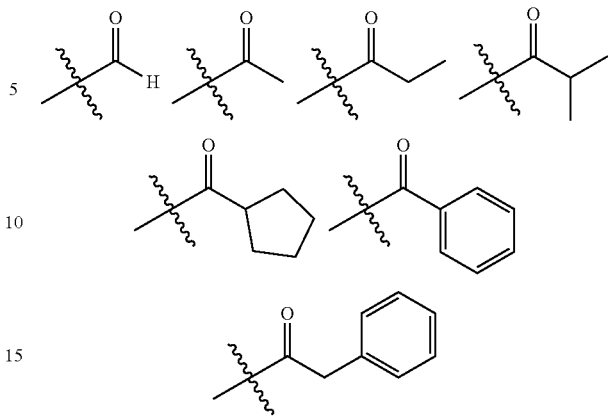

In the present disclosure, an ester group may have a structure in which oxygen of the ester group may be substituted by a straight-chain, branched-chain, or a cyclic alkyl group having 1 to 25 carbon atoms, or an aryl group having 6 to 25 carbon atoms. Specifically, the ester group may be a compound having the following structural formulas, but is not limited thereto.

In the present disclosure, the carbon number of an imide group is not particularly limited, but is preferably 1 to 25. Specifically, the imide group may be a compound having the following structural formulas, but is not limited thereto.

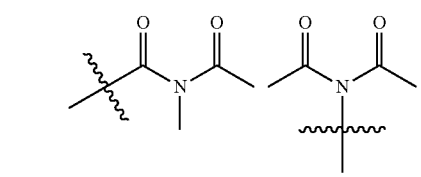

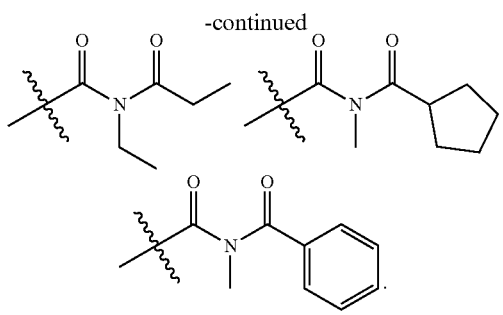

In the present disclosure, a silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but is not limited thereto.

In the present disclosure, a boron group specifically includes a trimethylboron group, a triethylboron group, a t-butyldimethylboron group, a triphenylboron group, and a phenylboron group, but is not limited thereto.

In the present disclosure, examples of a halogen group include fluorine, chlorine, bromine, or iodine.

In the present disclosure, the alkyl group may be straight-chain or branched-chain, and the carbon number thereof is not particularly limited, but is preferably 1 to 40. According to one embodiment, the carbon number of the alkyl group is 1 to 20. According to another embodiment, the carbon number of the alkyl group is 1 to 10. According to another embodiment, the carbon number of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present disclosure, the alkenyl group may be straight-chain or branched-chain, and the carbon number thereof is not particularly limited, but is preferably 2 to 40. According to one embodiment, the carbon number of the alkenyl group is 2 to 20. According to another embodiment, the carbon number of the alkenyl group is 2 to 10. According to still another embodiment, the carbon number of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present disclosure, a cycloalkyl group is not particularly limited, but the carbon number thereof is preferably 3 to 60. According to one embodiment, the carbon number of the cycloalkyl group is 3 to 30. According to another embodiment, the carbon number of the cycloalkyl group is 3 to 20. According to still another embodiment, the carbon number of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-m ethylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present disclosure, an aryl group is not particularly limited, but the carbon number thereof is preferably 6 to 60, and it may be a monocyclic aryl group or a polycyclic aryl group. According to one embodiment, the carbon number of the aryl group is 6 to 30. According to one embodiment, the carbon number of the aryl group is 6 to 20. The aryl group may be a phenyl group, a biphenyl group, a terphenyl group or the like as the monocyclic aryl group, but is not limited thereto. The polycyclic aryl group includes a naphthyl group, an anthracenyl group, a phenanthryl group, a pyrenyl group, a perylenyl group, a chrysenyl group, flurorenyl group or the like, but is not limited thereto.

In the present disclosure, the fluorenyl group may be substituted, and two substituents may be linked with each other to form a spiro structure. In the case where the fluorenyl group is substituted,

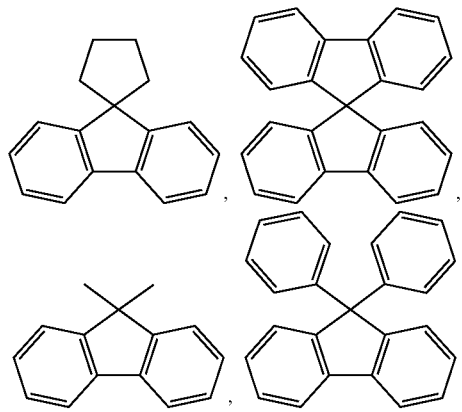

and the like can be formed. However, the structure is not limited thereto.

In the present disclosure, a heterocyclic group is a heterocyclic group containing one or more of O, N, Si and S as a heteroatom, and the carbon number thereof is not particularly limited, but is preferably 2 to 60. Examples of the heterocyclic group include a thiophene group, a furan group, a pyrrole group, an imidazole group, a thiazole group, an oxazol group, an oxadiazol group, a triazol group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzoimidazole group, a benzothiazol group, a benzocarbazole group, a benzothiophene group, a dibenzothiophene group, a benzofuranyl group, a phenanthroline group, an thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present disclosure, the aryl group in the aralkyl group, the aralkenyl group, the alkylaryl group and the arylamine group is the same as the aforementioned examples of the aryl group. In the present disclosure, the alkyl group in the aralkyl group, the alkylaryl group and the alkylamine group is the same as the aforementioned examples of the alkyl group. In the present disclosure, the heteroaryl in the heteroarylamine can be applied to the aforementioned description of the heterocyclic group. In the present disclosure, the alkenyl group in the aralkenyl group is the same as the aforementioned examples of the alkenyl group. In the present disclosure, the aforementioned description of the aryl group may be applied except that the arylene is a divalent group. In the present disclosure, the aforementioned description of the heterocyclic group can be applied except that the heteroarylene is a divalent group. In the present disclosure, the aforementioned description of the aryl group or cycloalkyl group can be applied except that the hydrocarbon ring is not a monovalent group but formed by combining two substituent groups. In the present disclosure, the aforementioned description of the heterocyclic group can be applied, except that the heterocyclic group is not a monovalent group but formed by combining two substituent groups.

One embodiment of the present disclosure provides a compound represented by the following Chemical Formula 1.

[Chemical Formula 1]

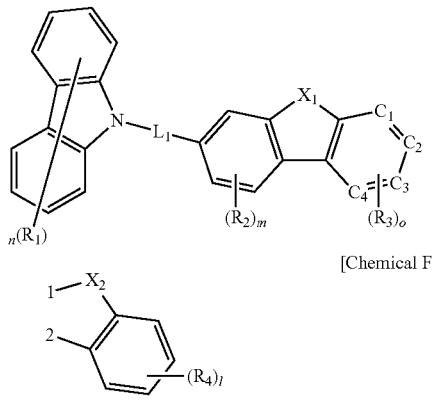

[Chemical Formula 2]

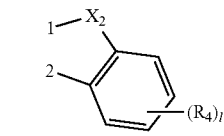

in the Chemical Formula 1, two adjacent carbons of $C_1$ to $C_4$ are respectively connected to 1 and 2 of Chemical Formula 2, where $C_1$ and $C_2$ are not connected to 2 and 1 of Chemical Formula 2 respectively, and $C_4$ and $C_3$ are not connected to 1 and 2 of Chemical Formula 2 respectively, $L_1$ is independently a direct bond; or a substituted or unsubstituted $C_{6-60}$ arylene, $R_1$ is hydrogen; deuterium; a substituted or unsubstituted $C_{1-60}$ alkyl; a substituted or unsubstituted $C_{6-60}$ aryl; or a substituted or unsubstituted $C_{5-60}$ heteroaryl containing at least one heteroatom selected from the group consisting of N, O and S, or is fused with an adjacent ring to form a benzene ring, $R_2$ to $R_4$ are each independently hydrogen; deuterium; a substituted or unsubstituted $C_{1-60}$ alkyl; a substituted or unsubstituted $C_{6-60}$ aryl; or a substituted or unsubstituted $C_{5-60}$ heteroaryl containing at least one heteroatom selected from the group consisting of N, O and S, n is an integer of 0 to 8, m and o are each independently an integer of 0 to 3, l is an integer of 0 to 4, $X_1$ is NR' and $X_2$ is O or S, or $X_1$ is O or S and $X_2$ is NR', R' is

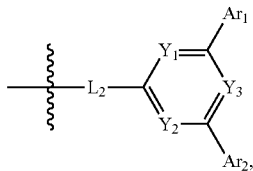

$L_2$ is a direct bond; or a substituted or unsubstituted $C_{6-60}$ arylene, $Y_1$, $Y_2$ and $Y_3$ are each independently CH; or N, and at least two of $Y_1$, $Y_2$ and $Y_3$ are N, and $Ar_1$ and $Ar_2$ are each independently a substituted or unsubstituted $C_{6-60}$ aryl; or a substituted or unsubstituted $C_{5-60}$ heteroaryl containing at least one heteroatom selected from the group consisting of N, O and S.

The connection relationship between Chemical Formula 1 and Chemical Formula 2 means, specifically, $C_1$-1 and $C_2$-2; $C_2$-1 and $C_3$-2; $C_3$-1 and $C_2$-2; $C_3$-1 and $C_4$-2.

Preferably, the compound represented by Chemical Formula 1 may be any one selected from the group consisting of compounds represented by the following Chemical Formulas 3 to 6:

[Chemical Formula 3]

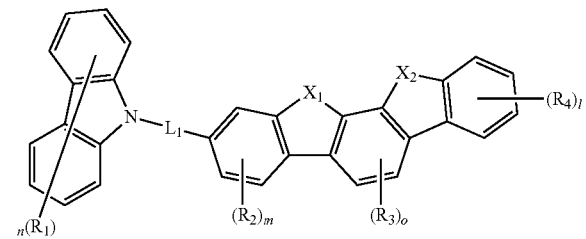

[Chemical Formula 4]

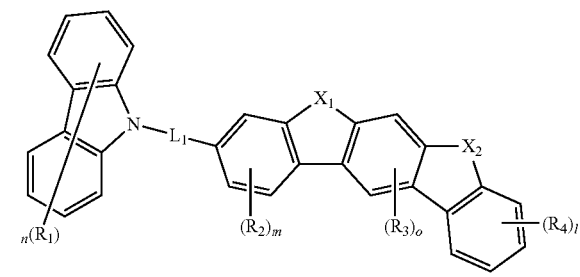

[Chemical Formula 5]

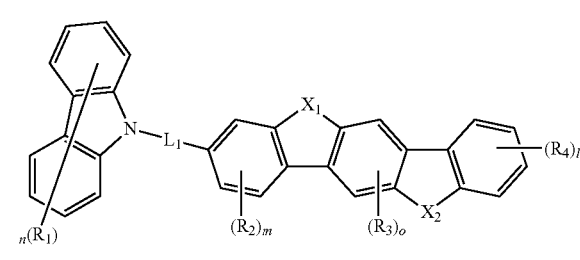

[Chemical Formula 6]

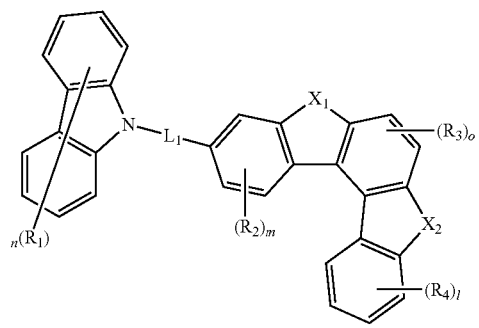

in the Chemical Formulas 3 to 6, $X_1$, $X_2$, $L_1$, $R_1$, $R_2$, $R_3$, $R_4$, n, m, o and l are the same as defined above.

Preferably, $L_1$ and $L_2$ are each independently a direct bond; phenylene unsubstituted or substituted with deuterium; or naphthylene unsubstituted or substituted with deuterium.

Preferably, $R_1$ is hydrogen; deuterium; methyl; ethyl; propyl; phenyl unsubstituted or substituted with deuterium; biphenylyl unsubstituted or substituted with deuterium; or is fused with an adjacent ring to form a benzene ring.

Preferably, $R_2$ to $R_4$ are each independently hydrogen; deuterium; methyl; ethyl; propyl; phenyl unsubstituted or substituted with deuterium; or biphenylyl unsubstituted or substituted with deuterium.

Preferably, $Ar_1$ and $Ar_2$ are each independently phenyl substituted or unsubstituted with deuterium; biphenylyl unsubstituted or substituted with deuterium; dibenzofuranyl unsubstituted or substituted with deuterium; or dibenzothiophenyl unsubstituted or substituted with deuterium.

The compound represented by Chemical Formula 1 is any one selected from the group consisting of:

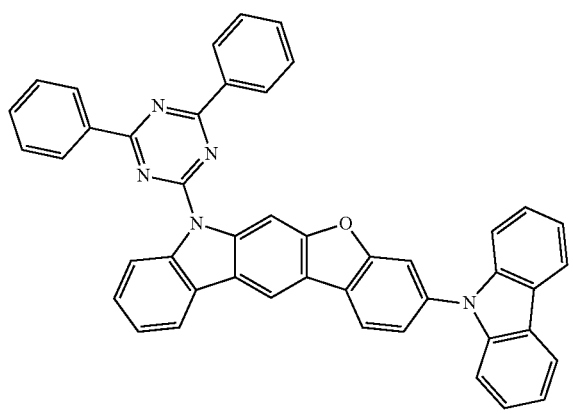

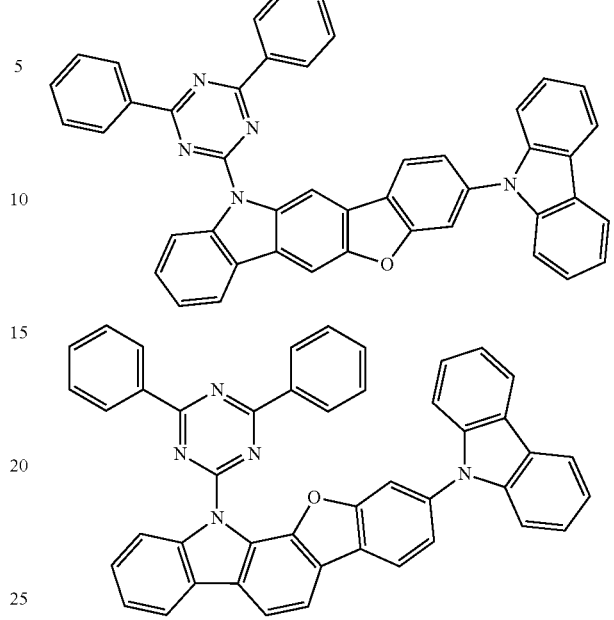

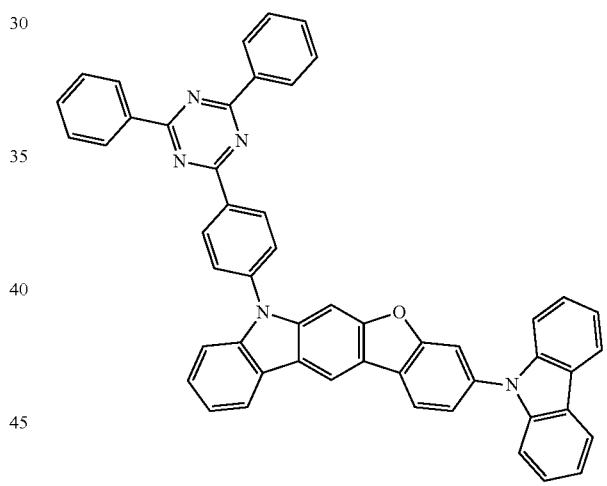

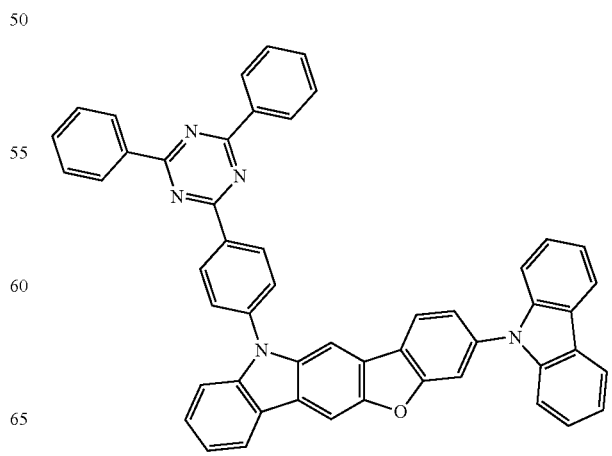

11
-continued
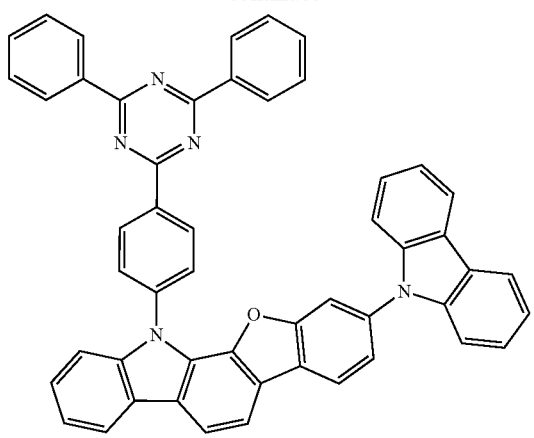
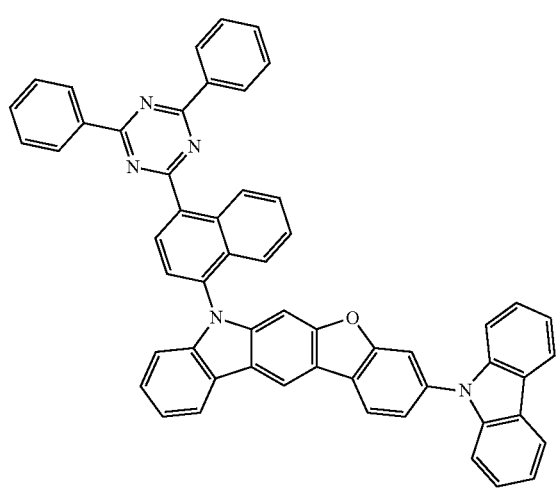
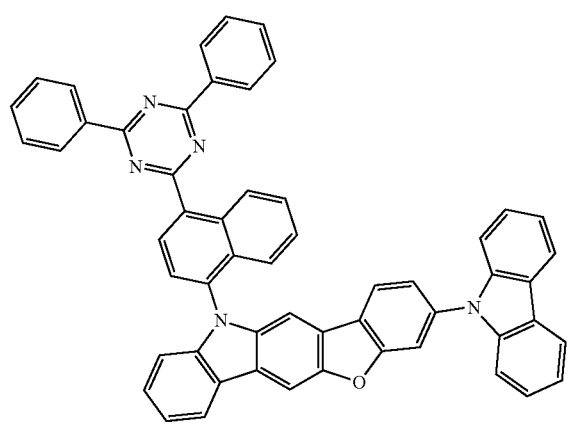
12
-continued
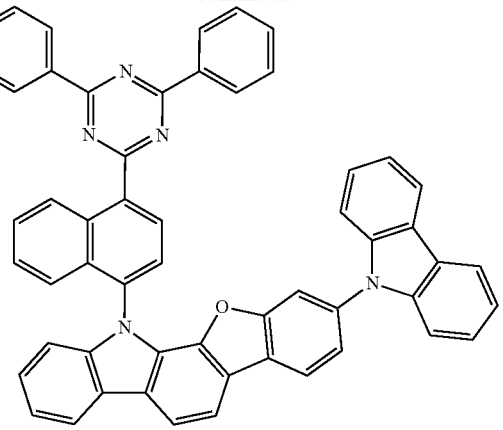
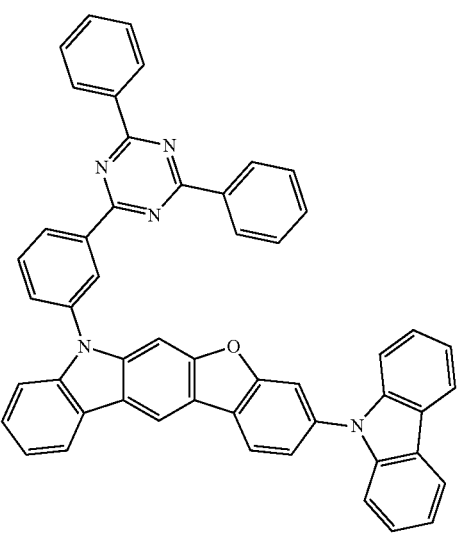
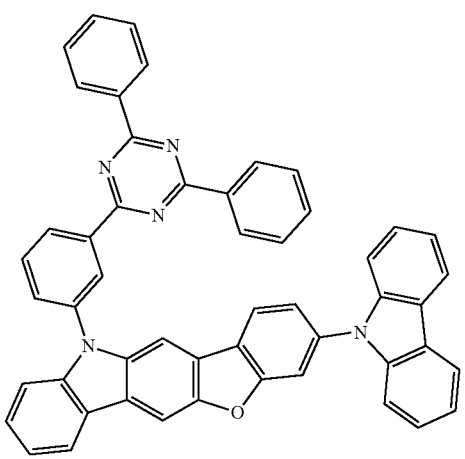

-continued
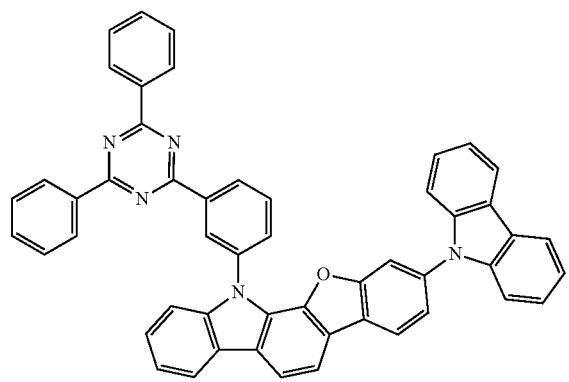
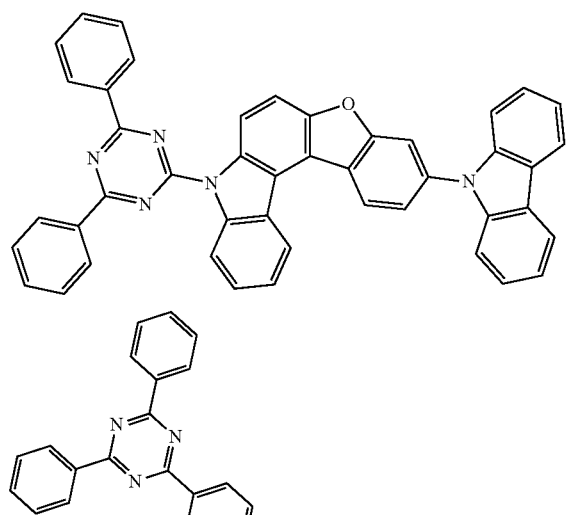
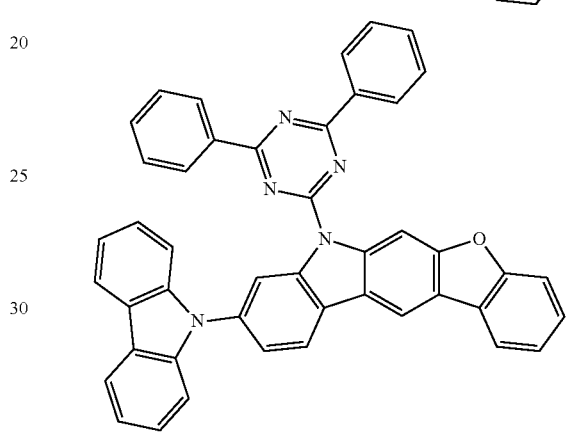
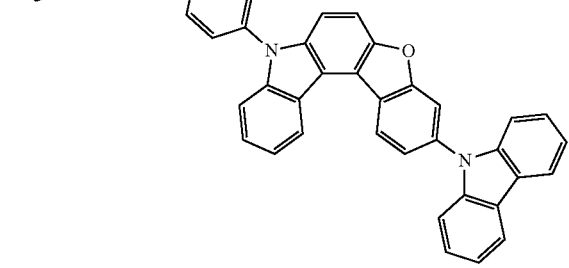
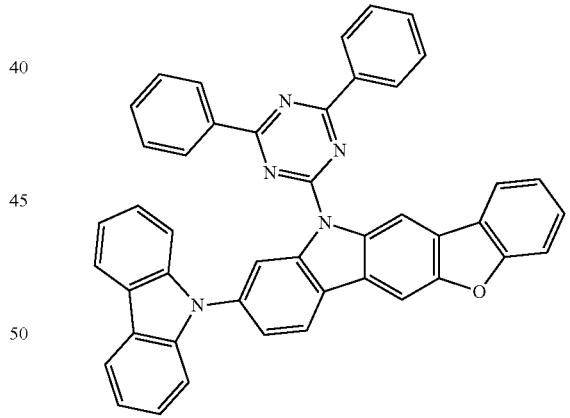
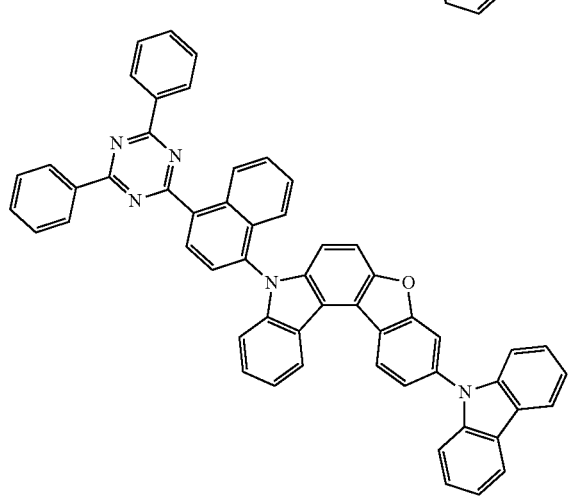
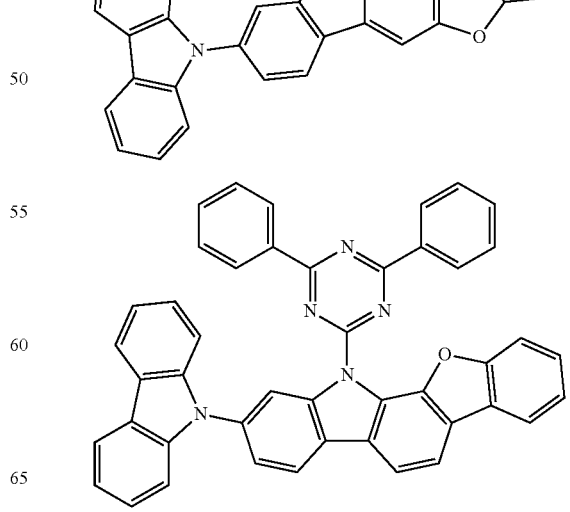

-continued
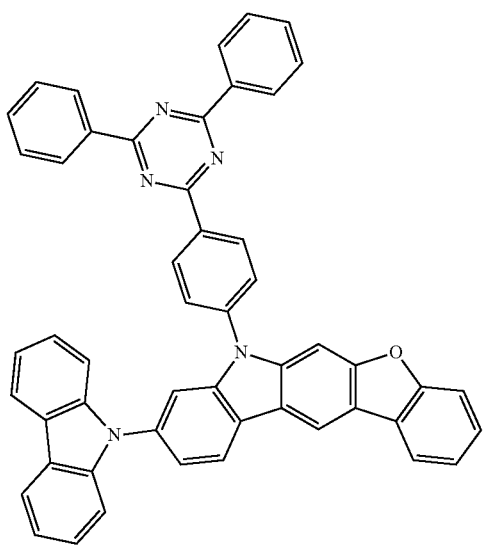
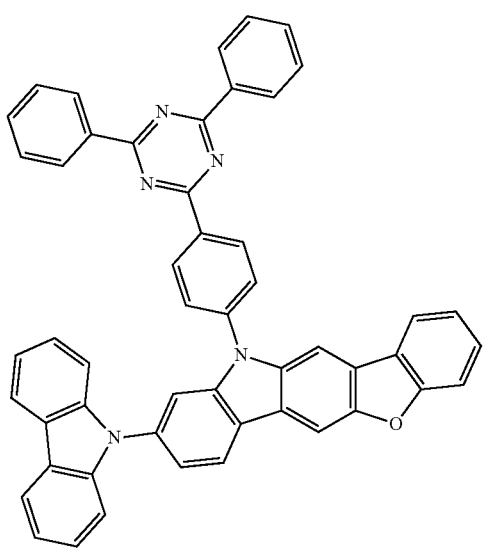
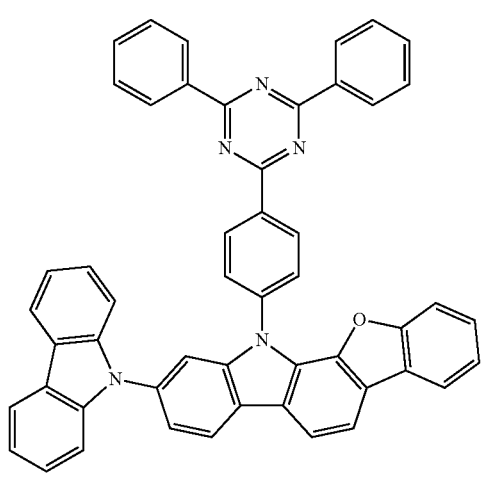
-continued
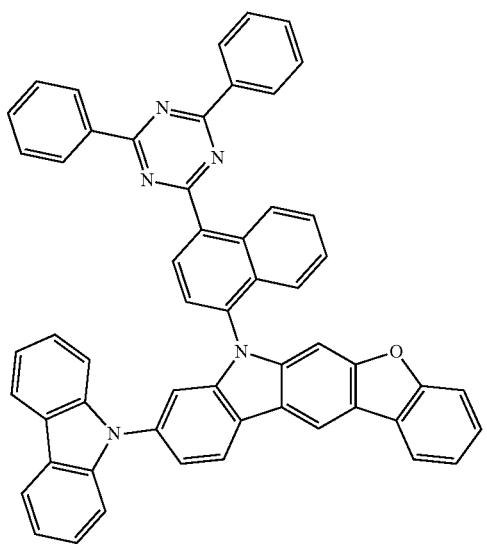
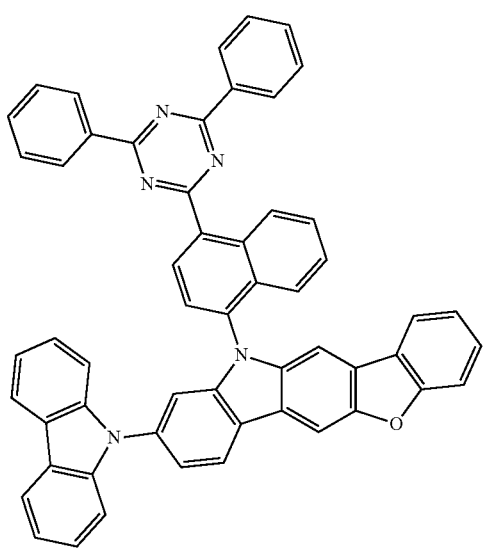
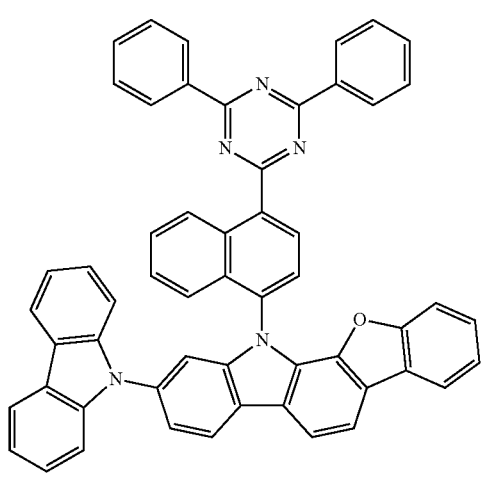

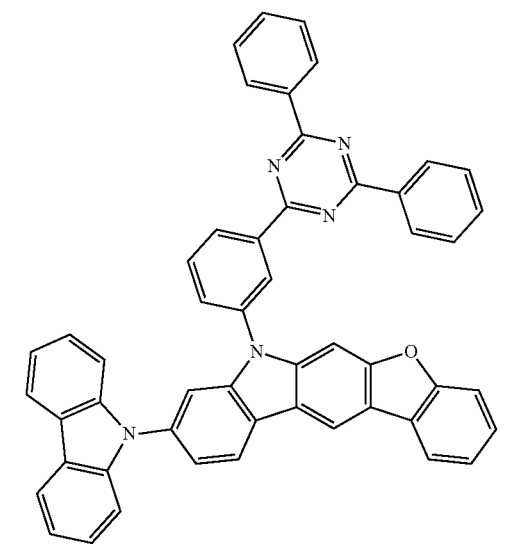
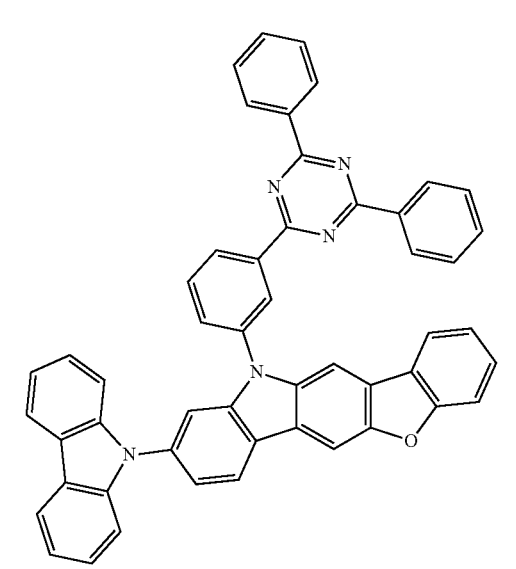
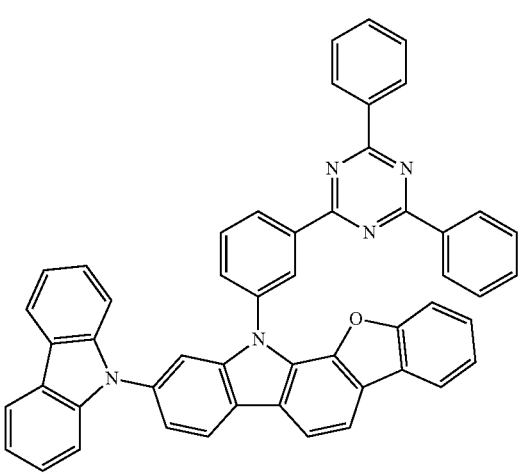
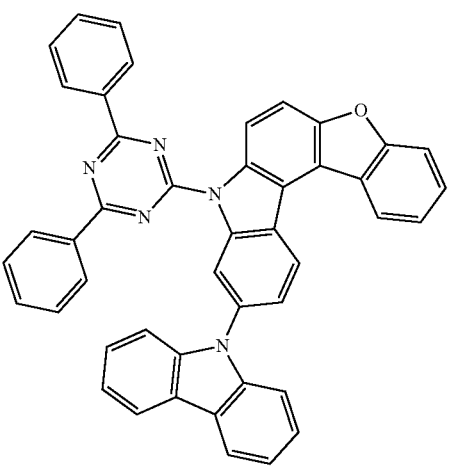
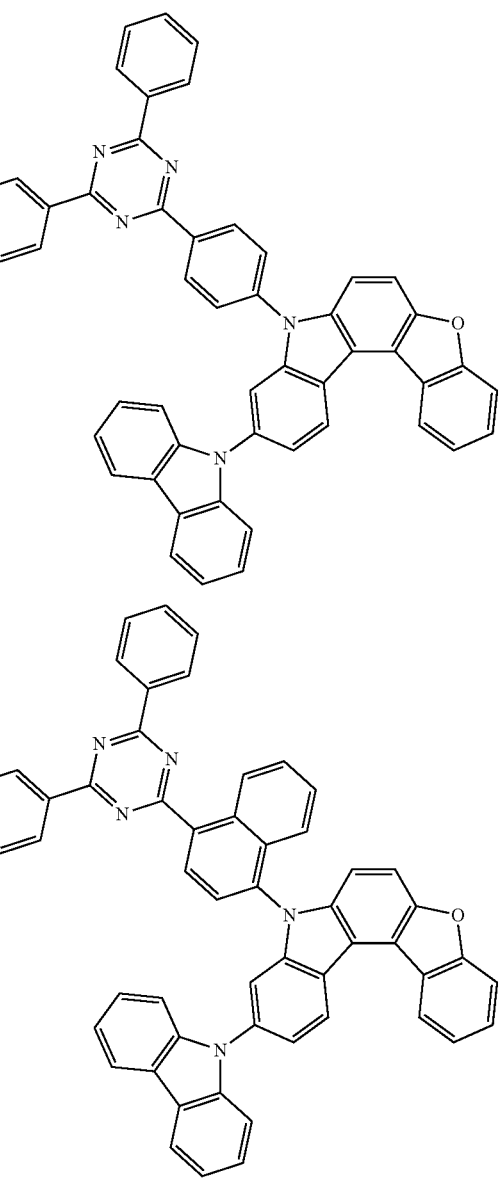

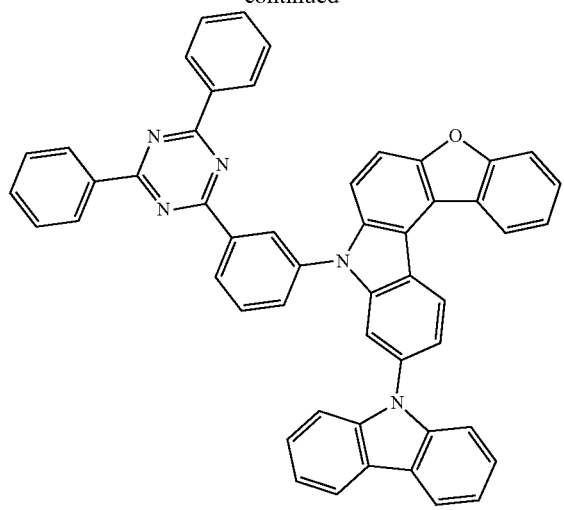
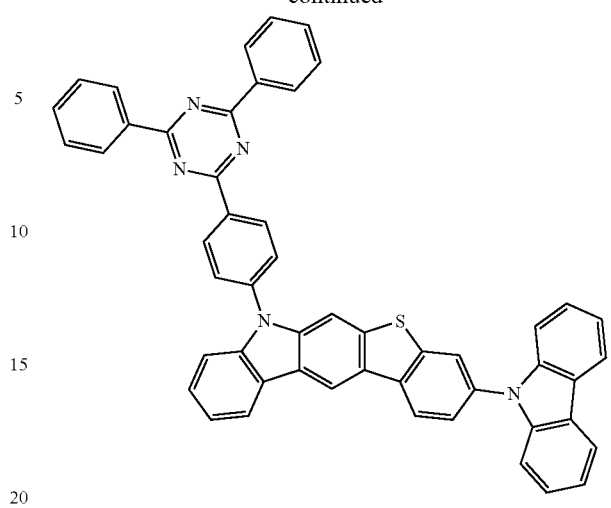
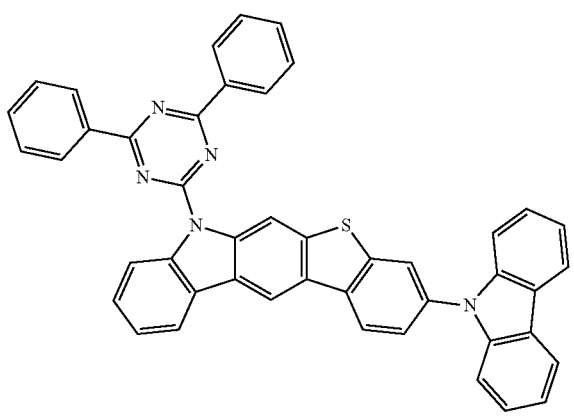
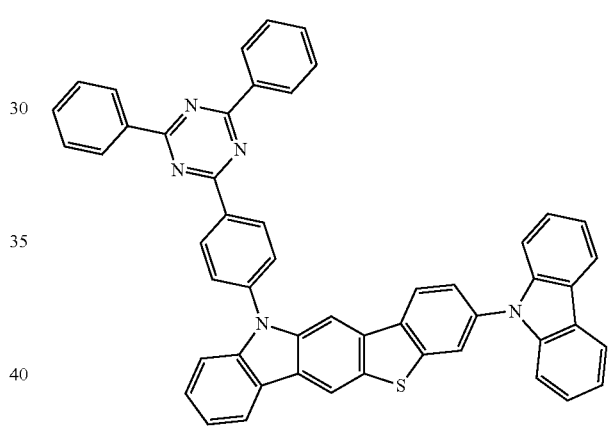
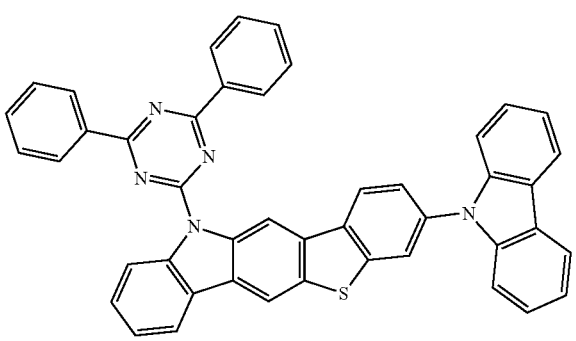
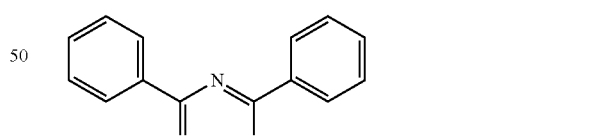
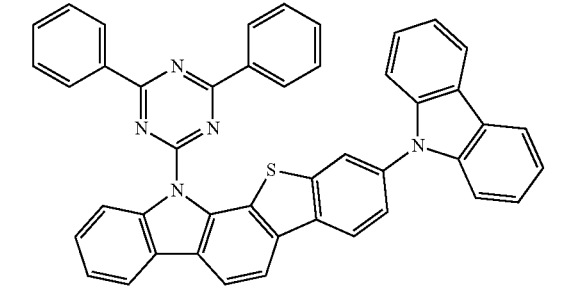
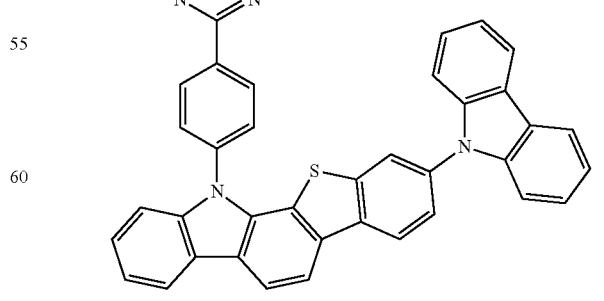

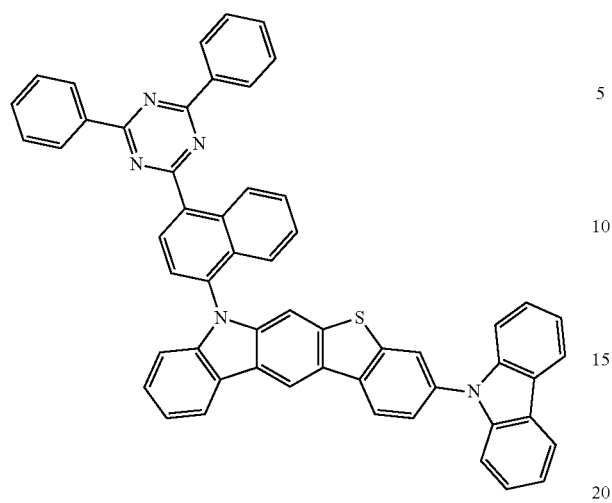
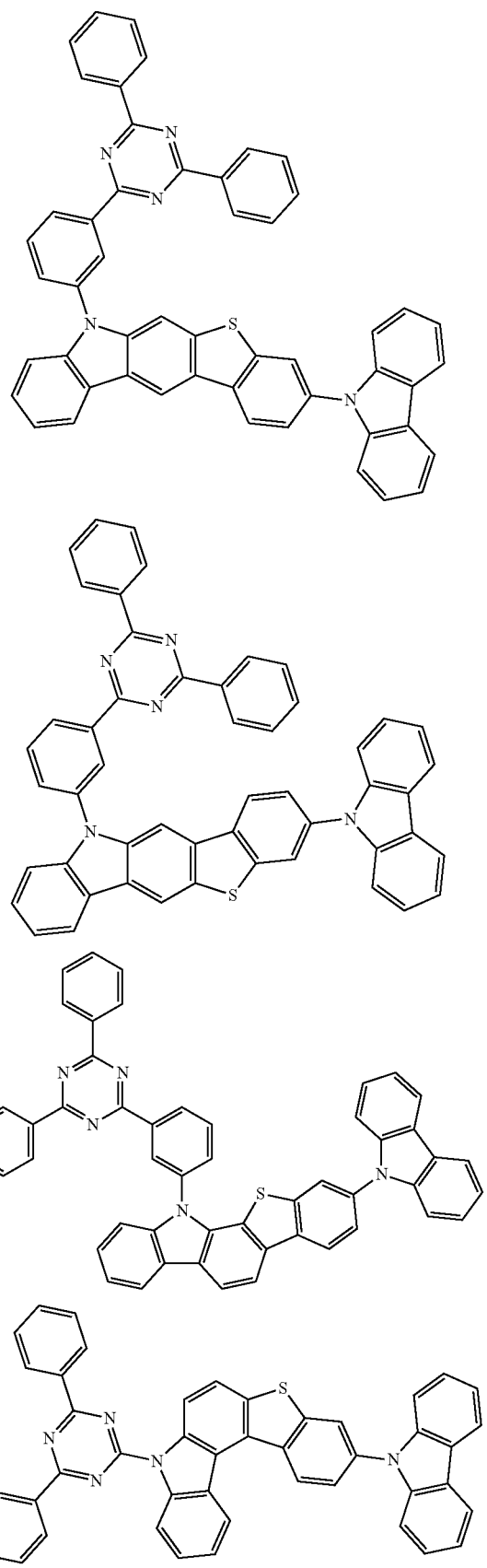

23
-continued
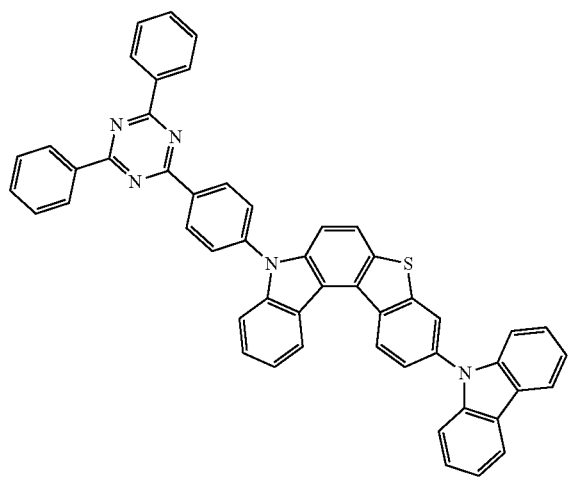
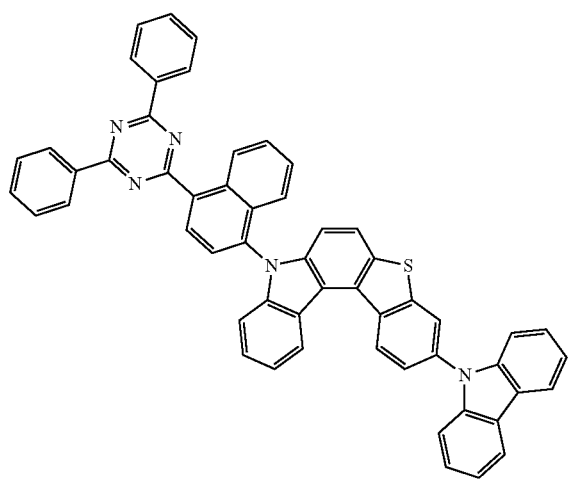
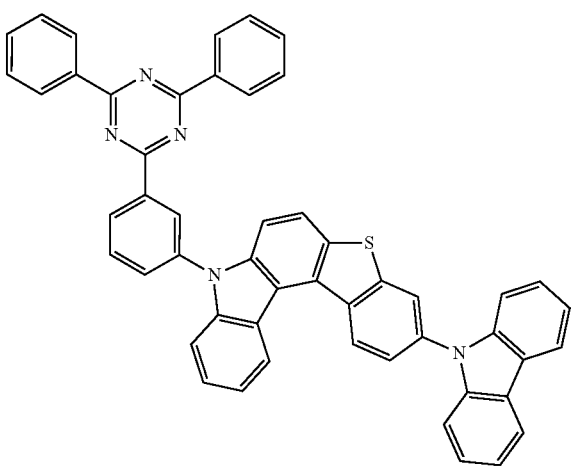
24
-continued
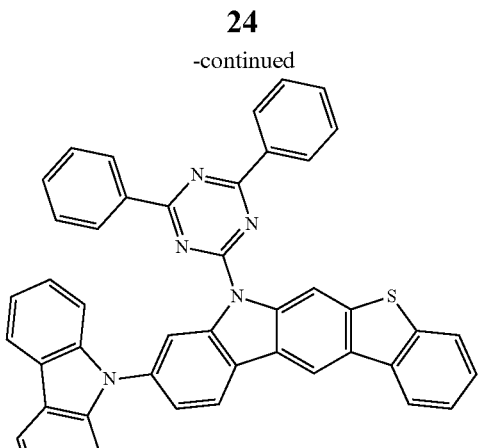
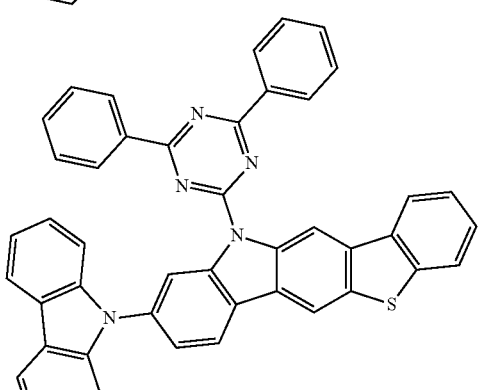
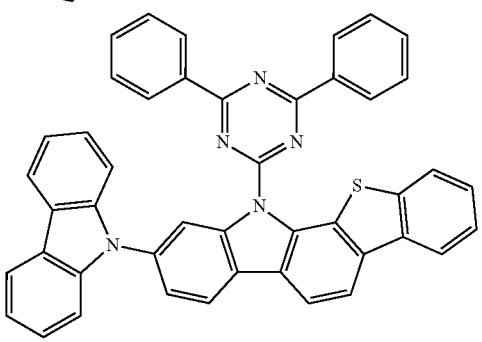
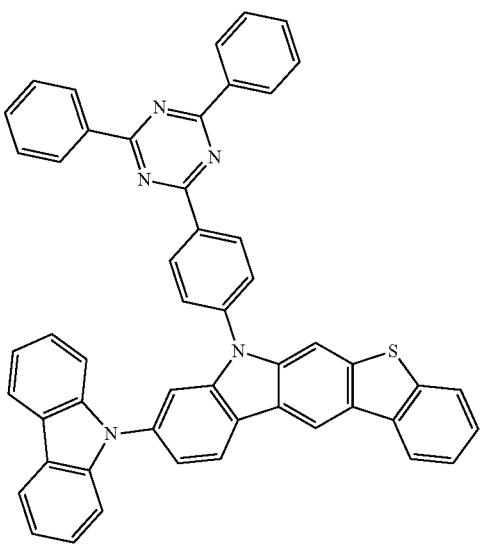

-continued
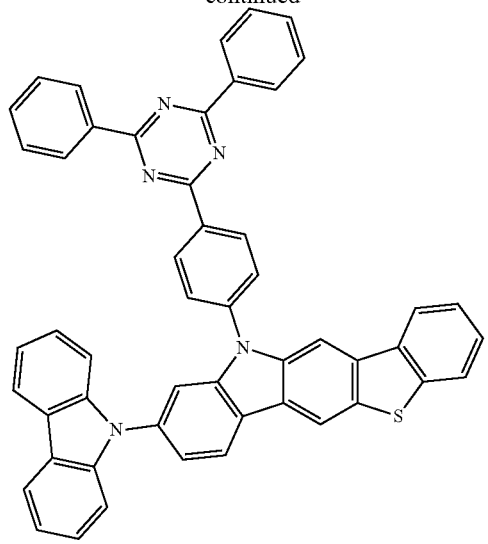
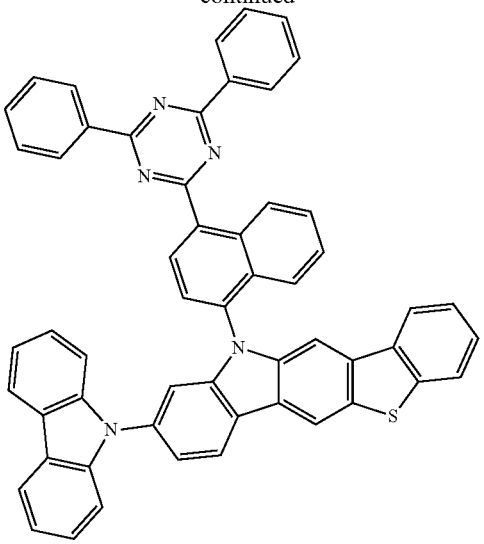
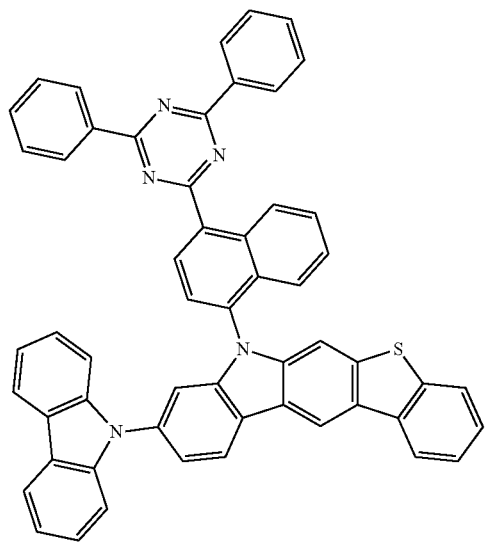
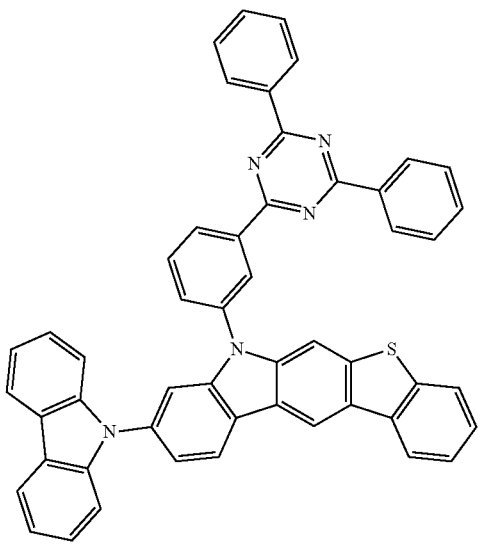

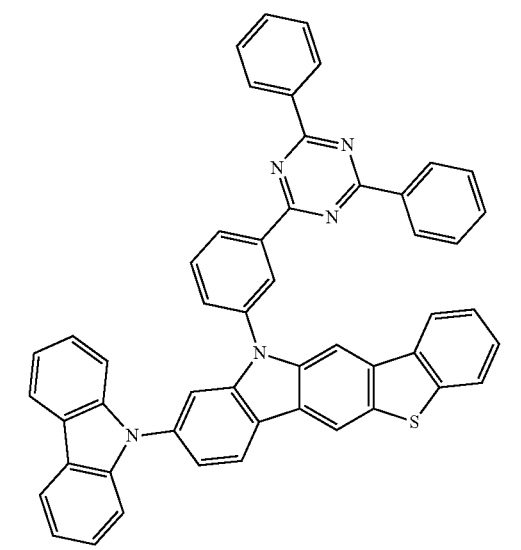
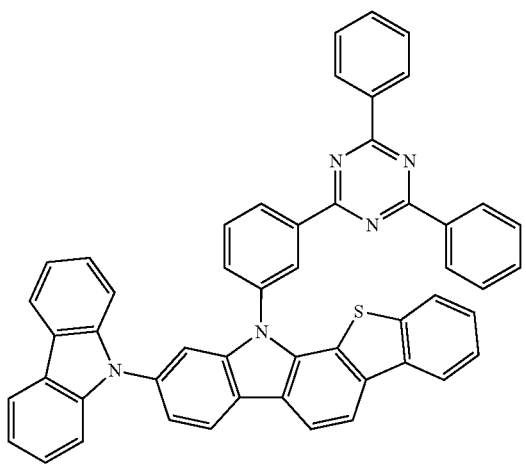
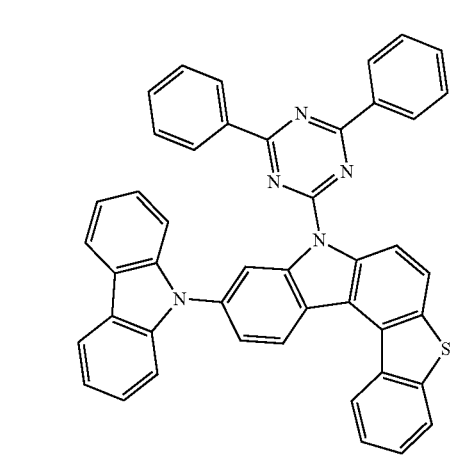
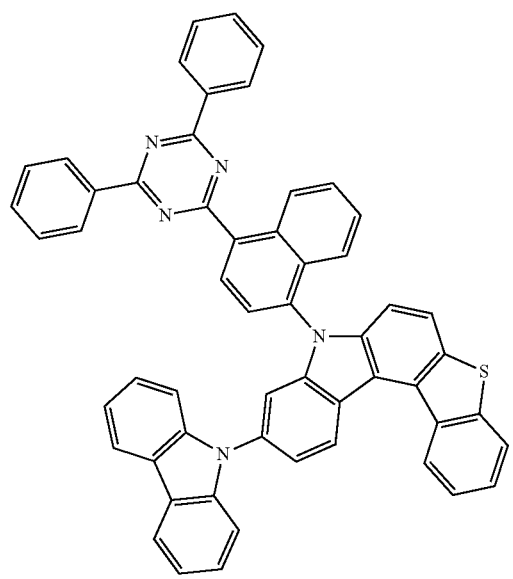
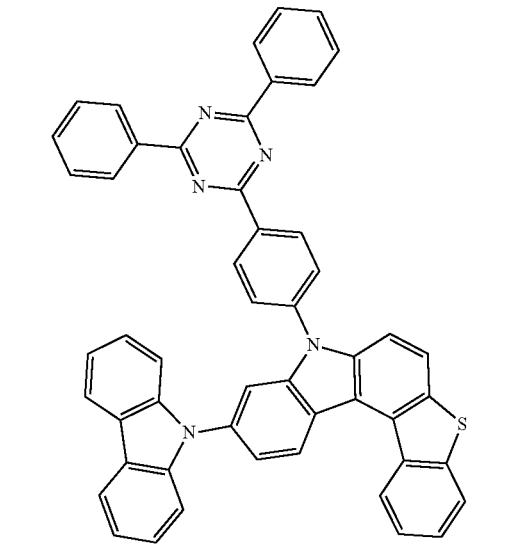

29
-continued
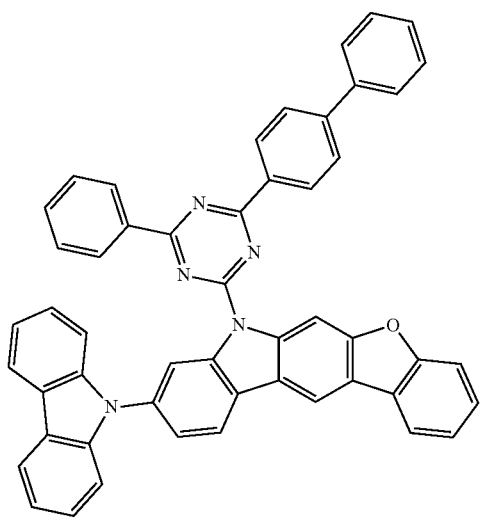
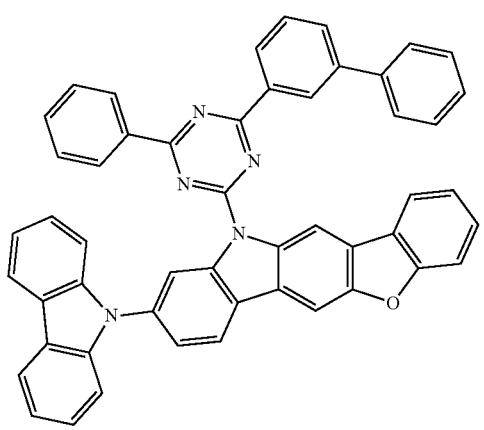
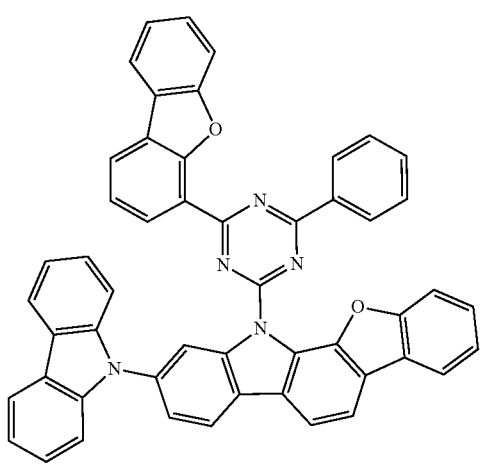
30
-continued
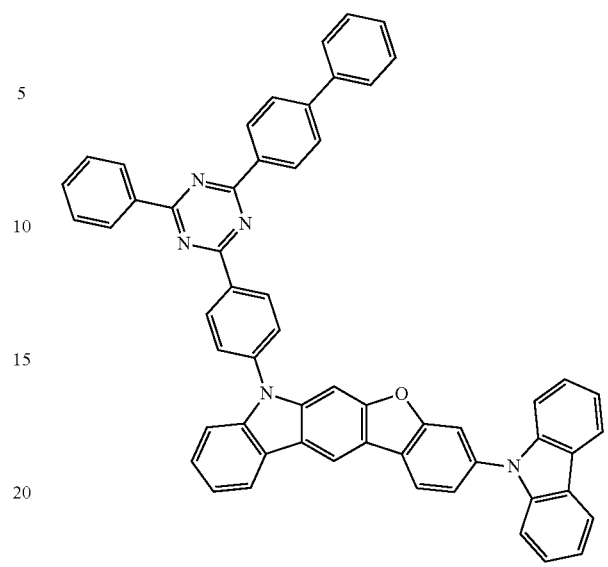
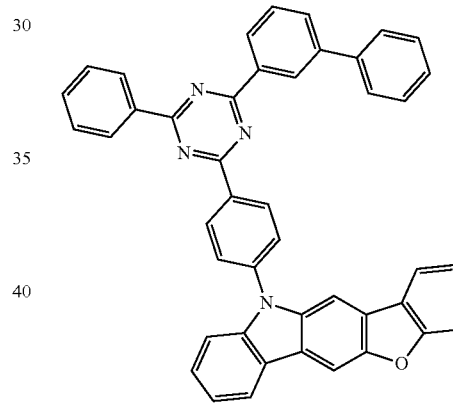
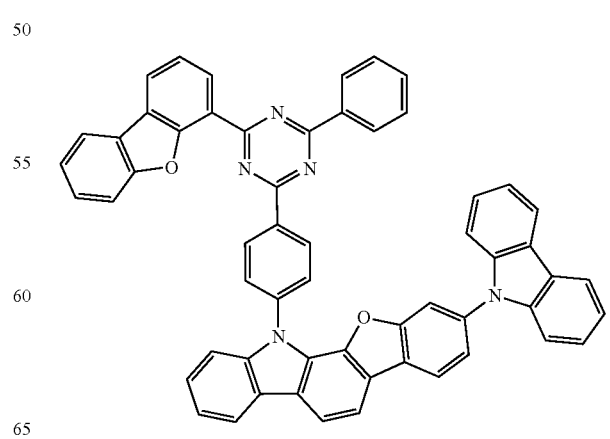

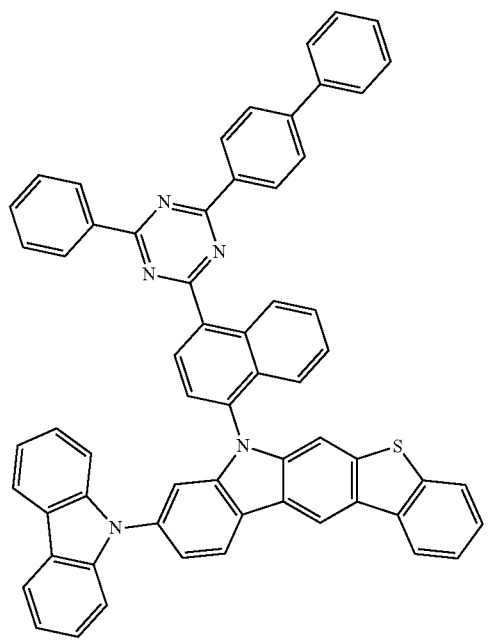
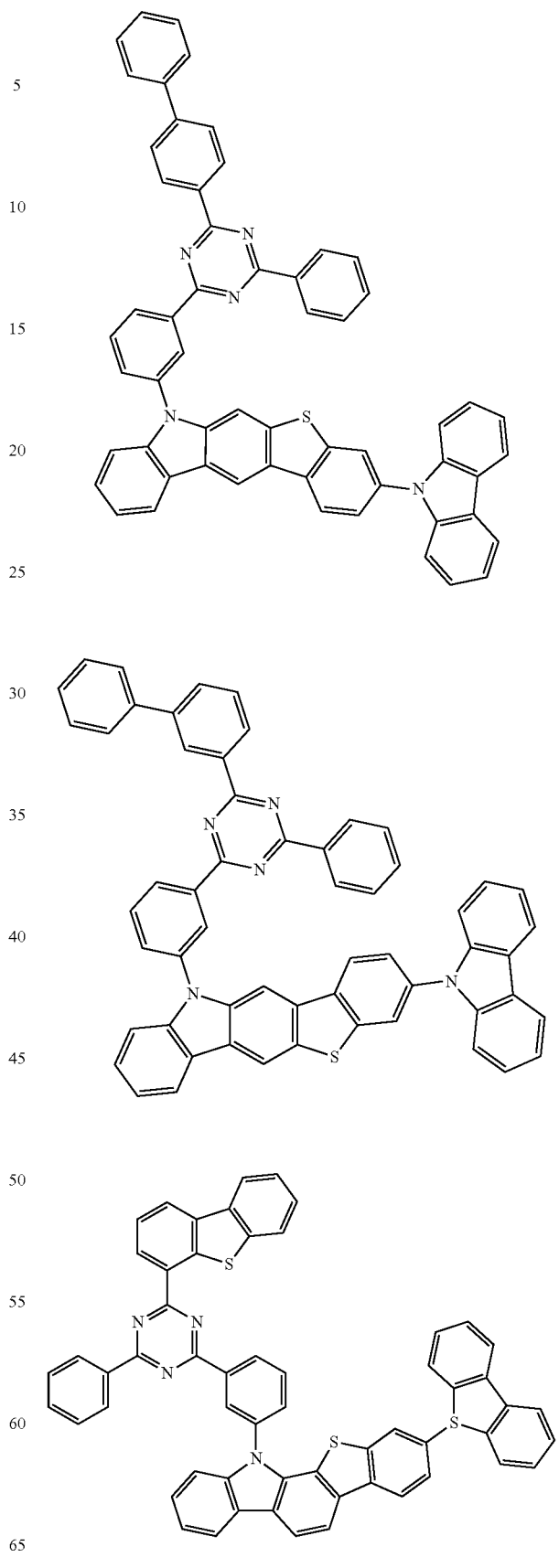

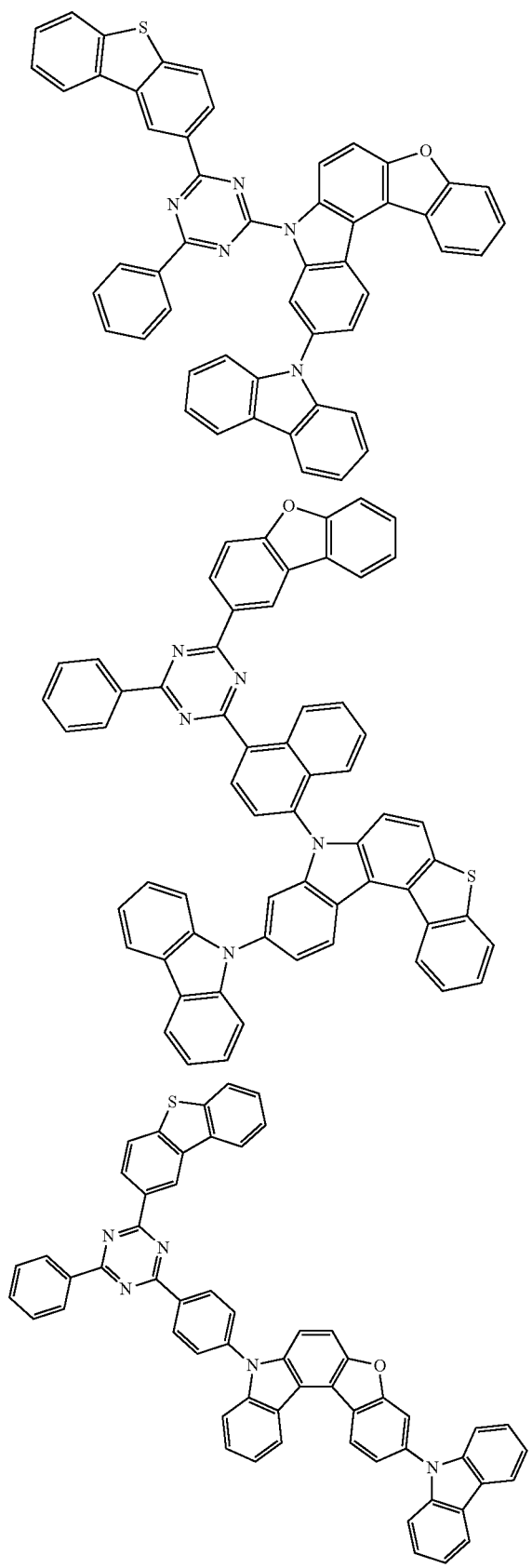
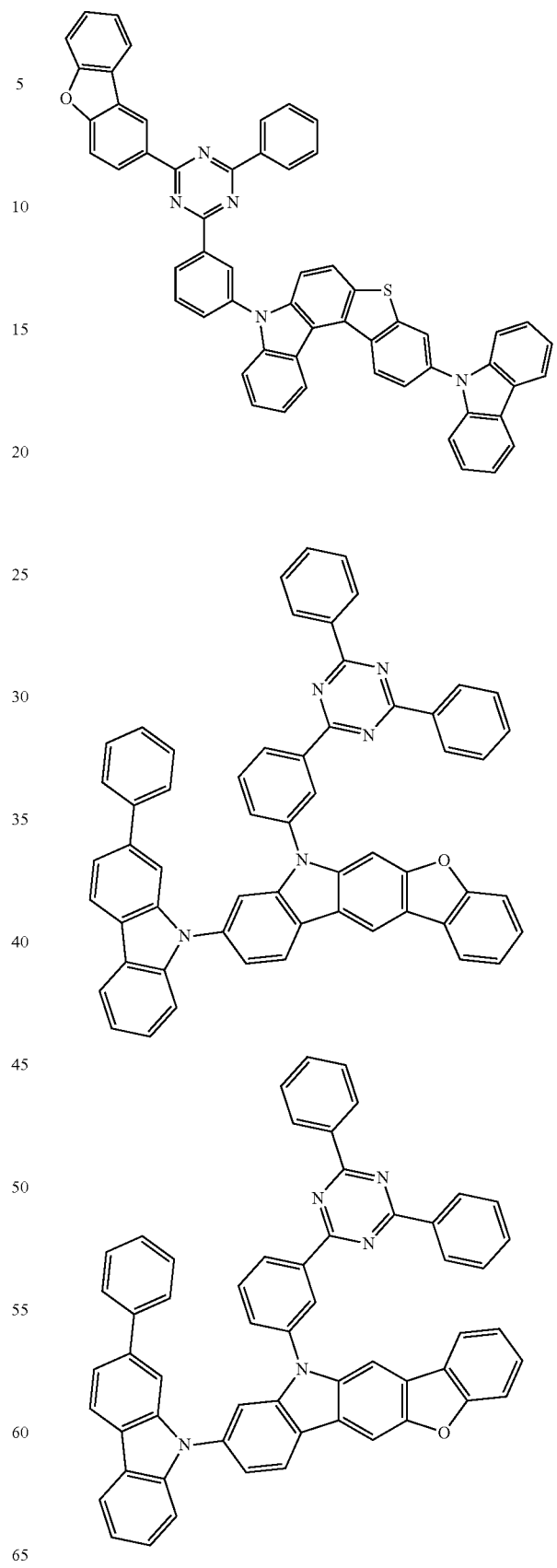

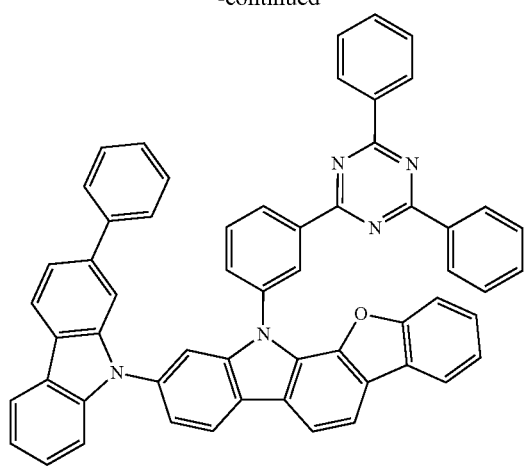
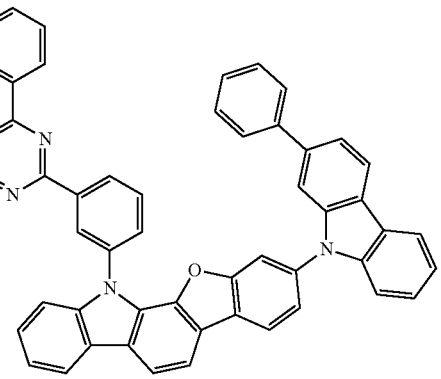
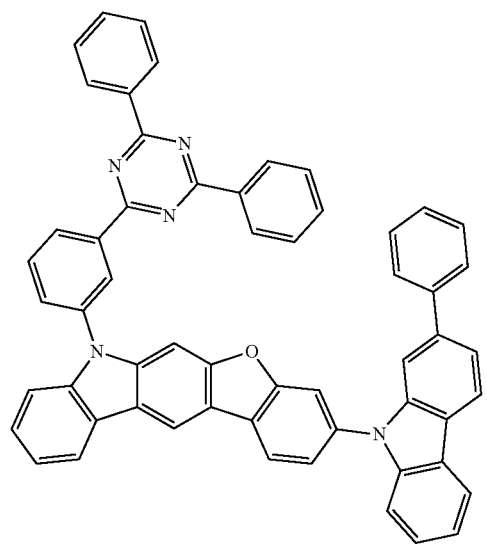
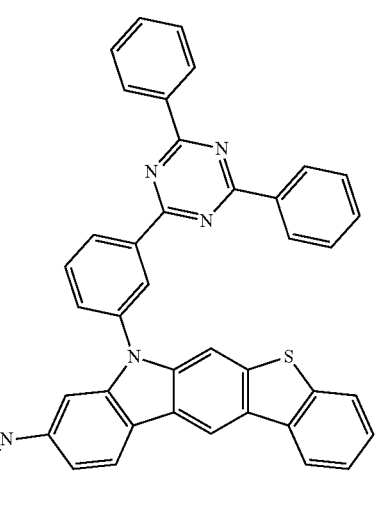
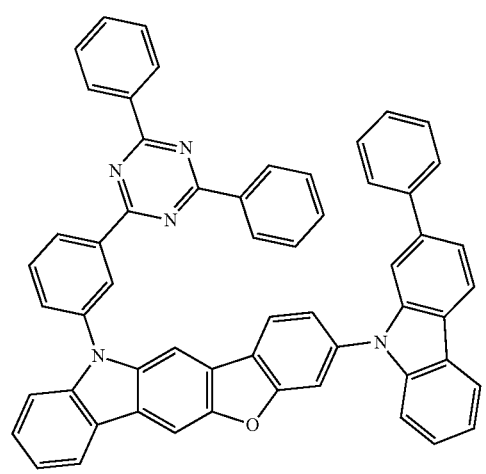
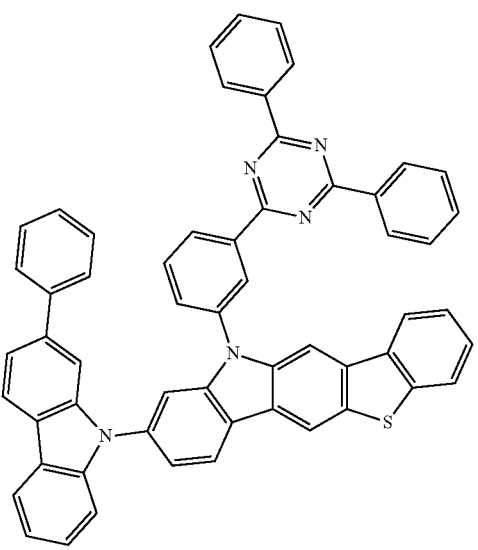

37
-continued
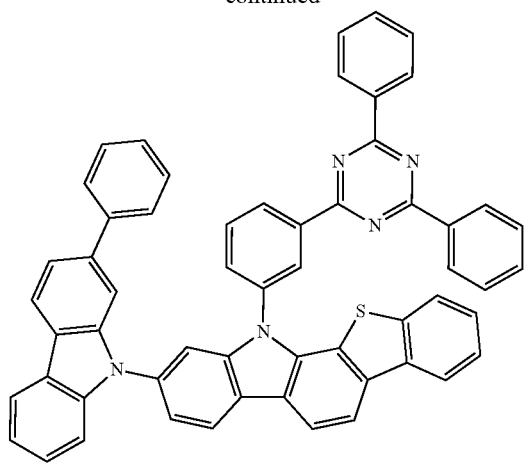
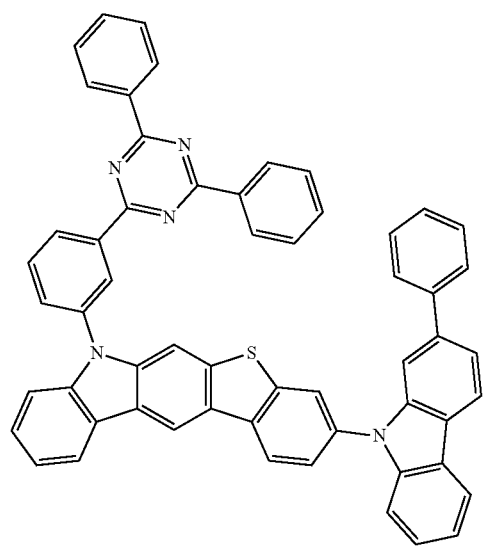
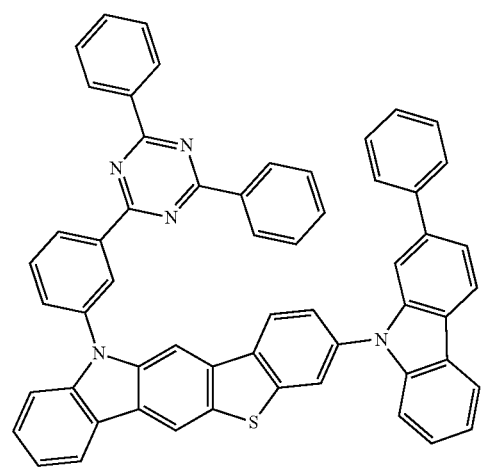
38
-continued
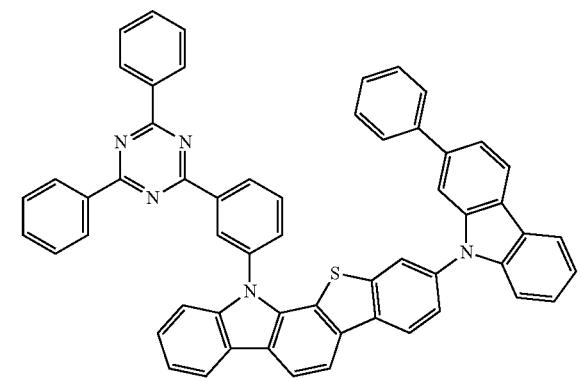
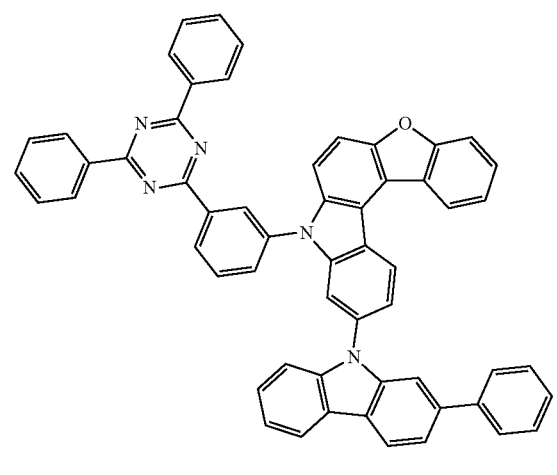
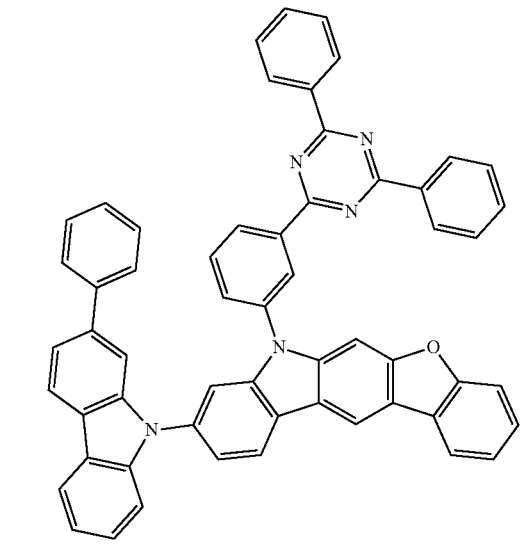

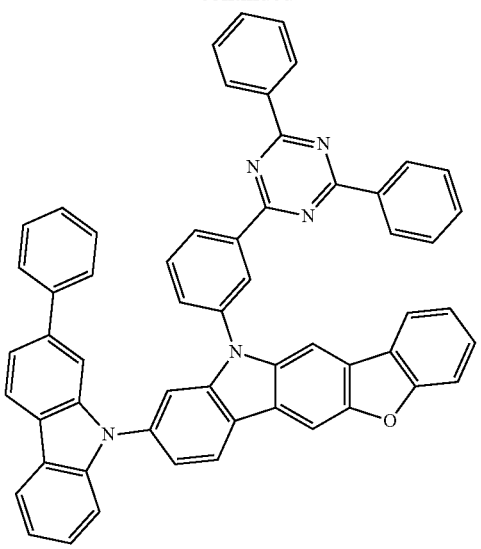
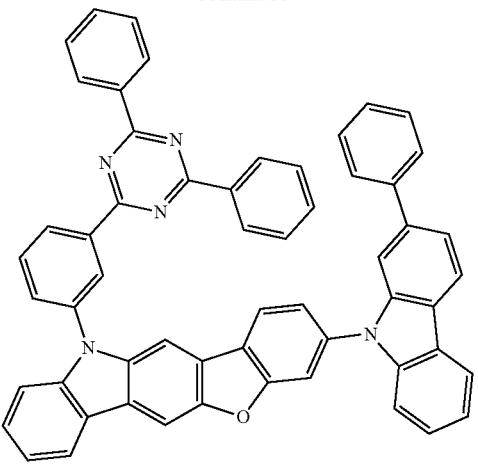
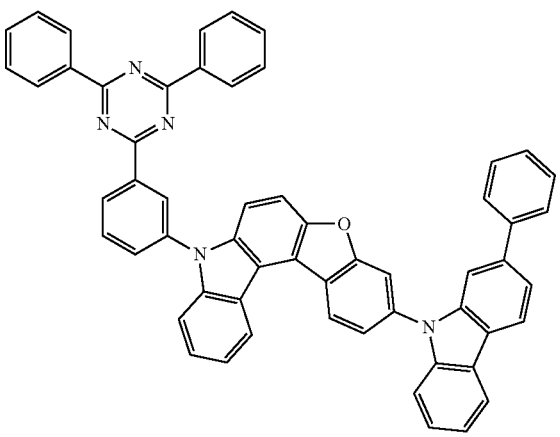
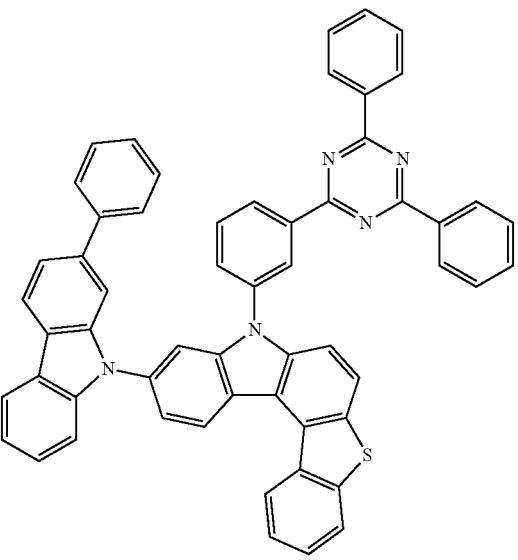
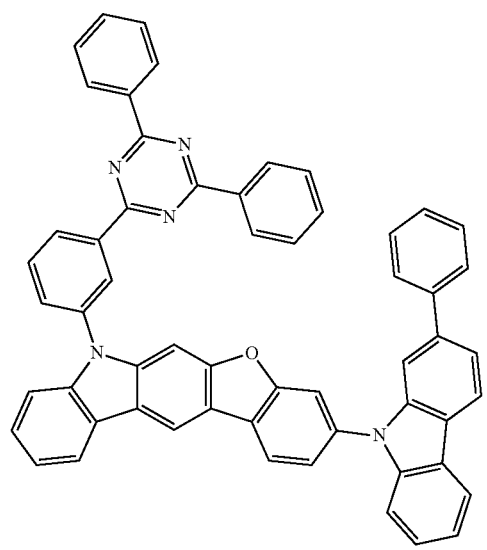

-continued
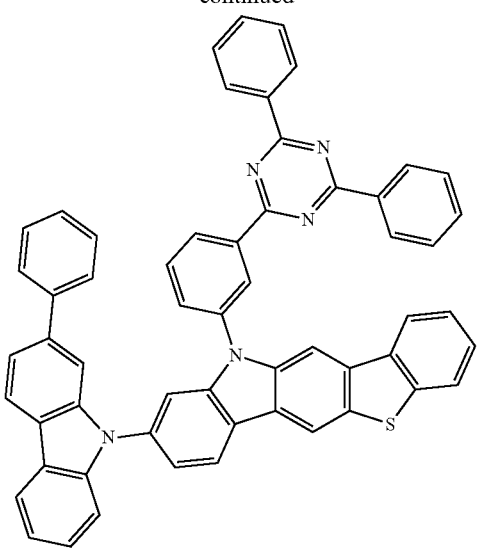
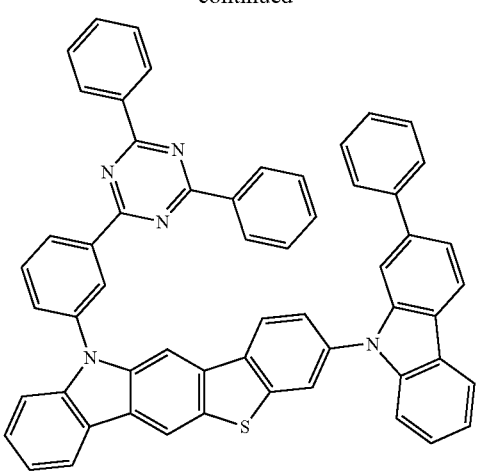
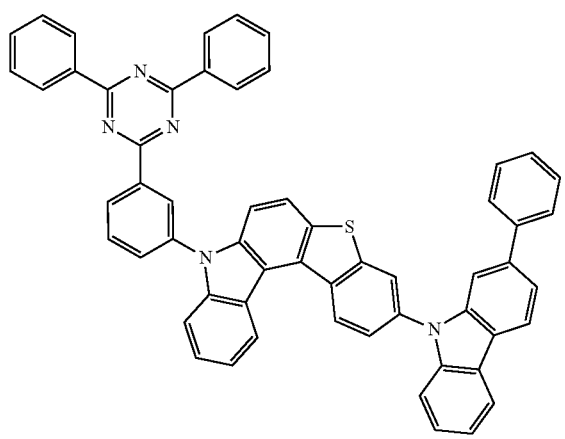
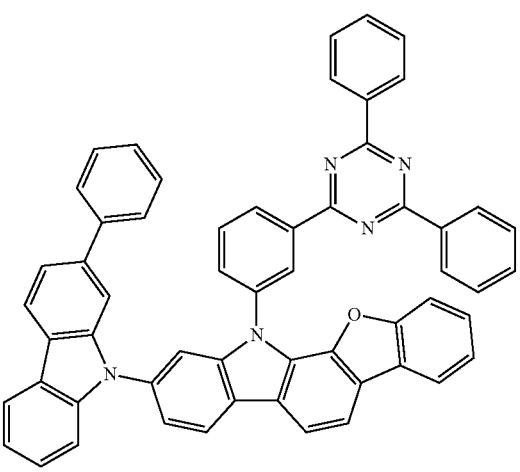
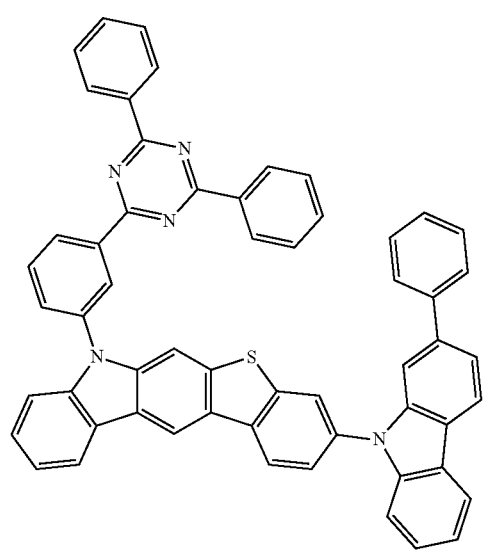
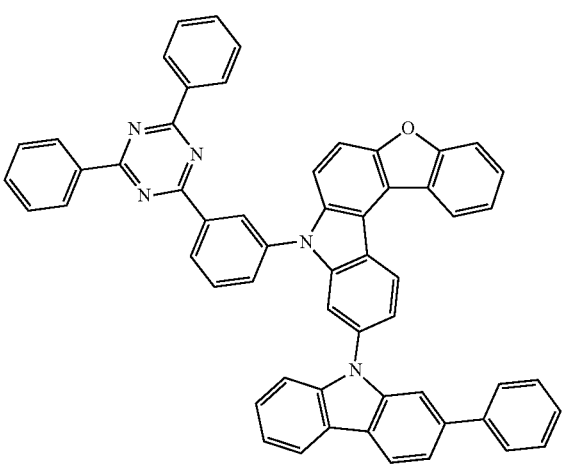

-continued
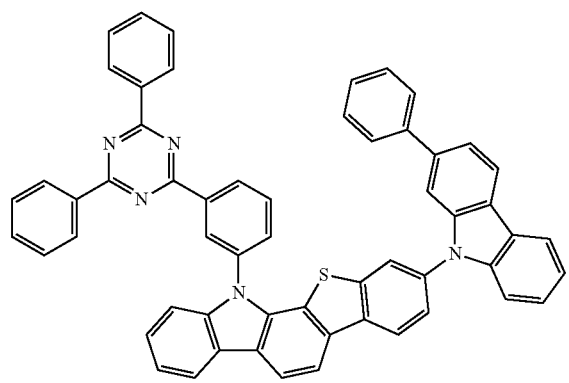
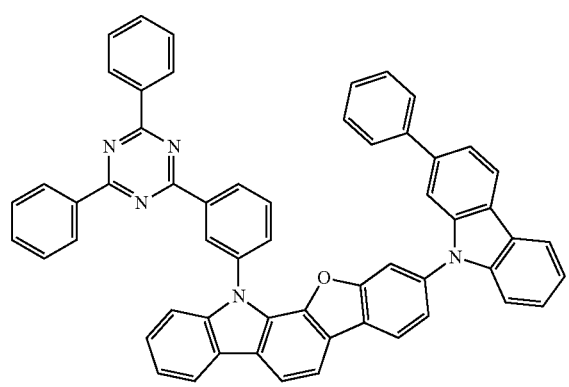
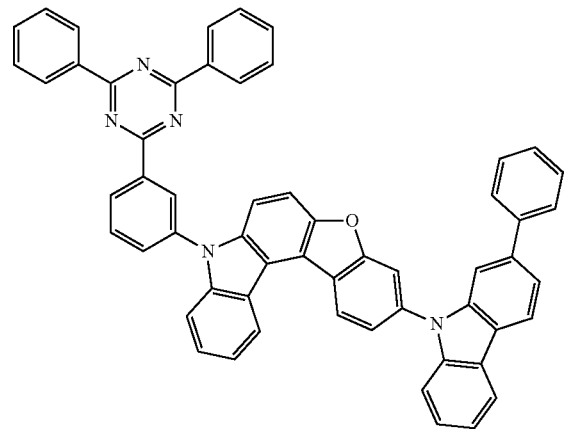
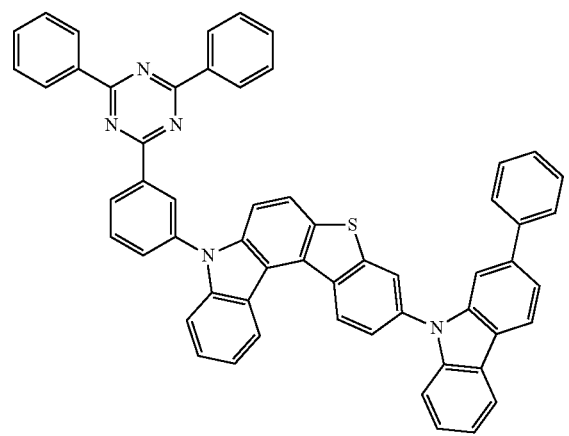
-continued
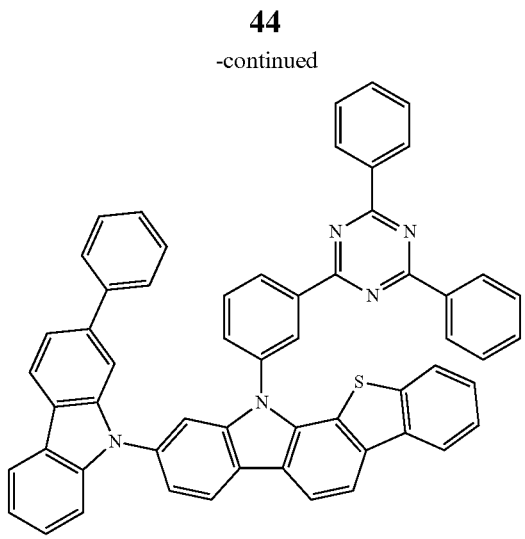
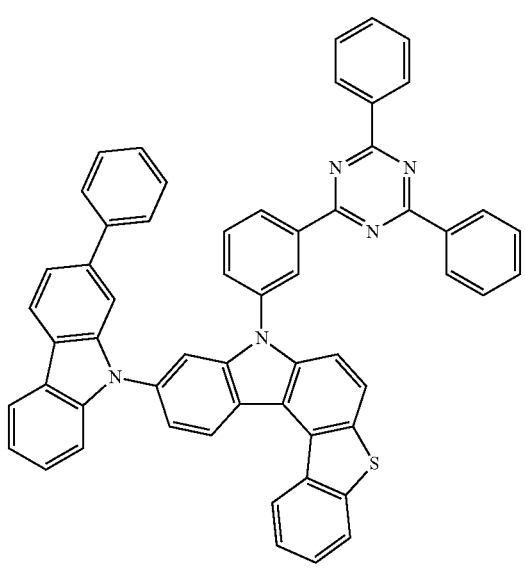
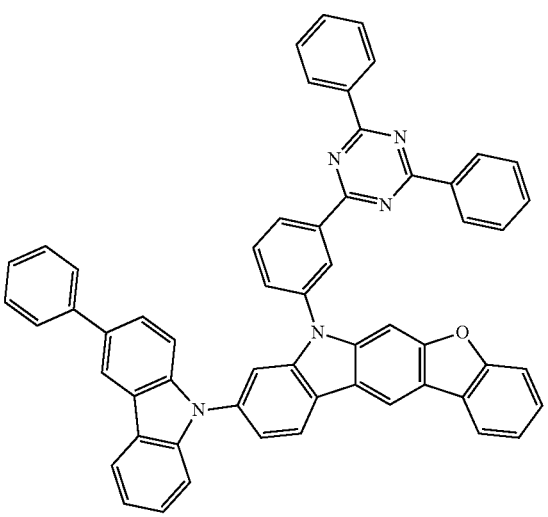

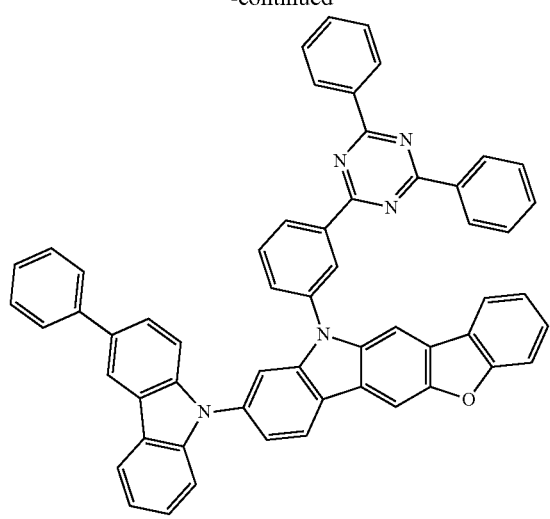
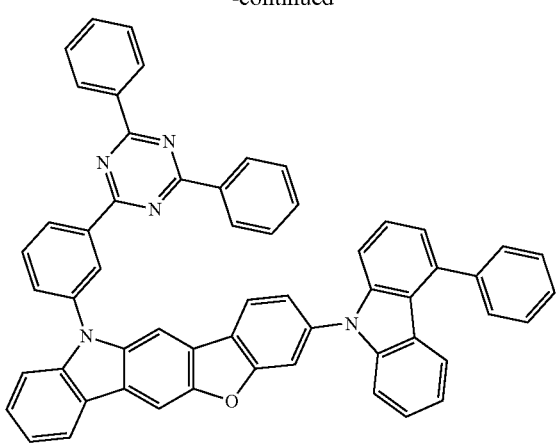
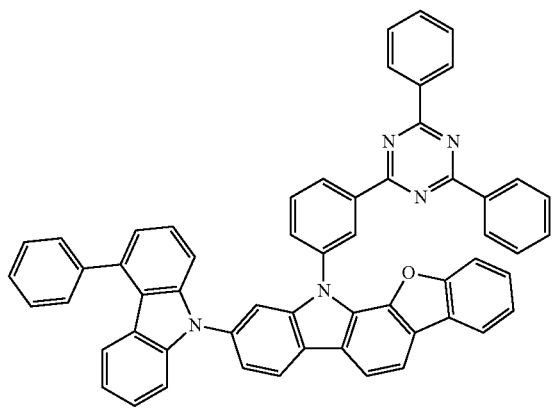
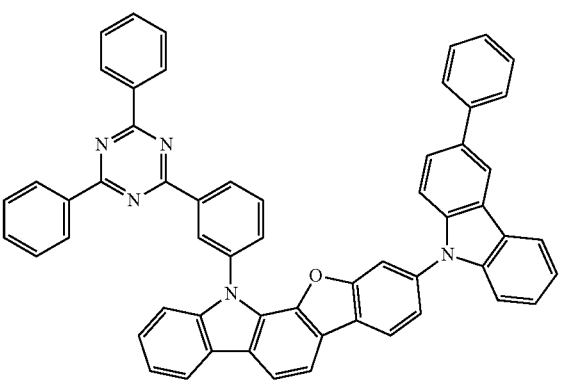
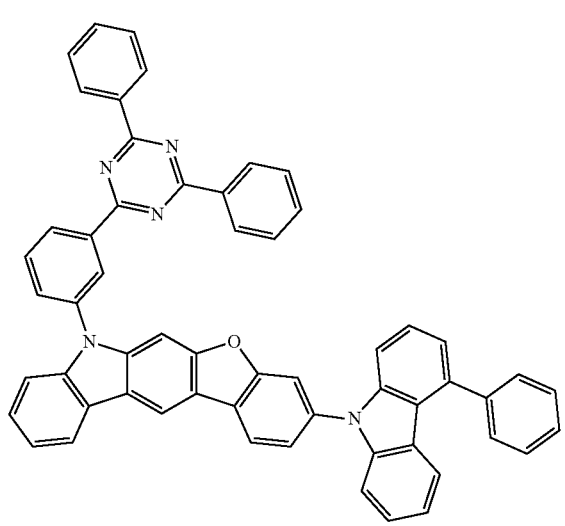

-continued
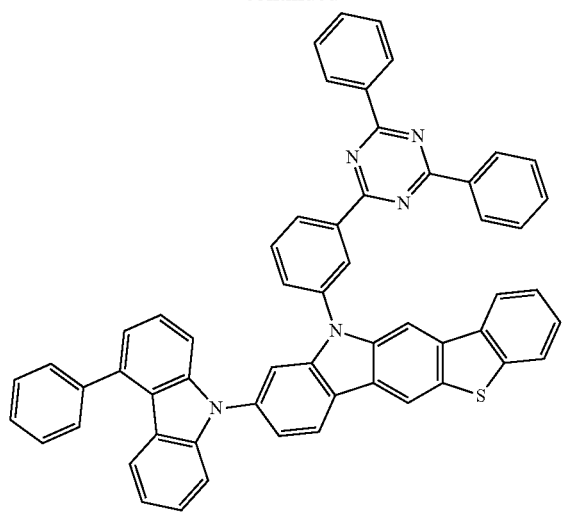
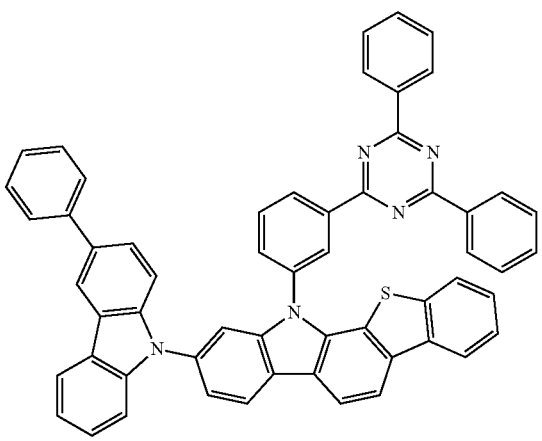
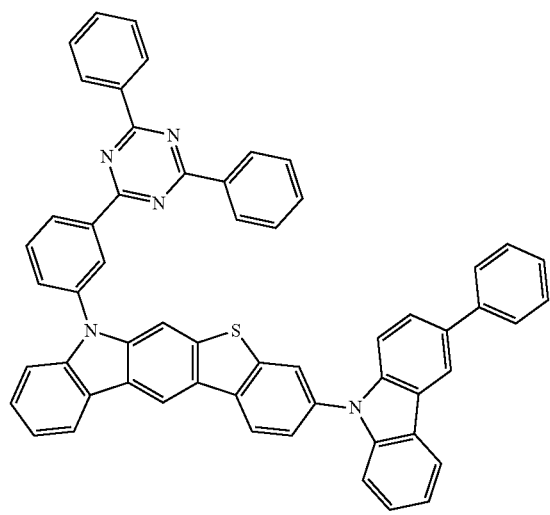
-continued
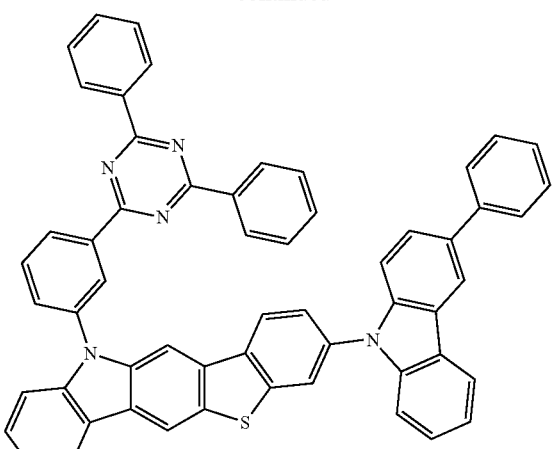
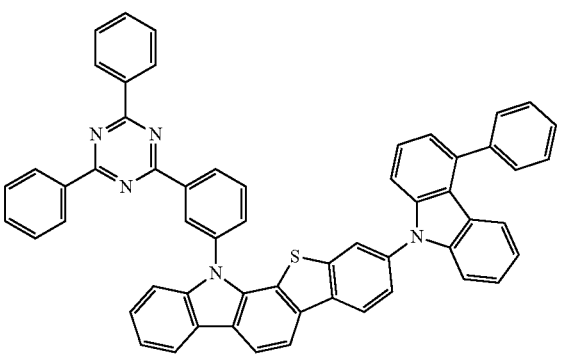
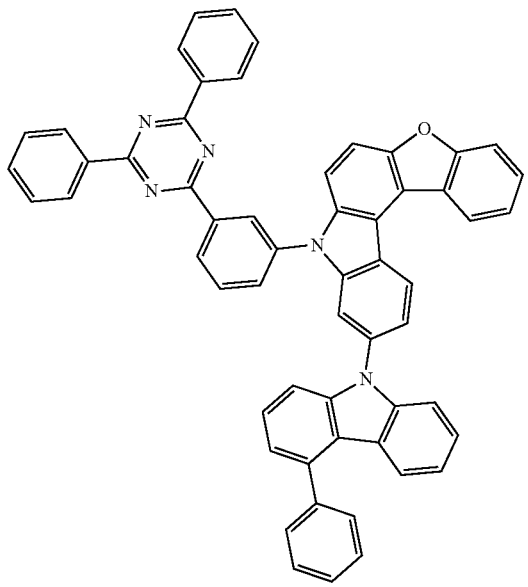

49
-continued
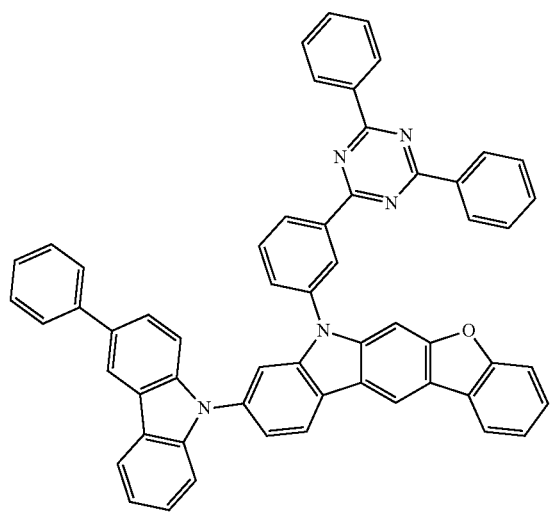
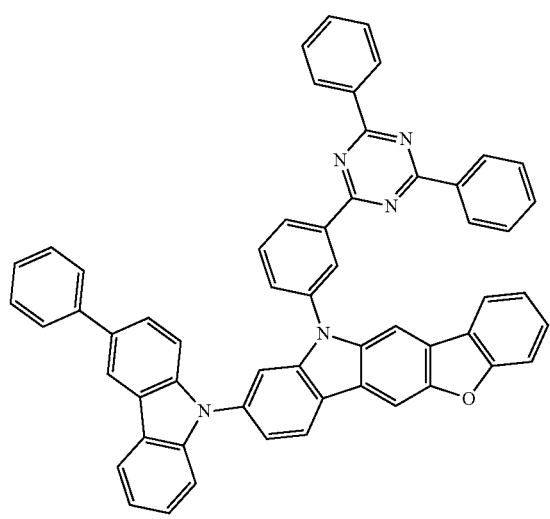
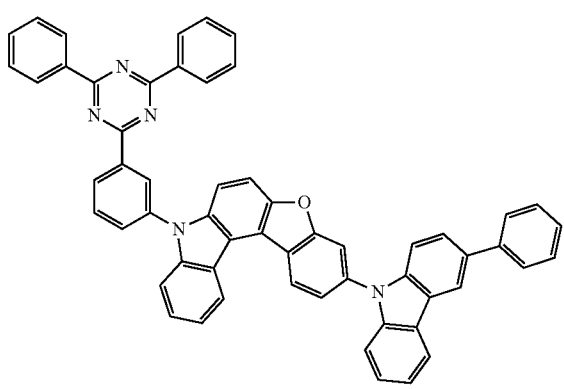
50
-continued
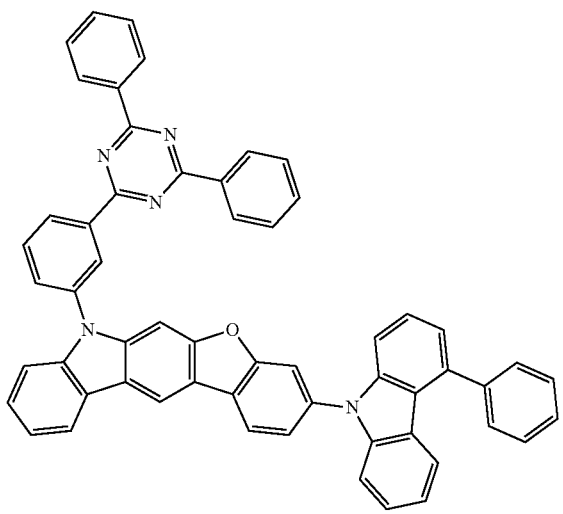
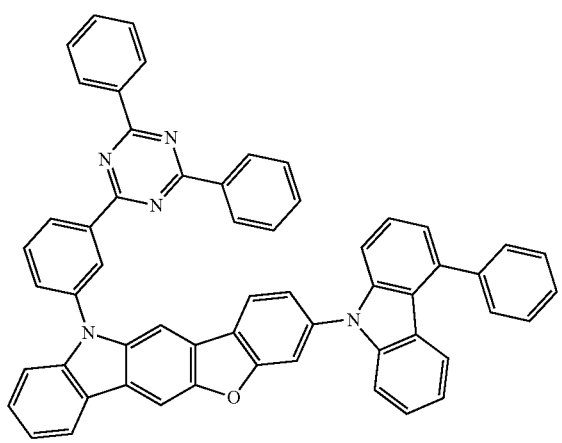
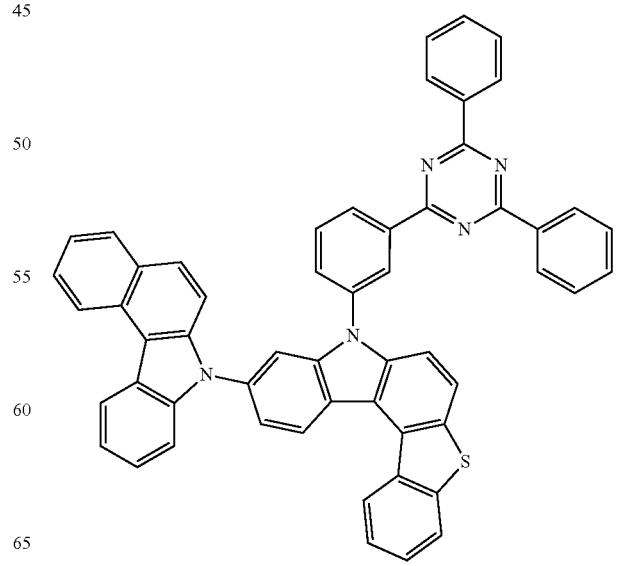

51
-continued
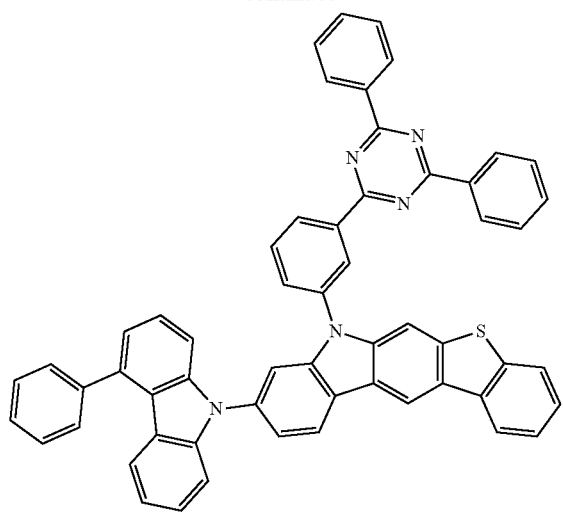
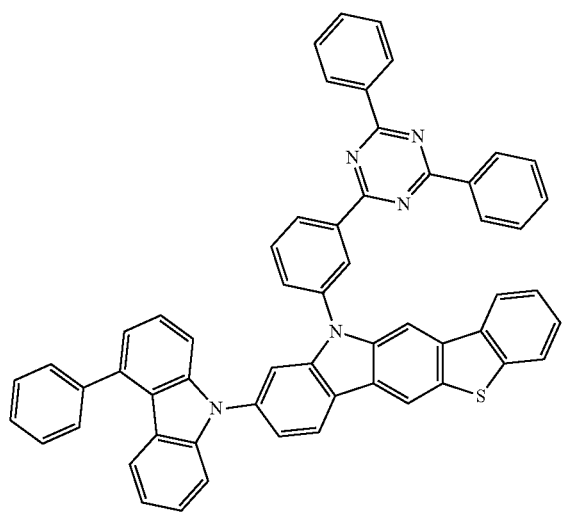
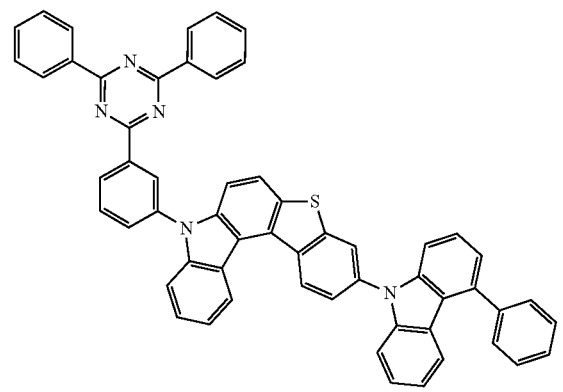
52
-continued
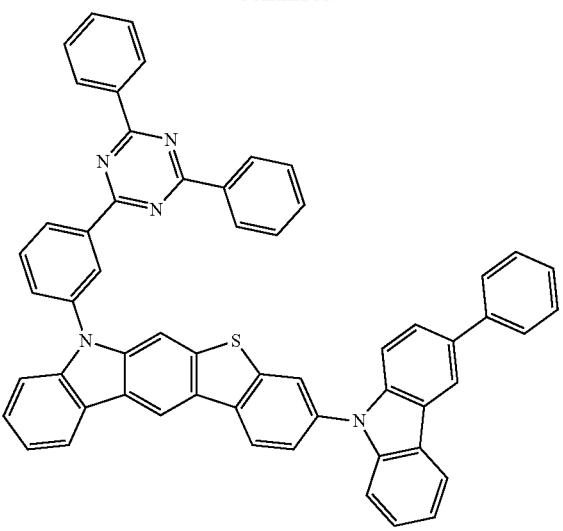
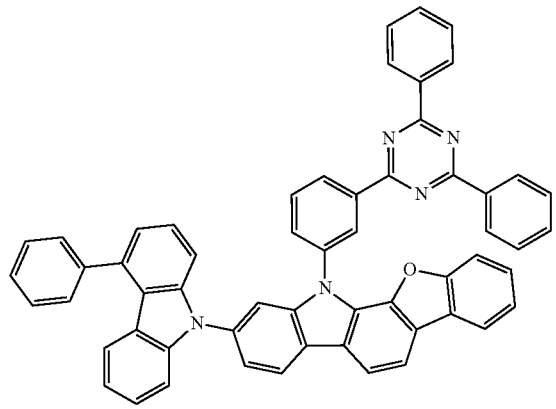

-continued
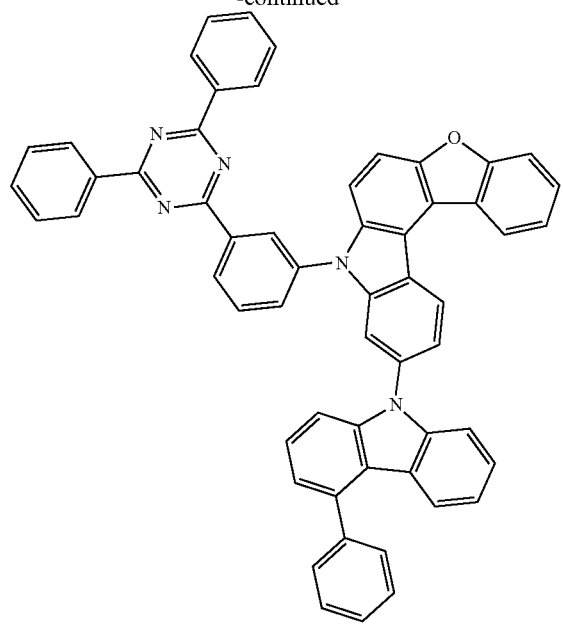
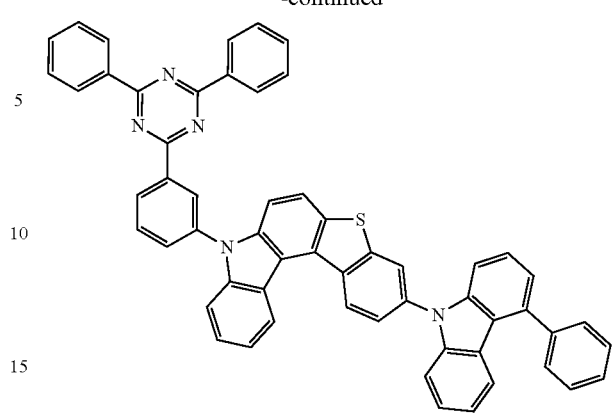
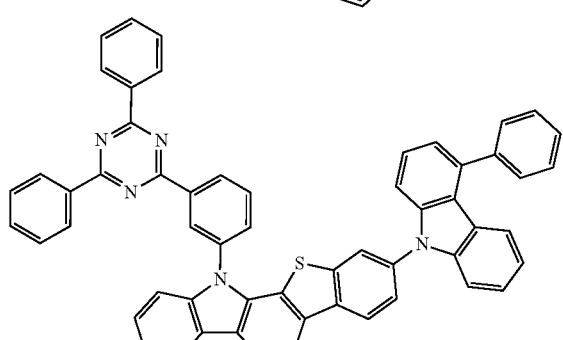
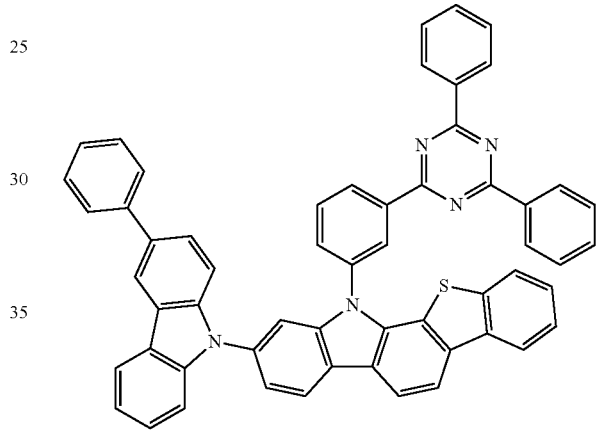
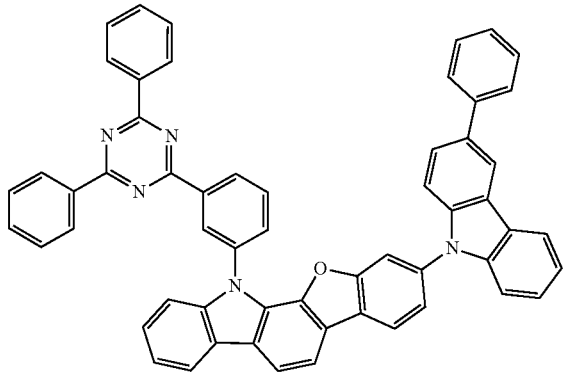
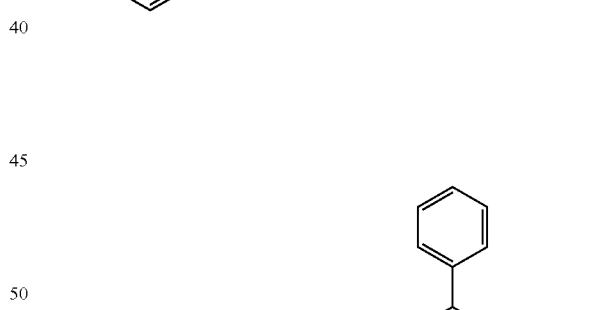
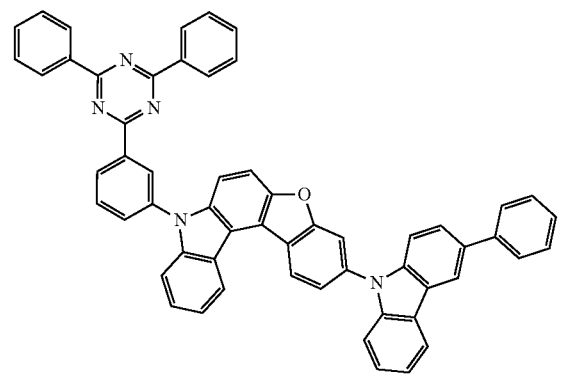
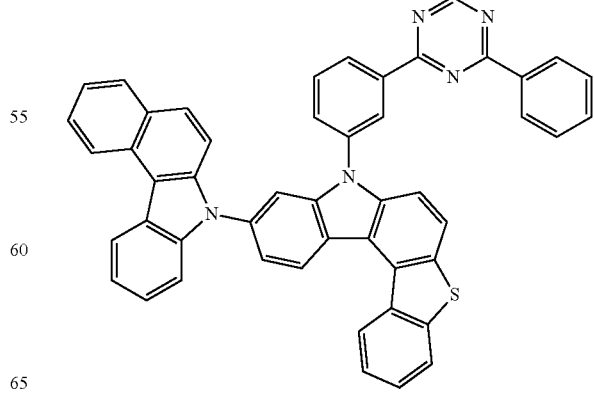

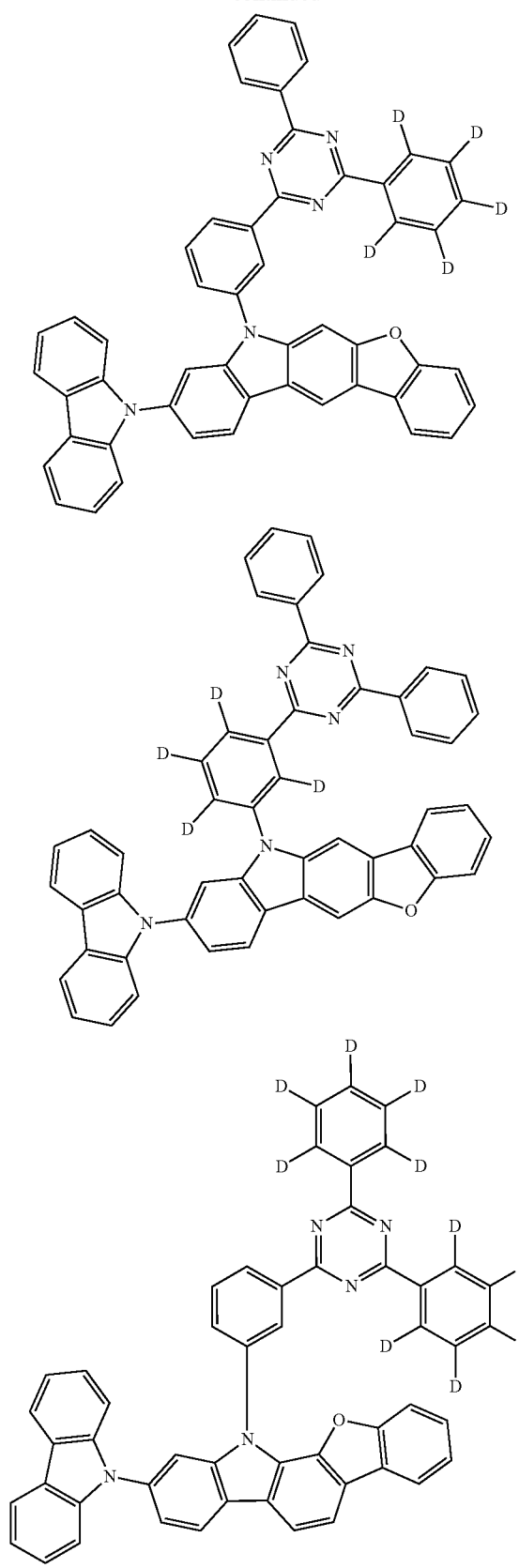
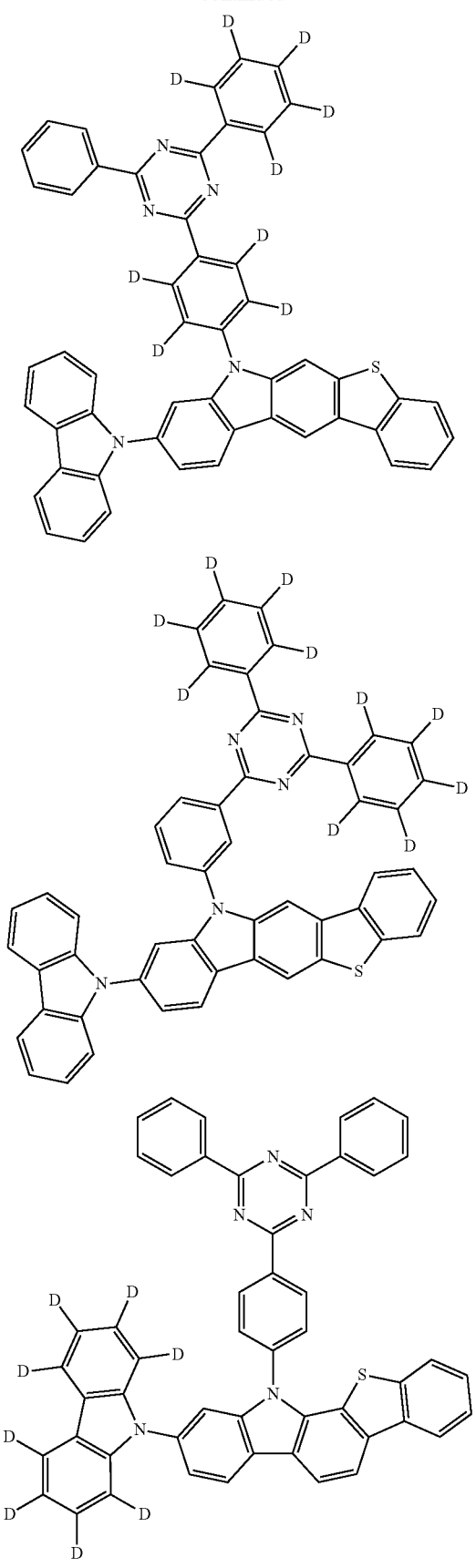

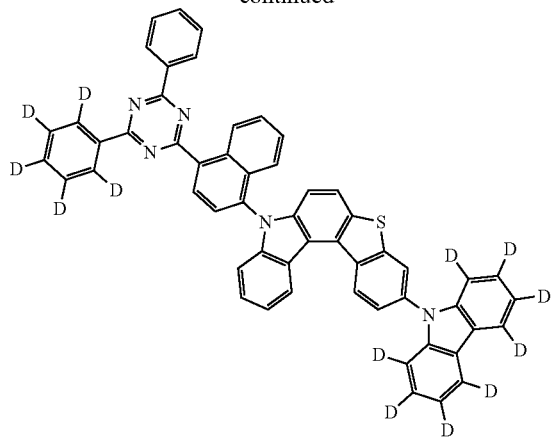

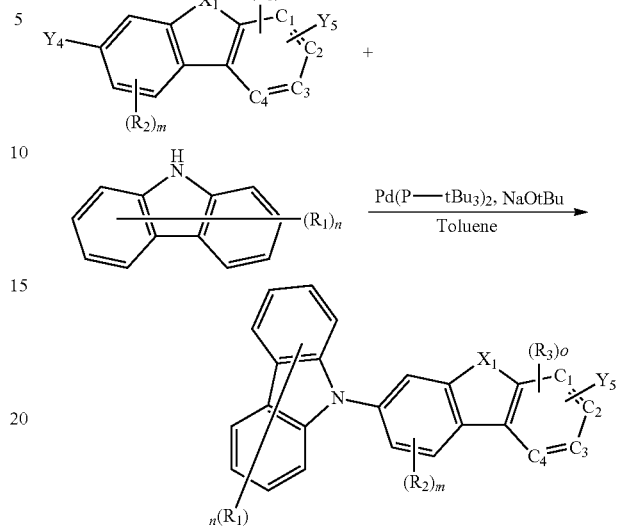

[Reaction Scheme 1a]

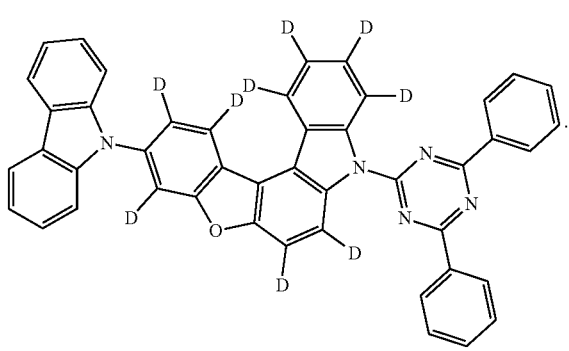

[Reaction Scheme 1b]

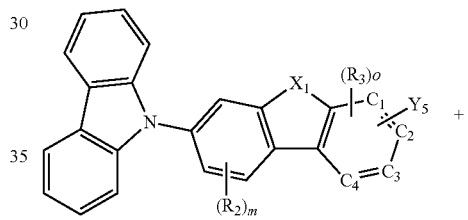

The compound represented by Chemical Formula 1 according to an embodiment of the present disclosure has a benzofurocarbazole or benzothiocarbazole which functions as an electron donor and a triazine part which functions as an electron acceptor, and thus, is advantageous for both hole transport and electron transport. The benzofurocarbazole or benzothiocarbazole has a very high material stability due to the structure in which five rings are fused. Also, in the structure of Chemical Formula 1, carbazole is substituted by a carbon-nitrogen bond at meta positions of N, O, and S of benzofurocarbazole or benzothiocarbazole. This plays the role of donating electrons from carbazole to benzofurocarbazole or benzothiocarbazole, which enhances electron-donating properties to increase hole transport properties, and also increases HOMO(highest occupied molecular orbital) levels to enhance hole injection properties. Thereby, when the compound of Chemical Formula 1 is applied as a light emitting layer host of an organic light emitting device, it may have high efficiency, low driving voltage, and long lifetime characteristics.

The compound represented by Chemical Formula 1 can be prepared through the following Reaction Scheme 1a, Reaction Scheme 1b, and Reaction Scheme 1c, or it can be prepared through Reaction Scheme 2a, Reaction Scheme 2b, and Reaction Scheme 2c. The preparation method will be further embodied in Preparation Examples described hereinafter.

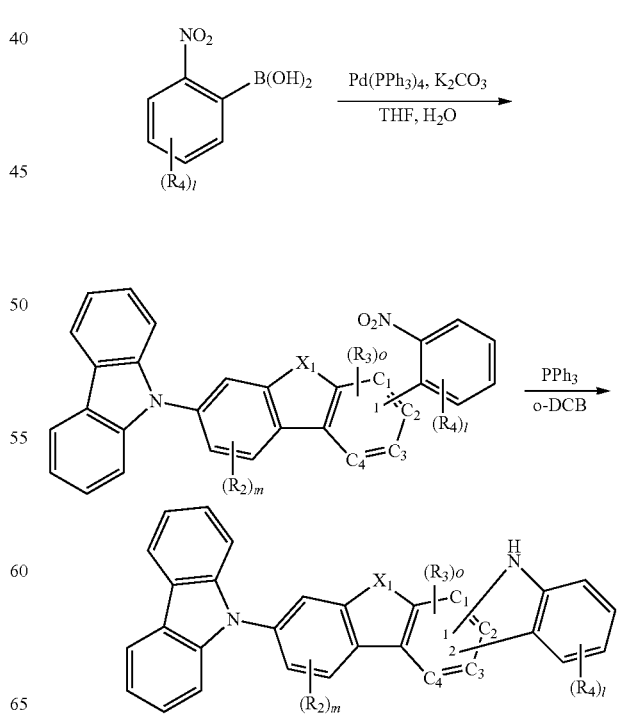

[Reaction Scheme 1c]

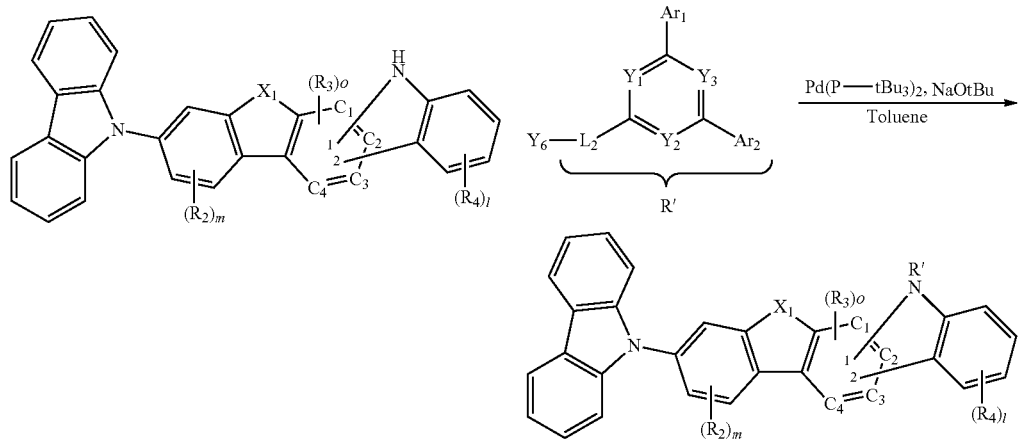

The Reaction Schemes 1a, 1b and 1c are synthetic reaction schemes where $X_2$ in Chemical Formula 1 is NR'. In the Reaction Schemes, the remaining variables except $Y_4$, $Y_5$ and $Y_6$ are as defined above, and $Y_4$, $Y_5$ and $Y_6$ are each independently halogen, preferably bromo or chloro.

[Reaction Scheme 2a]

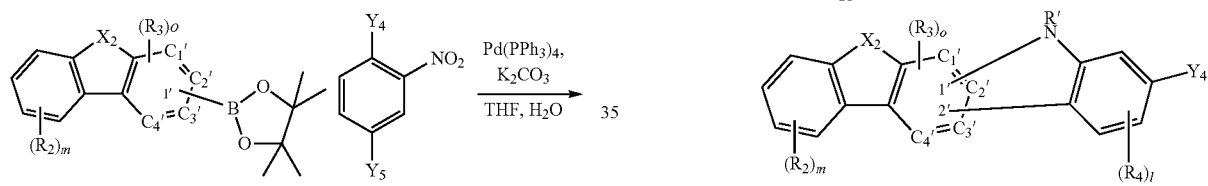

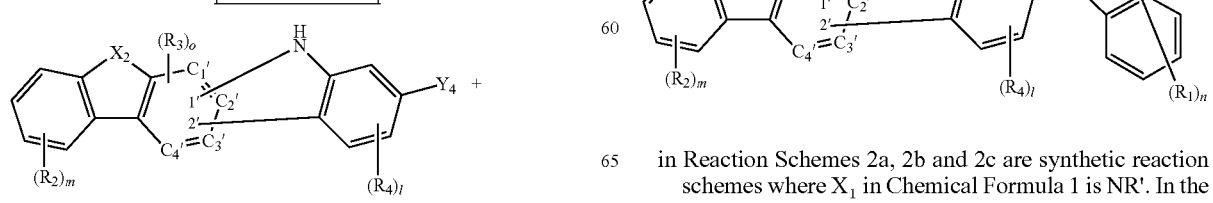

-continued

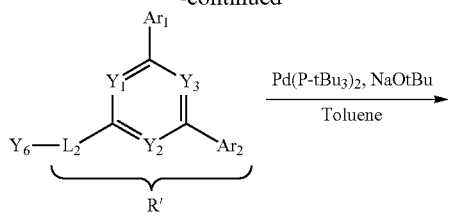

[Reaction Scheme 2c]

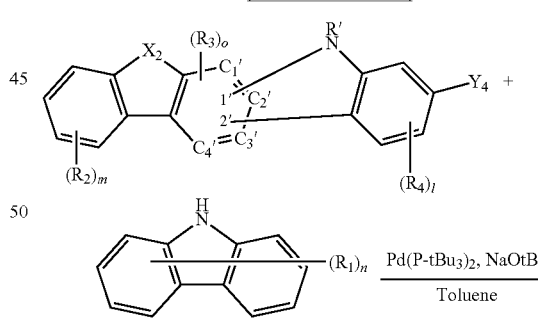

in Reaction Schemes 2a, 2b and 2c are synthetic reaction schemes where $X_1$ in Chemical Formula 1 is NR'. In the Reaction Schemes, the connection relationship of $C_1$, $C_2'$, $C_3'$, $C_4'$, 1' and 2' is identical to the connection relationship of $C_1$, $C_2$, $C_3$, $C_4$, 1 and 2 in Chemical Formula 1, the remaining variables except $Y_5$ and $Y_6$ are the same as defined above, and $Y_4$, $Y_5$ and $Y_6$ are each independently halogen, preferably bromo or chloro.

According to an embodiment of the present disclosure, there is provided an organic light emitting device comprising the compound represented by Chemical Formula 1. As an example, there is provided an organic light emitting device comprising: a first electrode; a second electrode that is provided to face the first electrode; and one or more organic material layers that are provided between the first electrode and the second electrode, wherein at least one layer of the organic material layers include the compound represented by Chemical Formula 1.

The organic material layer of the organic light emitting device of the present disclosure may have a single-layer structure, or it may have a multilayered structure in which two or more organic material layers are stacked. For example, the organic light emitting device of the present disclosure may have a structure comprising a hole injection layer, a hole transport layer, a light emitting layer, an electron transport layer, an electron injection layer and the like as the organic material layer. However, the structure of the organic light emitting device is not limited thereto, and it may include a smaller number of organic layers.

Further, the organic material layer may include a hole injection layer, a hole transport layer, or a layer for simultaneously performing hole injection and transport, wherein the hole injection layer, the hole transport layer, or the layer for simultaneously performing hole injection and transport includes the compound represented by Chemical Formula 1.

Also, the organic material layer may include an electron transport layer, or an electron injection layer, wherein the electron transport layer, or the electron injection layer includes the compound represented by Chemical Formula 1.

In addition, the organic material layer includes a light emitting layer and a hole transport layer, wherein the light emitting layer and the hole transport layer may include the compound represented by Chemical Formula 1.

Further, the organic material layer may include a light emitting layer, wherein the light emitting layer includes the compound represented by Chemical Formula 1. In particular, the compound represented by Chemical Formula 1 according to the present disclosure can have high efficiency, low driving voltage and long lifetime characteristics when applied as a light emitting layer host of a device.

Further, the organic light emitting device according to the present disclosure may be a normal type organic light emitting device in which an anode, one or more organic material layers, and a cathode are sequentially stacked on a substrate. Further, the organic light emitting device according to the present disclosure may be an inverted type organic light emitting device in which a cathode, one or more organic material layers, and an anode are sequentially stacked on a substrate. For example, the structure of an organic light emitting device according to an embodiment of the present disclosure is illustrated in FIGS. 1 and 2.

FIG. 1 depicts an example of an organic light emitting device comprising a substrate 1, an anode 2, a light emitting layer 3 and a cathode 4. In such a structure, the compound represented by Chemical Formula 1 may be included in the light emitting layer.

FIG. 2 depicts an example of an organic light emitting device comprising a substrate 1, an anode 2, a hole injection layer 5, a hole transport layer 6, a light emitting layer 7, an electron transport layer 8 and a cathode 4. In such a structure, the compound represented by Chemical Formula 1 may be included in one or more layers of the hole injection layer, the hole transport layer, the light emitting layer and the electron transport layer.

In the organic light emitting device according to the present disclosure, the organic material layer including the compound represented by Chemical Formula 1 may be a light emitting layer, and preferably, the light emitting layer may further include a compound represented by the following Chemical Formula 7:

[Chemical Formula 7]

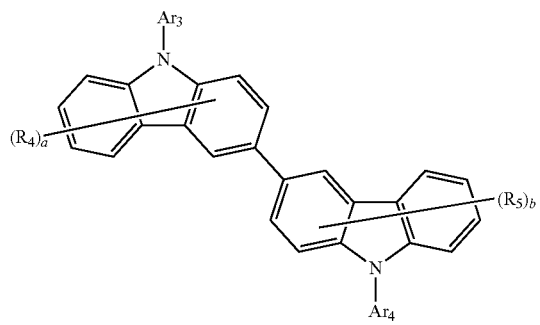

in the Chemical Formula 7, $Ar_4$ and $Ar_4$ are each independently a substituted or unsubstituted $C_{6-60}$ aryl; or a substituted or unsubstituted $C_{2-60}$ heteroaryl comprising any one or more heteroatoms selected from the group consisting of N, O and S, $R_4$ and $R_5$ are each independently hydrogen; deuterium; halogen; cyano; nitro; amino; a substituted or unsubstituted $C_{1-60}$ alkyl; a substituted or unsubstituted $C_{3-60}$ cycloalkyl; or a substituted or unsubstituted $C_{2-60}$ alkenyl; a substituted or unsubstituted $C_{6-60}$ aryl; or a substituted or unsubstituted $C_{2-60}$ heteroaryl containing any one or more heteroatoms selected from the group consisting of N, O and S, and a and b are each independently an integer of 0 to 7.

Preferably, $Ar_3$ and $Ar_4$ may be each independently phenyl, biphenylyl, terphenylyl, naphthyl, dibenzofuranyl, dibenzothiophenyl, or dimethylfluorenyl.

Preferably, $R_4$ and $R_5$ may be hydrogen.

Preferably, the compound represented by Chemical Formula 7 may be any one selected from the group consisting of the following:

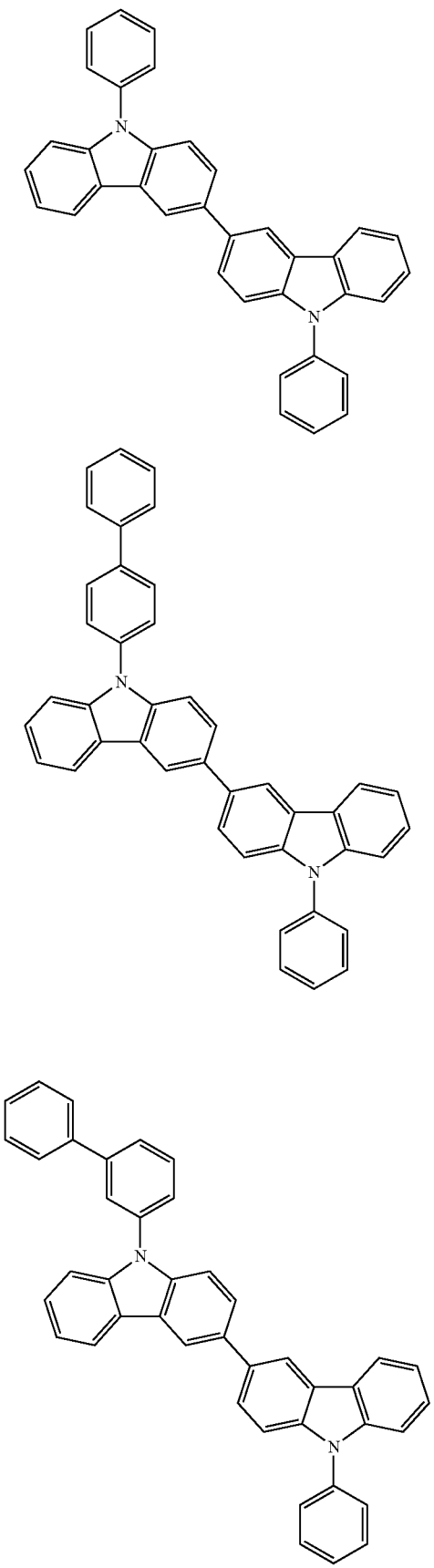
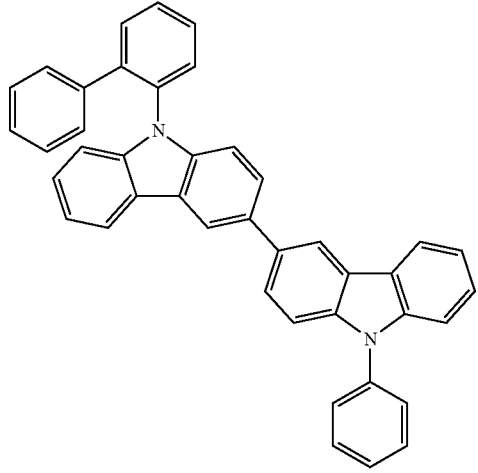
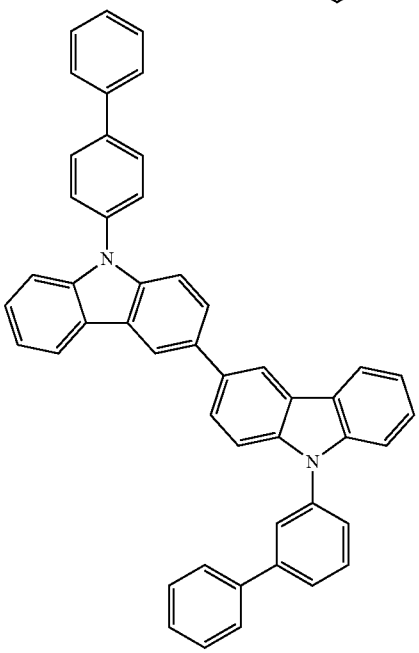
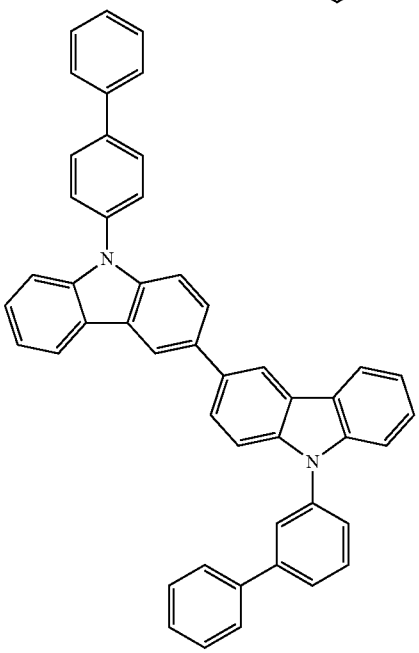

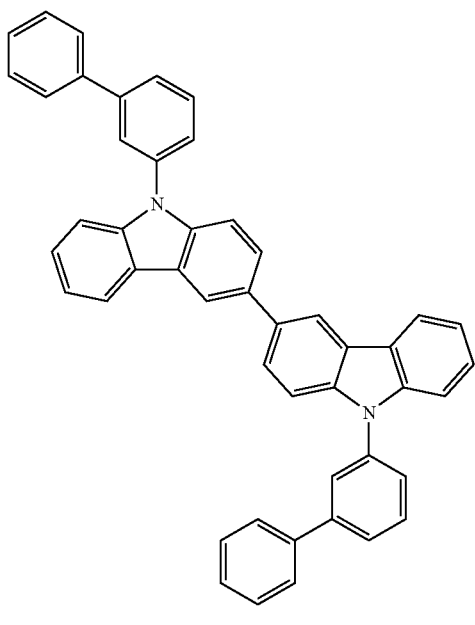
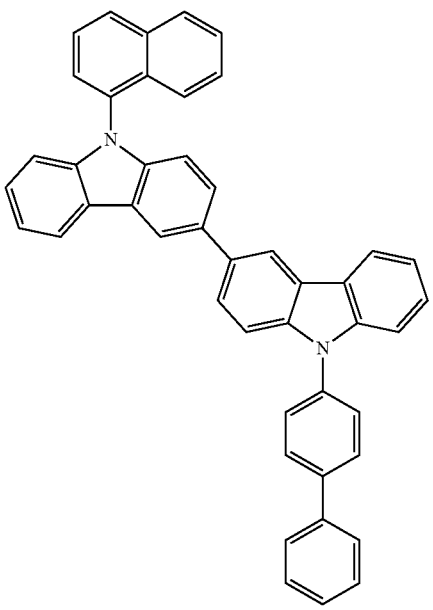
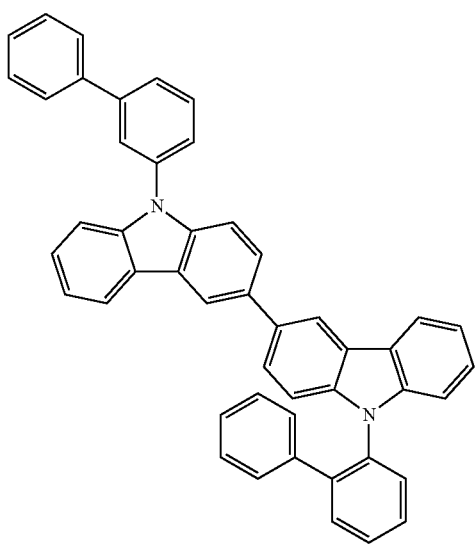
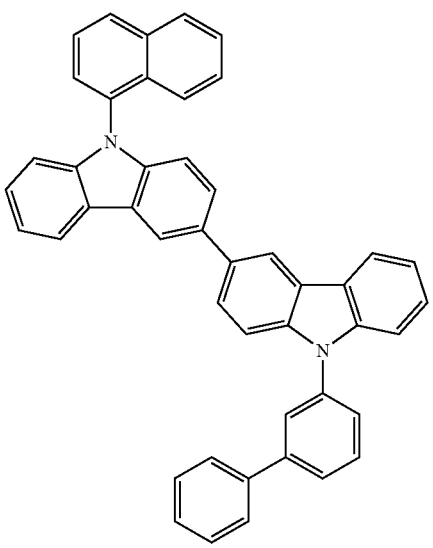
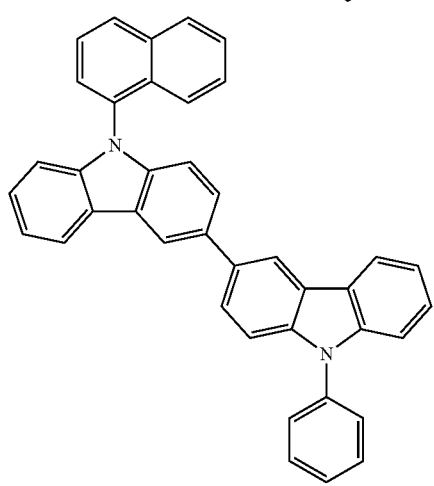

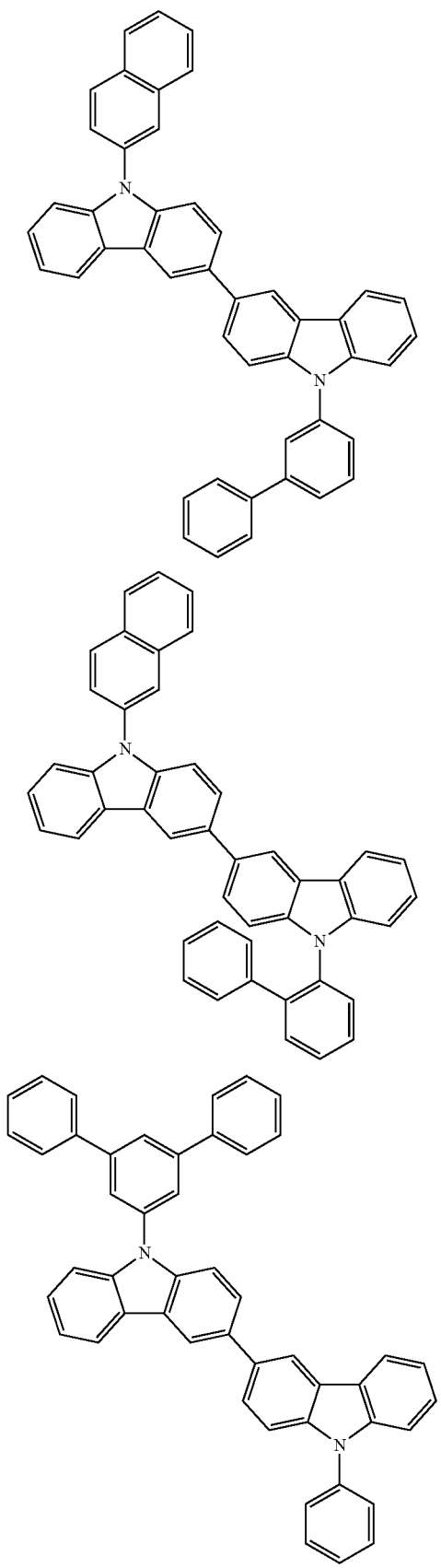
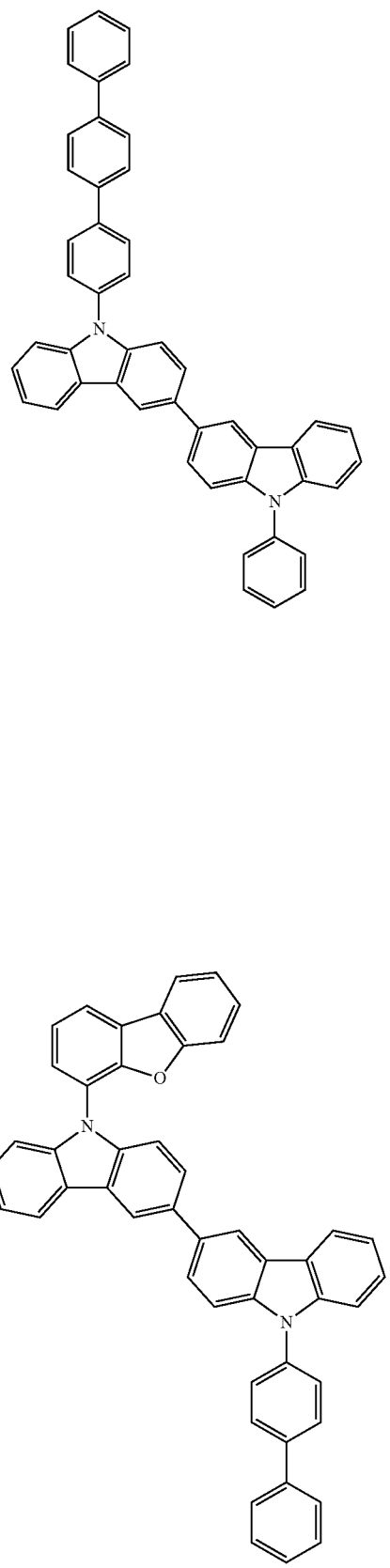

-continued
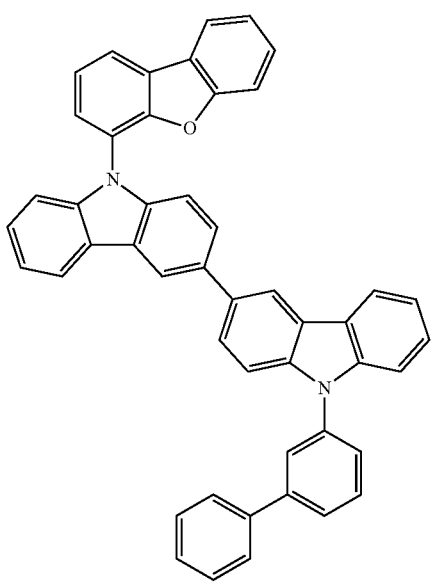
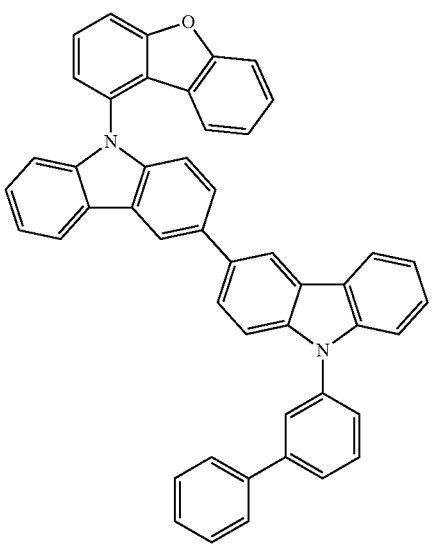
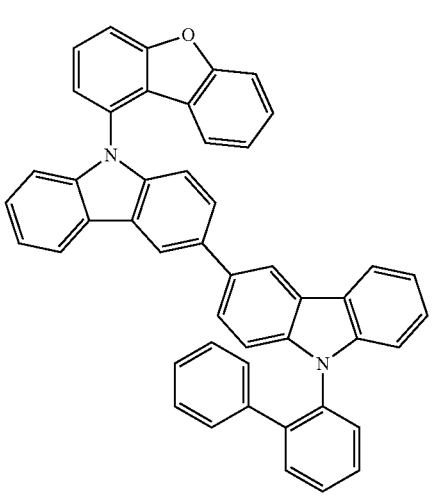
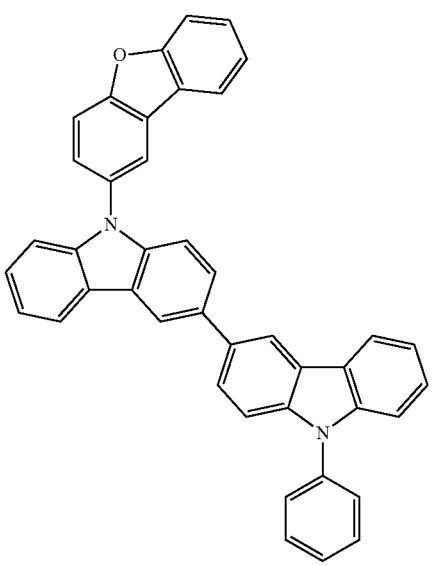

71
-continued
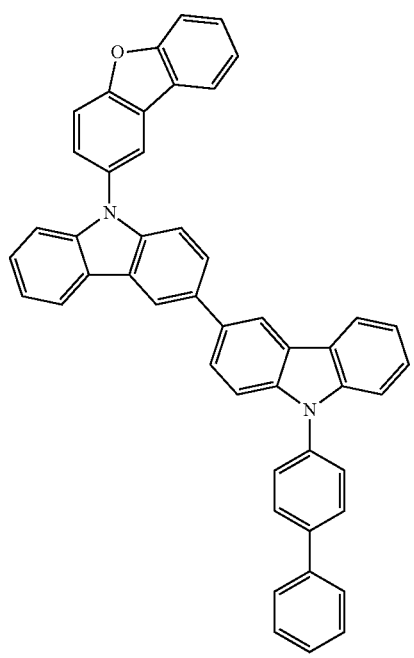
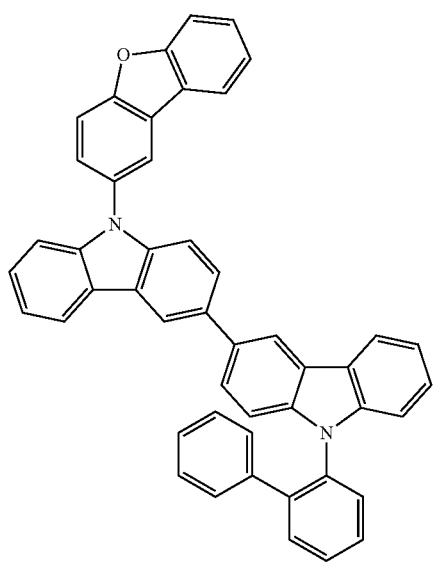
72
-continued
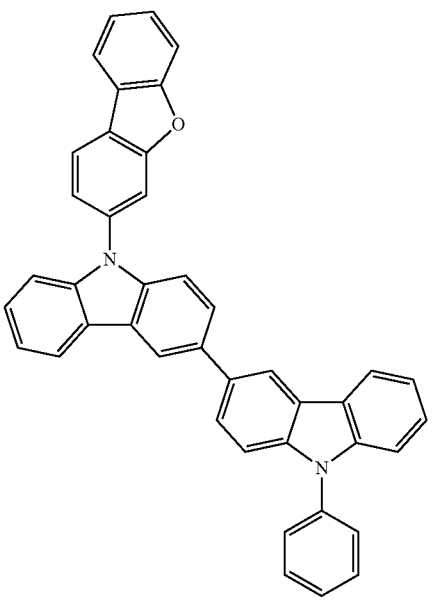
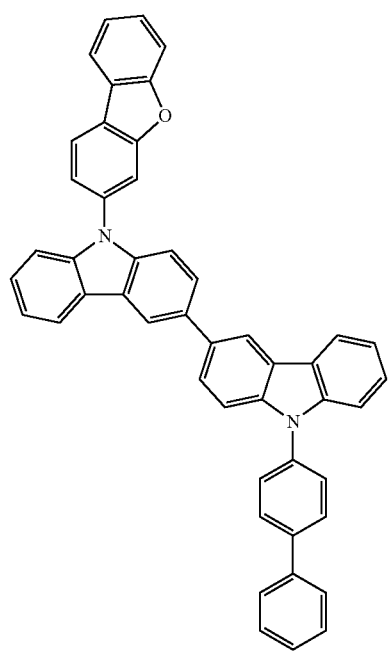

73
-continued
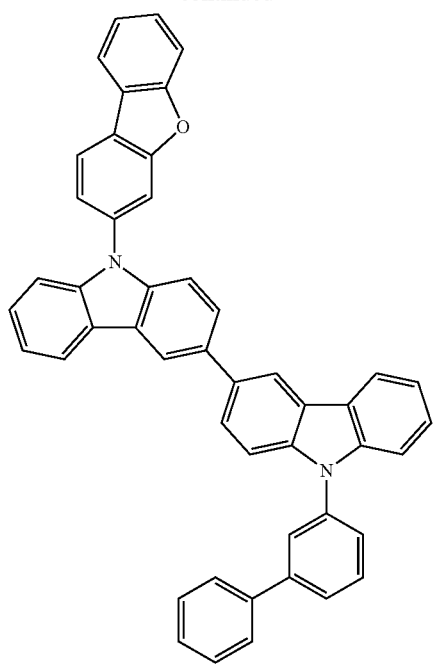
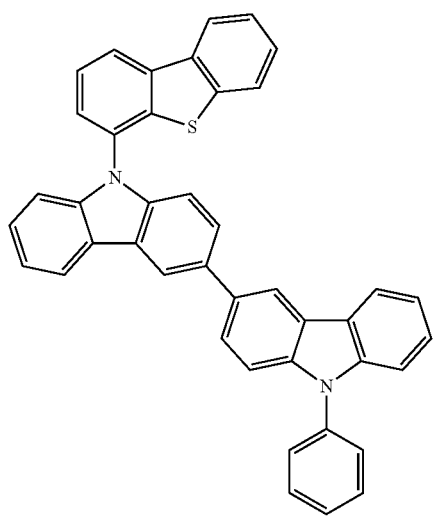
74
-continued
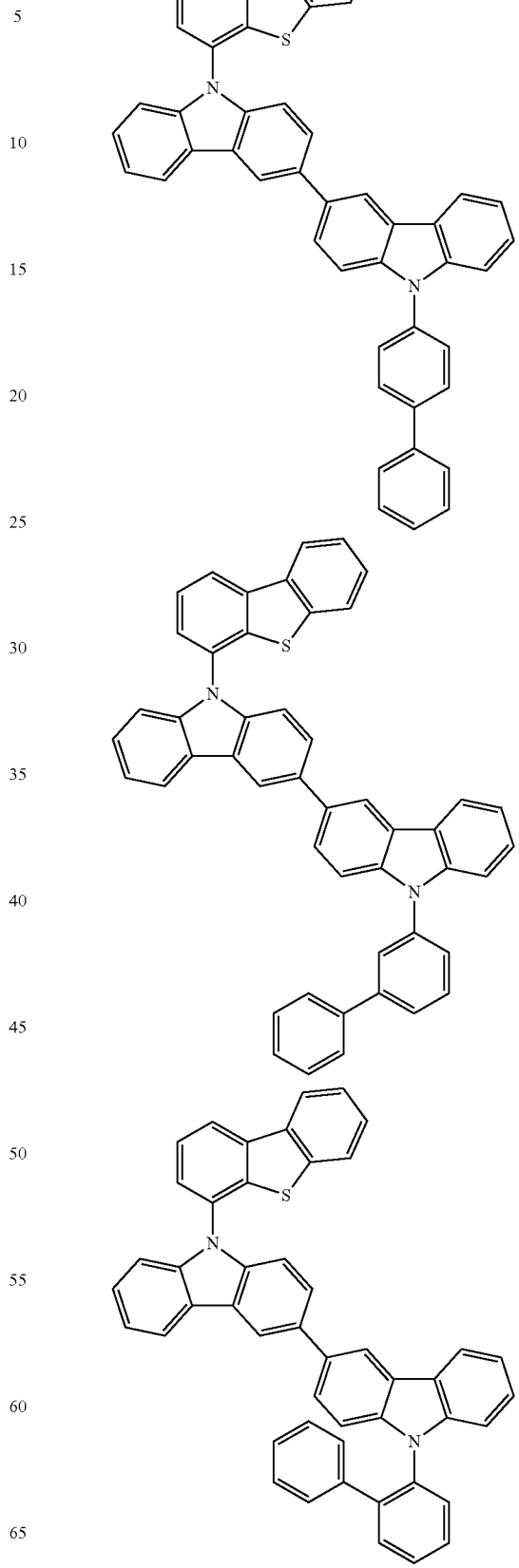

75
-continued
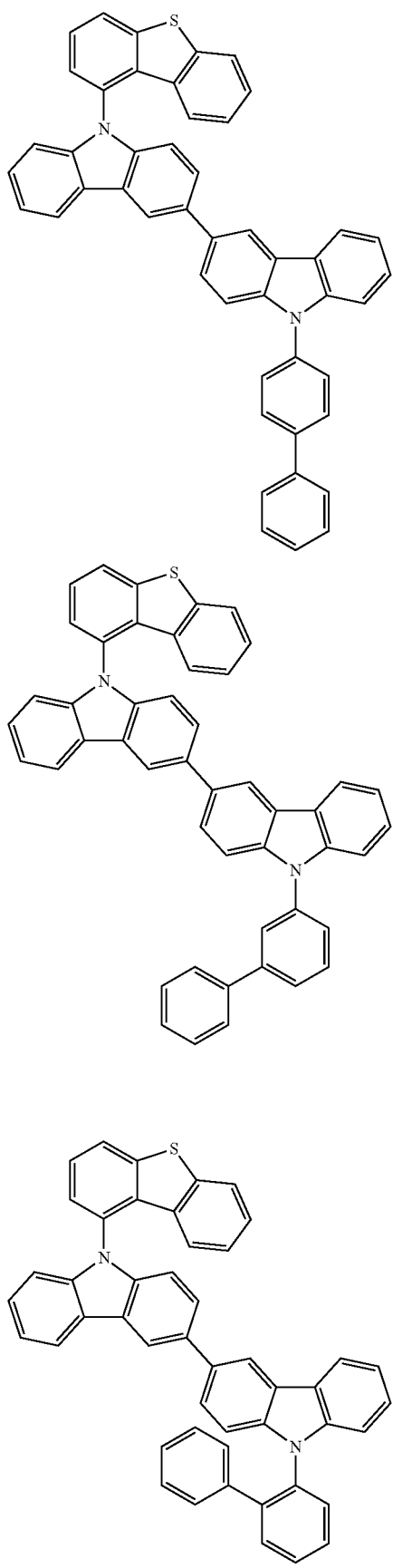
76
-continued
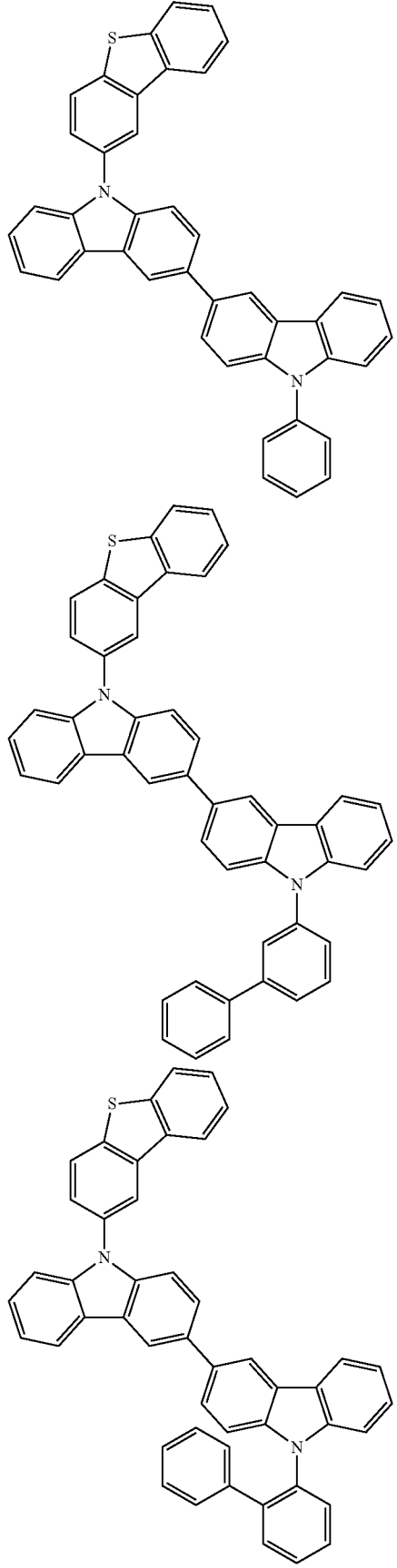

77
-continued
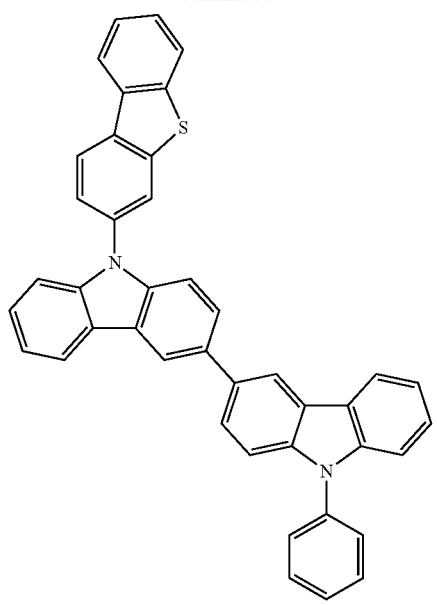
78
-continued
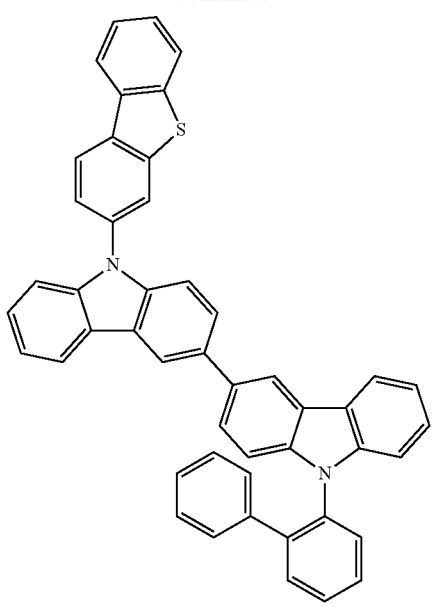
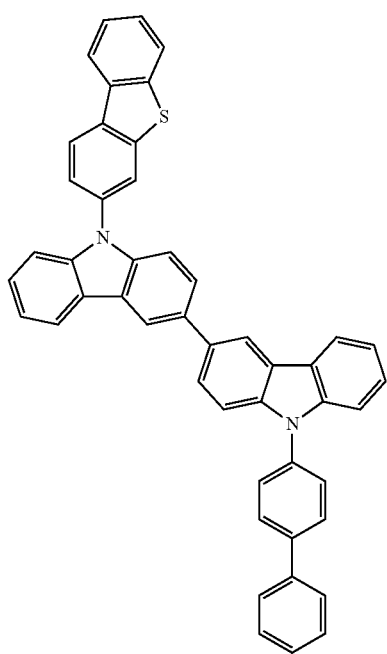
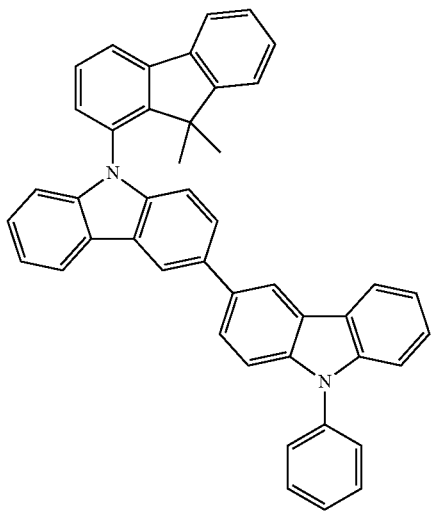

79
-continued
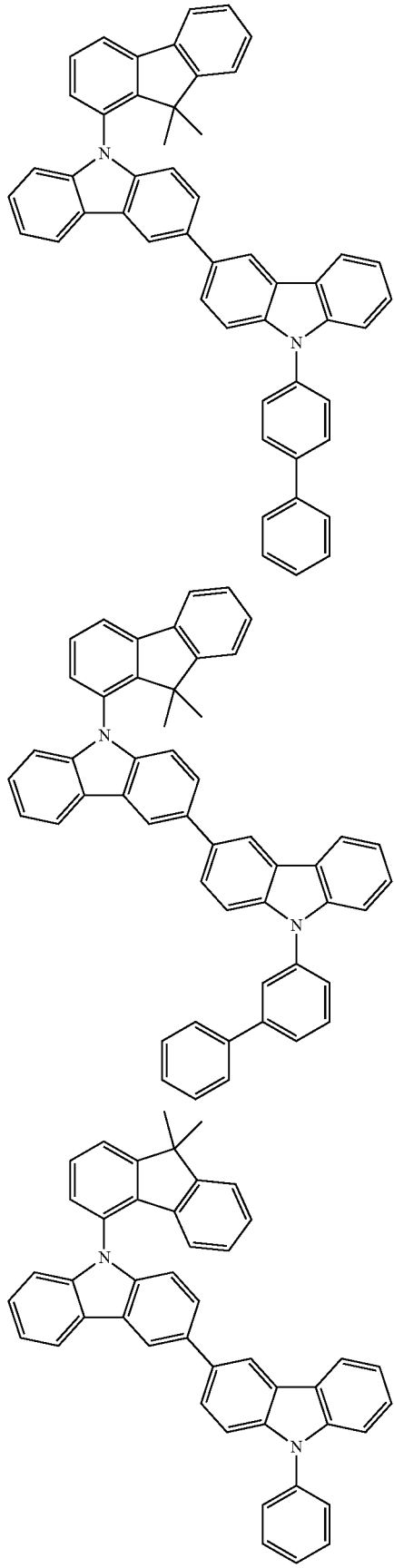
80
-continued
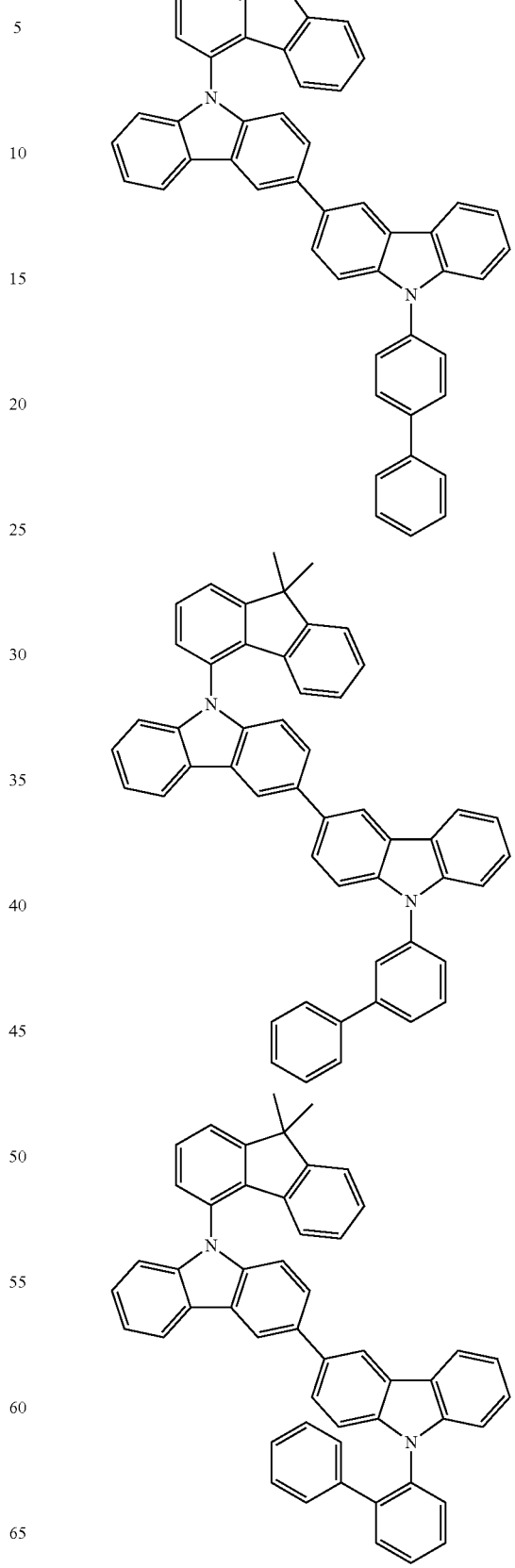

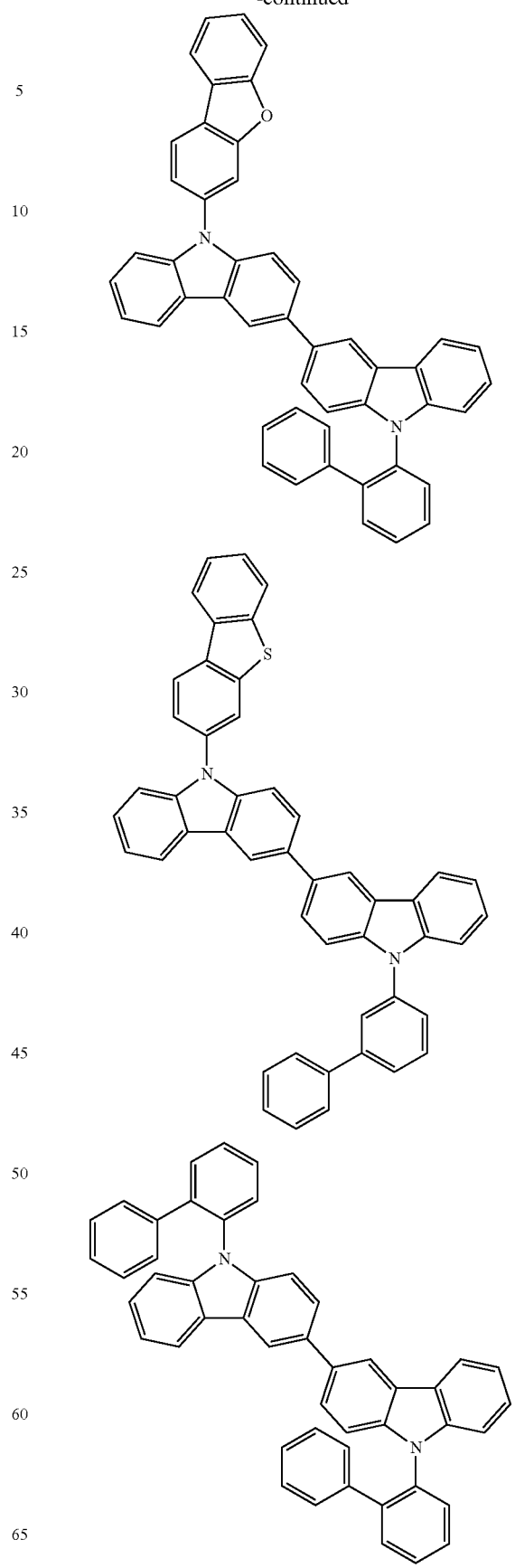

83
-continued
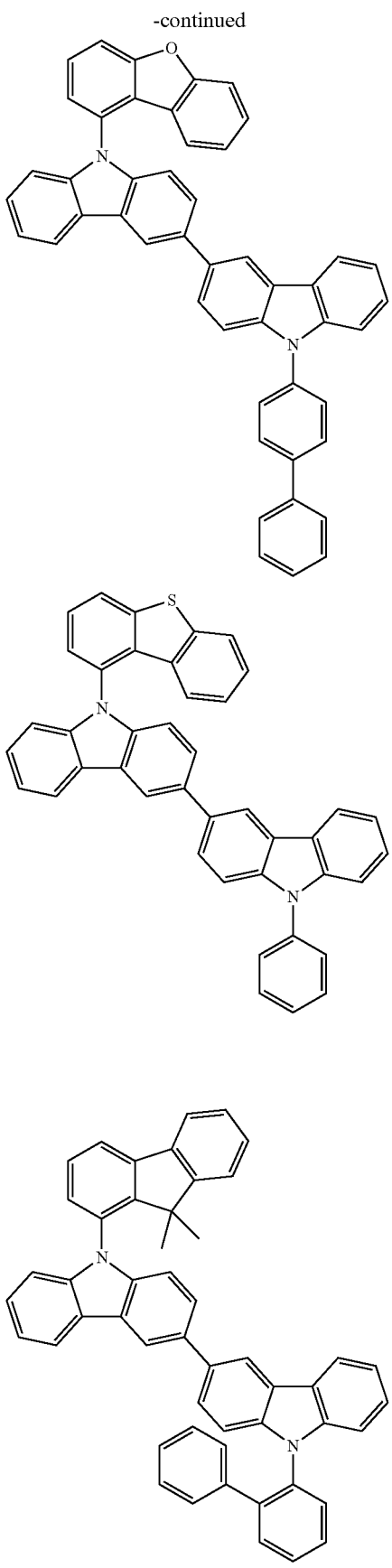
84
-continued
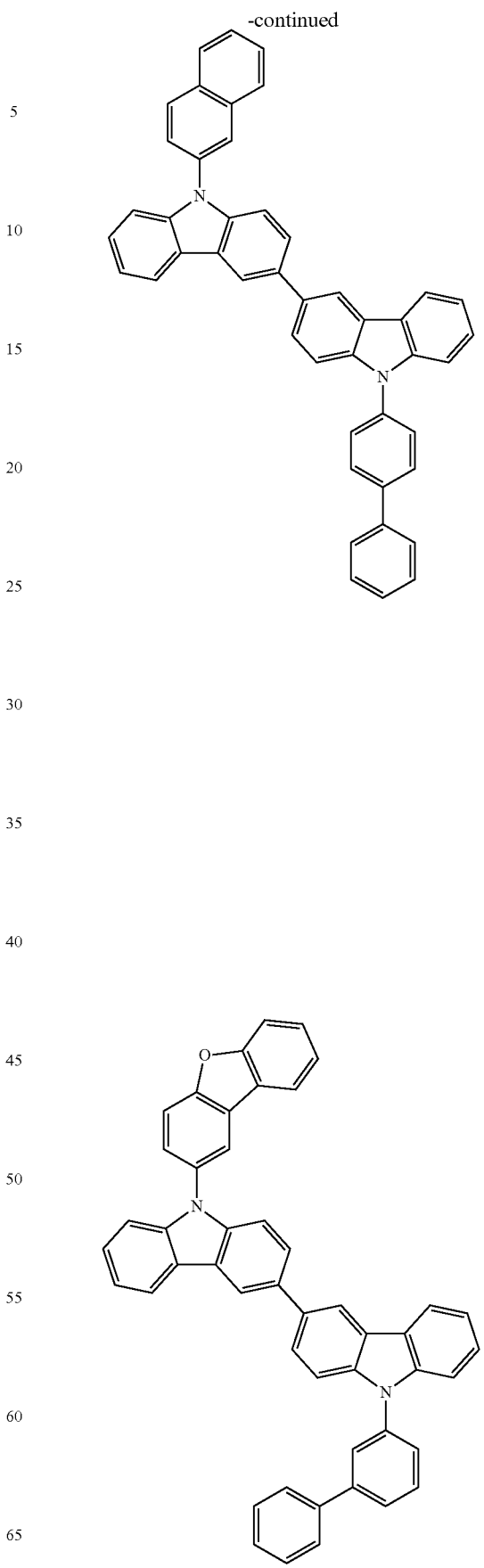

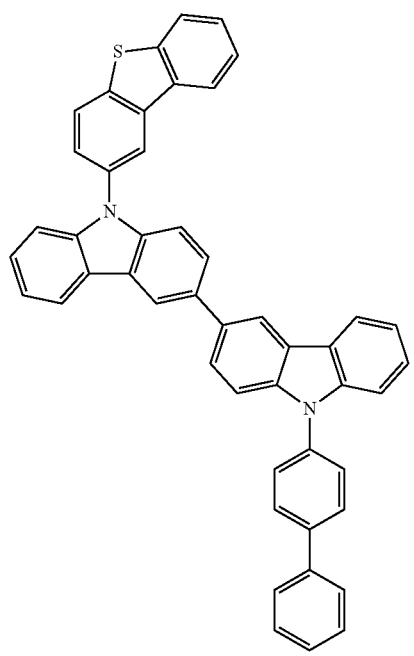
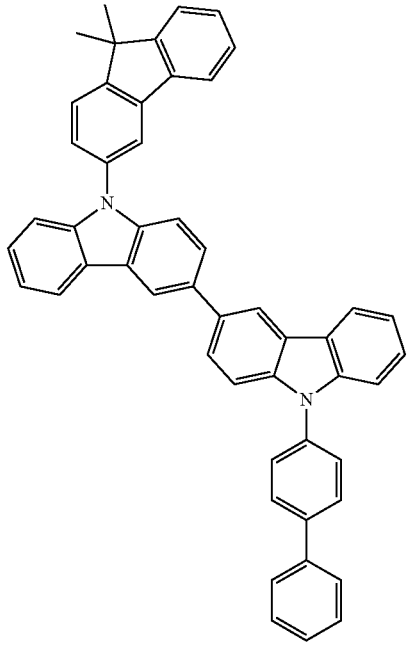
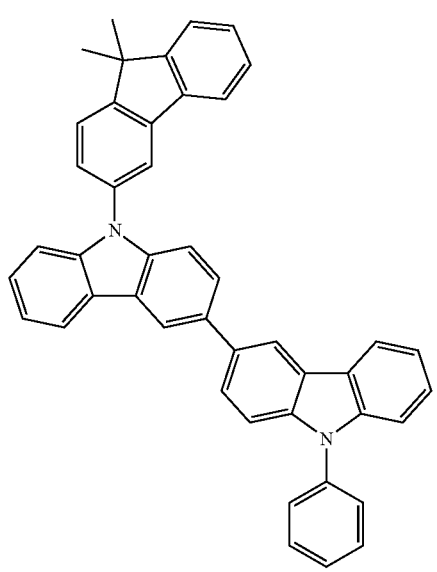
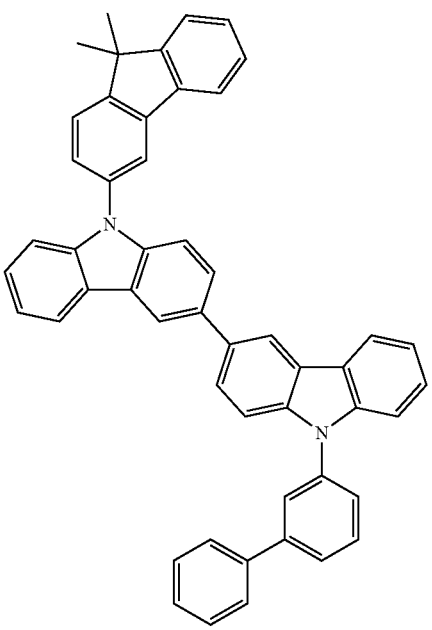

87
-continued
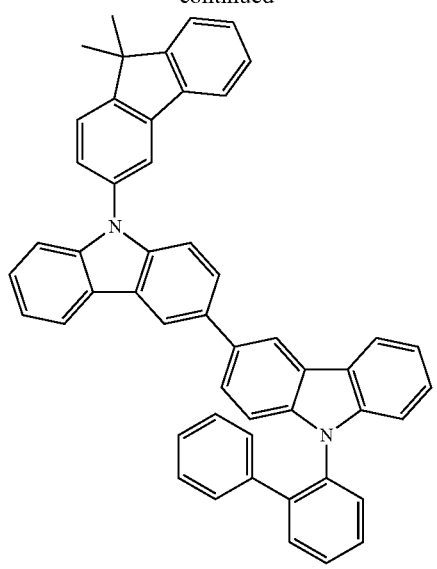
88
-continued
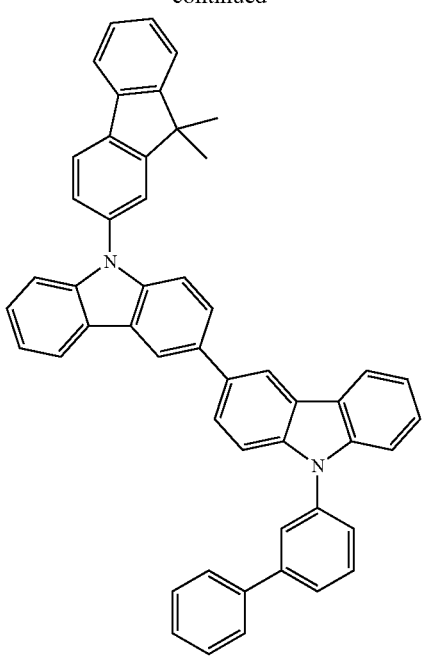
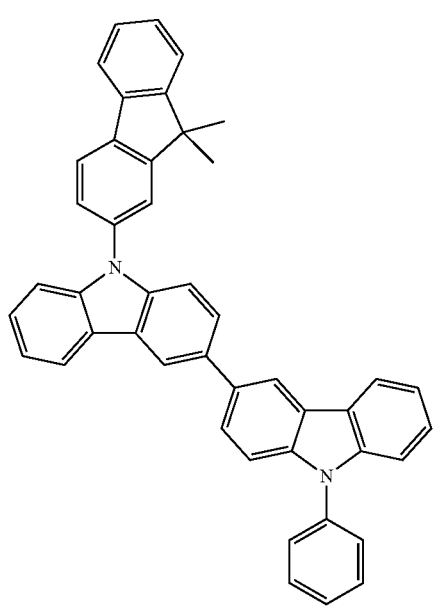
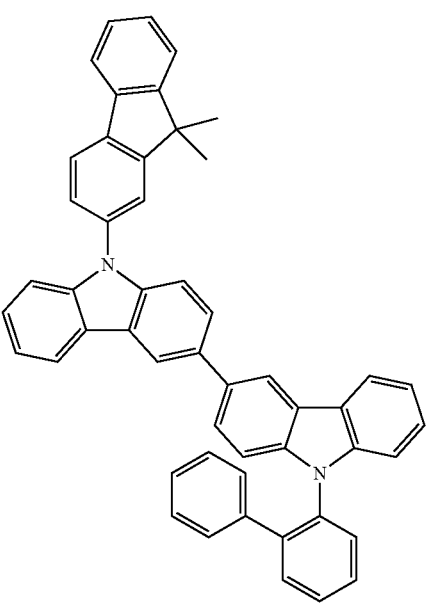

-continued

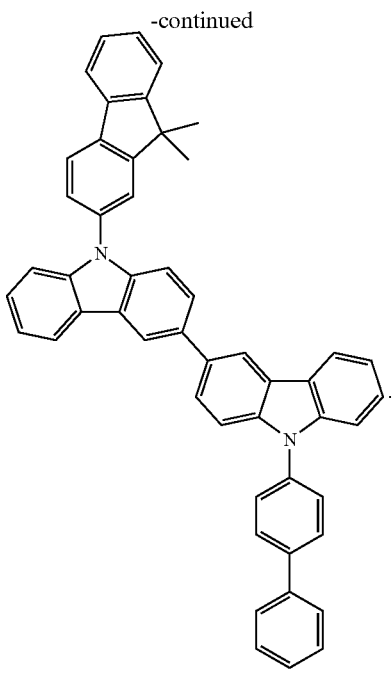

The organic light emitting device according to the present disclosure uses a combination of the compound represented by Chemical Formula 1 and the compound represented by Chemical Formula 7 in the light emitting layer, thereby exhibiting the synergistic effect resulting therefrom, that is, significantly improving low voltage, high efficiency and long lifetime characteristics.

The organic light emitting device according to the present disclosure may be manufactured by materials and methods known in the art, except that one or more layers of the organic material layers include the compound represented by Chemical Formula 1. Moreover, when the organic light emitting device includes a plurality of organic material layers, the organic material layers may be formed of the same material or different materials.

For example, the organic light emitting device according to the present disclosure can be manufactured by sequentially stacking a first electrode, an organic material layer and a second electrode on a substrate. In this case, the organic light emitting device may be manufactured by depositing a metal, metal oxides having conductivity, or an alloy thereof on the substrate using a PVD (physical vapor deposition) method such as a sputtering method or an e-beam evaporation method to form an anode, forming organic material layers including the hole injection layer, the hole transport layer, the light emitting layer and the electron transport layer thereon, and then depositing a material that can be used as the cathode thereon. In addition to such a method, the organic light emitting device may be manufactured by sequentially depositing a cathode material, an organic material layer and an anode material on a substrate.

Further, the compound represented by Chemical Formula 1 may be formed into an organic layer by a solution coating method as well as a vacuum deposition method at the time of manufacturing an organic light emitting device. Herein, the solution coating method means a spin coating, a dip coating, a doctor blading, an inkjet printing, a screen printing, a spray method, a roll coating, or the like, but is not limited thereto.

In addition to such a method, the organic light emitting device may be manufactured by sequentially depositing a cathode material, an organic material layer and an anode material on a substrate (International Publication WO2003/012890). However, the manufacturing method is not limited thereto.

As an example, the first electrode is an anode, and the second electrode is a cathode, or alternatively, the first electrode is a cathode and the second electrode is an anode.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SnO_2$:Sb, conductive polymers such as poly(3-methylthiophene), poly[3,4-(ethylene-1,2-dioxy)thiophene](PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al, and the like, but are not limited thereto.

The hole injection layer is a layer for injecting holes from the electrode, and the hole injection material is preferably a compound which has a capability of transporting the holes, thus has a hole injecting effect in the anode and an excellent hole-injecting effect to the light emitting layer or the light emitting material, prevents excitons produced in the light emitting layer from moving to an electron injection layer or the electron injection material, and is excellent in the ability to form a thin film. It is preferable that a HOMO (highest occupied molecular orbital) of the hole injection material is between the work function of the anode material and a HOMO of a peripheral organic material layer. Specific examples of the hole injection material include metal porphyrine, oligothiophene, an arylamine-based organic material, a hexanitrilehexaazatriphenylene-based organic material, a quinacridone-based organic material, a perylene-based organic material, anthraquinone, polyaniline and polythiophene-based conductive polymer, and the like, but are not limited thereto.

The hole transport layer is a layer that receives holes from a hole injection layer and transports the holes to the light emitting layer. The hole transport material is suitably a material having large mobility to the holes, which may receive holes from the anode or the hole injection layer and transfer the holes to the light emitting layer. Specific examples thereof include an arylamine-based organic material, a conductive polymer, a block copolymer in which a conjugate portion and a non-conjugate portion are present together, and the like, but are not limited thereto.

The light emitting material is preferably a material which may receive holes and electrons transported from a hole transport layer and an electron transport layer, respectively, and combine the holes and the electrons to emit light in a visible ray region, and has good quantum efficiency to fluorescence or phosphorescence. Specific examples thereof include an 8-hydroxy-quinoline aluminum complex ($Alq_3$); a carbazole-based compound; a dimerized styryl compound; BAlq; a 10-hydroxybenzoquinoline-metal compound; a benzoxazole, benzthiazole and benzimidazole-based compound; a poly(p-phenylenevinylene)(PPV)-based polymer; a spiro compound; polyfluorene, lubrene, and the like, but are not limited thereto.

The light emitting layer may include a host material and a dopant material. The host material may be a fused aromatic ring derivative, a heterocycle-containing compound or the like. Specific examples of the fused aromatic ring derivatives include anthracene derivatives, pyrene derivatives, naphthalene derivatives, pentacene derivatives, phenanthrene compounds, fluoranthene compounds, and the like. Examples of the heterocyclic-containing compounds include carbazole derivatives, dibenzofuran derivatives, ladder-type furan compounds, pyrimidine derivatives, and the like, but are not limited thereto.

Examples of the dopant material include an aromatic amine derivative, a styrylamine compound, a boron complex, a fluoranthene compound, a metal complex, and the like. Specifically, the aromatic amine derivative is a substituted or unsubstituted fused aromatic ring derivative having an arylamino group, and examples thereof include pyrene, anthracene, chrysene, periflanthene and the like, which have an arylamino group. The styrylamine compound is a compound where at least one arylvinyl group is substituted in substituted or unsubstituted arylamine, in which one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, the metal complex includes an iridium complex, a platinum complex, and the like, but is not limited thereto.

The electron transport layer is a layer which receives electrons from an electron injection layer and transports the electrons to a light emitting layer, and an electron transport material is suitably a material which may receive electrons well from a cathode and transfer the electrons to a light emitting layer, and has a large mobility for electrons. Specific examples of the electron transport material include: an Al complex of 8-hydroxyquinoline; a complex including $Alq_3$; an organic radical compound; a hydroxyflavone-metal complex, and the like, but are not limited thereto. The electron transport layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a cathode and an excellent effect of injecting electrons into a light emitting layer or a light emitting material, prevents excitons produced from the light emitting layer from moving to a hole injection layer, and is also excellent in the ability to form a thin film. Specific examples of the electron injection layer include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris (2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

The organic light emitting device according to the present disclosure may be a front side emission type, a backside emission type, or a double-sided emission type according to the used material.

In addition, the compound represented by Chemical Formula 1 may be included in an organic solar cell or an organic transistor in addition to an organic light emitting device.

The preparation of the compound represented by Chemical Formula 1 and the organic light emitting device containing the same will be described in detail in the following examples. However, these examples are presented for illustrative purposes only, and are not intended to limit the scope of the present disclosure.

SYNTHESIS EXAMPLES

Synthesis Example 1: Synthesis of Intermediate A

Reaction Scheme 1-1) Synthesis of Intermediate A-1

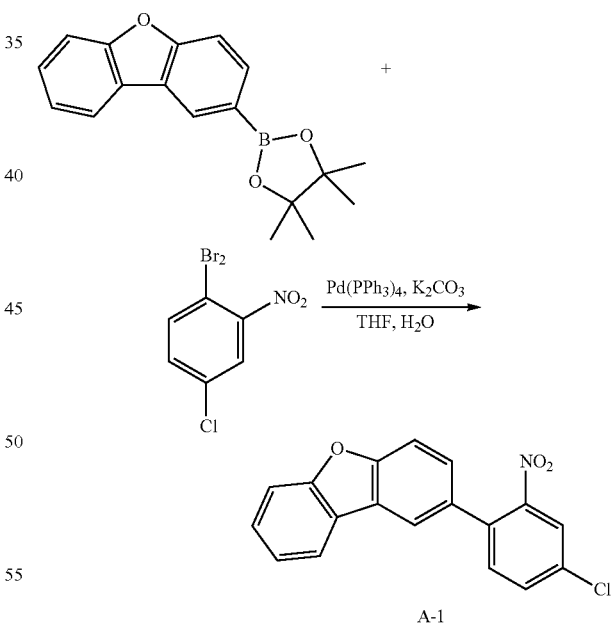

A-1

In a three-necked flask, 2-(dibenzo[b,d]furan-2-yl)-4,4,5,5-tetramethyl-1,3,2-dioxaborolane (30.0 g, 102.0 mmol), and 1-bromo-4-chloro-2-nitrobenzene (27.0 g, 114.2 mmol) were dissolved in 450 ml of THF, and potassium carbonate (56.4 g, 407.9 mmol) dissolved in 150 ml of $H_2O$ was added. Tetrakis(triphenylphosphine)palladium(0) (5.9 g, 5.1 mmol) was added thereto, and the mixture was stirred at reflux for 8 hours under an argon atmosphere. After completion of the reaction, the reaction solution was cooled to room temperature, then transferred to a separatory funnel, and extracted with ethyl acetate. The extract was dried over MgSO₄, filtered, concentrated, and then recrystallized to give 28.1 g of Intermediate A-1. (Yield: 85%, MS[M+H]⁺=323)

Reaction Scheme 1-2) Synthesis of Intermediate A

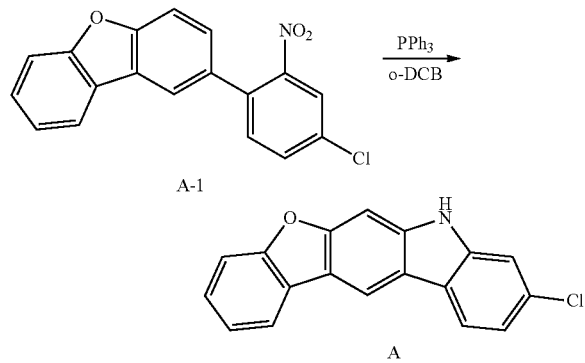

In two-necked flask was placed Compound A-1 (25.0 g, 77.2 mmol), triphenylphosphine (16.0 g, 115.8 mmol) and 250 ml of o-dichlorobenzene, and the mixture was stirred at reflux for 24 hours. After completion of the reaction, the reaction solution was cooled to room temperature, distilled under reduced pressure to remove the solvent, and then extracted with CH₂Cl₂. The extract was dried over MgSO₄, filtered and concentrated, and then the sample was purified by silica gel column chromatography to give 16.9 g of Intermediate A. (Yield: 75%, MS [M+H]⁺=291)

Synthesis Example 2: Synthesis of Intermediate B and Intermediate C

Reaction Scheme 2-1)

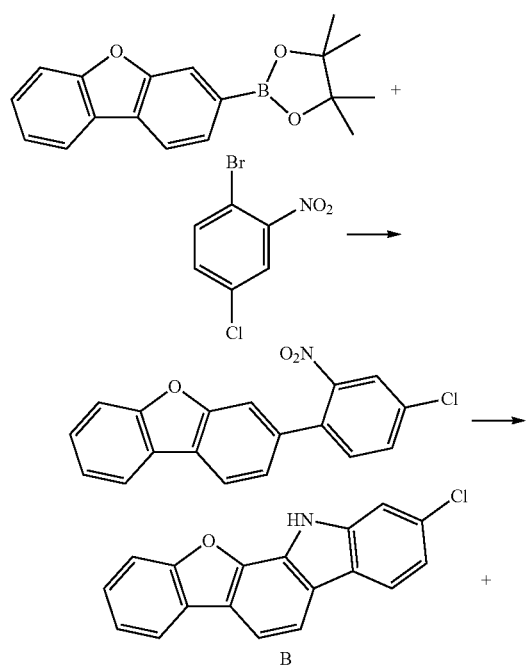

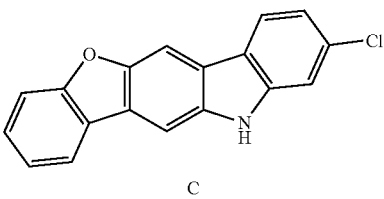

It was synthesized in the same manner as in the preparation method of Intermediate A, except that 2-(dibenzo[b,d]furan-3-yl)-4,4,5,5-tetramethyl-1,3,2-dioxaborolane was used instead of 2-(dibenzo[b,d]furan-2-yl)-4,4,5,5-tetramethyl-1,3,2-dioxaborolane in Synthesis Example 1, and then separated by silica gel column chromatography to give Intermediate B and Intermediate C. (MS[M+H]⁺=291)

Synthesis Example 3: Synthesis of Intermediate D

Reaction Scheme 3-1)

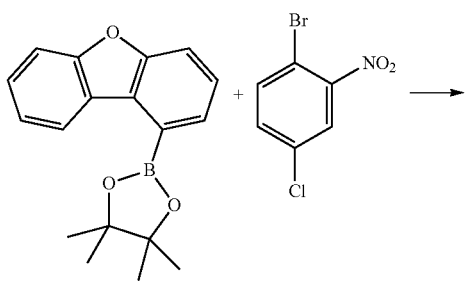

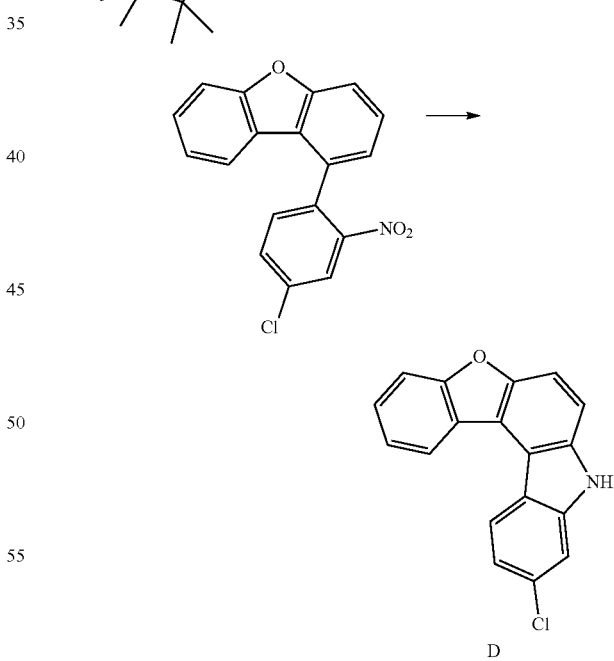

Intermediate D was prepared in the same manner as in the preparation method of Intermediate A, except that 2-(dibenzo[b,d]furan-1-yl)-4,4,5,5-tetramethyl-1,3,2-dioxaborolane was used instead of 2-(dibenzo[b,d]furan-2-yl)-4,4,5,5-tetramethyl-1,3,2-dioxaborolane in Synthesis Example 1. (MS[M+H]⁺=291)

Synthesis Example 4: Synthesis of Intermediate E

Reaction Scheme 4-1)

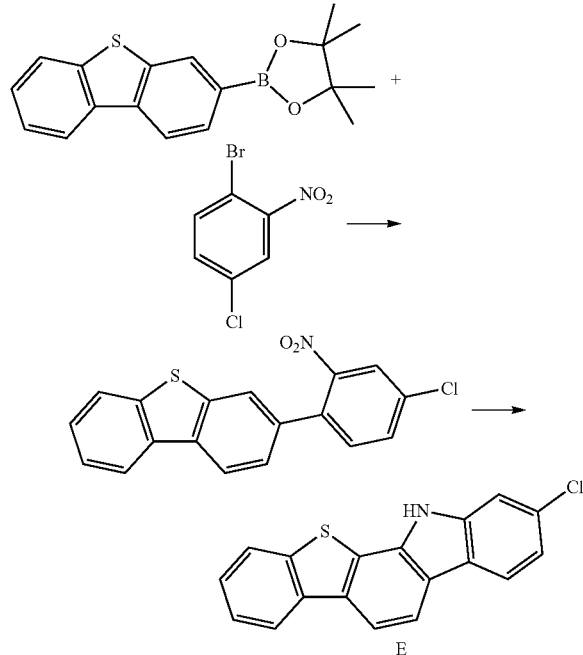

Intermediate E was prepared in the same manner as in the preparation method of Intermediate A, except that 2-(dibenzo[b,d]thiophen-3-yl)-4,4,5,5-tetramethyl-1,3,2-dioxaborolane was used instead of 2-(dibenzo[b,d]furan-2-yl)-4,4,5,5-tetramethyl-1,3,2-dioxaborolane in Synthesis Example 1. (MS[M+H]$^+$=307)

Synthesis Example 5: Synthesis of Intermediate F

Reaction Scheme 5-1)

Intermediate F was prepared in the same manner as in the preparation method of Intermediate A, except that 2-(dibenzo[b,d]thiophen-1-yl)-4,4,5,5-tetramethyl-1,3,2-dioxaborolane was used instead of 2-(dibenzo[b,d]furan-2-yl)-4,4,5,5-tetramethyl-1,3,2-dioxaborolane in Synthesis Example 1. (MS[M+H]$^+$=307)

Synthesis Example 6: Synthesis of Intermediate G

Reaction Scheme 6-1) Synthesis of Intermediate G-1

In a three-necked flask, 3-bromo-7-chlorodibenzo[b,d]furan (25.0 g, 88.8 mmol) and 9H-carbazole (15.6 g, 93.2 mmol) were dissolved in 750 ml of toluene, and sodium tert-butoxide (12.8 g, 133.2 mmol) and bis(tri-tert-butylphosphine)palladium(0) (0.9 g, 1.8 mmol) were added, and then the mixture was stirred at reflux for 6 hours under an argon atmosphere. After completion of the reaction, the reaction temperature was cooled to room temperature, then H$_2$O was added, and the reaction solution was transferred to a separatory funnel, and extracted. The extract was dried over MgSO$_4$ and concentrated, and then the sample was purified by silica gel column chromatography to give 24.8 g of Intermediate G-1. (Yield: 76%, MS [M+H]$^+$=367)

Reaction Scheme 6-2) Synthesis of Intermediate G-2

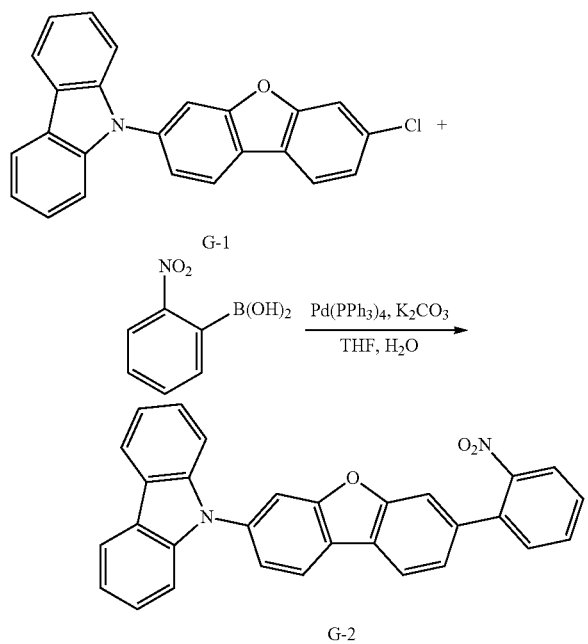

G-2

In a three-necked flask, Intermediate G-1 (20.0 g, 54.4 mmol) and (2-nitrophenyl)boronic acid (10.0 g, 59.8 mmol) were dissolved in 300 ml of THF, and potassium carbonate (30.1 g, 217.5 mmol) dissolved in 100 ml of H$_2$O was added. Tetrakis(triphenylphosphine)palladium(0) (3.1 g, 2.7 mmol) was added thereto, and then the mixture was stirred at reflux for 8 hours under an argon atmosphere. After completion of the reaction, the reaction solution was cooled to room temperature, then transferred to a separatory funnel, and extracted with ethyl acetate. The extract was dried over MgSO$_4$, filtered, concentrated, and then recrystallized to give 20.0 g of Intermediate G-2. (Yield: 81%, MS[M+H]$^+$=454)

Reaction Scheme 6-3) Synthesis of Intermediate G

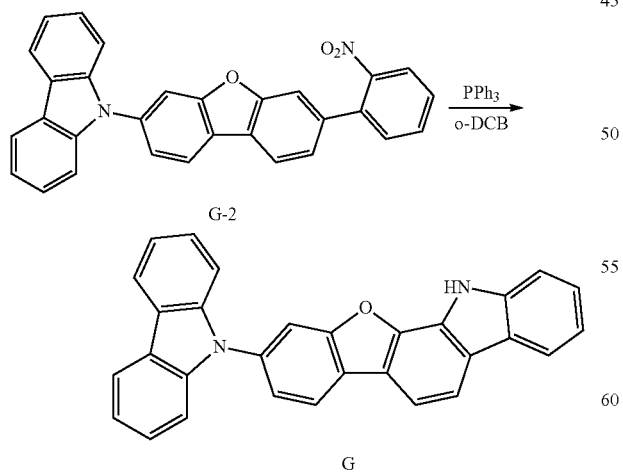

G

In two-necked flask was placed Intermediate G-2 (20.0 g, 44.0 mmol), triphenylphosphine (9.1 g, 66.0 mmol) and 200 ml of o-dichlorobenzene, and the mixture was stirred at reflux for 24 hours. After completion of the reaction, the reaction solution was cooled to room temperature, distilled under reduced pressure to remove the solvent, and then extracted with CH2Cl2. The extract was dried over MgSO$_4$, filtered and concentrated, and then the sample was purified by silica gel column chromatography to give 13.4 g of Intermediate G. (Yield: 72%, MS [M+H]+=422)

Synthesis Example 7: Synthesis of Intermediate H

Reaction Scheme 7-1)

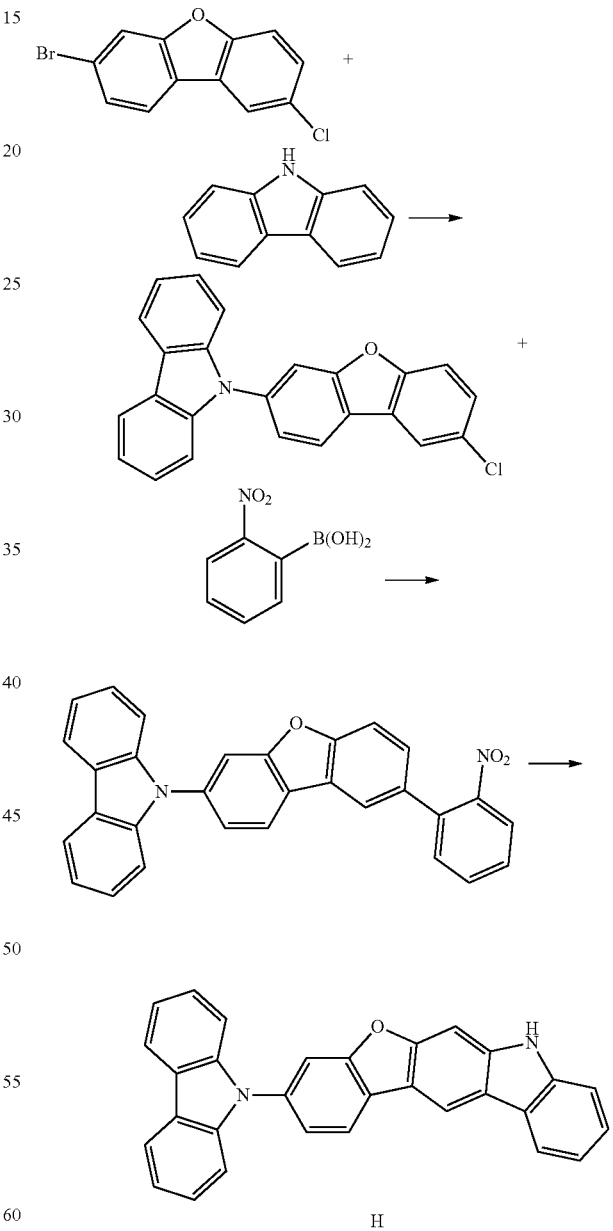

H

Intermediate H was prepared in the same manner as in the preparation method of Intermediate G, except that 7-bromo-2-chlorodibenzo[b,d]furan was used instead of 3-bromo-7-chlorodibenzo[b,d]furan in Synthesis Example F. (MS[M+H]$^+$=422)

EXAMPLES

Example 1: Synthesis of Compound 1

Reaction Scheme 1-A) Synthesis of Compound 1-1

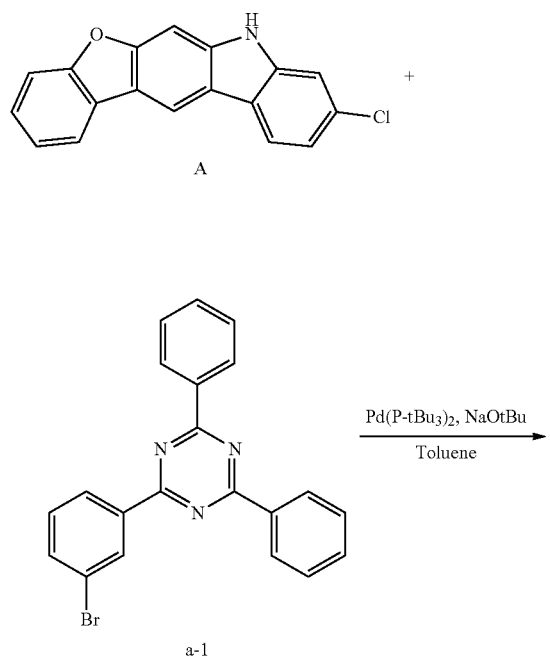

Reaction Scheme 1-B) Synthesis of Compound 1

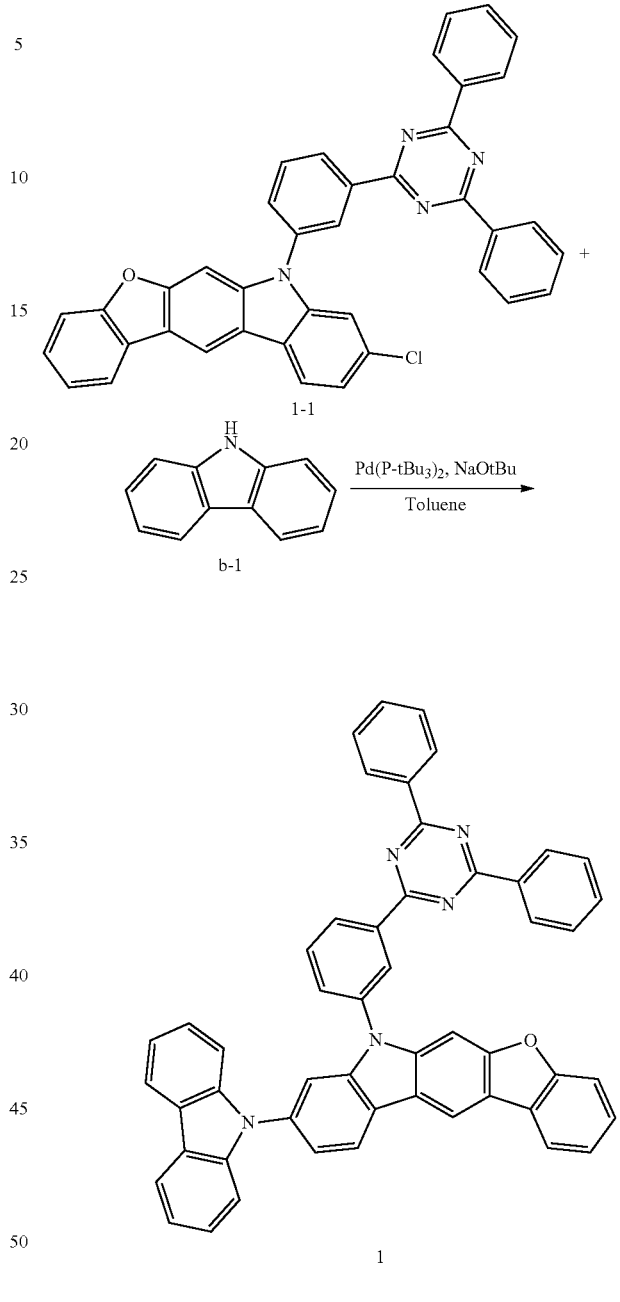

In a three-necked flask, Intermediate A (15.0 g, 51.4 mmol) and Intermediate a-1 (22.0 g, 56.6 mmol) were dissolved in 450 ml of toluene, and sodium tert-butoxide (7.4 g, 77.1 mmol) and bis(tri-tert-butylphosphine)palladium(0) (0.5 g, 1.0 mmol) were added, and then the mixture was stirred at reflux for 6 hours under an argon atmosphere. After completion of the reaction, the reaction temperature was cooled to room temperature, then H$_2$O was added, and the reaction solution was transferred to a separatory funnel, and extracted. The extract was dried over MgSO$_4$ and concentrated, and then the sample was purified by silica gel column chromatography to give 21.9 g of Compound 1-1. (Yield: 71%, MS [M+H]$^+$=599)

In a three-necked flask, Compound 1-1 (20.0 g, 33.4 mmol) and Intermediate b-1 (6.1 g, 36.7 mmol) were dissolved in 600 ml of toluene, and sodium tert-butoxide (4.8 g, 50.1 mmol) and bis(tri-tert-butylphosphine)palladium(0) (0.3 g, 0.7 mmol) were added, and then the mixture was stirred at reflux for 6 hours under an argon atmosphere. After completion of the reaction, the reaction temperature was cooled to room temperature, then H$_2$O was added, and the reaction solution was transferred to a separatory funnel, and extracted. The extract was dried over MgSO$_4$ and concentrated, and the sample was purified by silica gel column chromatography and then subjected to sublimation purification to give 7.8 g of Compound 1. (Yield: 32%, MS [M+H]$^+$=729)

Example 2: Synthesis of Compound 2
Reaction Scheme 2)
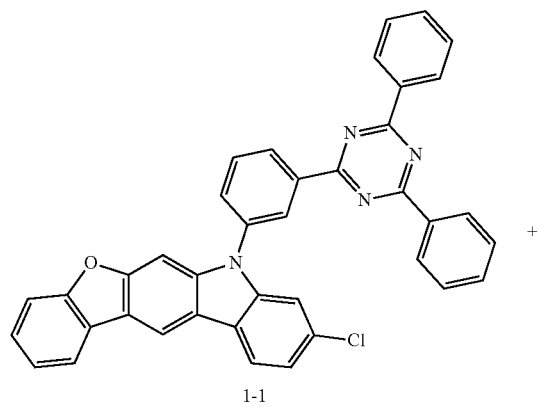
1-1
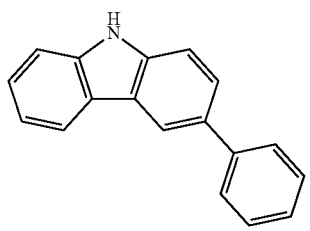
b-2
2
Compound 2 was prepared in the same manner as in the preparation method of Compound 1, except that Intermediate b-2 was used instead of Intermediate b-1 in Reaction Scheme 1-B of Example 1. (MS[M+H]$^+$=805)
Example 3: Synthesis of Compound 3
Reaction Scheme 3)
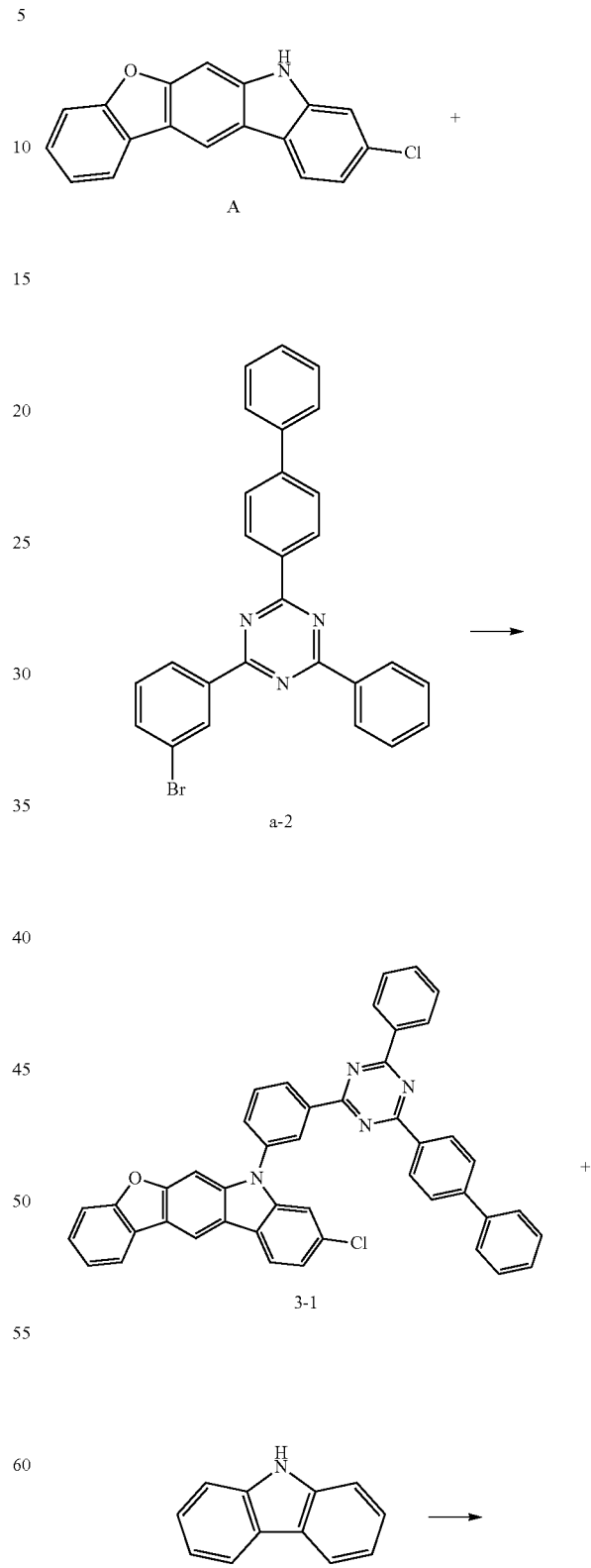

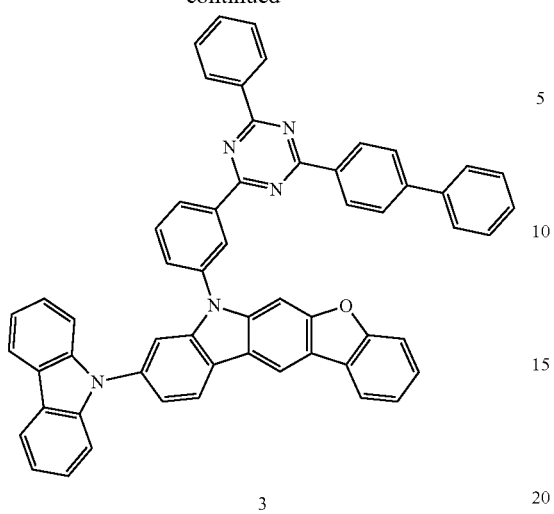

3

Compound 3 was prepared in the same manner as in the preparation method of Compound 1, except that Intermediate a-2 was used instead of Intermediate a-1 in Reaction Scheme 1-A of Example 1. (MS[M+H]⁺=805)

Example 4: Synthesis of Compound 4

Reaction Scheme 4)

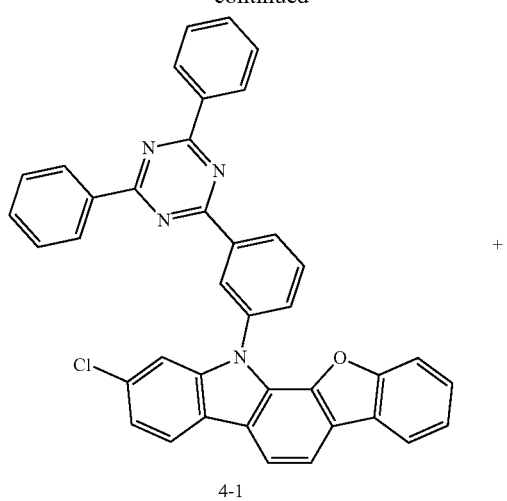

4-1

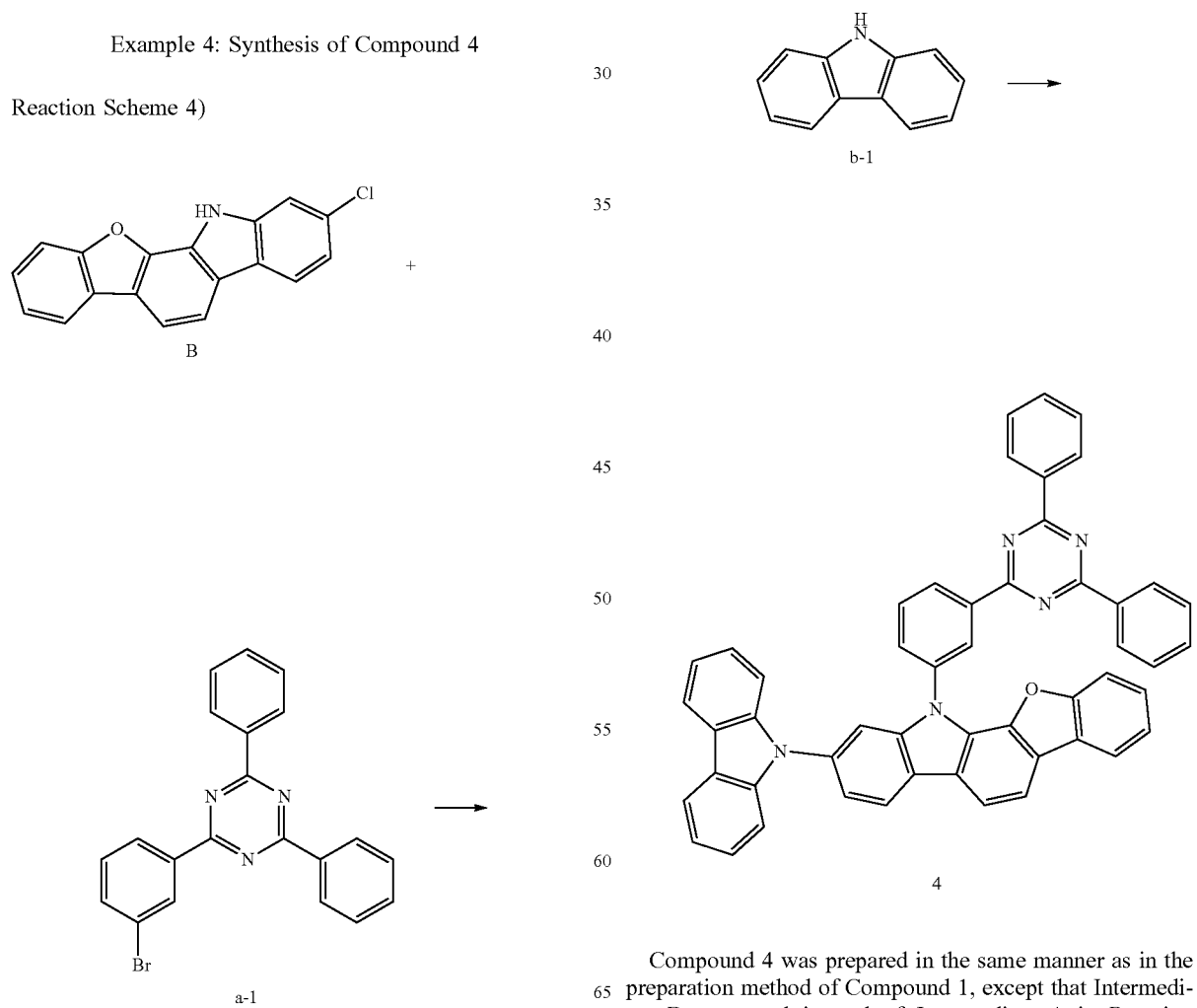

4

Compound 4 was prepared in the same manner as in the preparation method of Compound 1, except that Intermediate B was used instead of Intermediate A in Reaction Scheme 1-A of Example 1. (MS[M+H]⁺=729)

Example 5: Synthesis of Compound 5
Reaction Scheme 5)
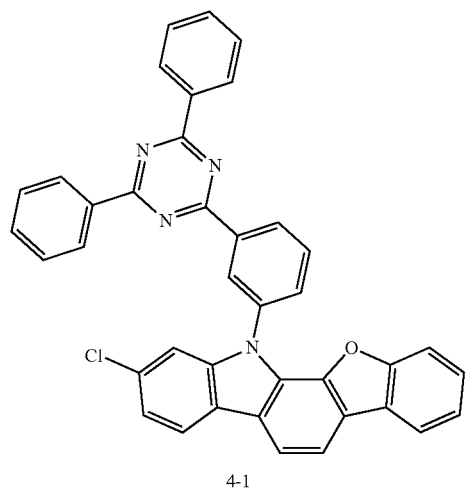
4-1
+
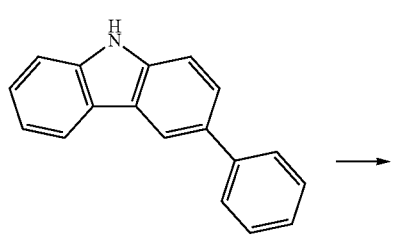
b-2
→
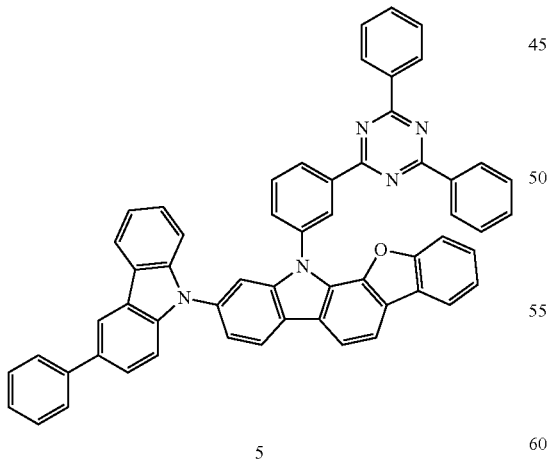
5
Compound 5 was prepared in the same manner as in the preparation method of Compound 1, except that Compound 4-1 was used instead of Compound 1-1 and Intermediate b-2 was used instead of Intermediate b-1 in Reaction Scheme 1-B of Example 1. (MS[M+H]⁺=805)
Example 6: Synthesis of Compound 6
Reaction Scheme 6)
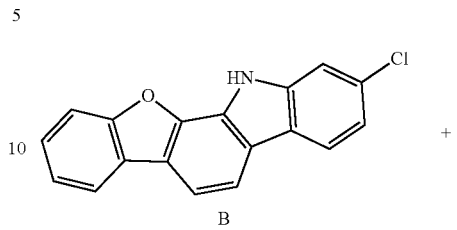
B
+
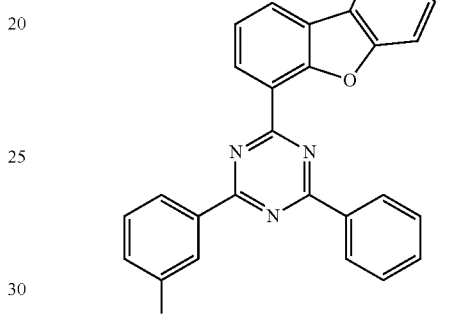
a-3
→
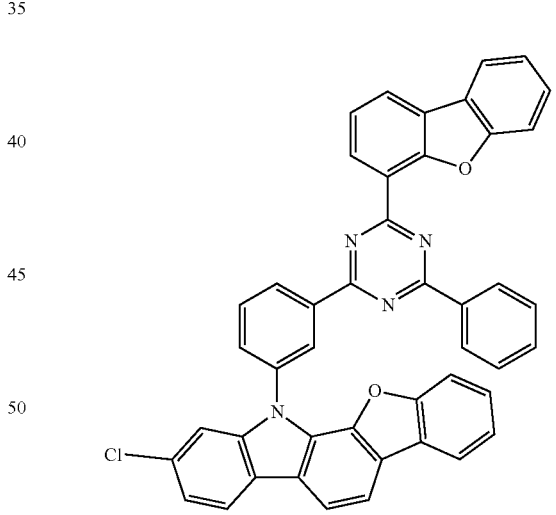
6-1
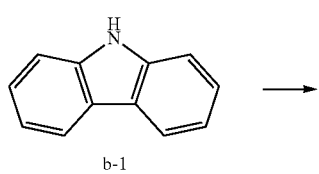
b-1
→

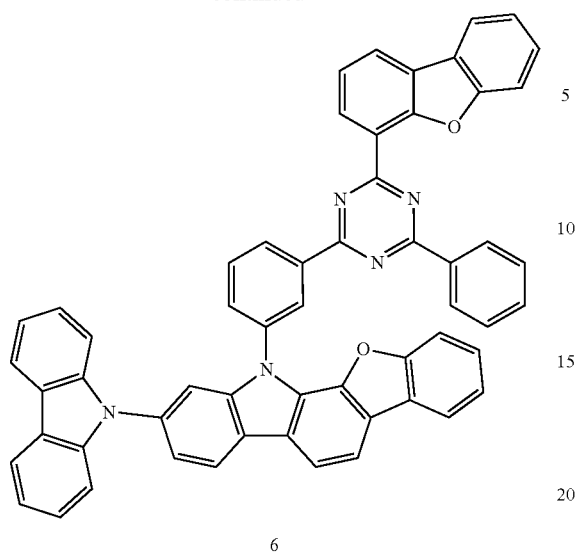

6

Compound 6 was prepared in the same manner as in the preparation method of Compound 1, except that Intermediate B was used instead of Intermediate A and Intermediate a-3 was used instead of Intermediate a-1 in Reaction Scheme 1-A of Example 1. (MS[M+H]⁺=819)

Example 7: Synthesis of Compound 7

Reaction Scheme 7)

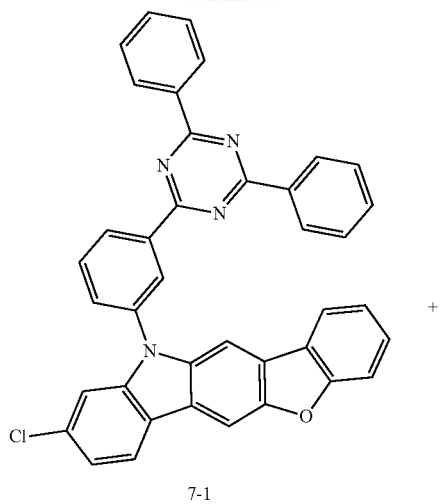

7-1

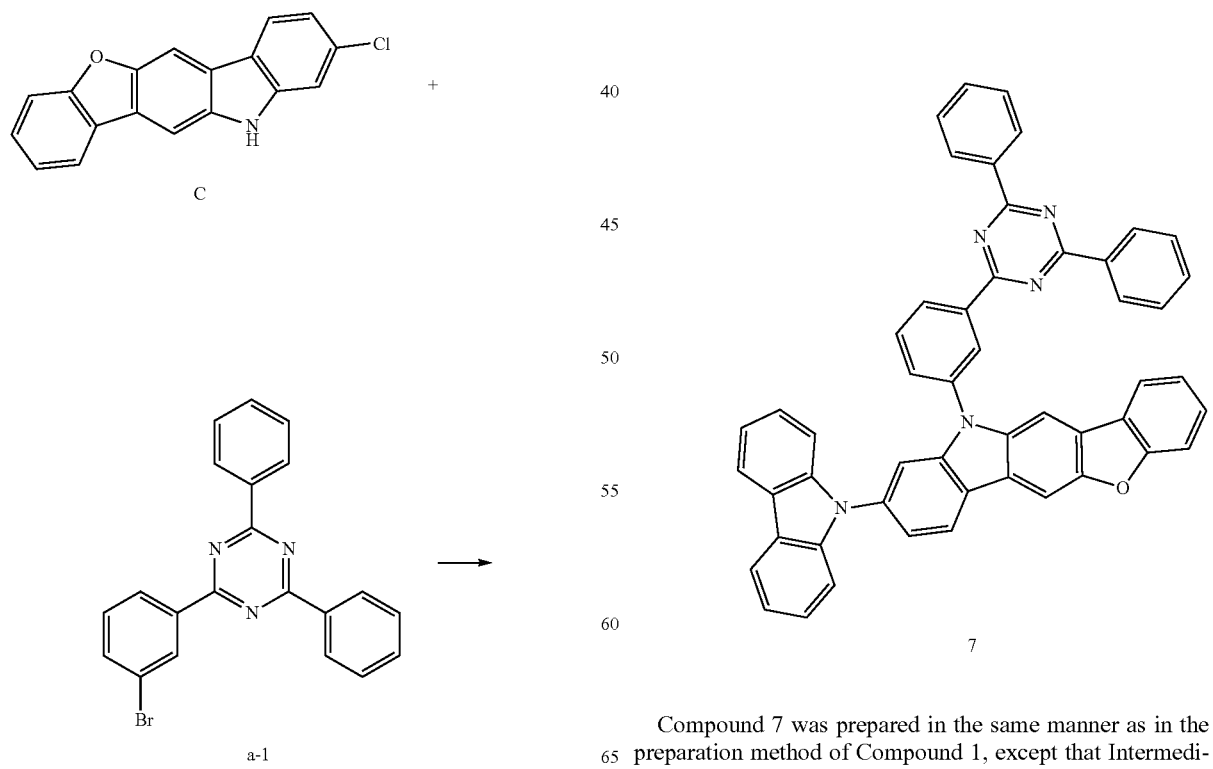

7

Compound 7 was prepared in the same manner as in the preparation method of Compound 1, except that Intermediate C was used instead of Intermediate A in Reaction Scheme 1-A of Example 1. (MS[M+H]⁺=729)

Example 8: Synthesis of Compound 8
Reaction Scheme 8)
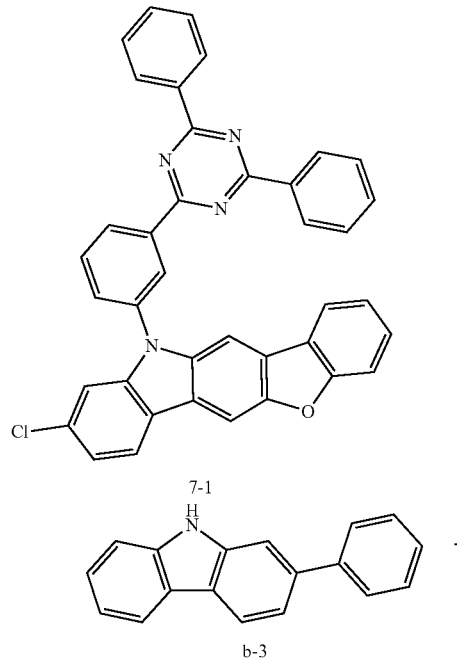
Compound 8 was prepared in the same manner as in the preparation method of Compound 1, except that Compound 7-1 was used instead of Compound 1-1 and Intermediate b-3 was used instead of Intermediate b-1 in Reaction Scheme 1-B of Example 1. (MS[M+H]$^+$=805)
Example 9: Synthesis of Compound 9
Reaction Scheme 9)
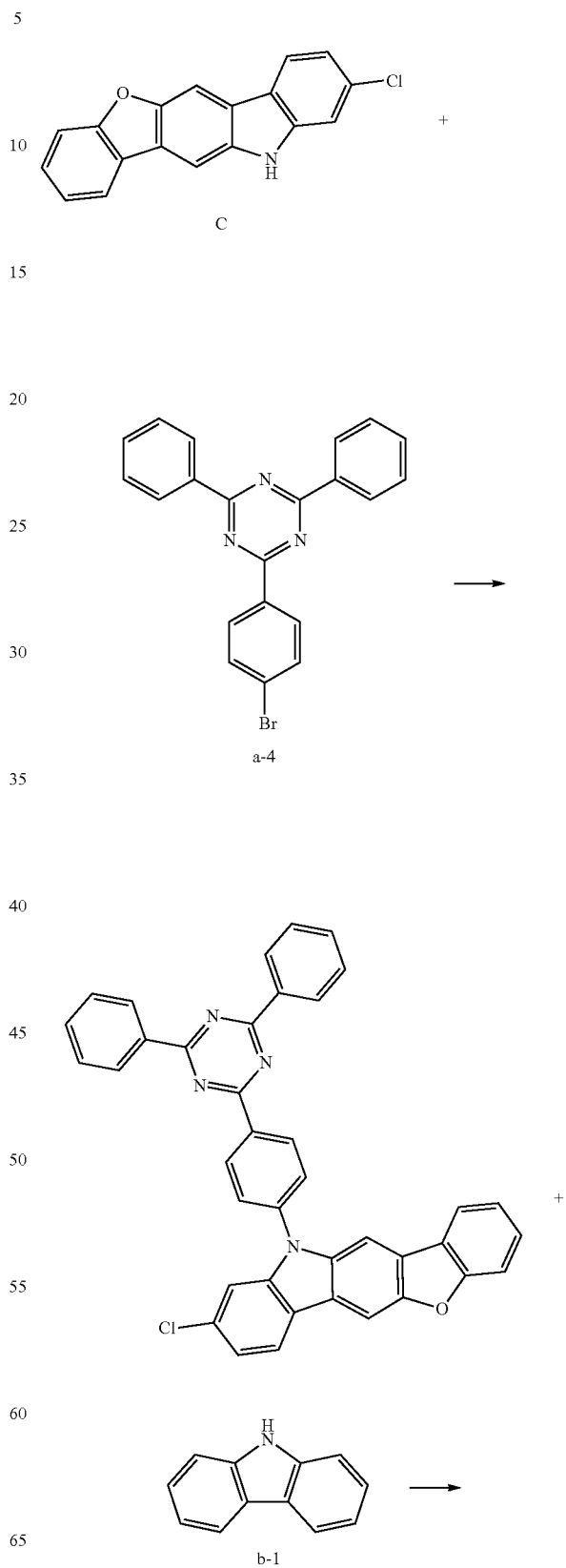

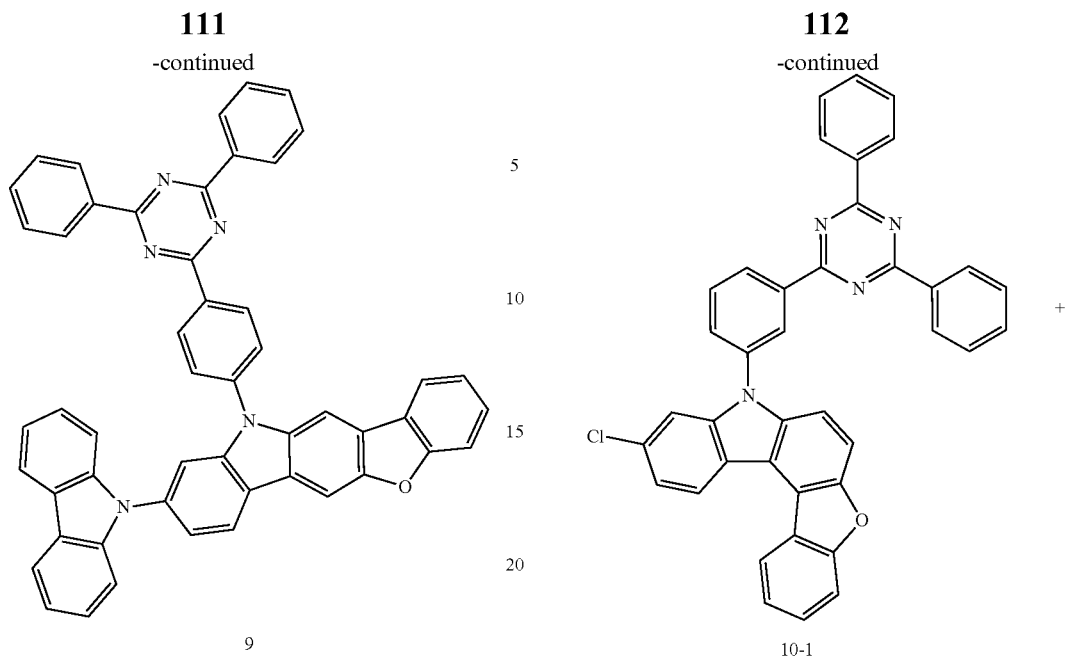

9

Compound 9 was prepared in the same manner as in the preparation method of Compound 1, except that Intermediate C was used instead of Intermediate A and Intermediate a-4 was used instead of Intermediate a-1 in Reaction Scheme 1-A of Example 1. (MS[M+H]$^+$=729)

Example 10: Synthesis of Compound 10

Reaction Scheme 10)

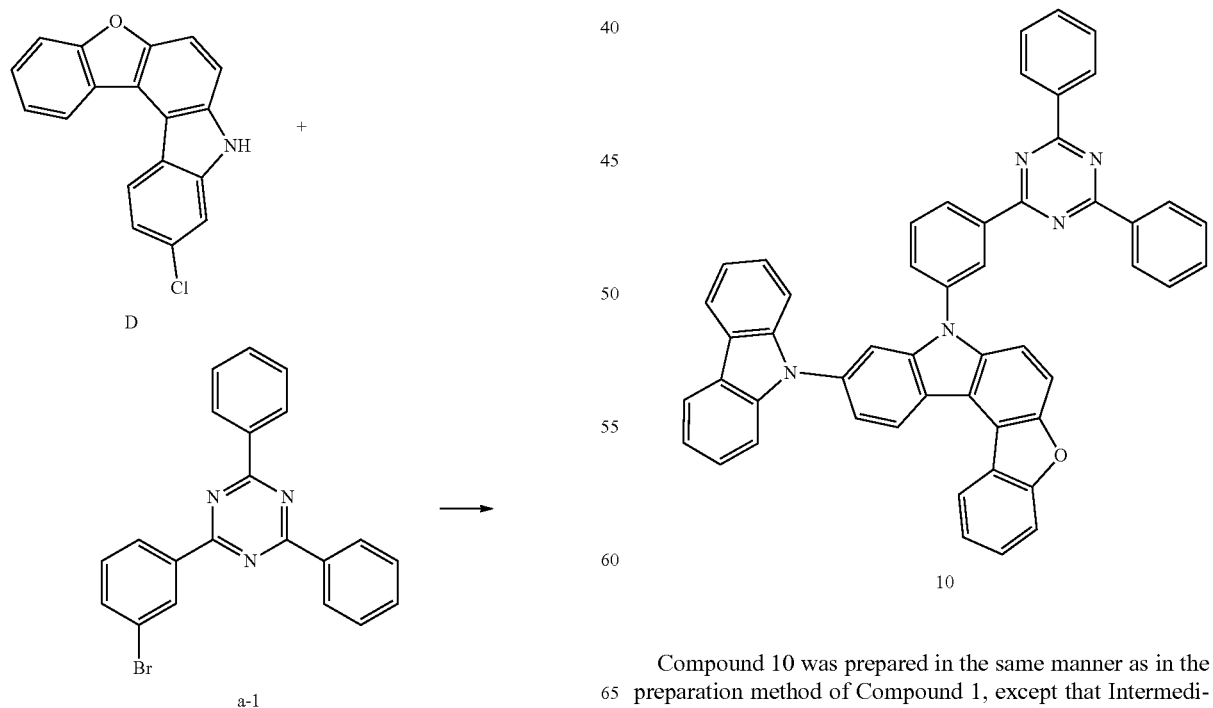

10-1

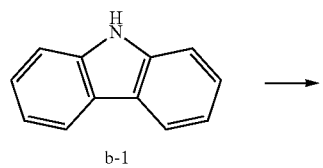

b-1

10

Compound 10 was prepared in the same manner as in the preparation method of Compound 1, except that Intermediate D was used instead of Intermediate A in Reaction Scheme 1-A of Example 1. (MS[M+H]$^+$=729)

Example 11: Synthesis of Compound 11
Reaction Scheme 11)
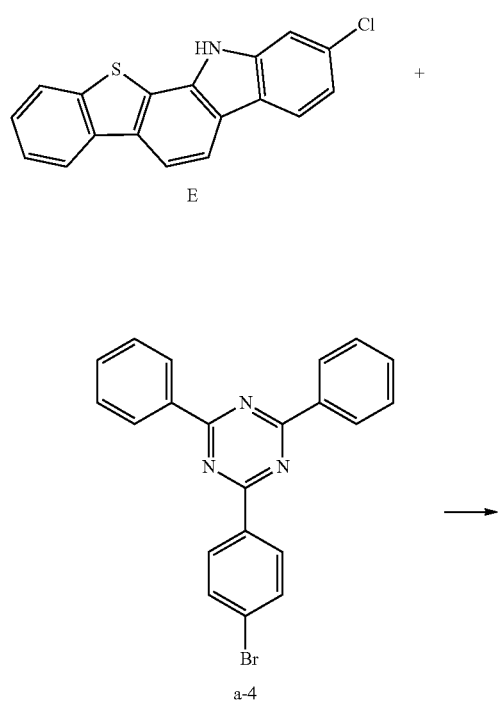
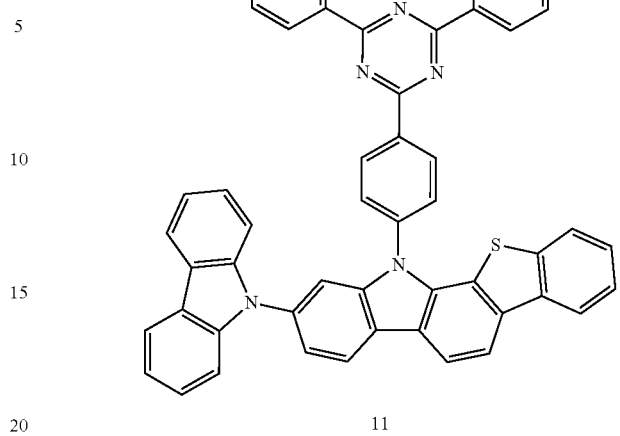
Compound 11 was prepared in the same manner as in the preparation method of Compound 1, except that Intermediate E was used instead of Intermediate A and Intermediate a-4 was used instead of Intermediate a-1 in Reaction Scheme 1-A of Example 1. (MS[M+H]$^+$=745)
Example 12: Synthesis of Compound 12
Reaction Scheme 12)
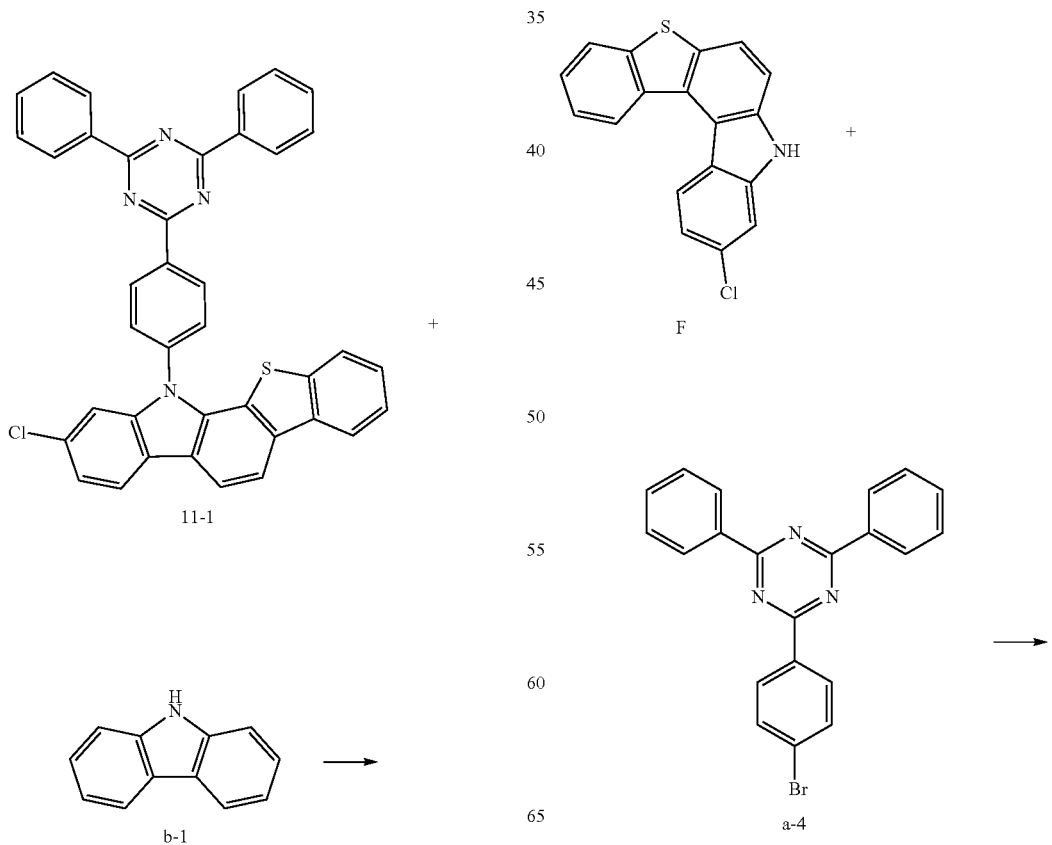

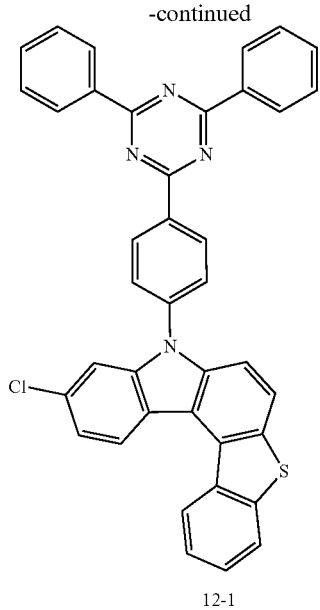
12-1
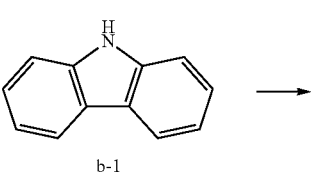
b-1
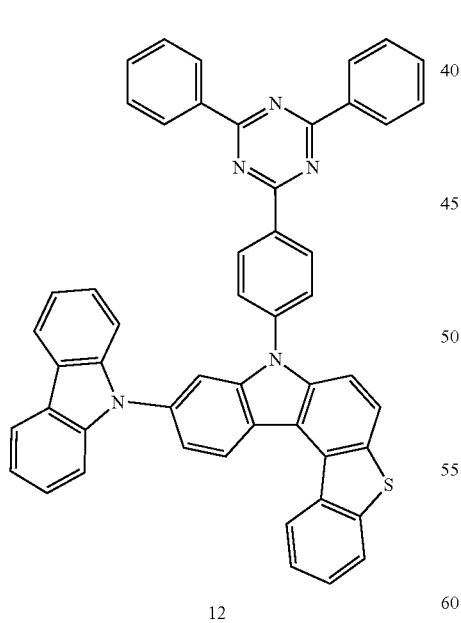
12
Compound 12 was prepared in the same manner as in the preparation method of Compound 1, except that Intermediate F was used instead of Intermediate A and Intermediate a-4 was used instead of Intermediate a-1 in Reaction Scheme 1-A of Example 1. (MS[M+H]$^+$=745)
Example 13: Synthesis of Compound 13
Reaction Scheme 13)
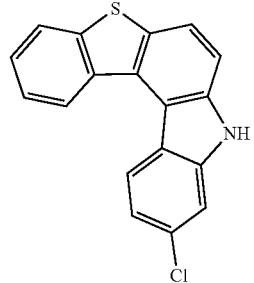
F
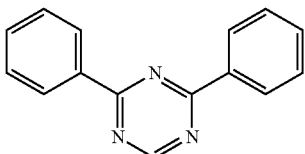
a-5
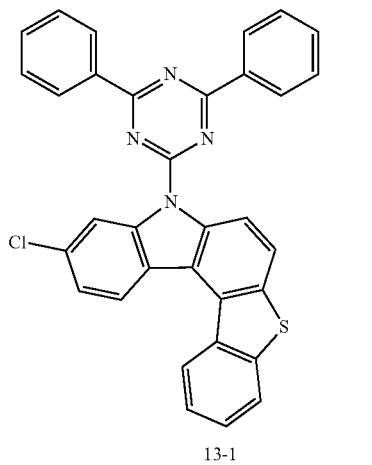
13-1
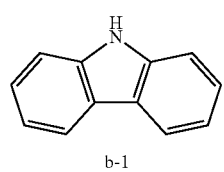
b-1

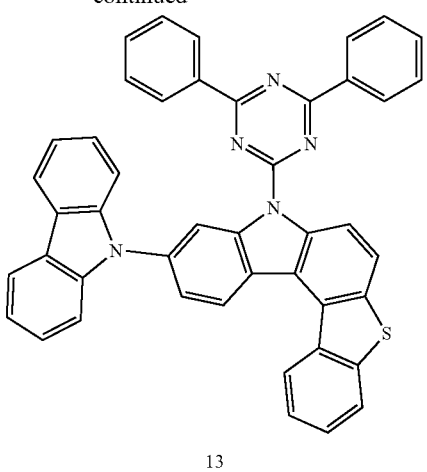

13

Compound 13 was prepared in the same manner as in the preparation method of Compound 1, except that Intermediate F was used instead of Intermediate A and Intermediate a-5 was used instead of Intermediate a-1 in Reaction Scheme 1-A of Example 1. (MS[M+H]⁺=669)

Example 14: Synthesis of Compound 14

Reaction Scheme 14)

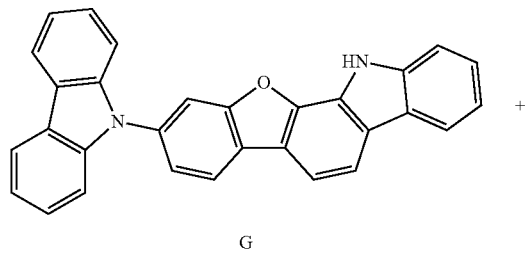

G

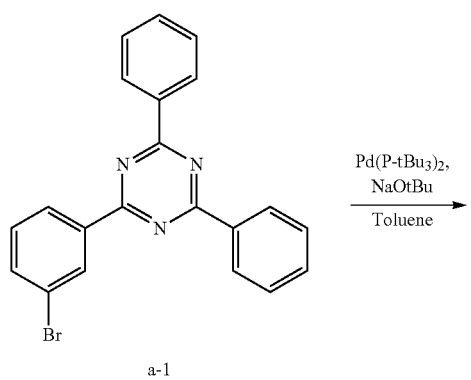

a-1

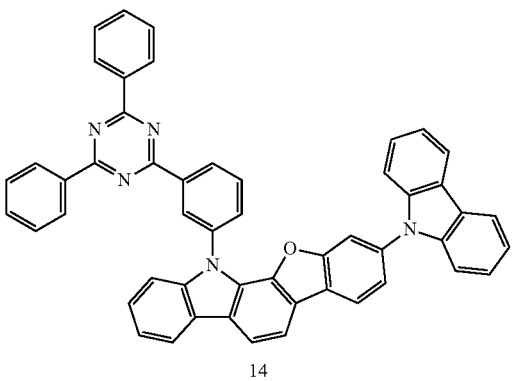

14

In a three-necked flask, Intermediate G (15.0 g, 35.5 mmol) and Intermediate a-1 (15.2 g, 39.1 mmol) were dissolved in 450 ml of toluene, and sodium tert-butoxide (5.1 g, 53.3 mmol) and bis(tri-tert-butylphosphine)palladium(0) (0.4 g, 0.7 mmol) were added, and the mixture was stirred at reflux for 6 hours under an argon atmosphere. After completion of the reaction, the reaction temperature was cooled to room temperature, then H$_2$O was added, and the reaction solution was transferred to a separatory funnel, and extracted. The extract was dried over MgSO$_4$ and concentrated, and the sample was purified by silica gel column chromatography and then subjected to sublimation purification to give 7.8 g of Compound 14. (Yield: 30%, MS [M+H]+=729)

Example 15: Synthesis of Compound 15

Reaction Scheme 15)

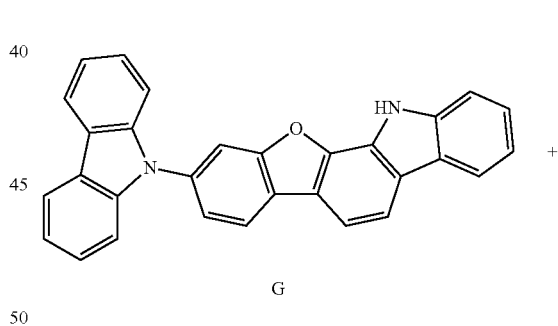

G

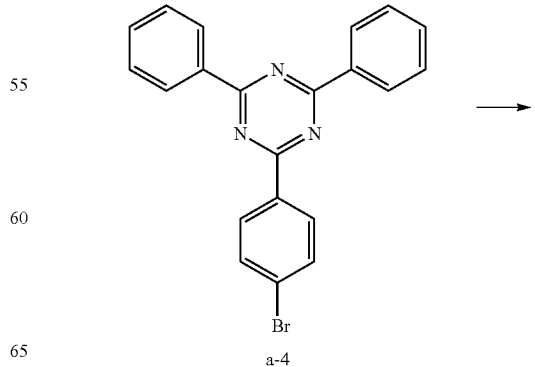

a-4

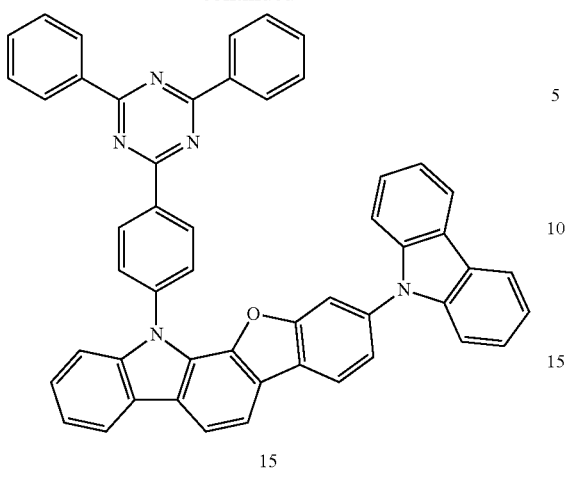

15

Compound 15 was prepared in the same manner as in the preparation method of Compound 14, except that Intermediate a-4 was used instead of Intermediate a-1 in Reaction Scheme 14 of Example 14. (MS[M+H]$^+$=729)

Example 16: Synthesis of Compound 16

Reaction Scheme 16)

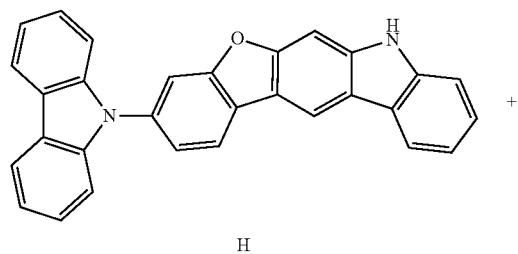

H

+

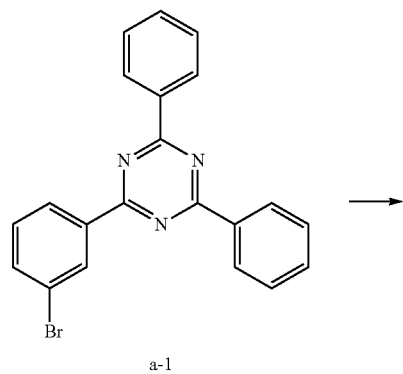

a-1

→

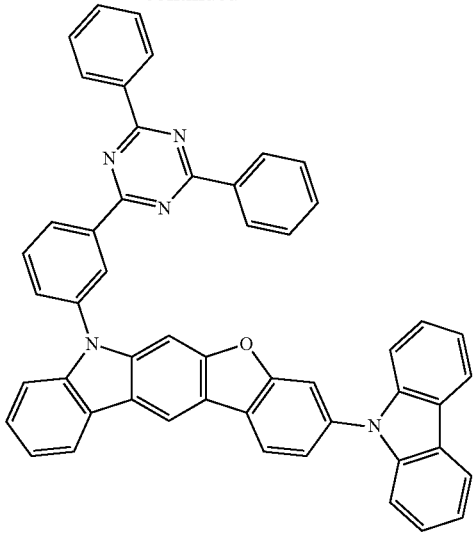

16

Compound 16 was prepared in the same manner as in the preparation method of Compound 14, except that Intermediate H was used instead of Intermediate G in Reaction Scheme 14 of Example 14. (MS[M+H]$^+$=729)

EXPERIMENTAL EXAMPLES

Experimental Example 1

A glass substrate on which ITO (indium tin oxide) was coated as a thin film to a thickness of 1,400 Å was put into distilled water in which a detergent was dissolved, and ultrasonically cleaned. At this time, a product manufactured by Fischer Co. was used as the detergent, and as the distilled water, distilled water filtered twice using a filter manufactured by Millipore Co. was used. After the ITO was cleaned for 30 minutes, ultrasonic cleaning was repeated twice using distilled water for 10 minutes. After the cleaning with distilled water was completed, the substrate was ultrasonically cleaned with solvents of isopropyl alcohol, acetone, and methanol, dried, and then transferred to a plasma cleaner. In addition, the substrate was cleaned for 5 minutes using oxygen plasma and then transferred to a vacuum depositor.

On the ITO transparent electrode thus prepared, a compound HT below and 5 wt % of a compound PD below were thermally vacuum deposited to a thickness of 100 Å, and then only a compound HT below was deposited to a thickness of 1150 Å to form a hole transport layer. A compound EB below was thermally vacuum-deposited to a thickness of 450 Å thereon as an electronic blocking layer. Then, vacuum deposition was performed to a thickness of 400 Å by using a host containing a compound 1 below and 15 wt % of a compound GD as a dopant. Then, a compound ET-A below was vacuum-deposited to a thickness of 50 Å as a hole blocking layer. Then, compounds ET-B and Liq below were thermally vacuum-deposited in a ratio of 2:1 to a thickness of 250 Å as an electron transport and injection layer, and LiF and magnesium were then vacuum deposited in a ratio of 1:1 to a thickness of 30 Å. Magnesium and silver were deposited in a ratio of 1:4 to a thickness of 160 Å on the electron injection layer to form a cathode, thereby completing the manufacture of an organic light emitting device.

The voltage, efficiency and lifetime (T95) were measured by applying a current to the organic light emitting devices manufactured above, and the results are shown in Table 1 below. At this time, the voltage and efficiency were measured by applying a current density of 10 mA/cm², and T95 means the time required for the luminance to be reduced to 95% of the initial luminance at a current density of 20 mA/cm².

HT

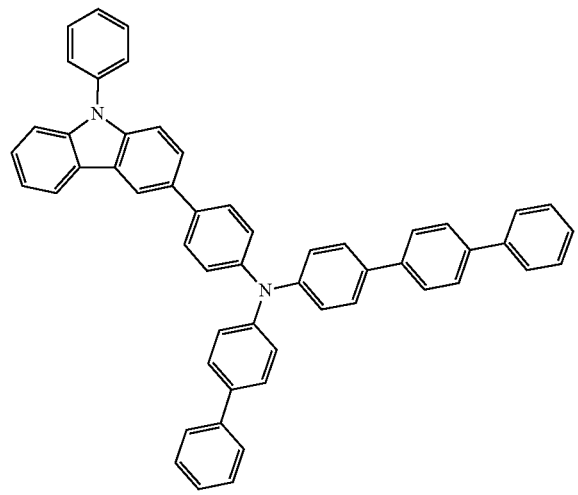

PD

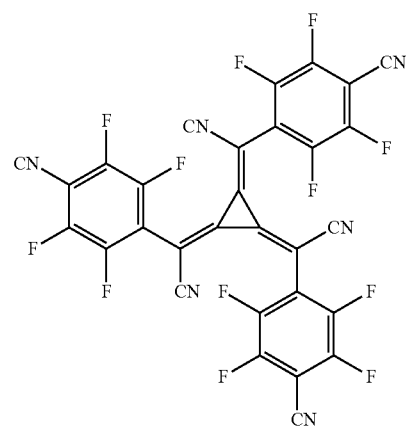

EB

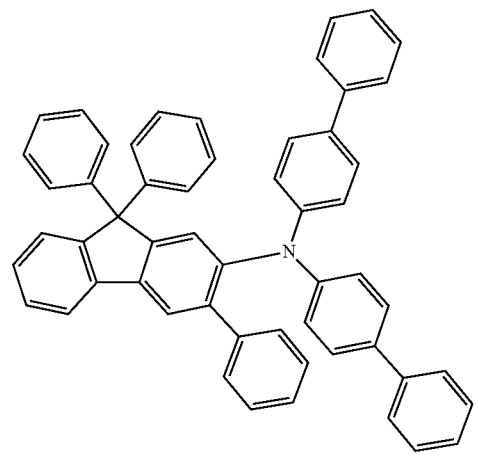

PGH

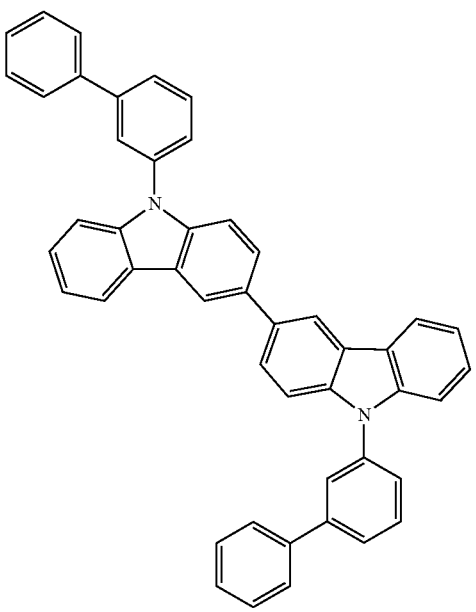

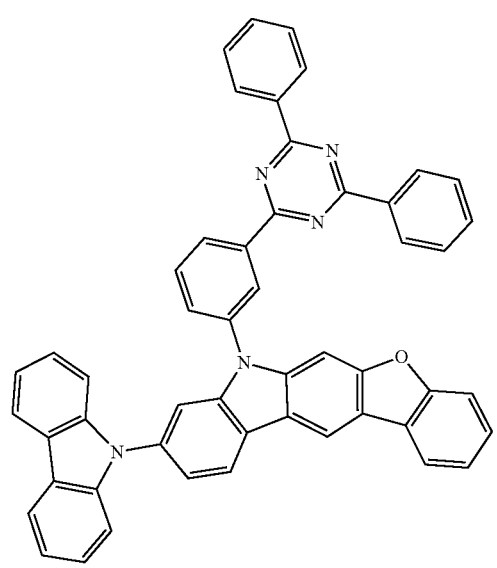

GD

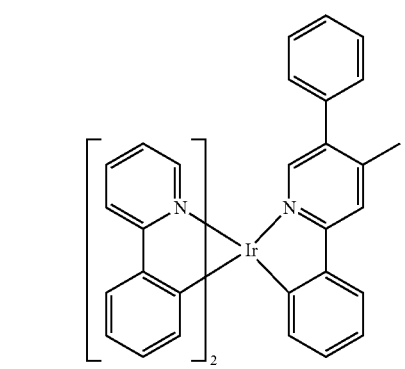

-continued

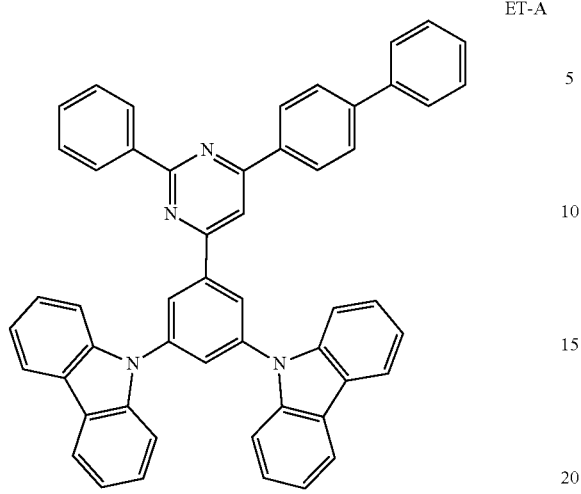
ET-A

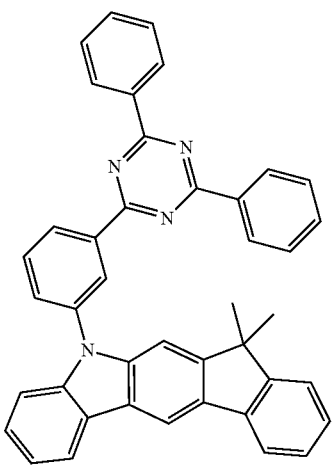
GH-A

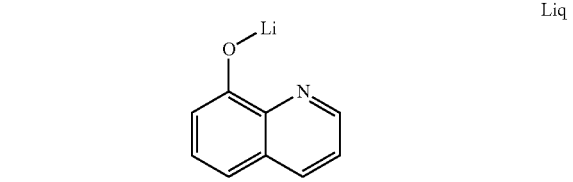
ET-B

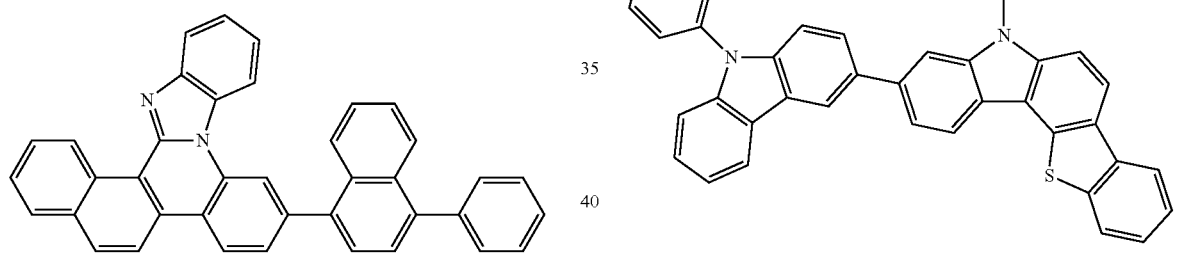
GH-B

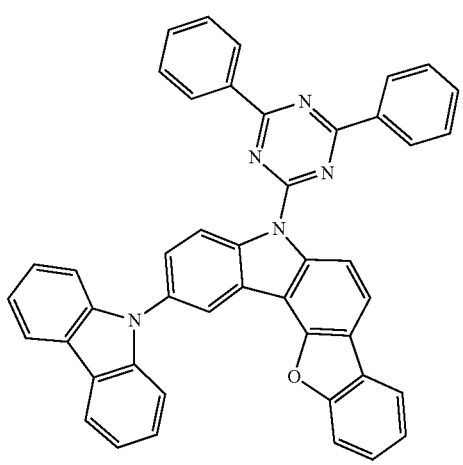
GH-C

Liq

Experimental Examples 2 to 19 and Comparative Experimental Examples 1 to 10

The organic light emitting devices of Experimental Examples 2 to 19 and Comparative Experimental Examples 1 to 10 were respectively manufactured in the same manner as in Experimental Example 1, except that the host material was changed as shown in Table 1 below. The voltage, efficiency and lifetime (T95) were measured by applying a current to the organic light emitting devices manufactured above, and the results are shown in Table 1 below. In this case, when a mixture of two kinds of compounds was used as the host, the parenthesis means the weight ratio between the host compounds.

GH-D

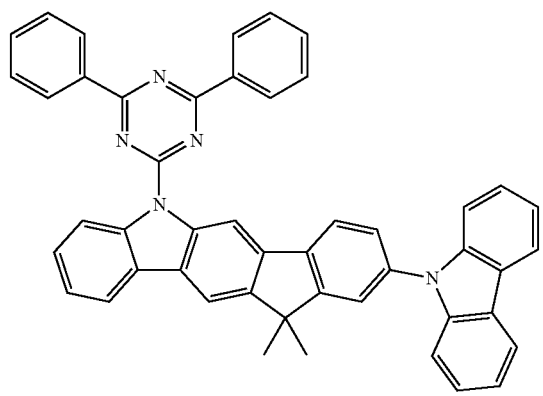

GH-G

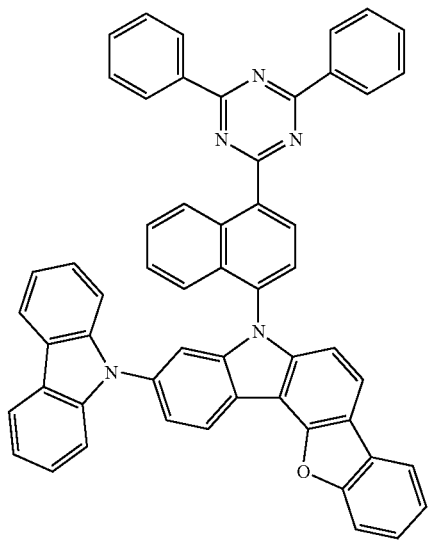

GH-E

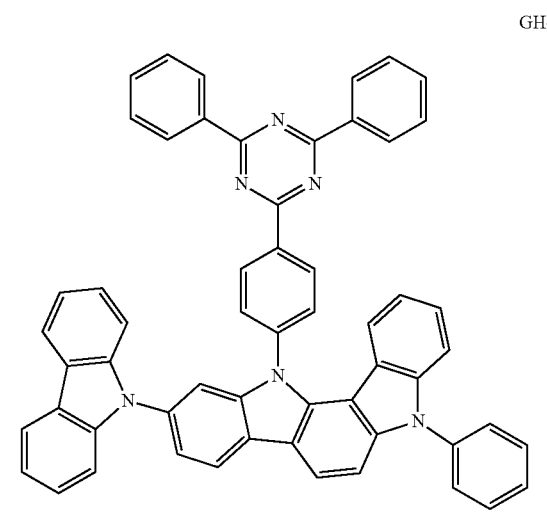

GH-H

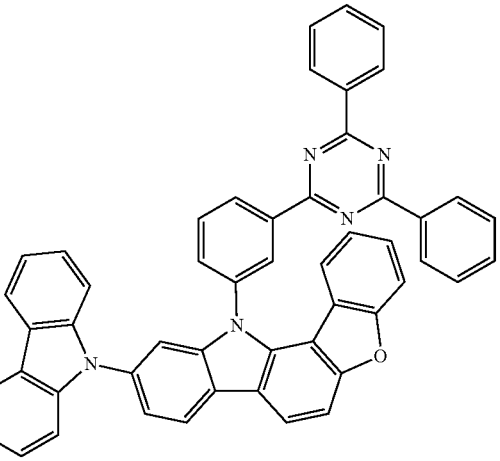

GH-F

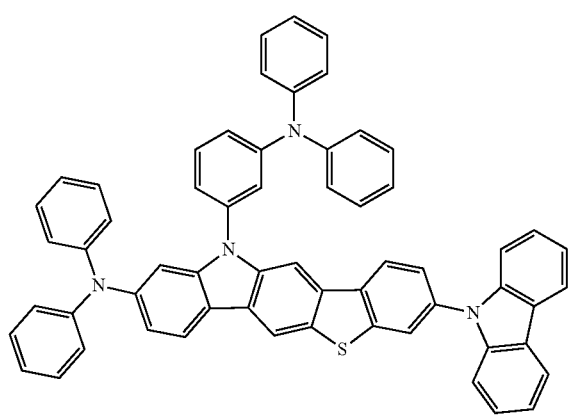

TABLE 1

| Category | Host material | @ 10 mA/cm² | | @ 20 mA/cm² |
| --- | --- | --- | --- | --- |
| | | Voltage (V) | Efficiency (cd/A) | Lifetime (T95, hr) |
| Experimental Example 1 | Compound 1 | 4.68 | 48.5 | 110 |
| Experimental Example 2 | Compound 2 | 4.69 | 48.1 | 110 |
| Experimental Example 3 | Compound 3 | 4.69 | 48.9 | 105 |
| Experimental Example 4 | Compound 4 | 4.60 | 49.2 | 120 |
| Experimental Example 5 | Compound 5 | 4.62 | 50.0 | 110 |
| Experimental Example 6 | Compound 6 | 4.63 | 49.6 | 125 |
| Experimental Example 7 | Compound 7 | 4.67 | 48.5 | 120 |
| Experimental Example 8 | Compound 8 | 4.68 | 49.1 | 110 |
| Experimental Example 9 | Compound 9 | 4.65 | 48.4 | 115 |
| Experimental Example 10 | Compound 10 | 4.68 | 50.2 | 125 |

TABLE 1-continued

| | | @ 10 mA/cm² | | @ 20 mA/cm² |
|---|---|---|---|---|
| Category | Host material | Voltage (V) | Efficiency (cd/A) | Lifetime (T95, hr) |
| Experimental Example 11 | Compound 11 | 4.74 | 47.1 | 125 |
| Experimental Example 12 | Compound 12 | 4.77 | 47.4 | 110 |
| Experimental Example 13 | Compound 13 | 4.71 | 48.2 | 120 |
| Experimental Example 14 | Compound 14 | 4.64 | 49.1 | 125 |
| Experimental Example 15 | Compound 15 | 4.67 | 49.4 | 110 |
| Experimental Example 16 | Compound 16 | 4.61 | 49.2 | 120 |
| Experimental Example 17 | PGH:Compound 1 (60:40) | 4.38 | 56.5 | 145 |
| Experimental Example 18 | PGH:Compound 5 (60:40) | 4.37 | 56.1 | 140 |
| Experimental Example 19 | PGH:Compound 14 (60:40) | 4.33 | 54.5 | 145 |
| Comparative Experimental Example 1 | GH-A | 4.88 | 45.8 | 80 |
| Comparative Experimental Example 2 | GH-B | 5.21 | 38.1 | 70 |
| Comparative Experimental Example 3 | GH-C | 5.51 | 21.0 | 65 |
| Comparative Experimental Example 4 | GH-D | 4.88 | 40.1 | 80 |
| Comparative Experimental Example 5 | GH-E | 5.97 | 35.3 | 70 |
| Comparative Experimental Example 6 | GH-F | 6.85 | 21.9 | 5 |
| Comparative Experimental Example 7 | GH-G | 6.71 | 20.1 | 10 |
| Comparative Experimental Example 8 | GH-H | 4.85 | 46.6 | 75 |
| Comparative Experimental Example 9 | PGH:GH-B (60:40) | 4.82 | 48.0 | 90 |
| Comparative Experimental Example 10 | PGH:GH-H (60:40) | 4.71 | 49.5 | 95 |

As shown in Table 1 above, it was confirmed that when the compound of Chemical Formula 1 was used as a host of light emitting layer in the organic light emitting device, it exhibited low voltage, high efficiency, and long lifetime characteristics. In addition, it was confirmed that the synergistic effect was realized when the compound of Chemical Formula 1 was used in combination with a compound of Chemical Formula 7 such as PGH.

DESCRIPTION OF REFERENCE NUMERALS

1: substrate
2: anode
3: light emitting layer
4: cathode
5: hole injection layer
6: hole transport layer
7: light emitting layer
8: electron transport layer

The invention claimed is:

1. A compound represented by Chemical Formula 1:

[Chemical Formula 1]

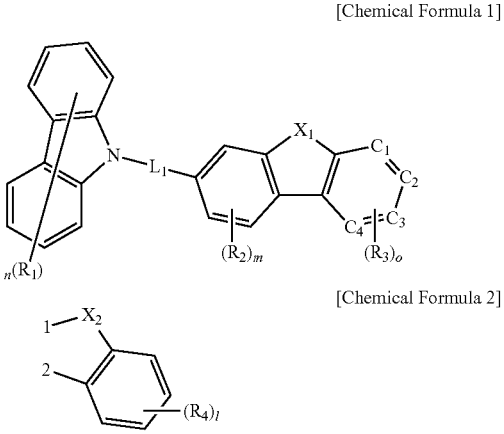

[Chemical Formula 2]

wherein, in Chemical Formula 1, two adjacent carbons of $C_1$ to $C_4$ are respectively connected to 1 and 2 of Chemical Formula 2, where $C_1$ and $C_2$ are not connected to 2 and 1 of Chemical Formula 2 respectively, and $C_4$ and $C_3$ are not connected to 1 and 2 of Chemical Formula 2 respectively, $L_1$ is a direct bond; or a substituted or unsubstituted $C_{6-60}$ arylene, $R_1$ is hydrogen; deuterium; a substituted or unsubstituted $C_{1-60}$ alkyl; or a substituted or unsubstituted $C_{6-60}$ aryl, or is fused with an adjacent ring to form a benzene ring, $R_2$ to $R_4$ are each independently hydrogen; deuterium; a substituted or unsubstituted $C_{1-60}$ alkyl; a substituted or unsubstituted $C_{6-60}$ aryl; or a substituted or unsubstituted $C_{5-60}$ heteroaryl containing at least one heteroatom selected from the group consisting of N, O and S, n is an integer of 0 to 8, m and o are each independently an integer of 0 to 3, l is an integer of 0 to 4, $X_1$ is NR' and $X_2$ is O or S; or $X_1$ is O or S and $X_2$ is NR', R' is

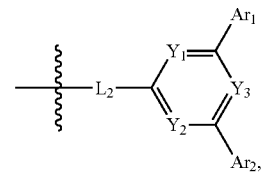

$L_2$ is a direct bond; or a substituted or unsubstituted $C_{6-60}$ arylene, $Y_1$, $Y_2$ and $Y_3$ are each independently CH or N, and at least two of $Y_1$, $Y_2$ and $Y_3$ are N, and $Ar_1$ and $Ar_2$ are each independently a substituted or unsubstituted $C_{6-60}$ aryl; or a substituted or unsubstituted $C_{5-60}$ heteroaryl containing at least one heteroatom selected from the group consisting of N, O and S.

2. The compound of claim 1, wherein the compound is any one selected from the group consisting of compounds represented by Chemical Formulas 3 to 6:

[Chemical Formula 3]

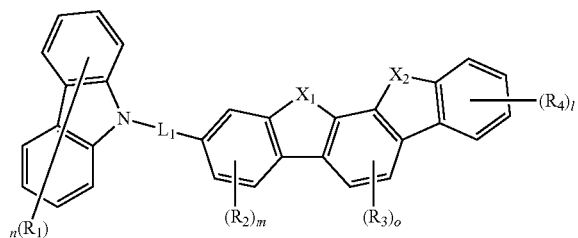

[Chemical Formula 4]

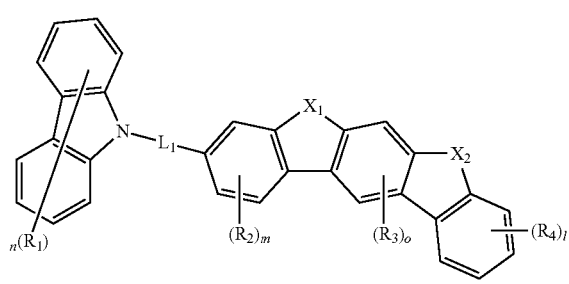

[Chemical Formula 5]

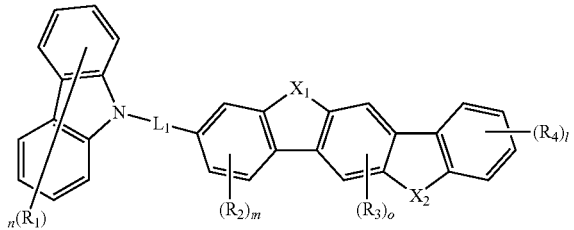

[Chemical Formula 6]

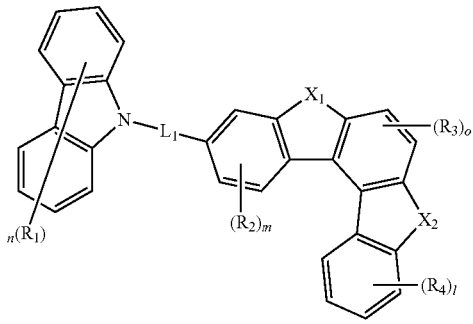

wherein, in Chemical Formulas 3 to 6,
$X_1$, $X_2$, $L_1$, $R_1$, $R_2$, $R_3$, $R_4$, n, m, o and l are the same as defined in claim 1.

3. The compound of claim 1
wherein $L_1$ and $L_2$ are each independently a direct bond; phenylene unsubstituted or substituted with deuterium; or naphthylene unsubstituted or substituted with deuterium.

4. The compound of claim 1,
wherein $R_1$ is hydrogen; deuterium; methyl; ethyl; propyl; phenyl unsubstituted or substituted with deuterium; biphenylyl unsubstituted or substituted with deuterium; or is fused with an adjacent ring to form a benzene ring.

5. The compound of claim 1,
wherein $R_2$ to $R_4$ are each independently hydrogen; deuterium; methyl; ethyl; propyl; phenyl unsubstituted or substituted with deuterium; or biphenylyl unsubstituted or substituted with deuterium.

6. The compound of claim 1,
wherein $Ar_1$ and $Ar_2$ are each independently phenyl substituted or unsubstituted with deuterium; biphenylyl unsubstituted or substituted with deuterium; dibenzofuranyl unsubstituted or substituted with deuterium; or dibenzothiophenyl unsubstituted or substituted with deuterium.

7. The compound of claim 1,
wherein the compound represented by Chemical Formula 1 is any one selected from the group consisting of:

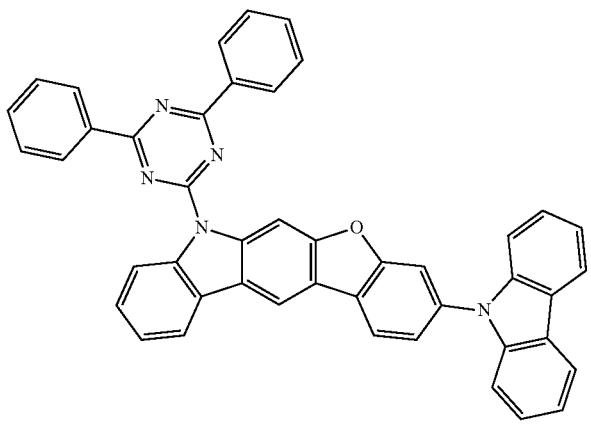

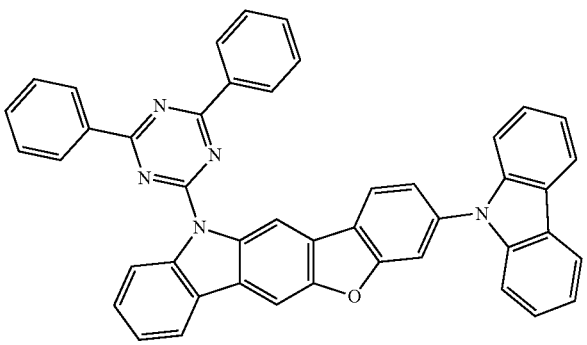

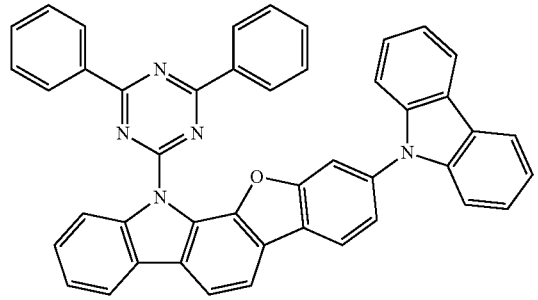
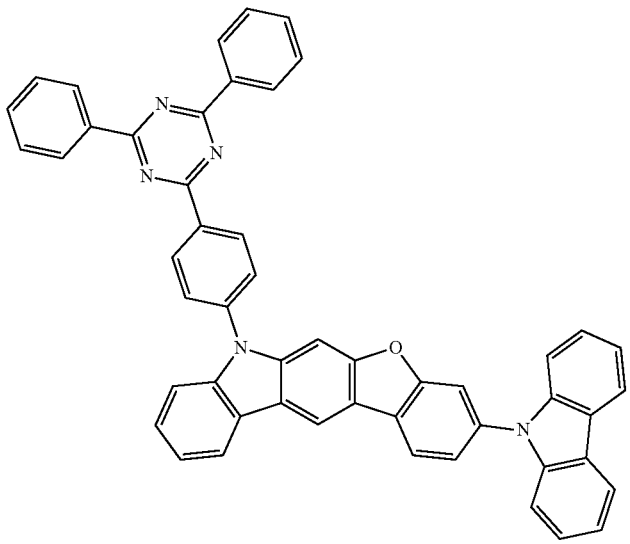
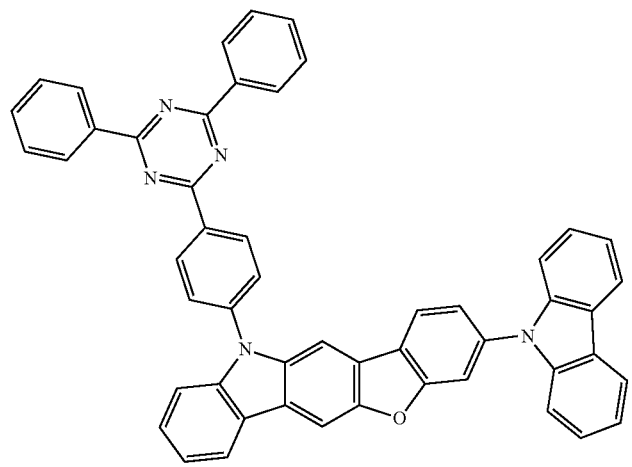
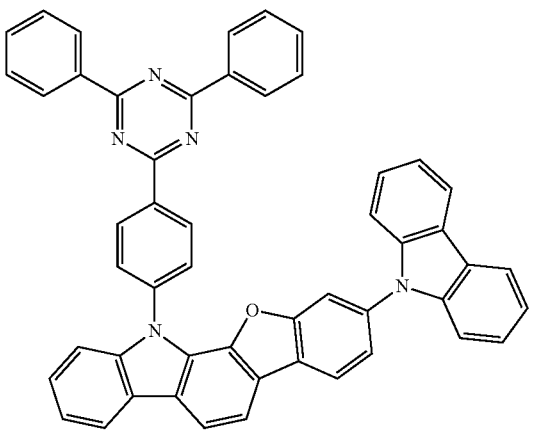
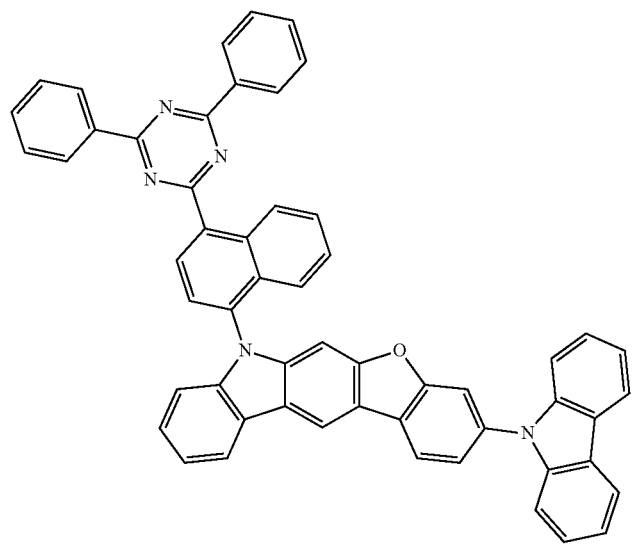

133 134
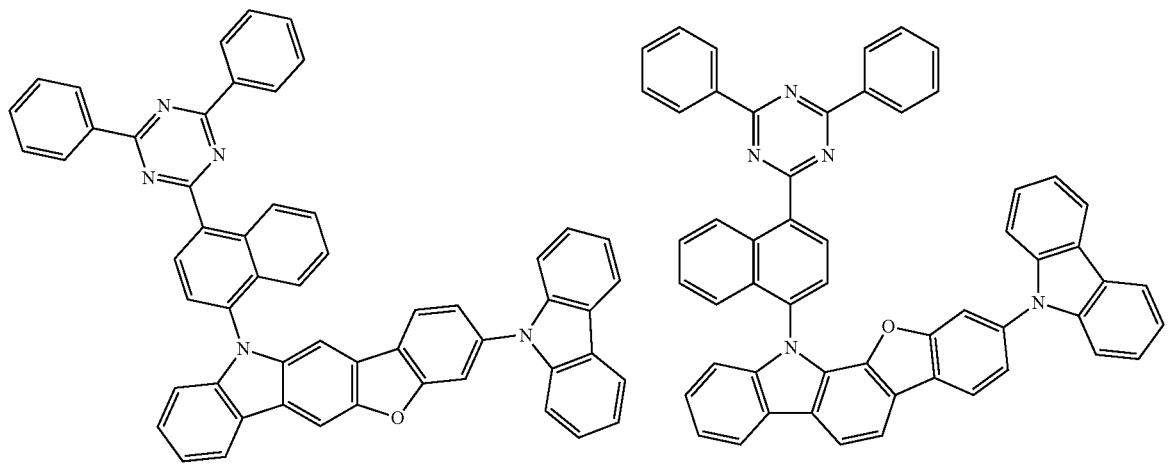
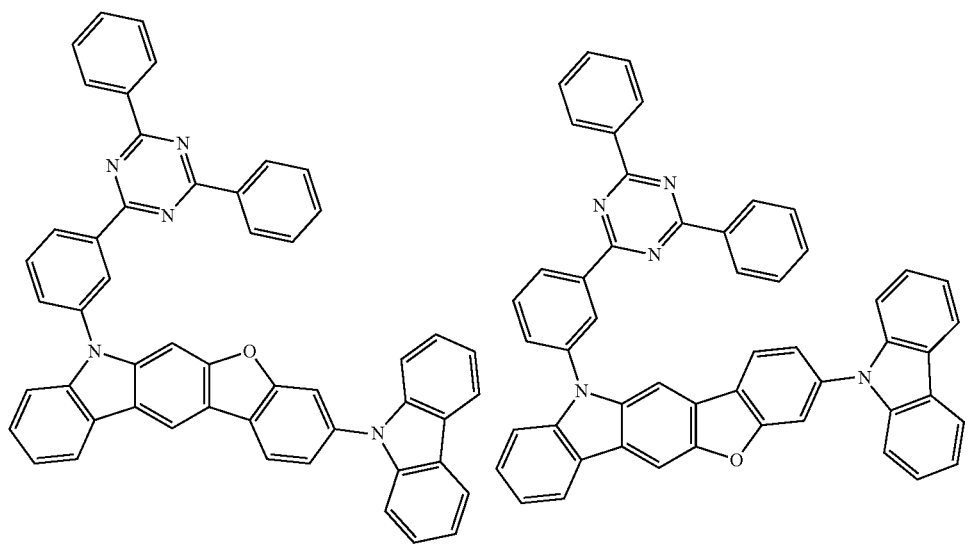
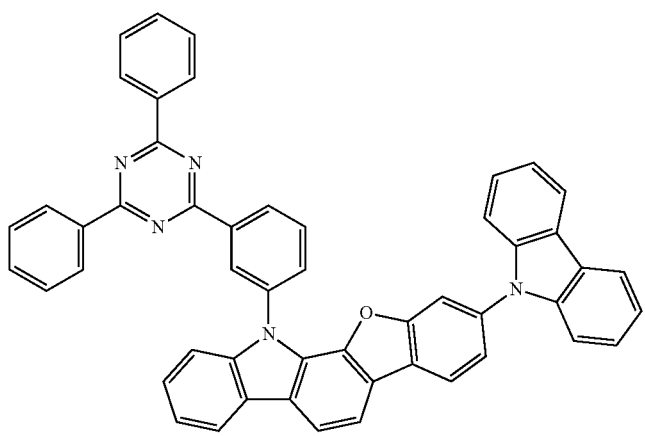

-continued
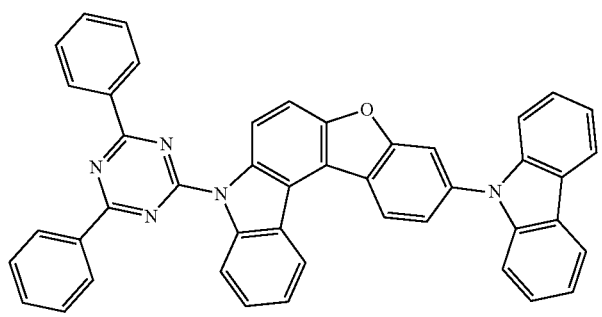
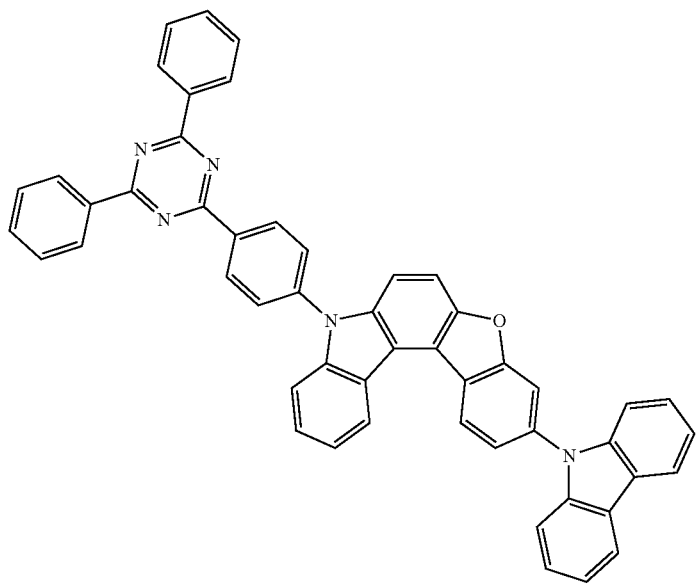
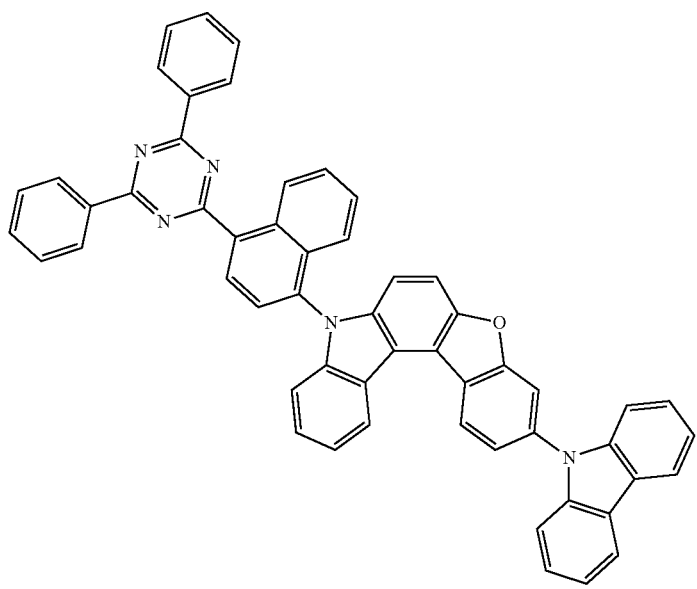

-continued
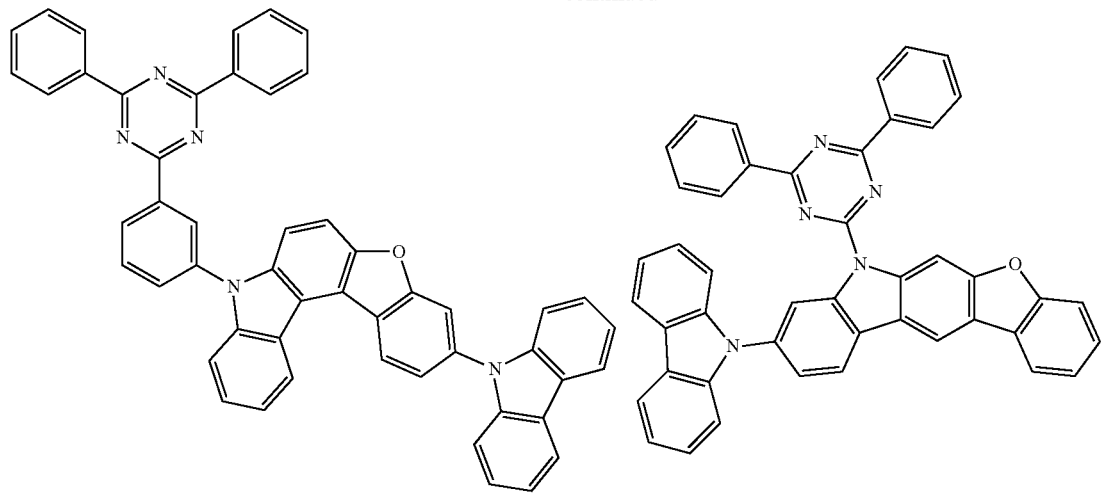
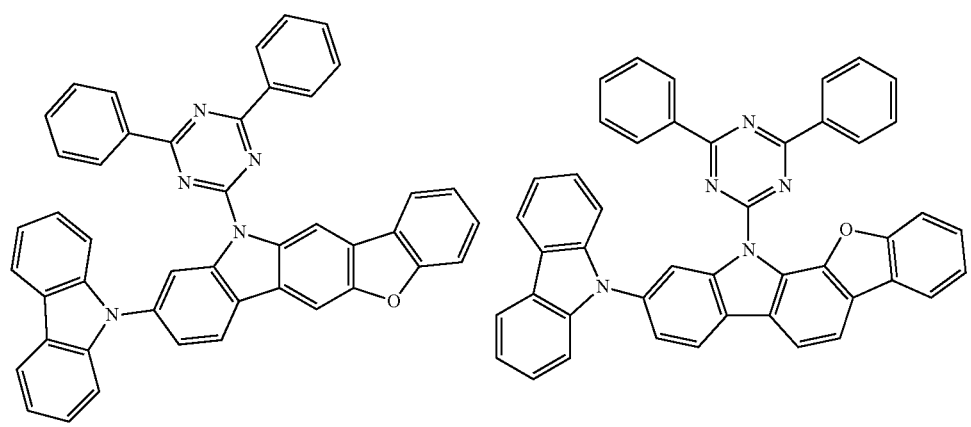
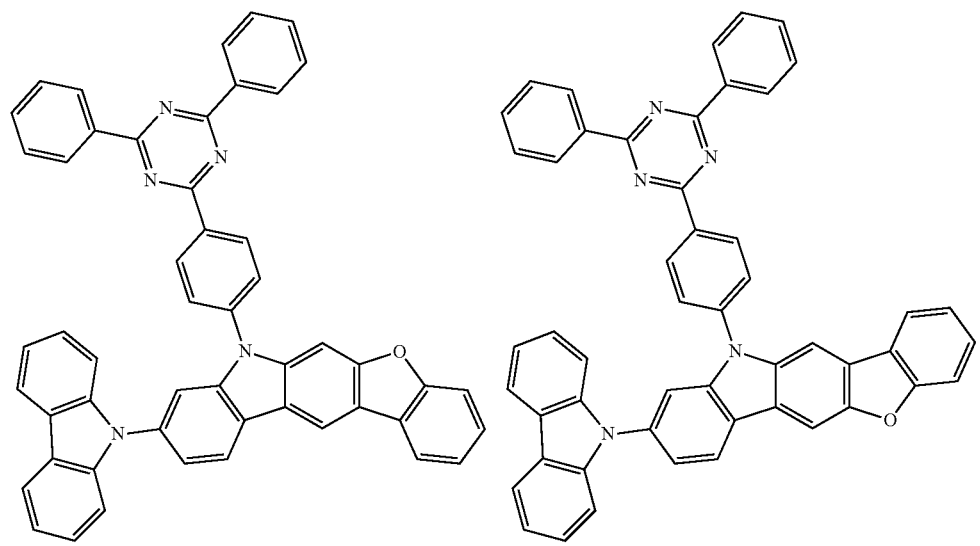

-continued
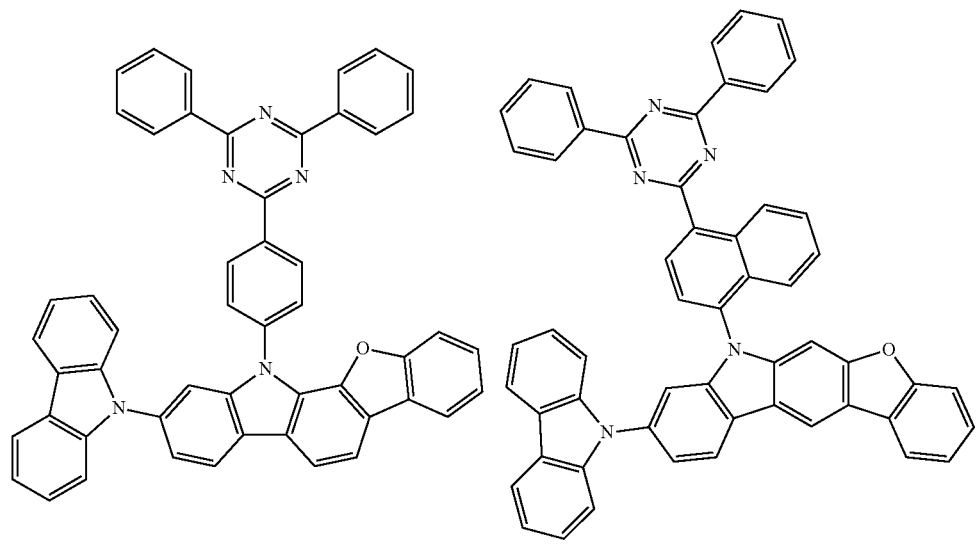
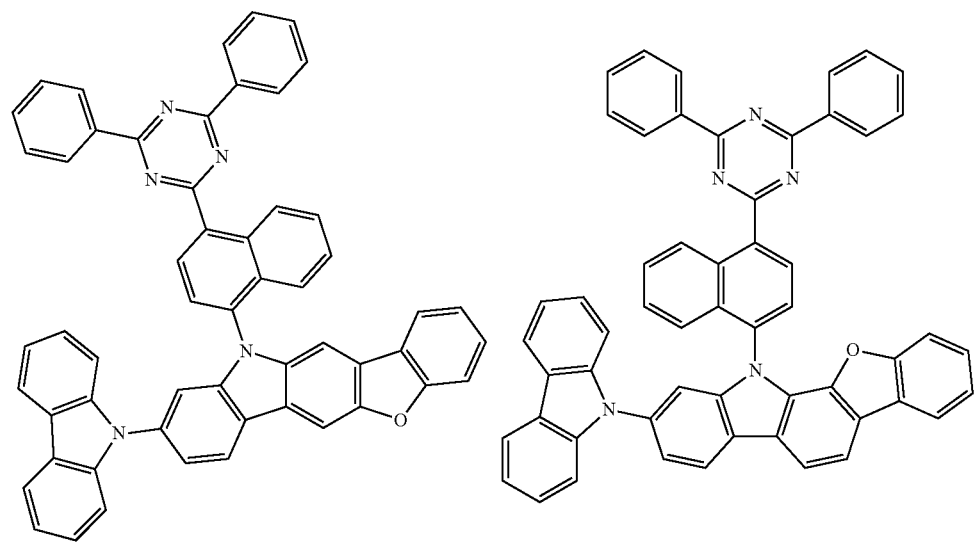
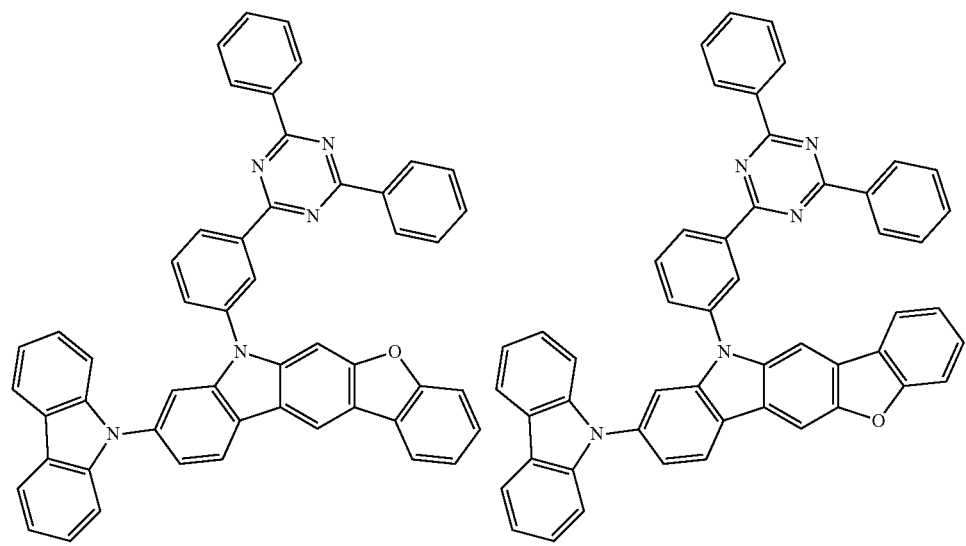

-continued
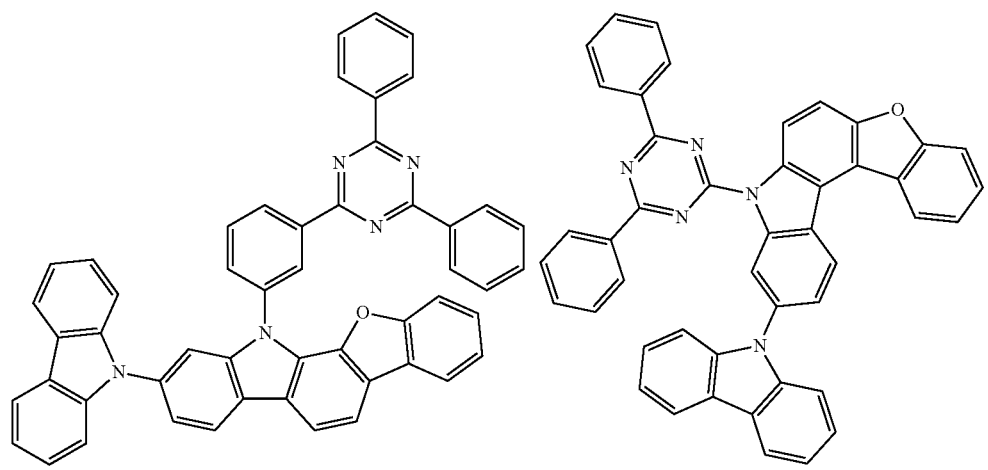
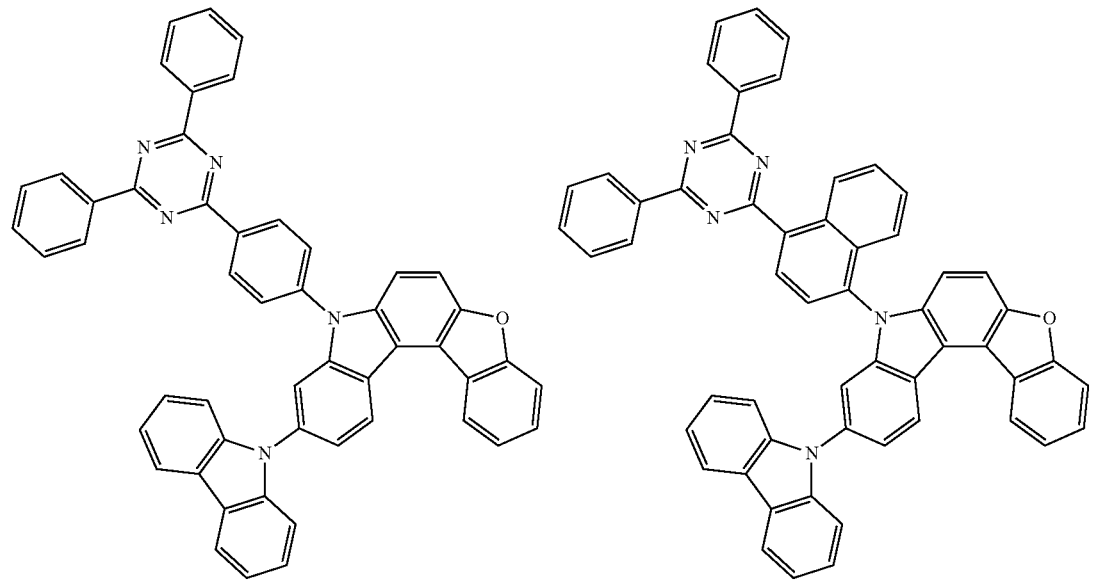
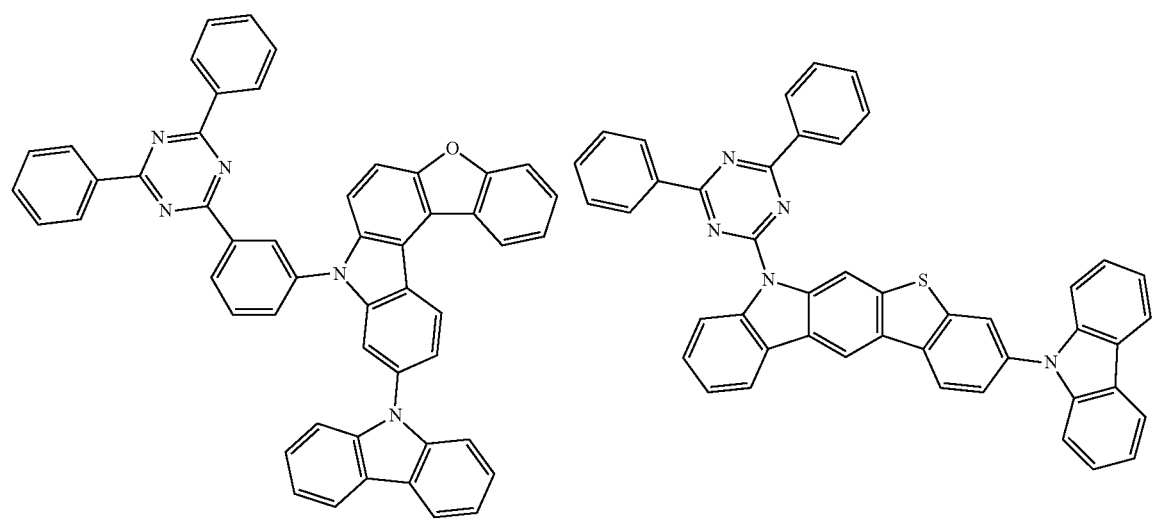

-continued
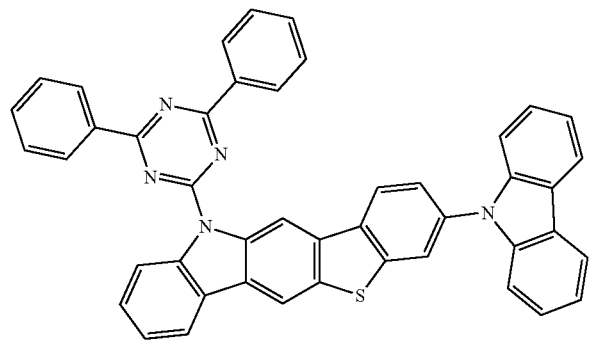 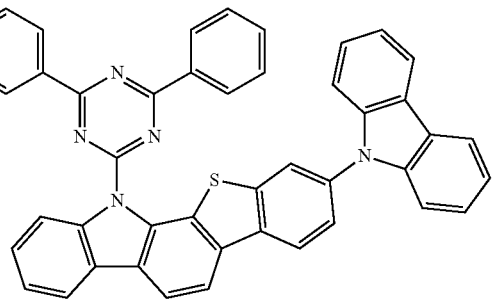
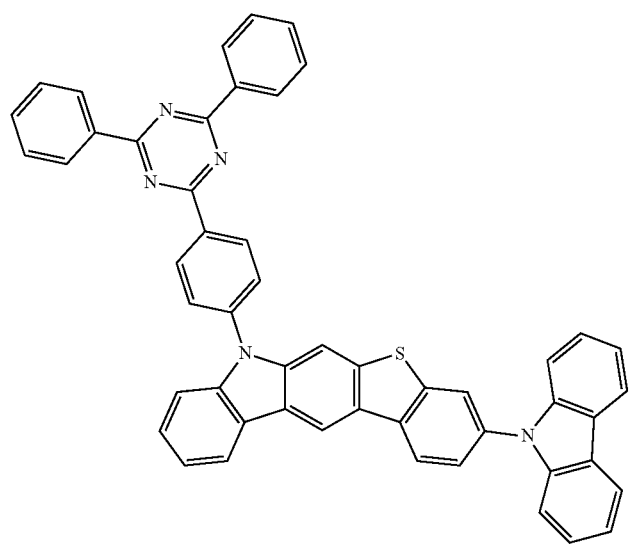
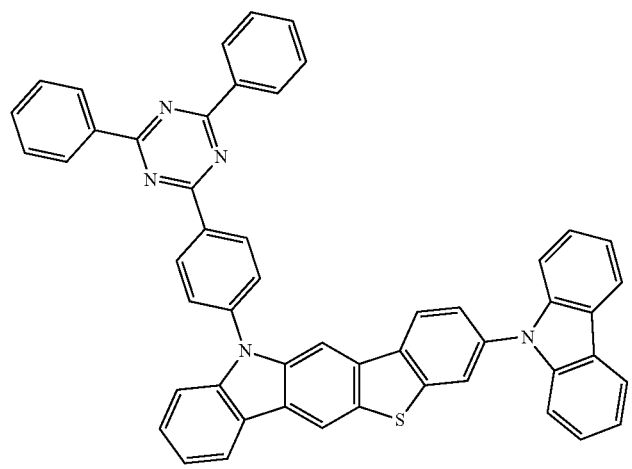 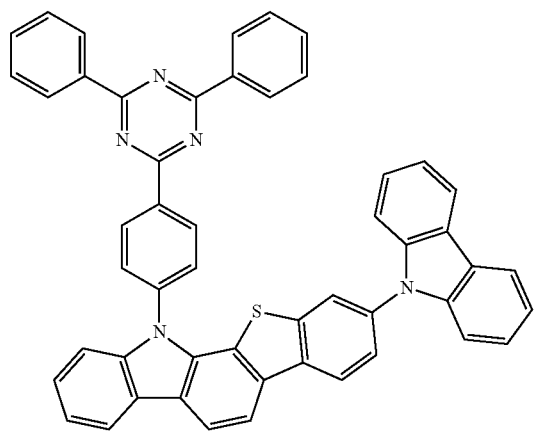

-continued
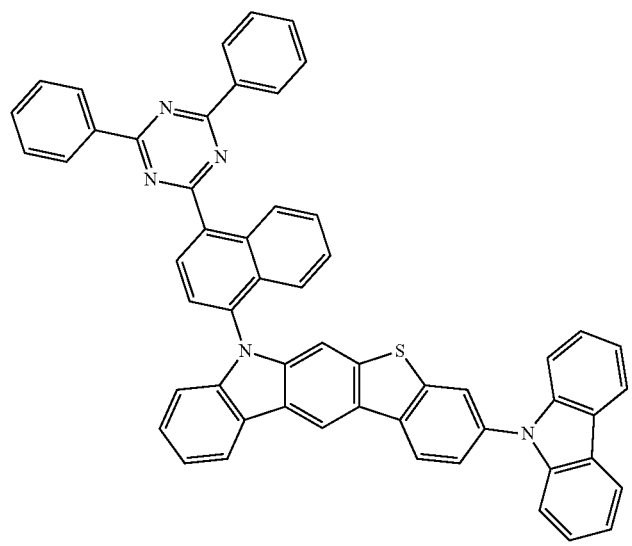
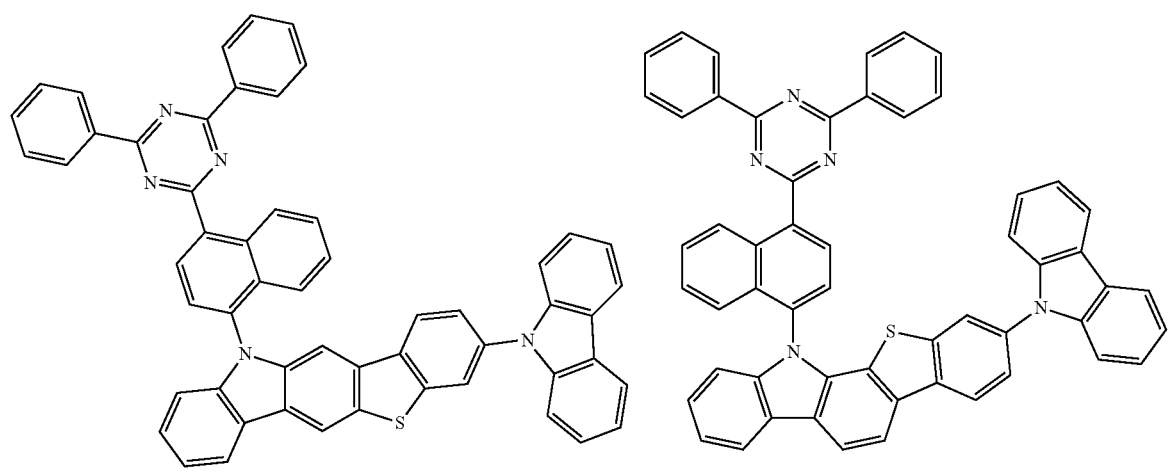
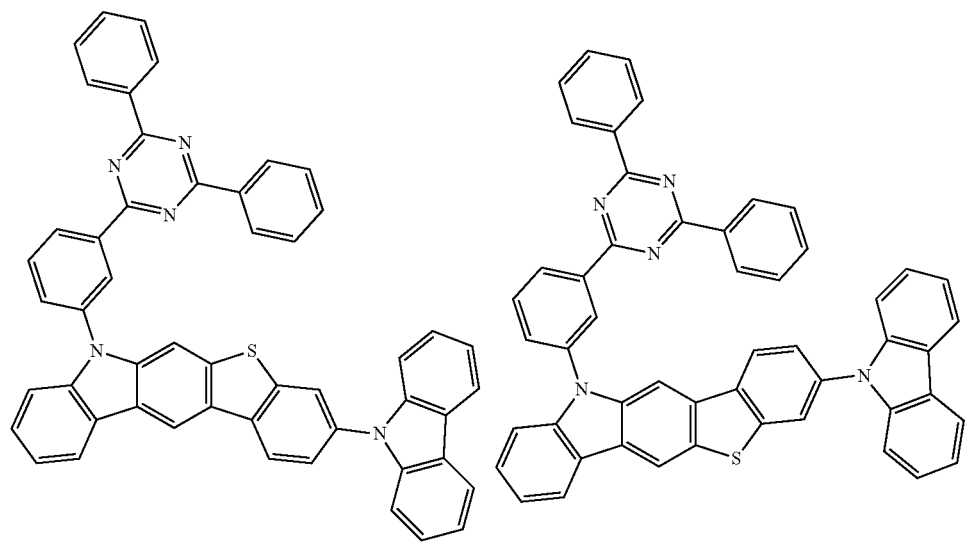

-continued
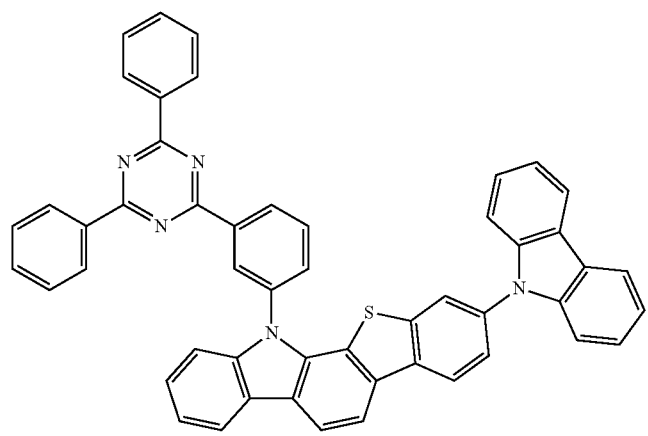
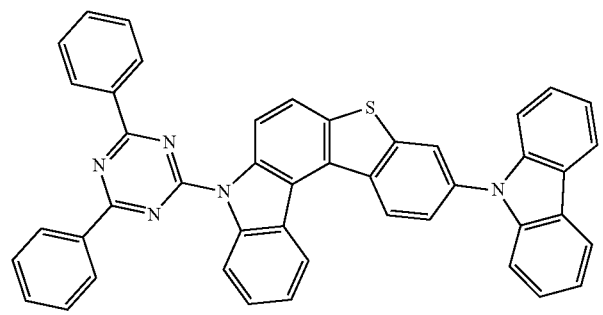
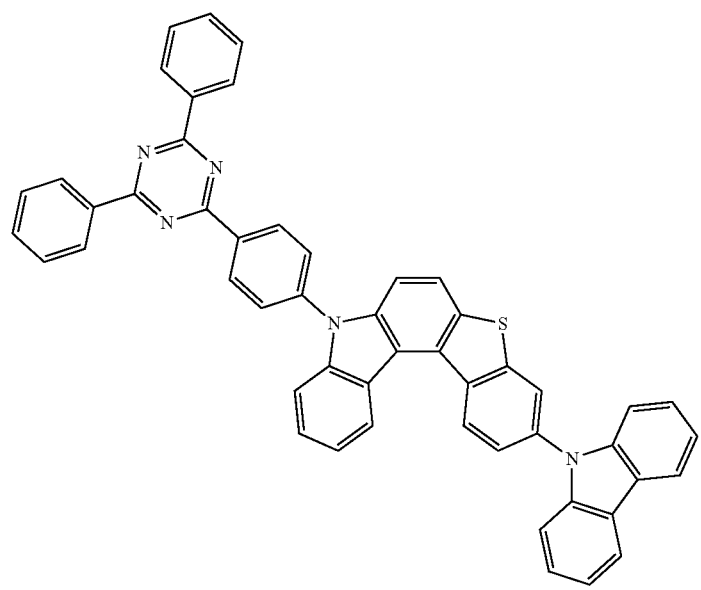

-continued
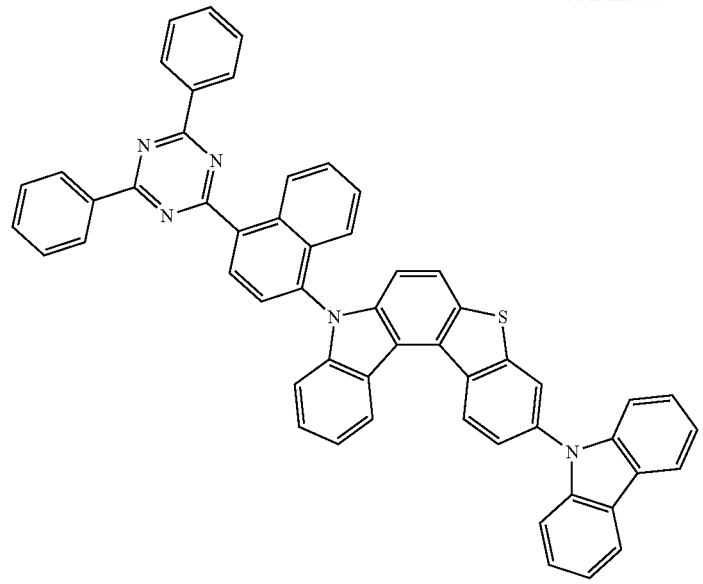
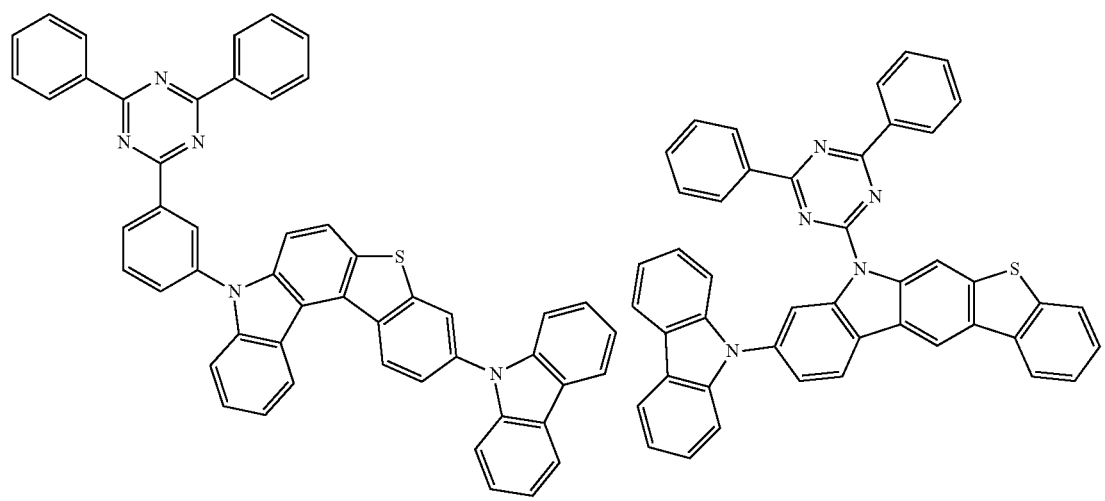
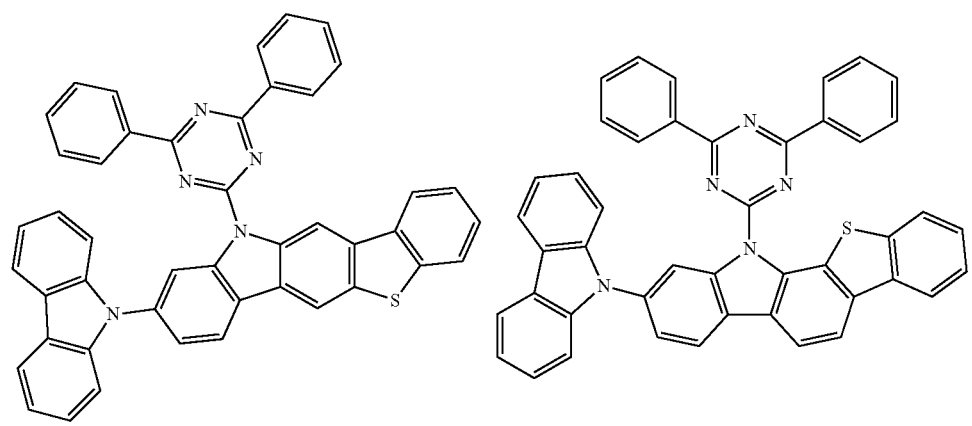

-continued
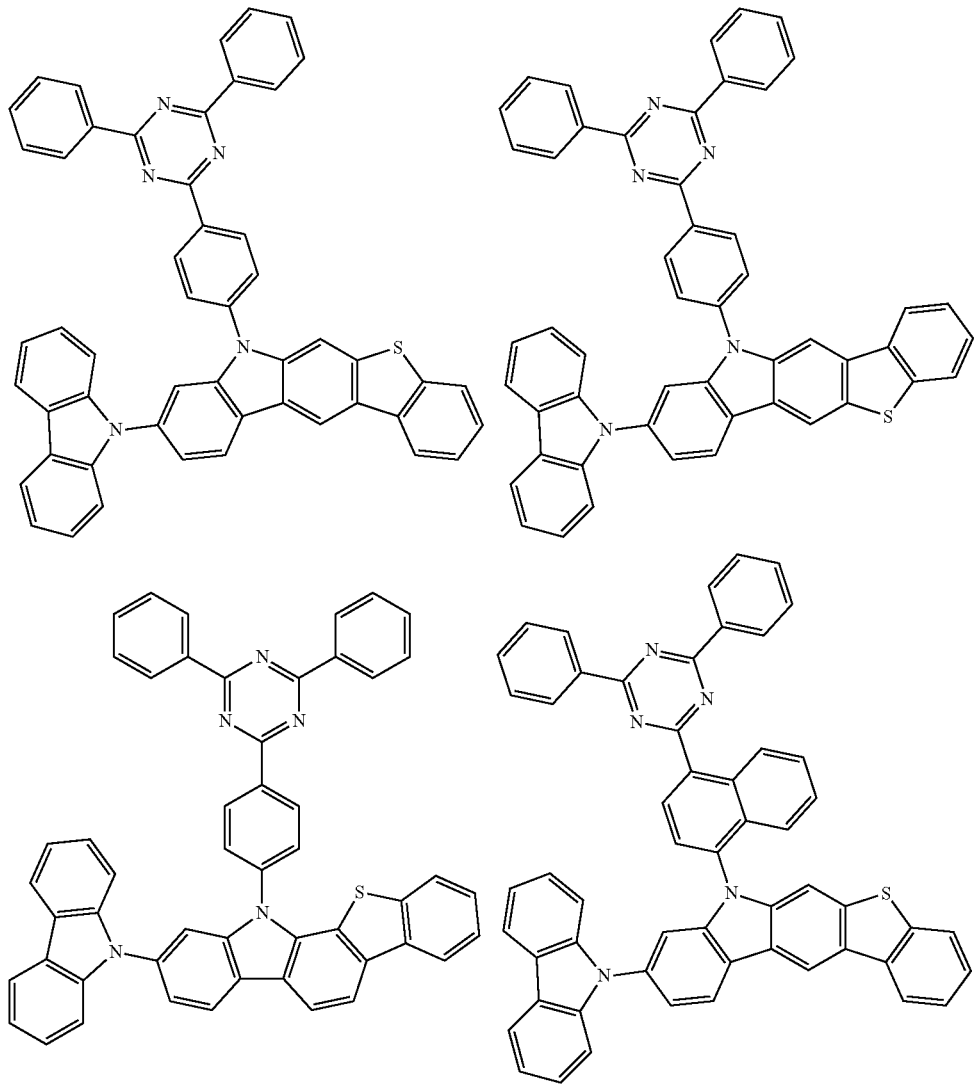
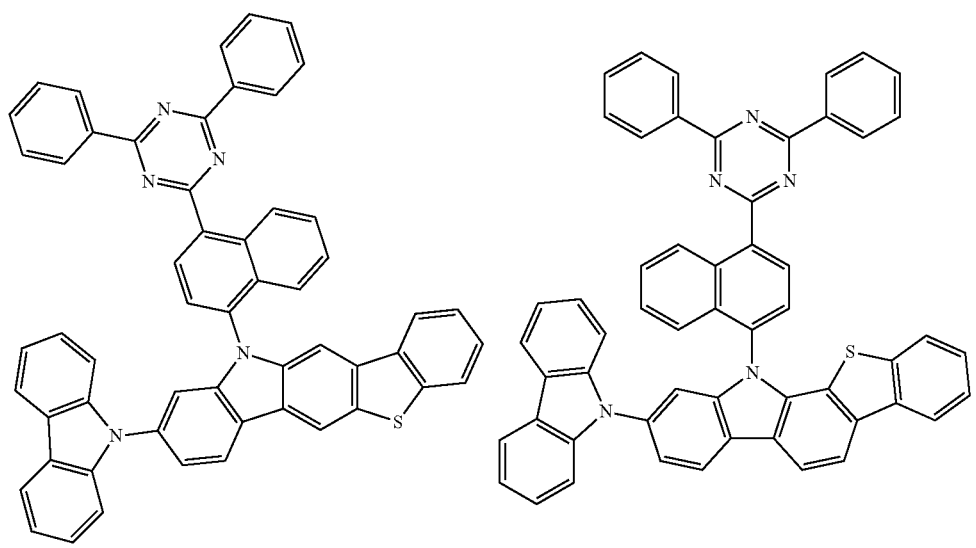

-continued
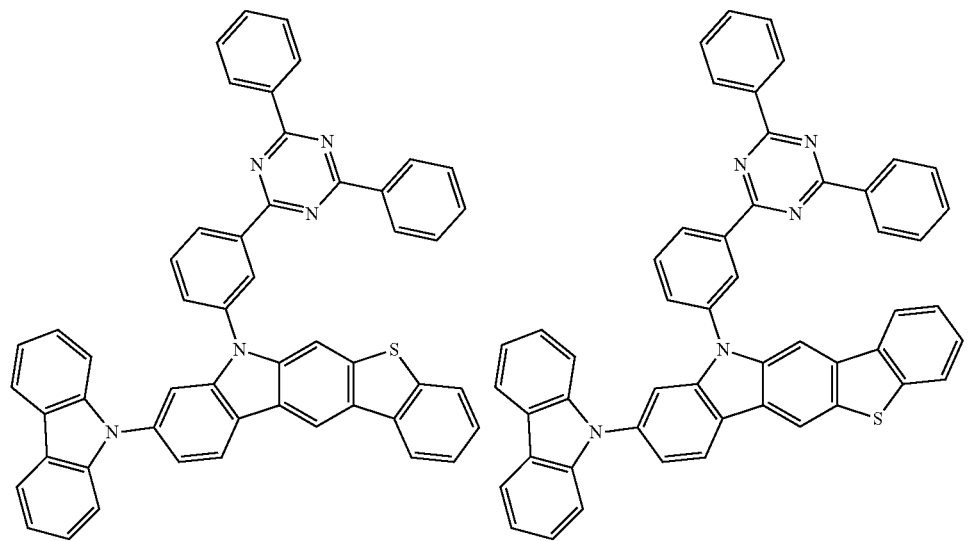
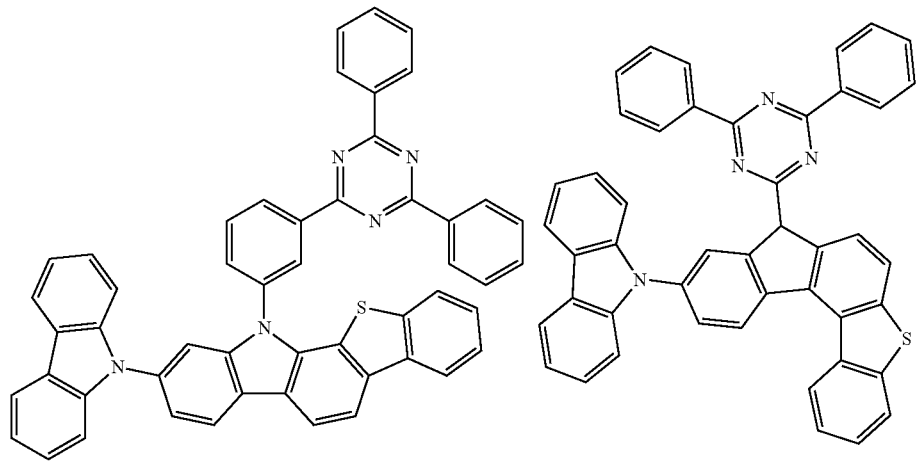
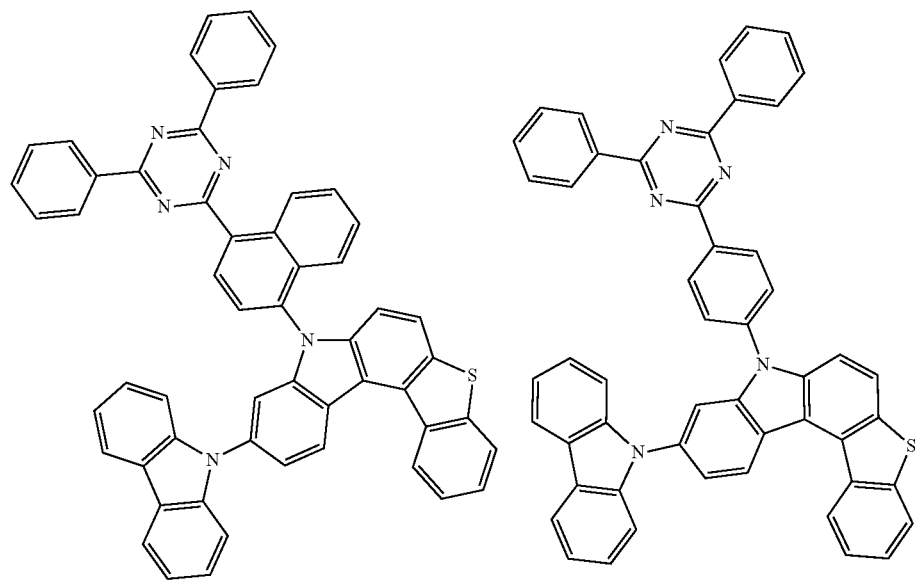

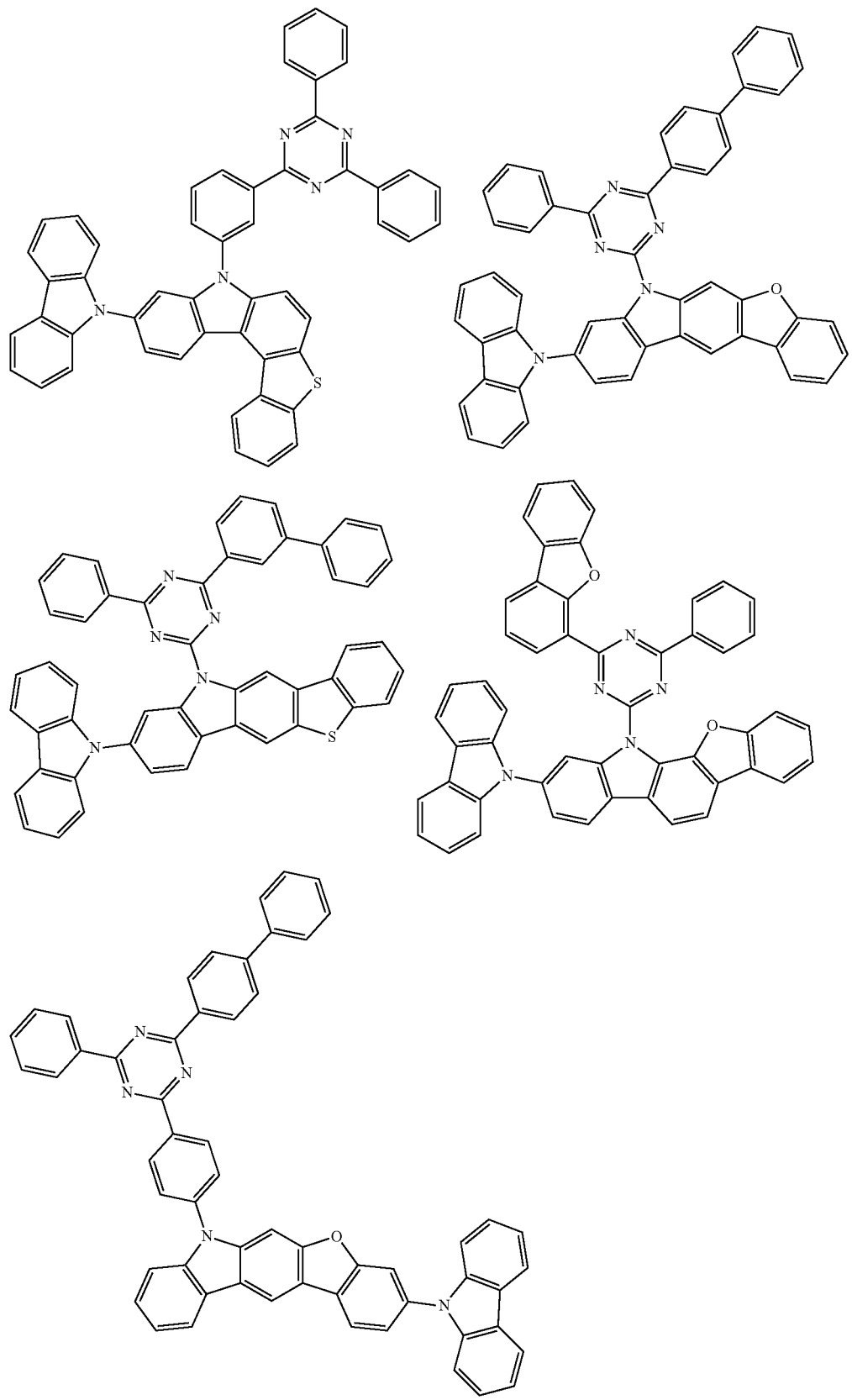

-continued
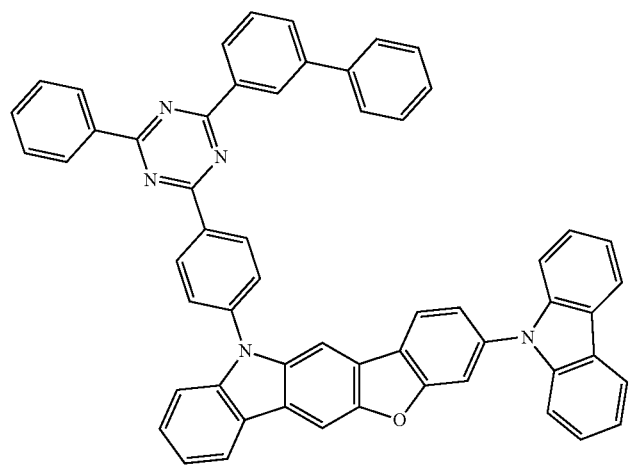
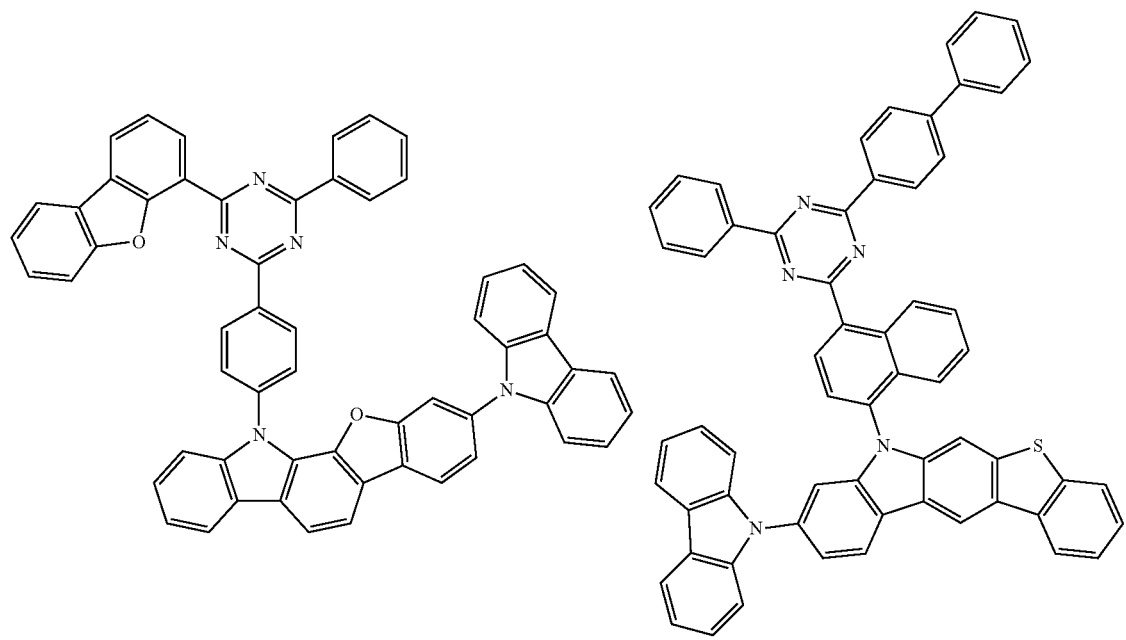
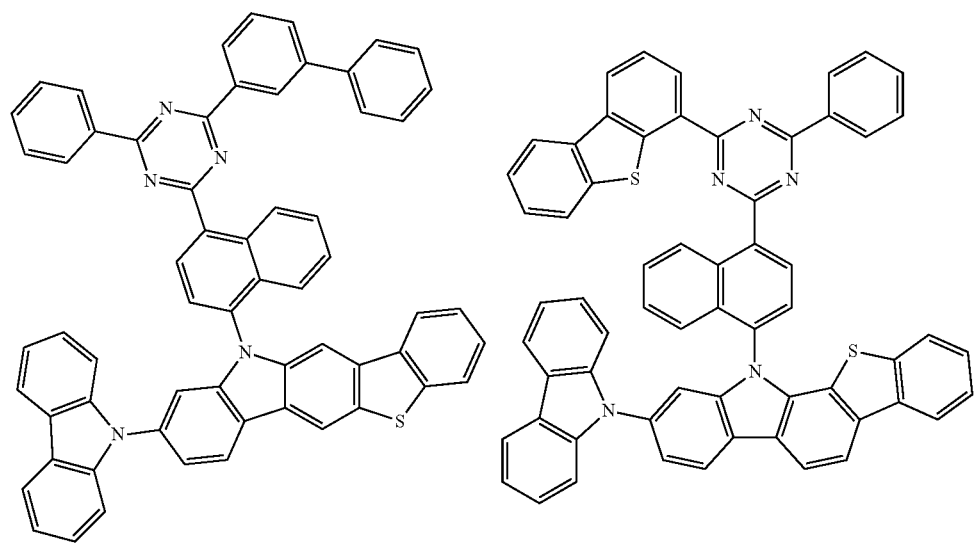

-continued
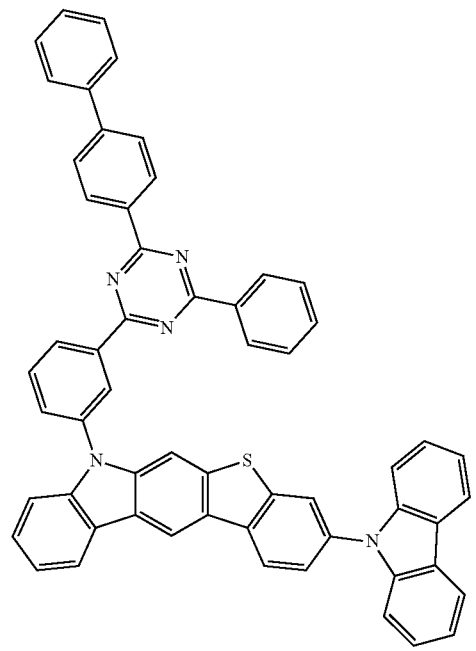
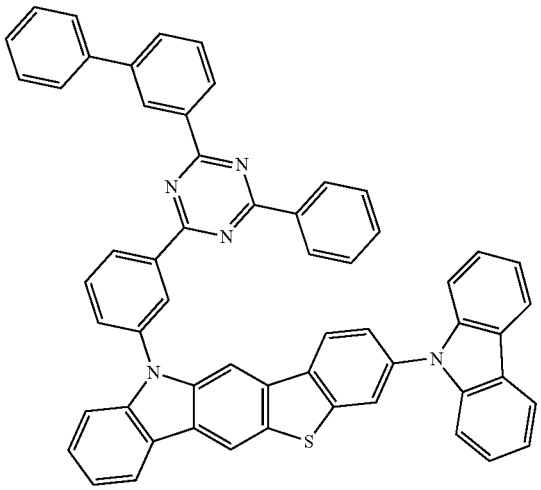
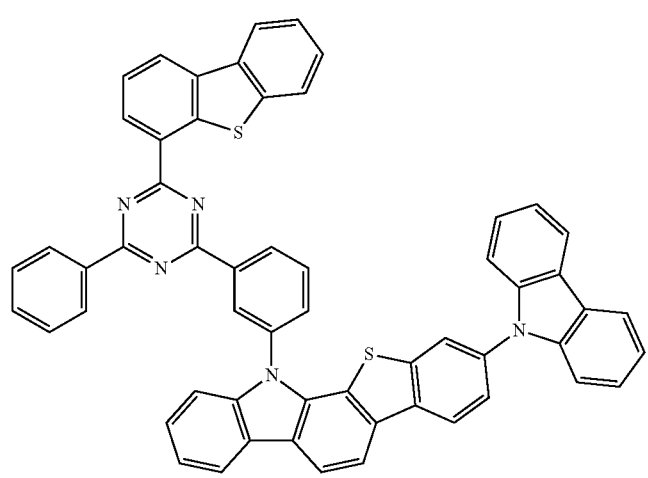
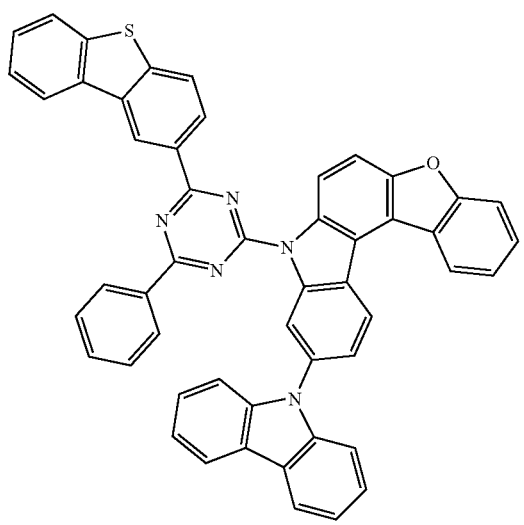

161
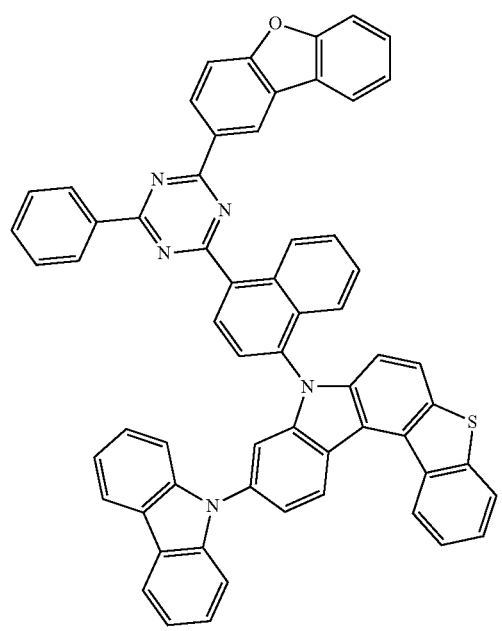
162
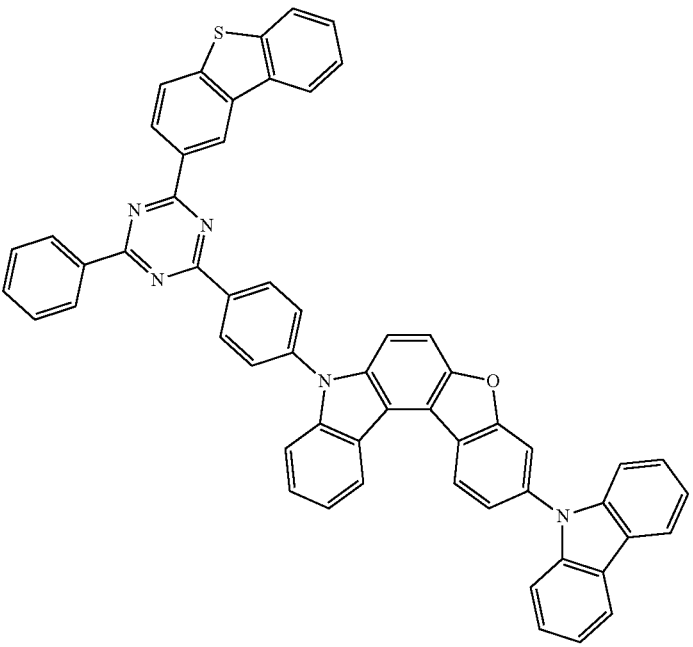
-continued
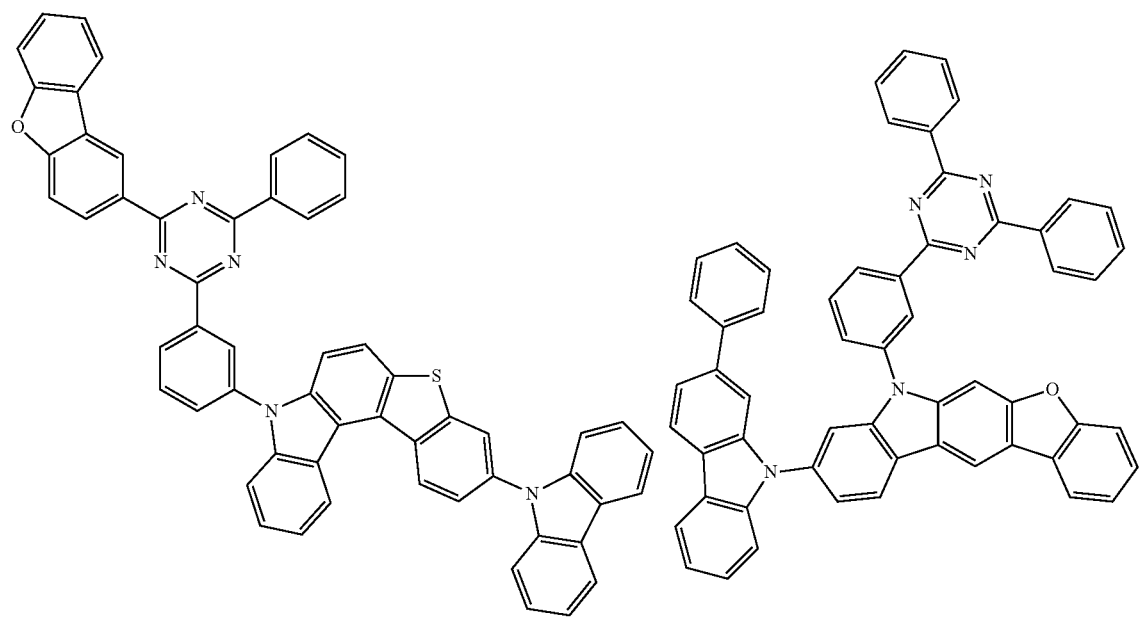

-continued
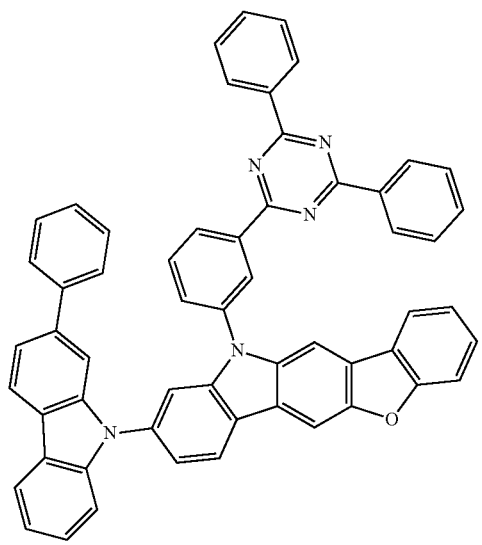
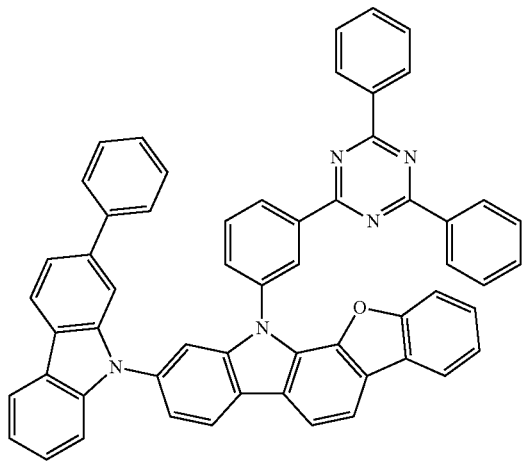
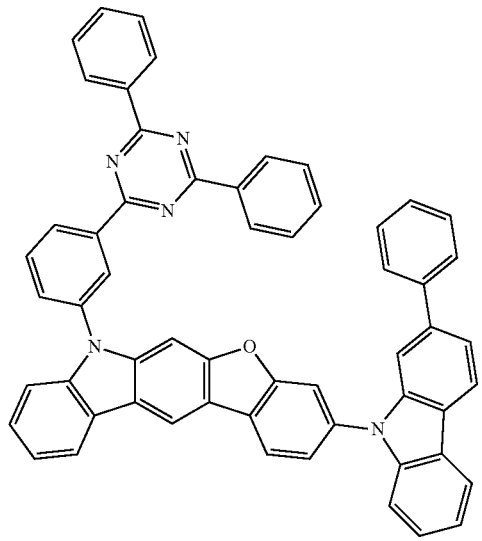
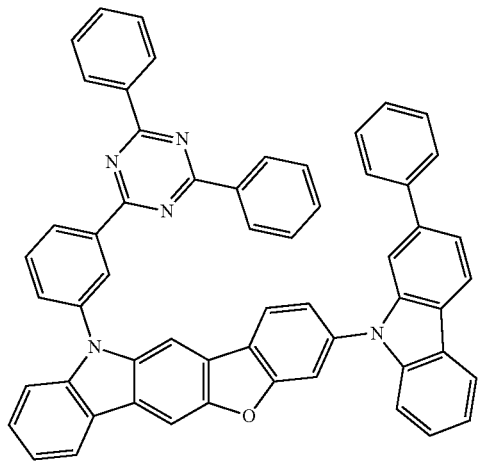
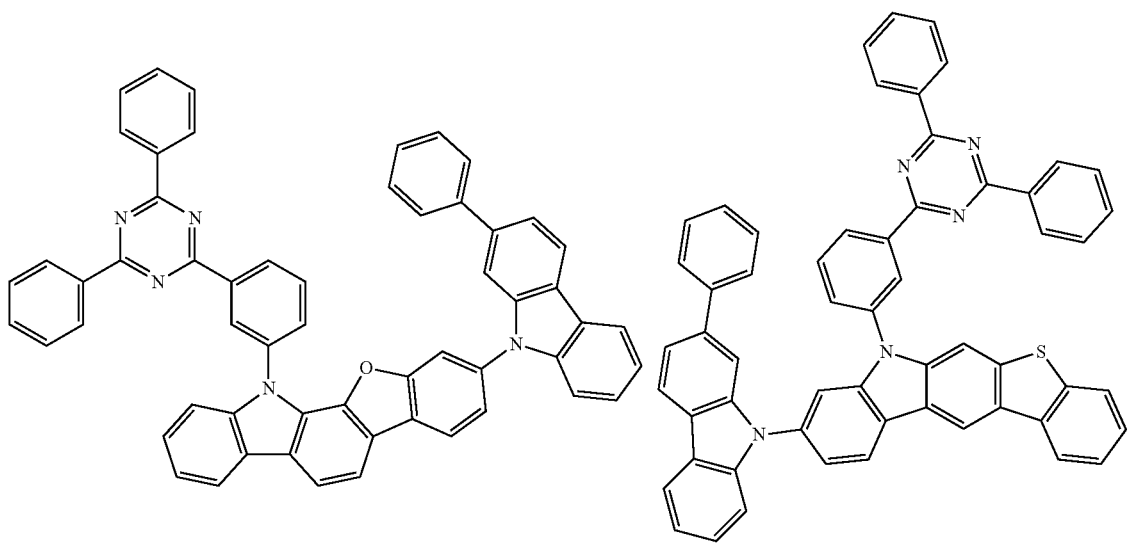

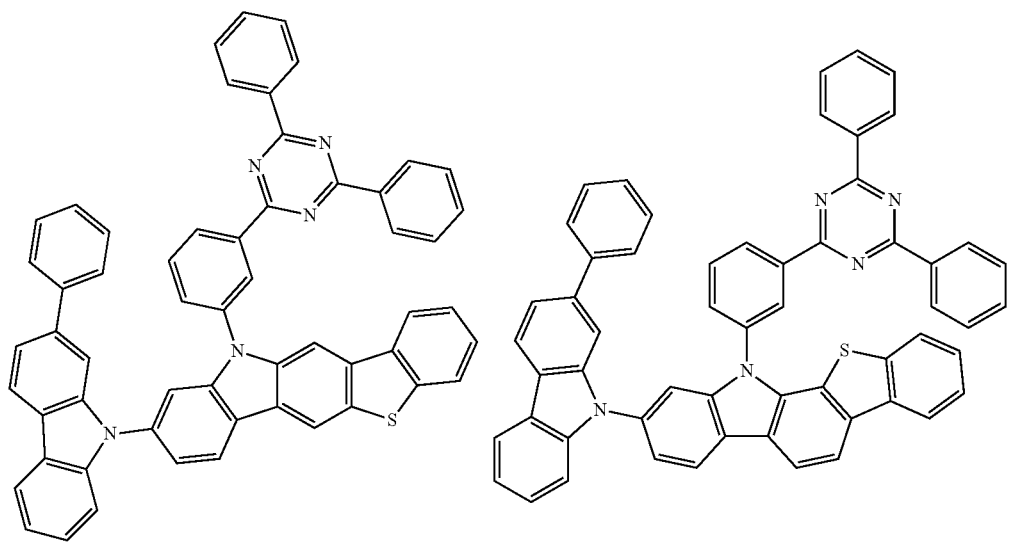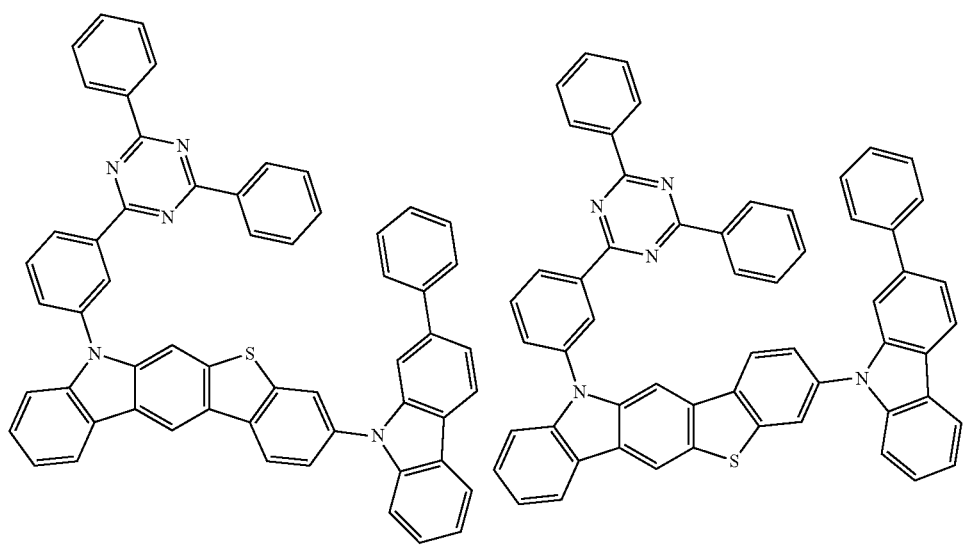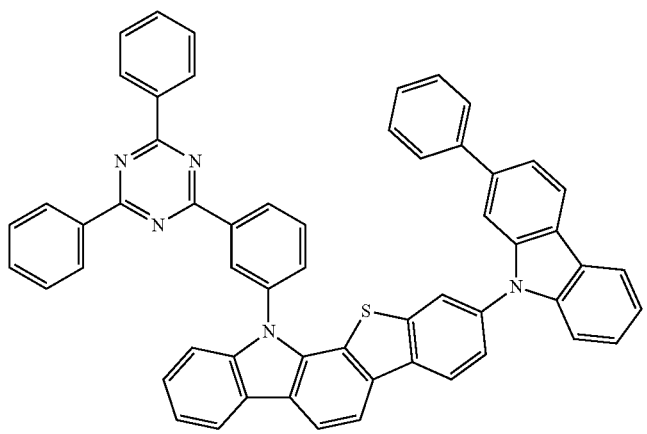

167
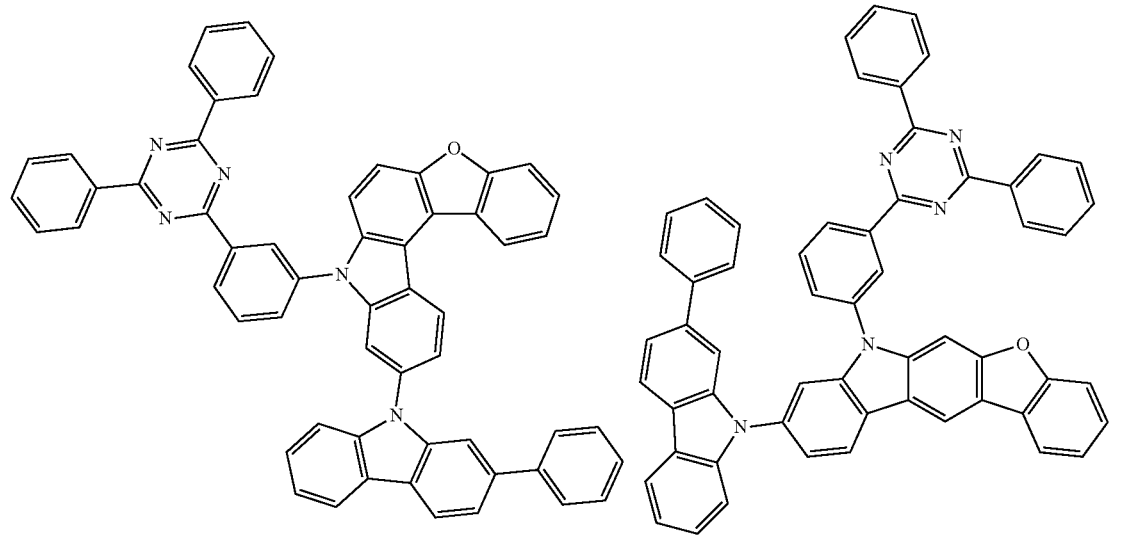
168
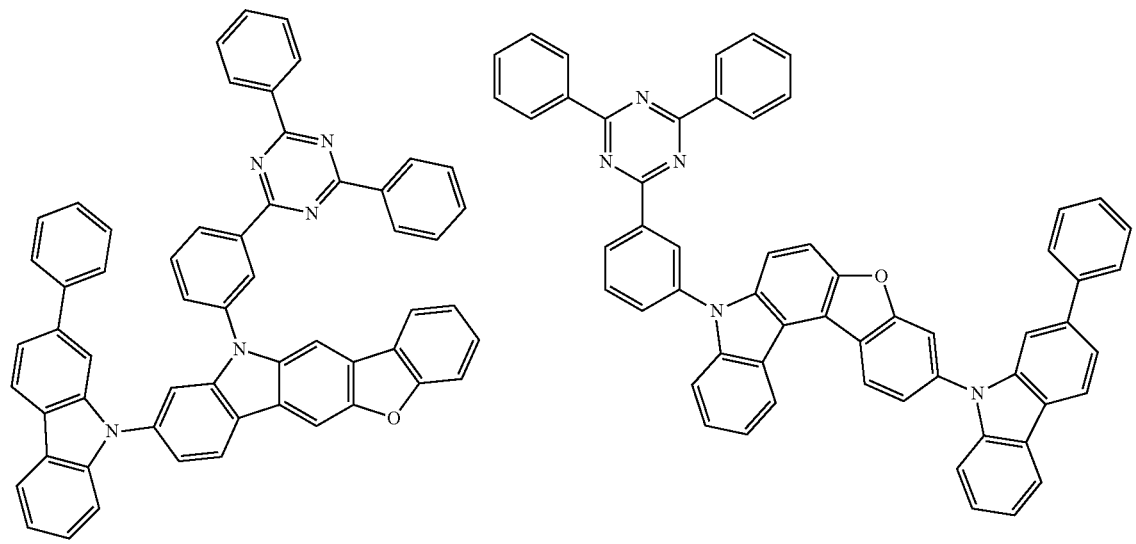
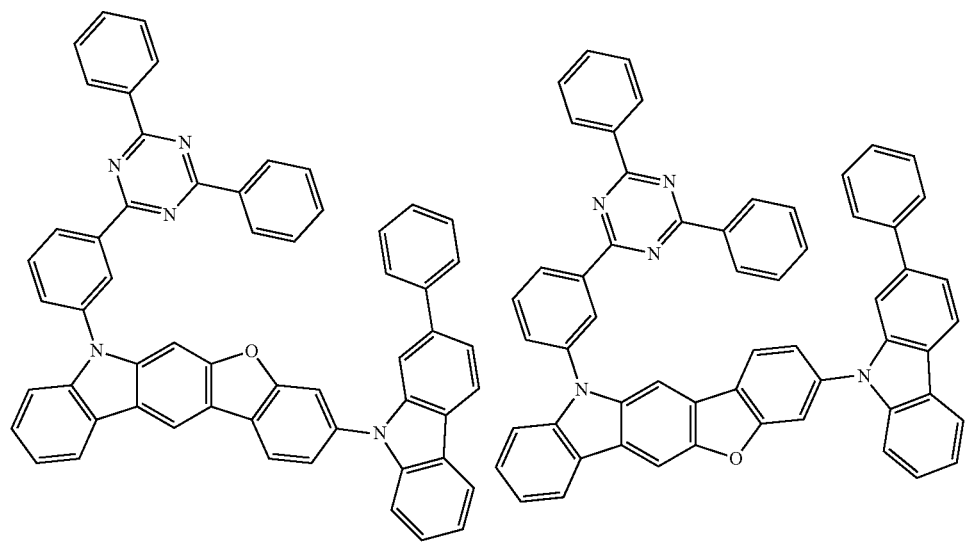

-continued
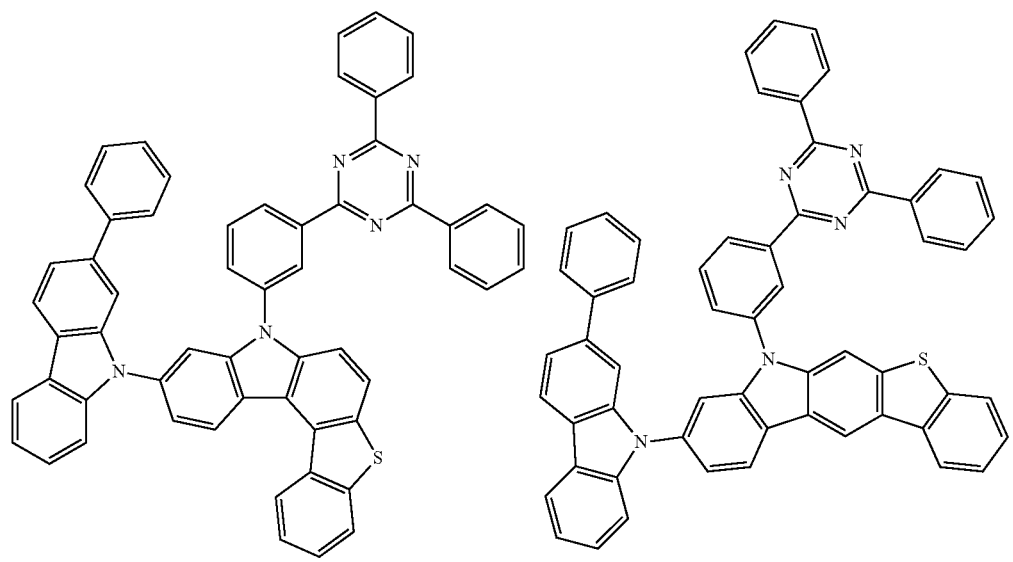
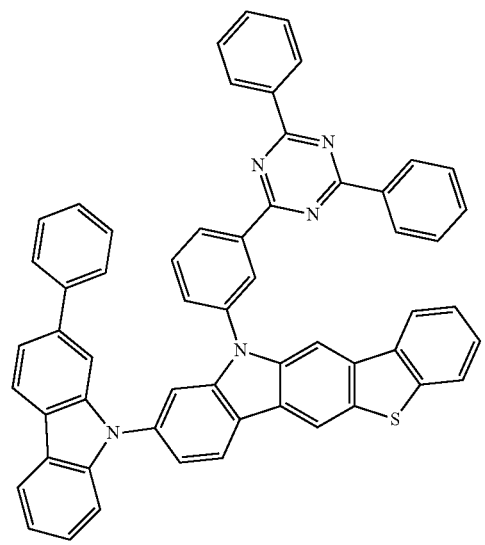
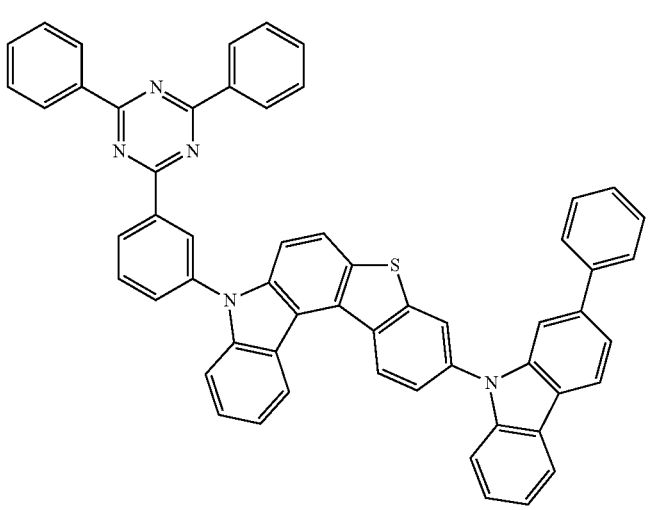
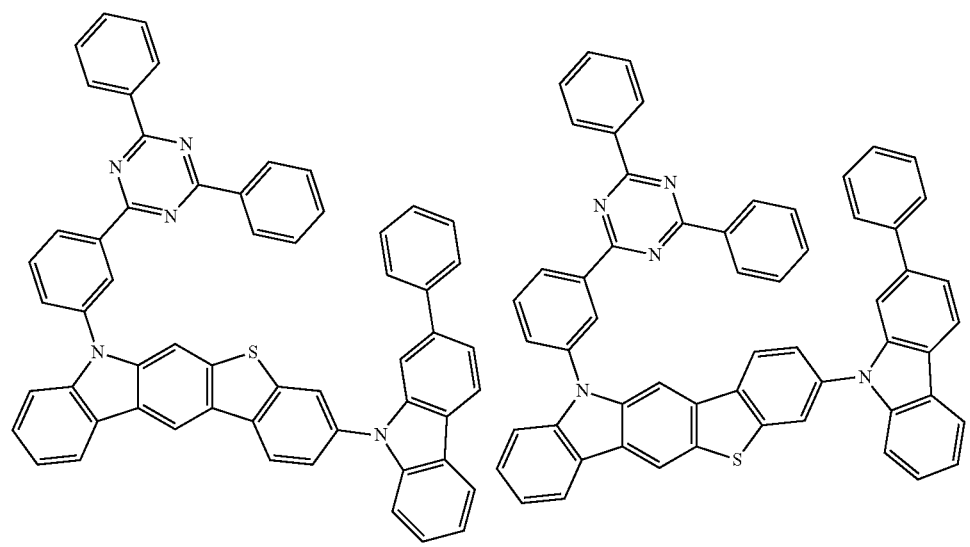

171 172
-continued
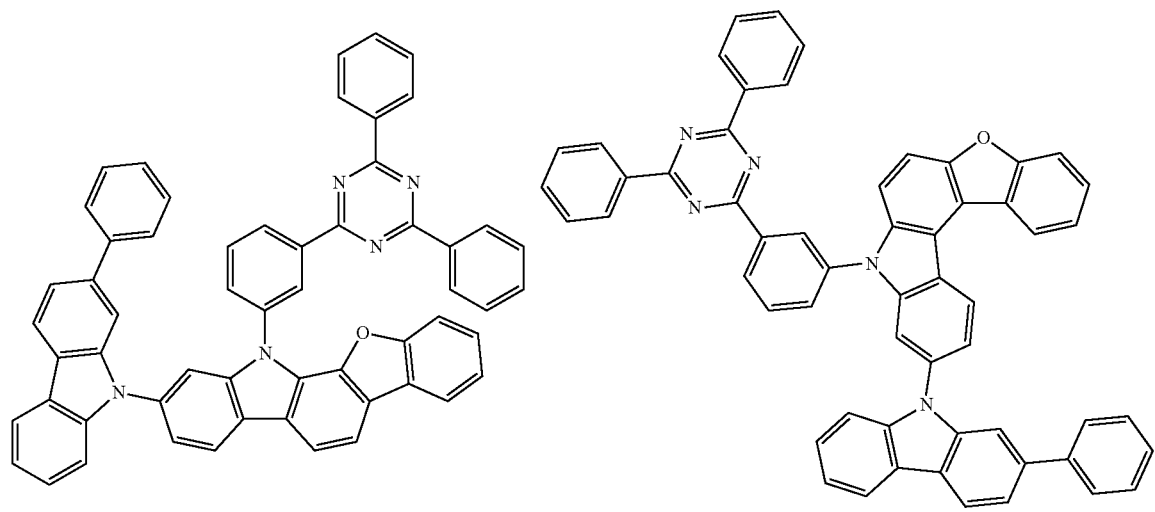
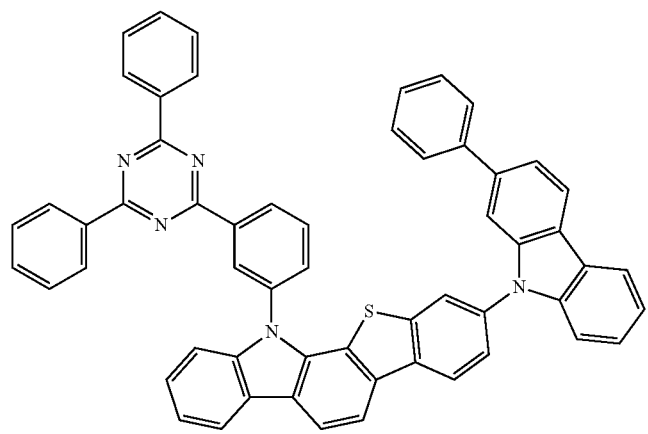
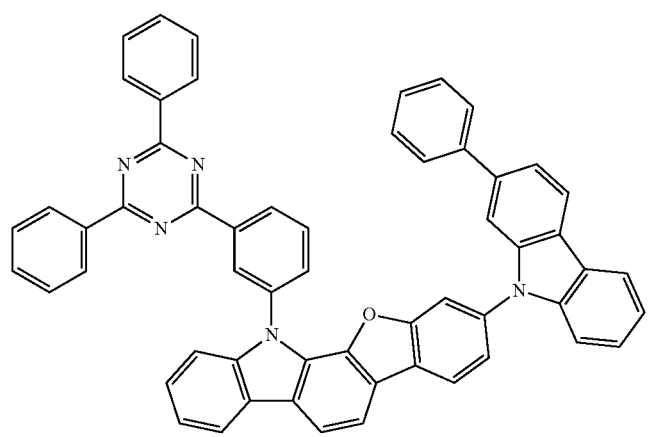

-continued
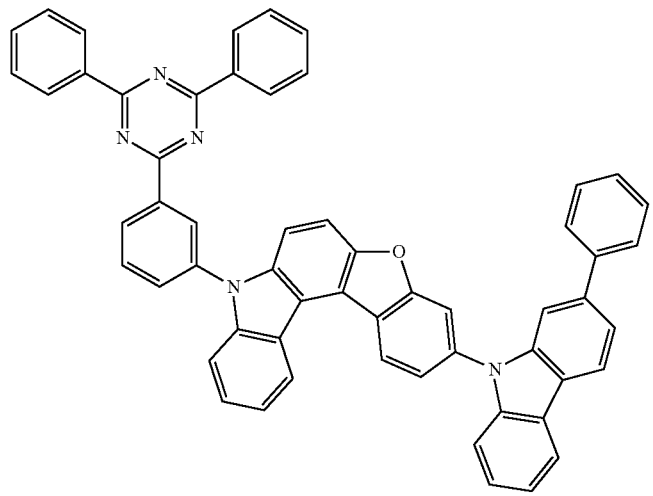
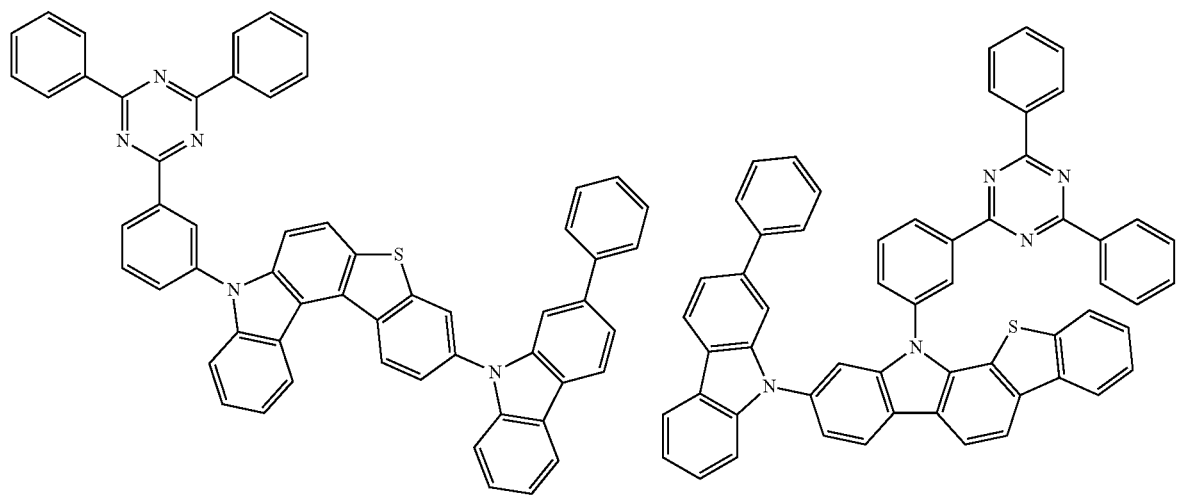
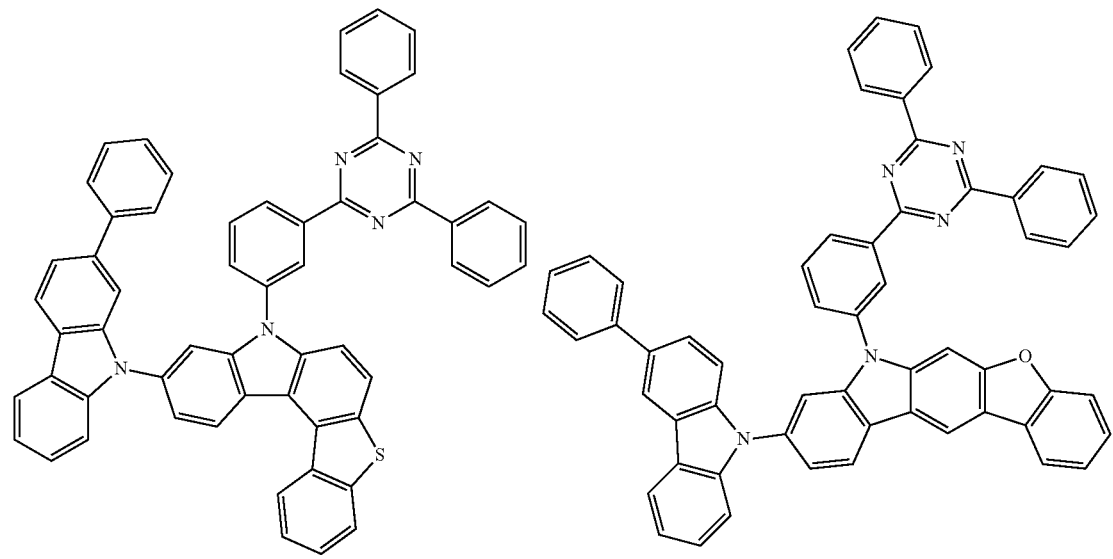

-continued
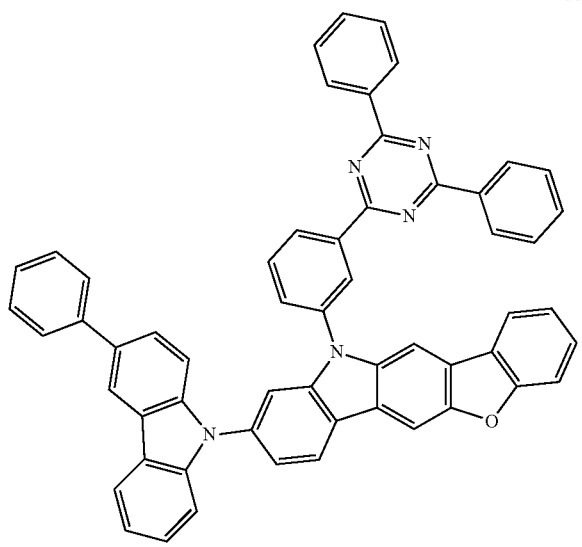
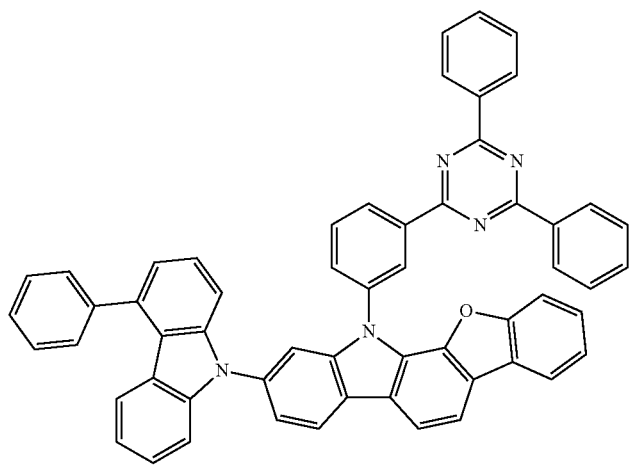
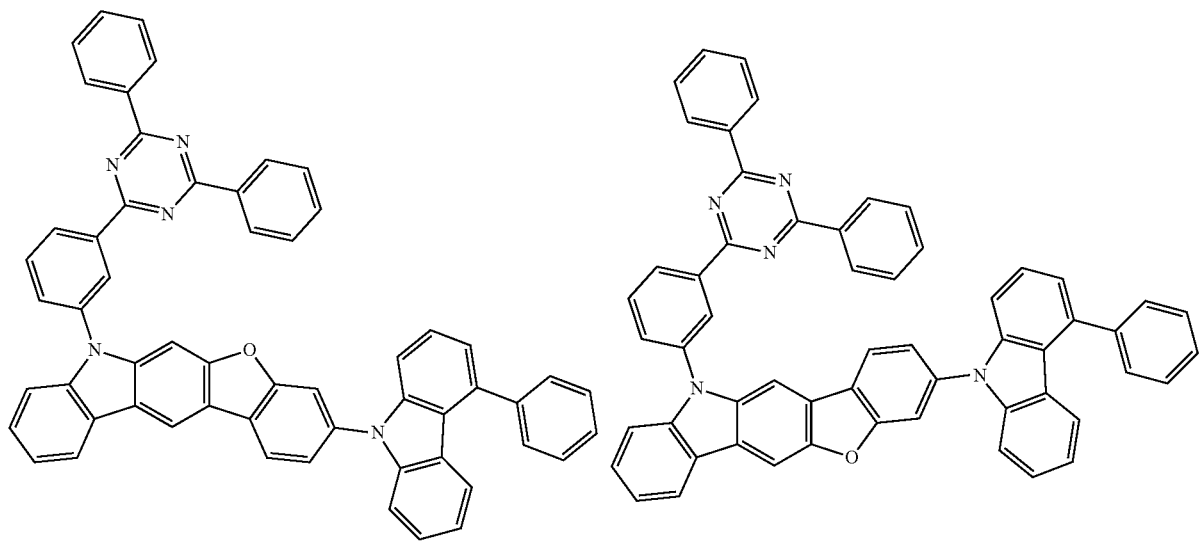

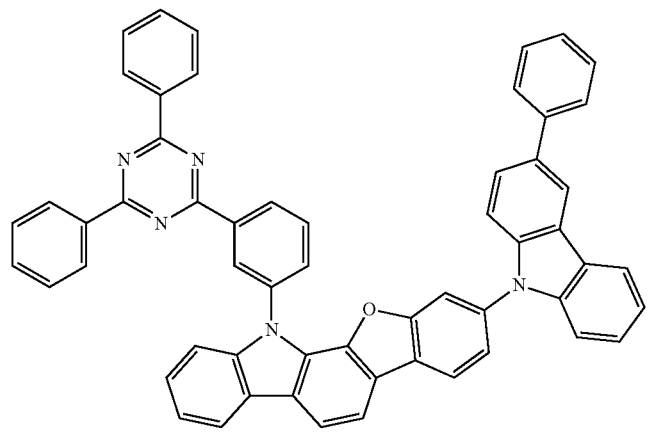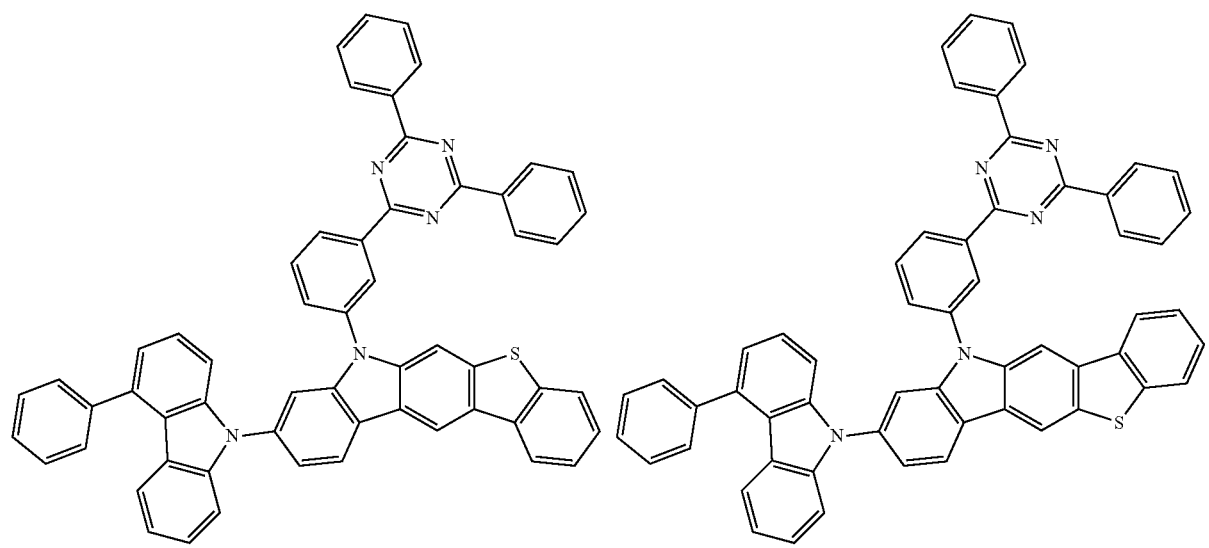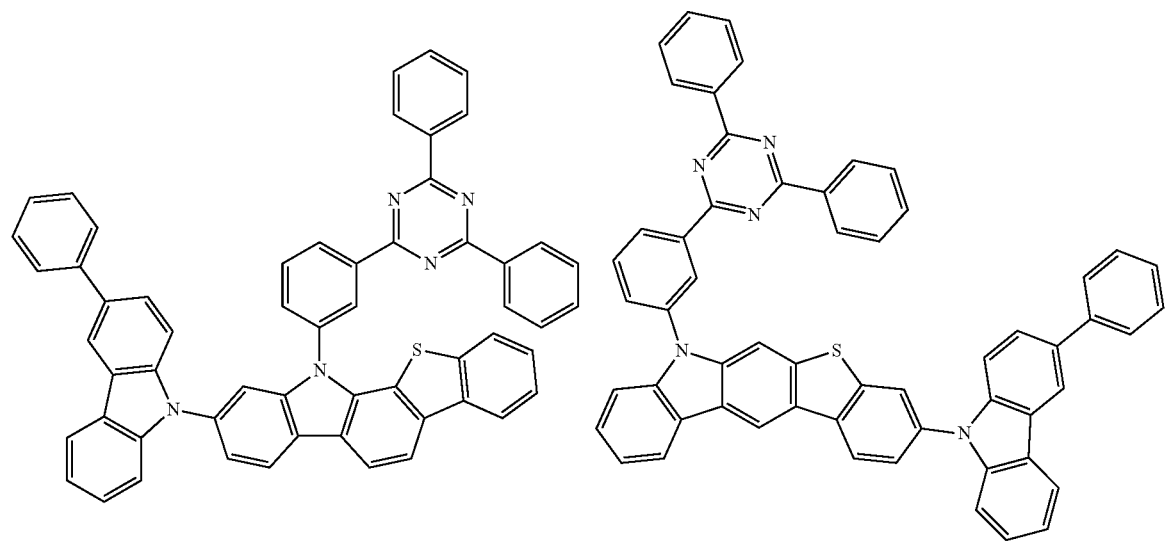

-continued
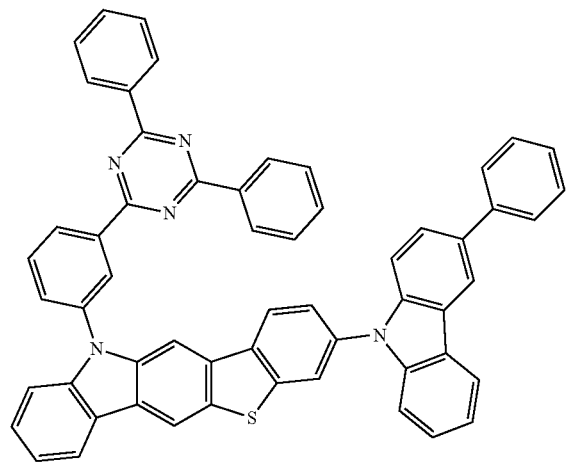
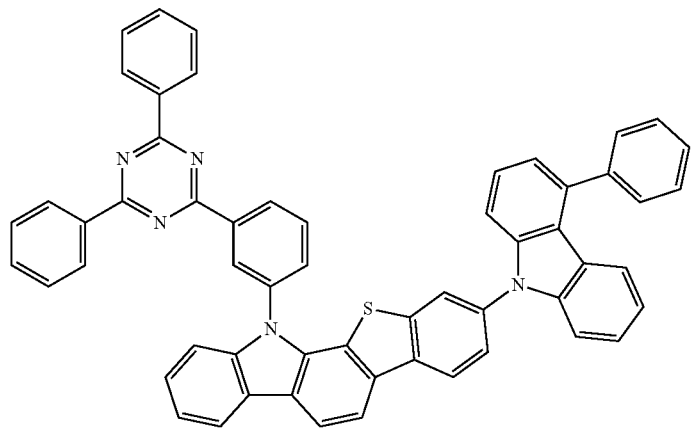
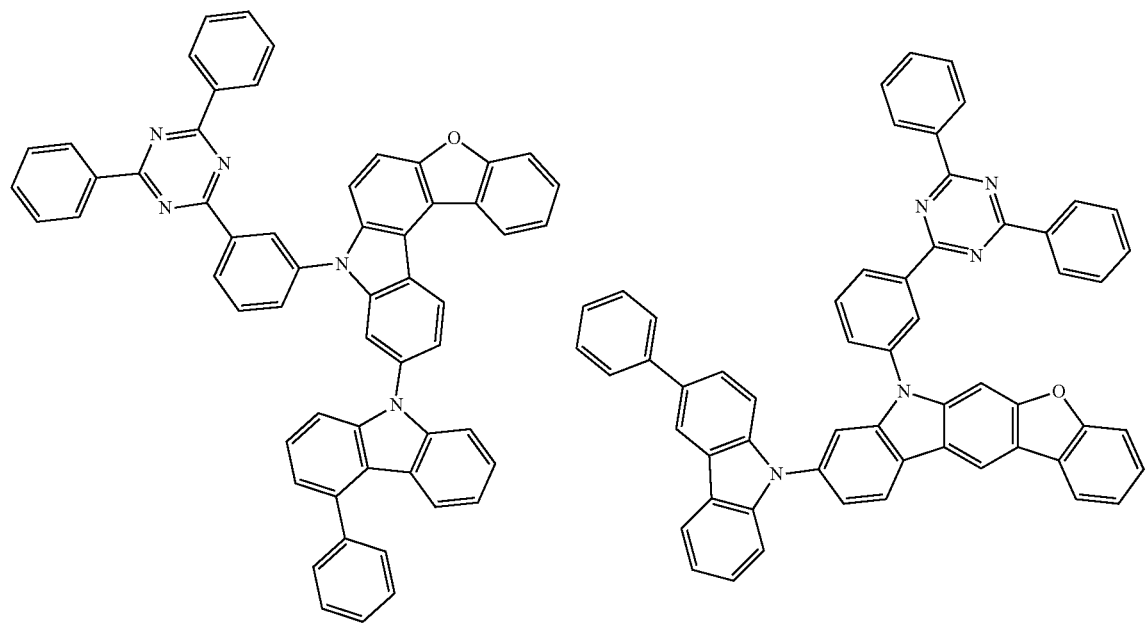

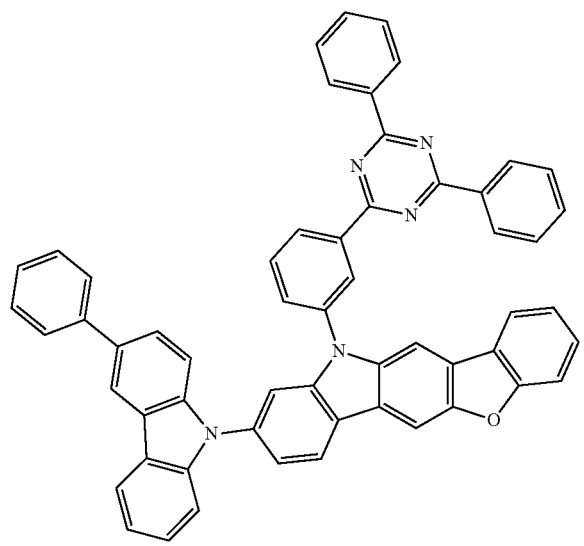
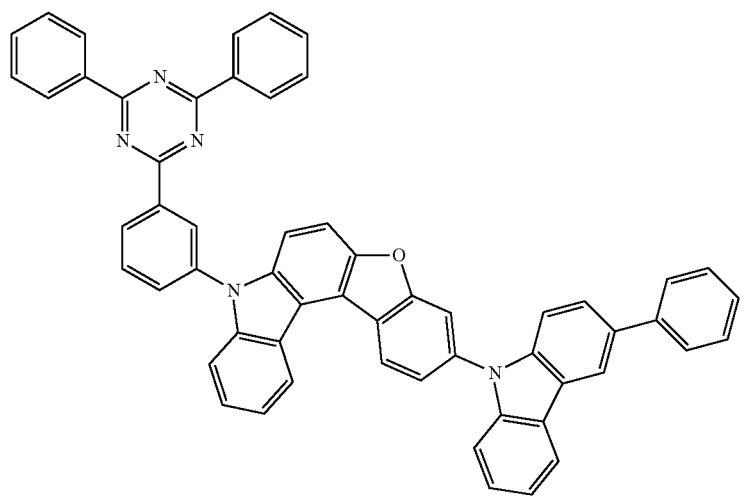
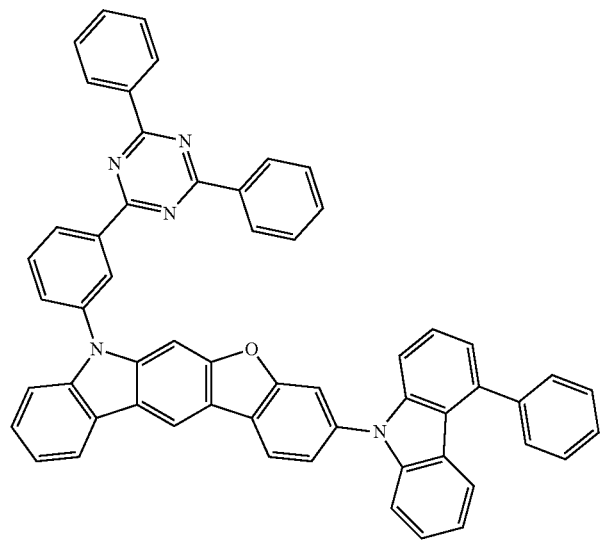
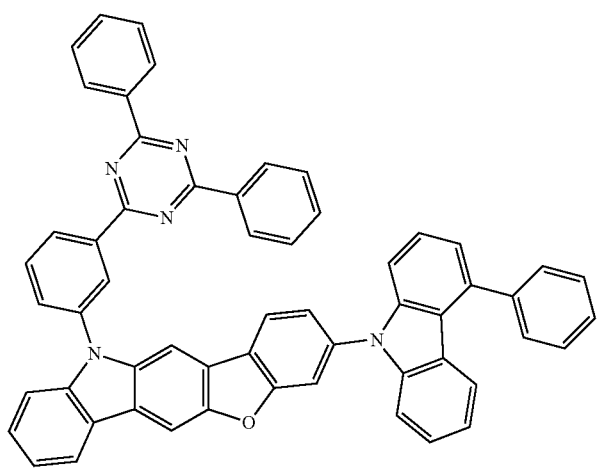

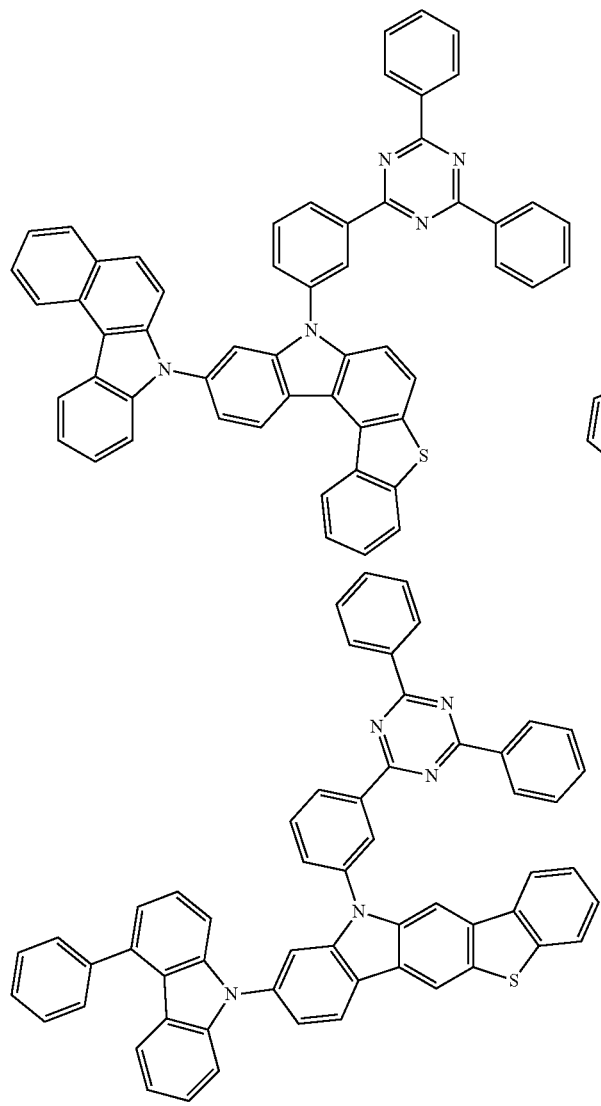
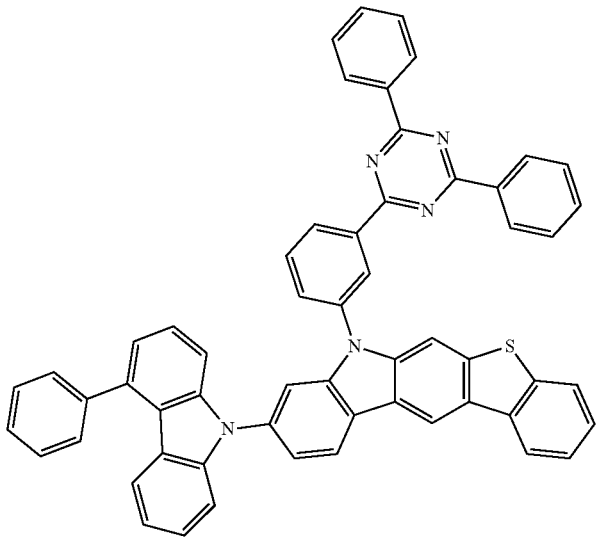
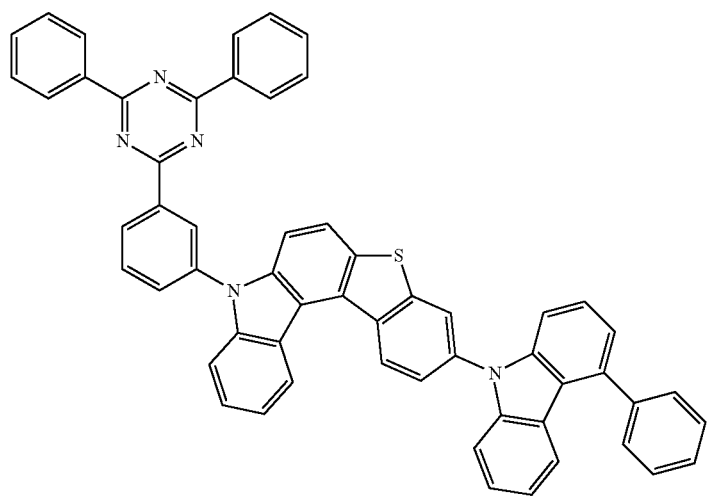

-continued
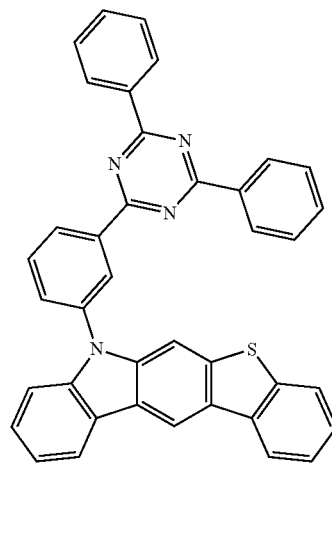
185
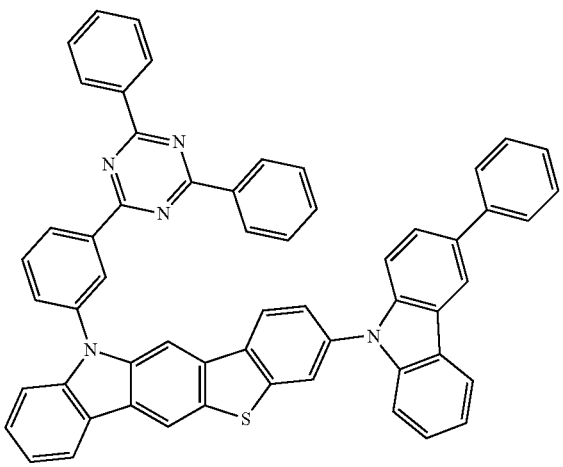
186
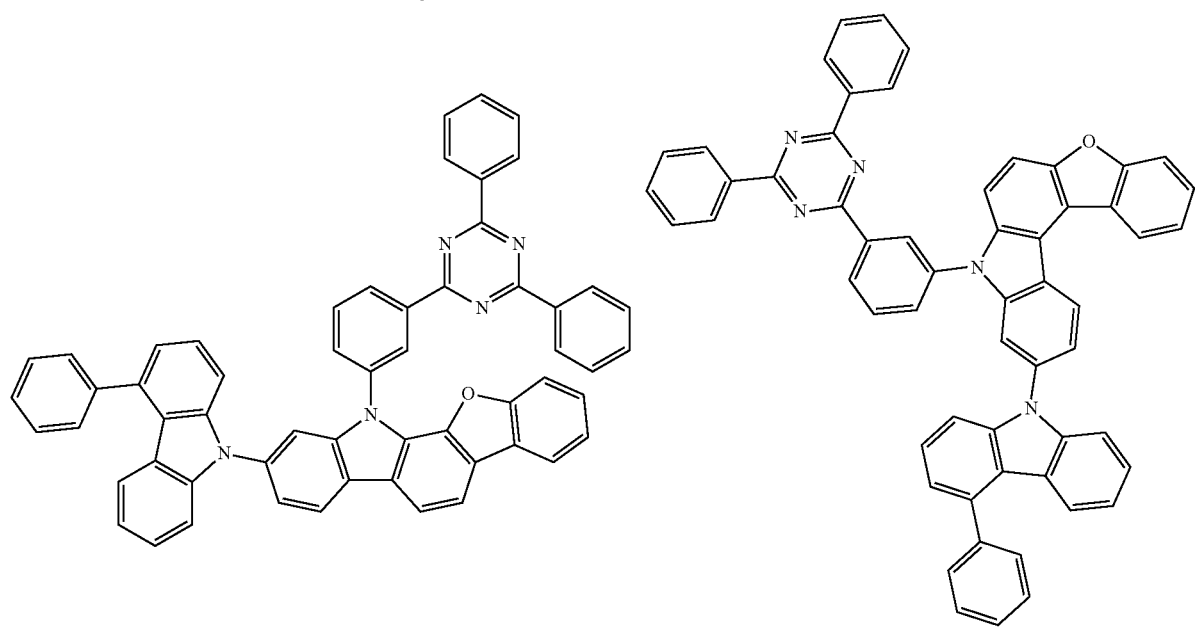
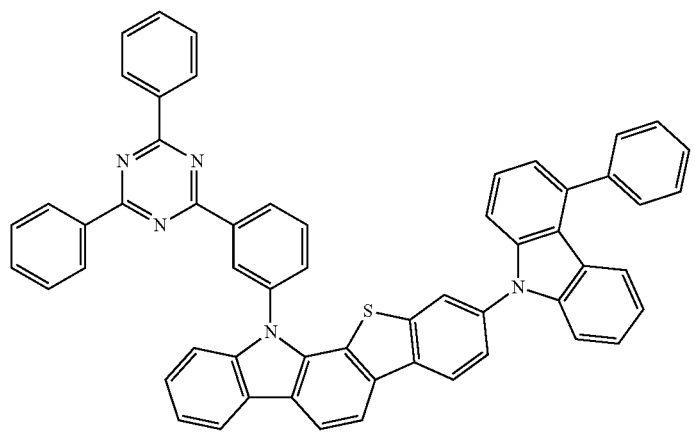

-continued
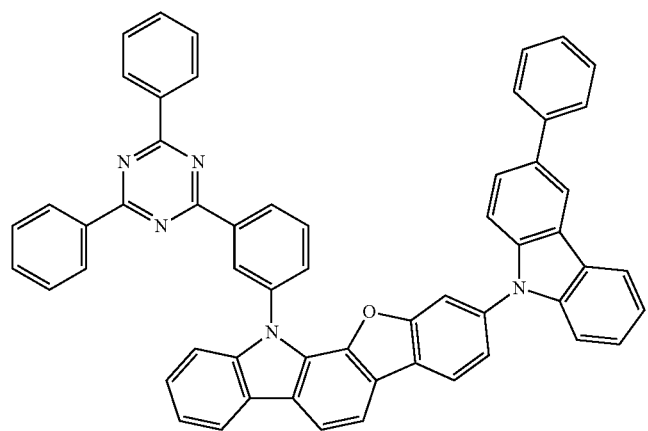
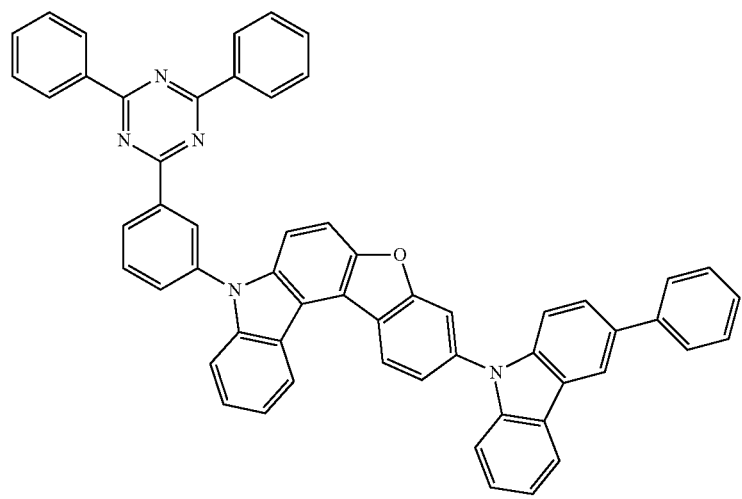
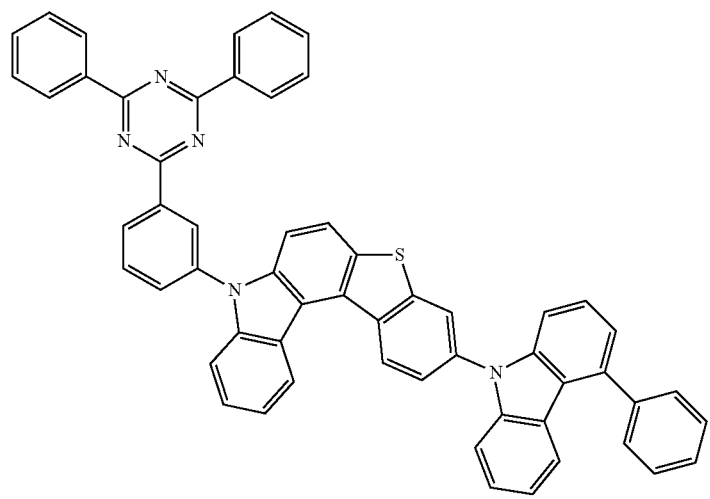

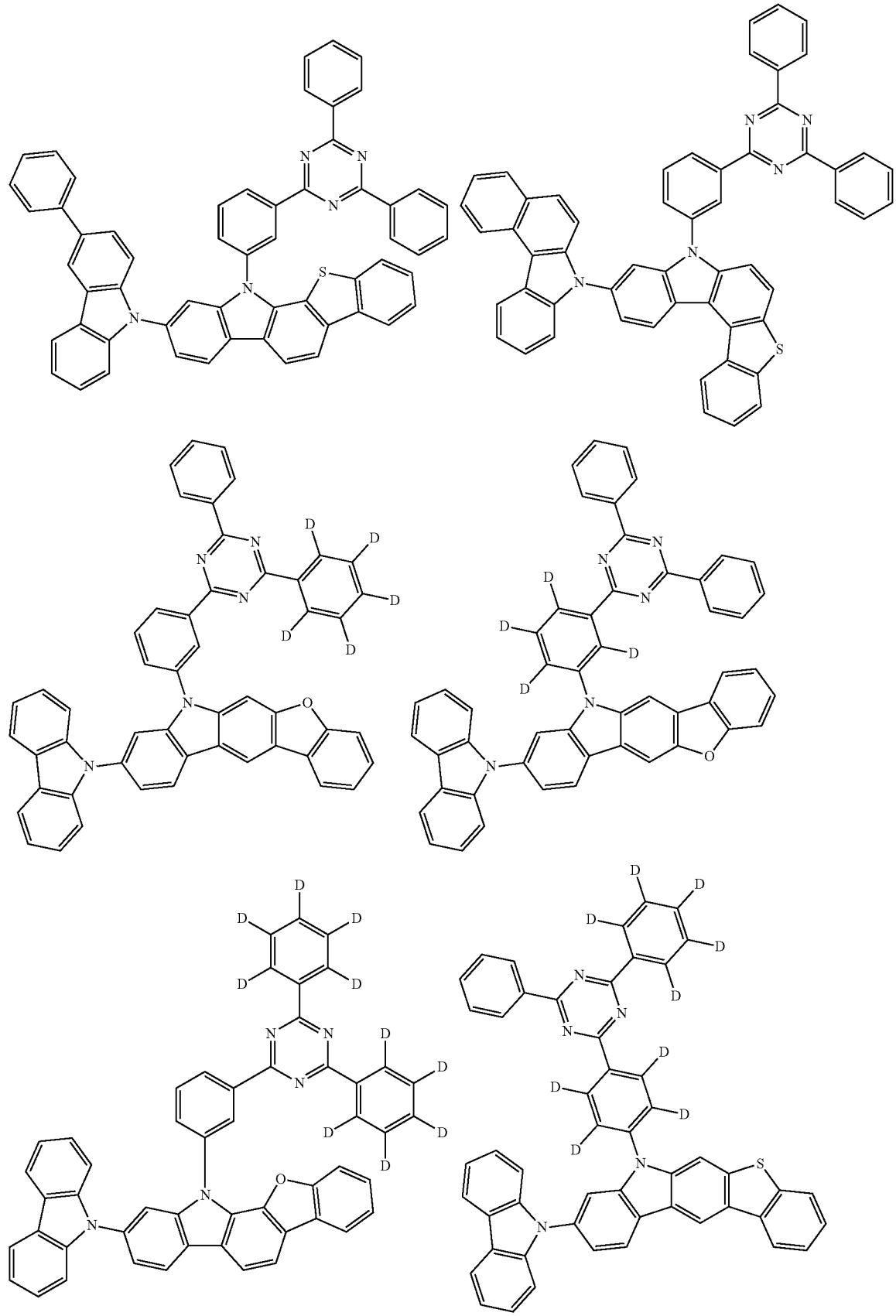

191
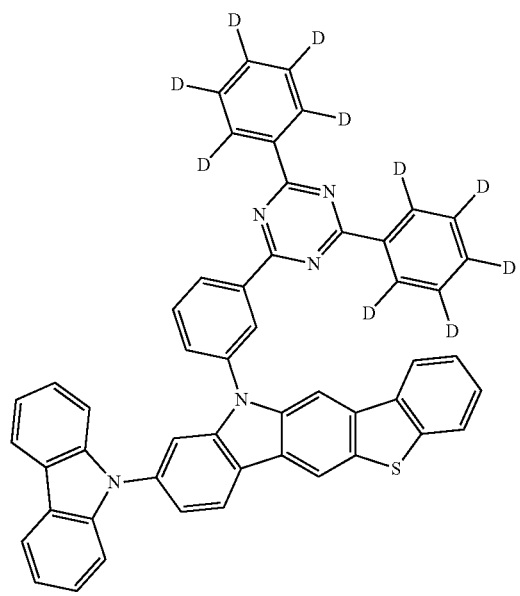
192
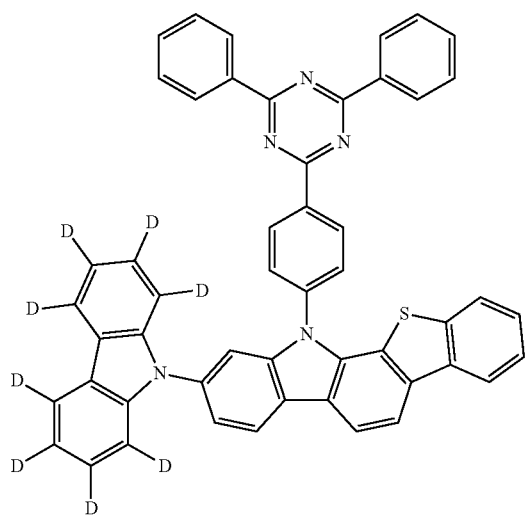
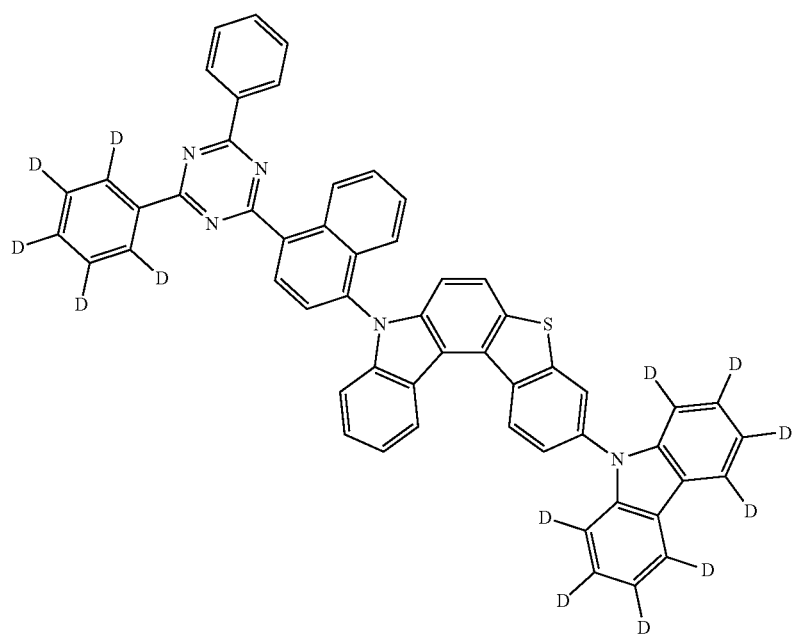
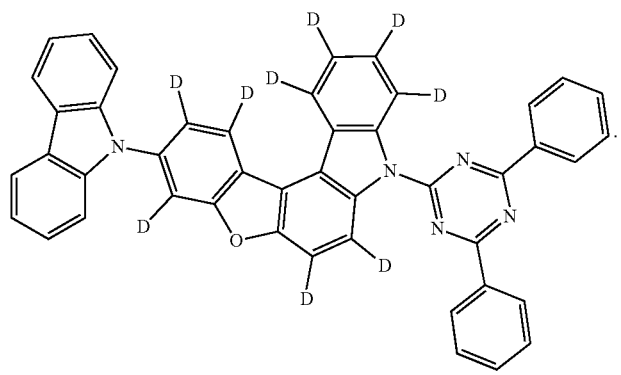

8. An organic light emitting device comprising: a first electrode; a second electrode provided to face the first electrode; and one or more organic material layers that are provided between the first electrode and the second electrode, wherein at least one layer of the organic material layers include the compound according to claim 1.

9. The organic light emitting device of claim 8, wherein the organic material layer including the compound is a light emitting layer.

10. The organic light emitting device of claim 9, wherein the light emitting layer further includes a compound represented by Chemical Formula 7:

[Chemical Formula 7]

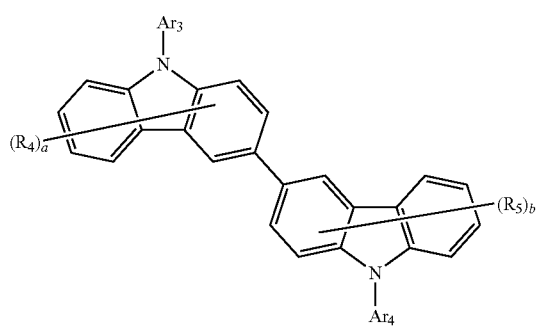

wherein, in Chemical Formula 7, $Ar_3$ and $Ar_4$ are each independently a substituted or unsubstituted $C_{6-60}$ aryl; or a substituted or unsubstituted $C_{2-60}$ heteroaryl comprising any one or more heteroatoms selected from the group consisting of N, O and S, $R_4$ and $R_5$ are each independently hydrogen; deuterium; halogen; cyano; nitro; amino; a substituted or unsubstituted $C_{1-60}$ alkyl; a substituted or unsubstituted $C_{3-60}$ cycloalkyl; or a substituted or unsubstituted $C_{2-60}$ alkenyl; a substituted or unsubstituted $C_{6-60}$ aryl; or a substituted or unsubstituted $C_{2-60}$ heteroaryl containing any one or more heteroatoms selected from the group consisting of N, O and S, and a and b are each independently an integer of 0 to 7.

11. The organic light emitting device of claim 10, wherein $Ar_3$ and $Ar_4$ are each independently phenyl, biphenylyl, terphenylyl, naphthyl, dibenzofuranyl, dibenzothiophenyl, or dimethylfluorenyl.

12. The organic light emitting device of claim 10, wherein $R_4$ and $R_5$ are hydrogen.

13. The organic light emitting device of claim 10, wherein the compound represented by Chemical Formula 7 is any one selected from the group consisting of the following:

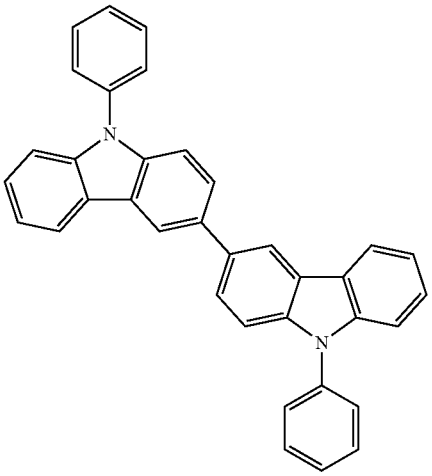

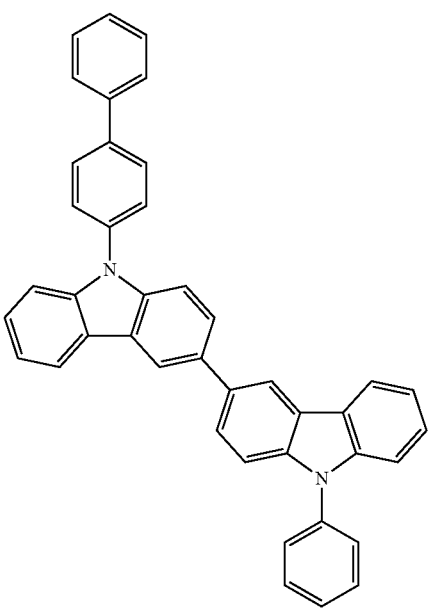

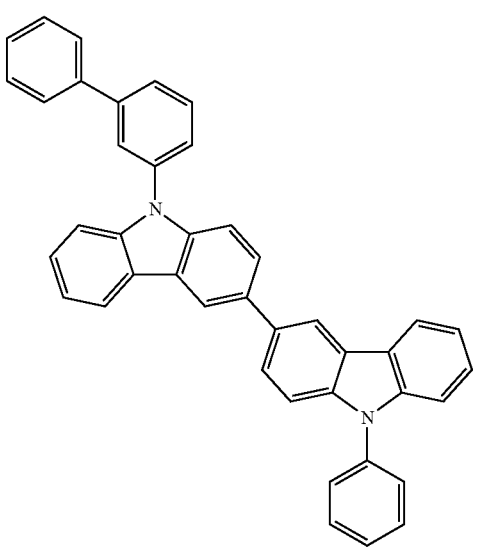

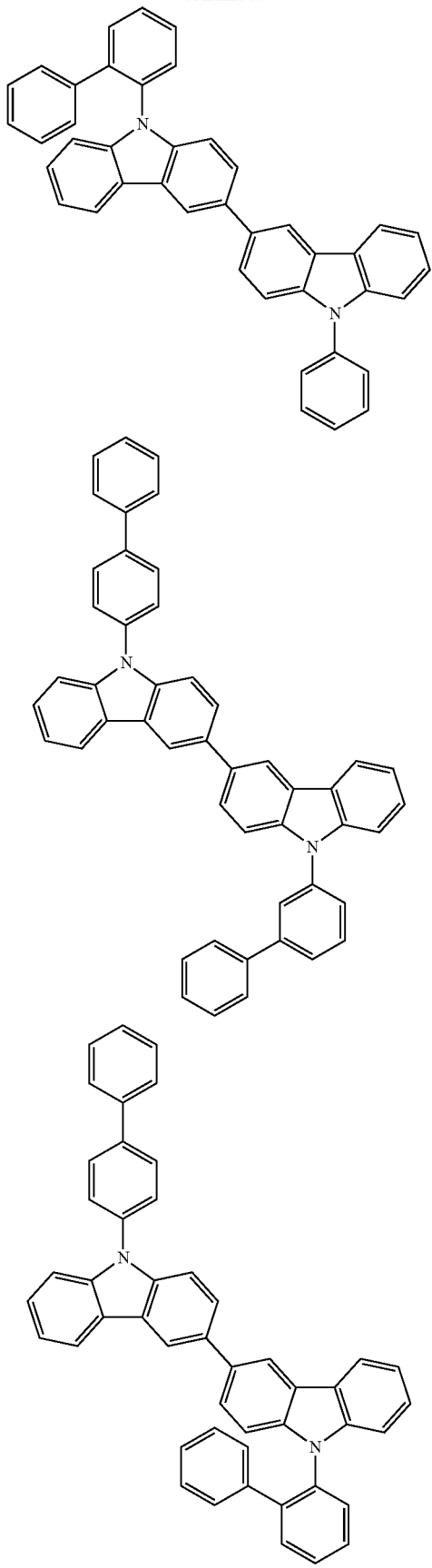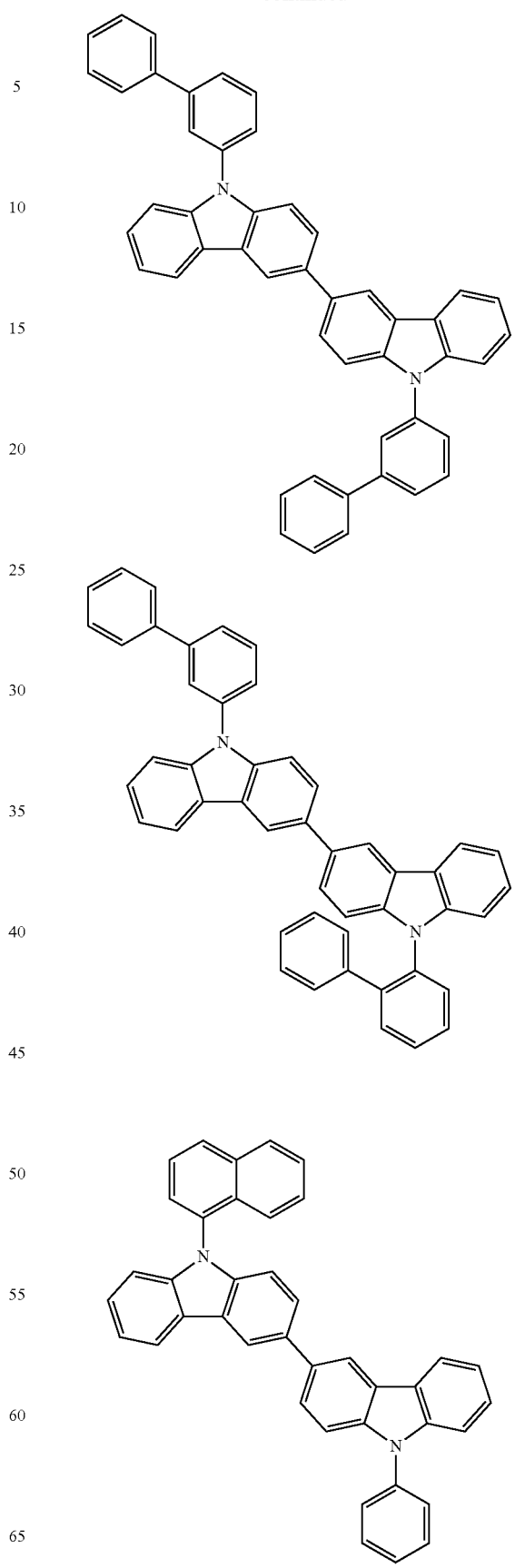

197
-continued
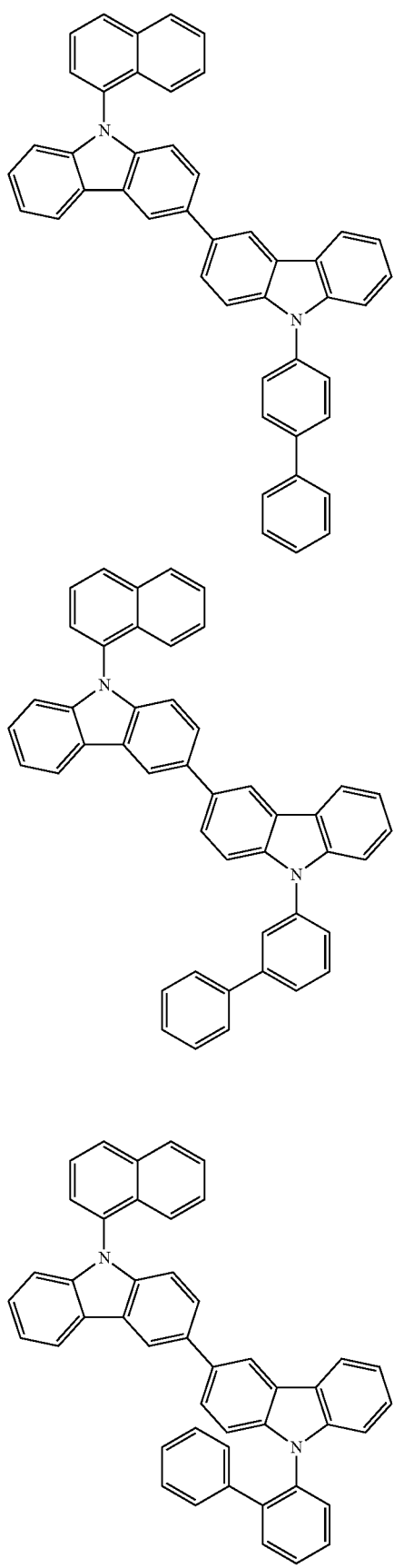
198
-continued
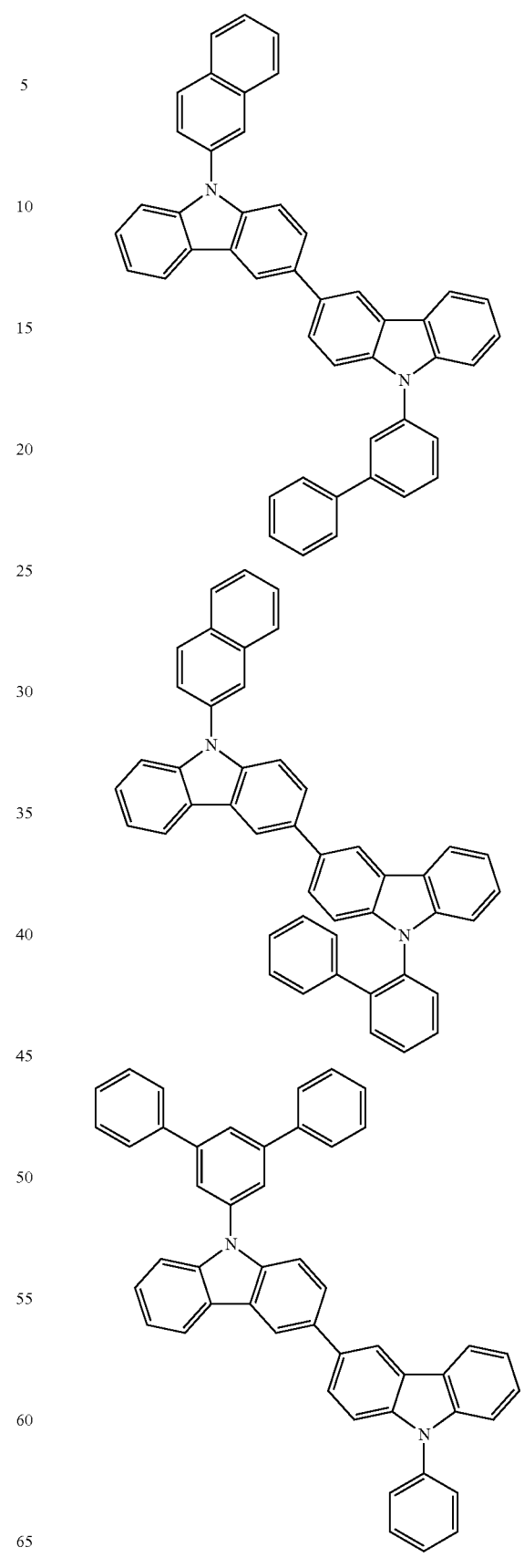

199
-continued
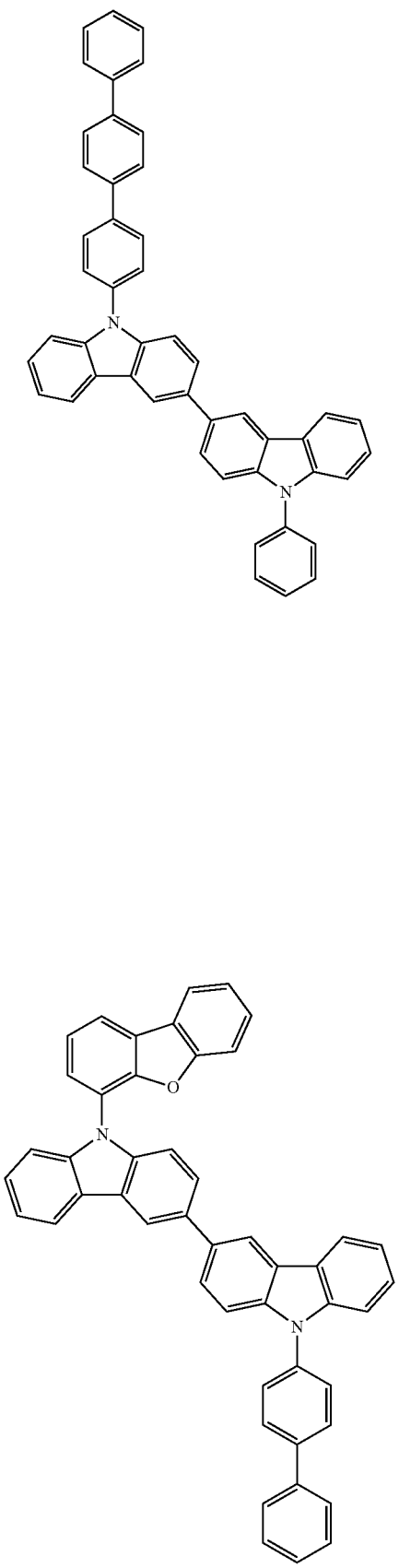
200
-continued
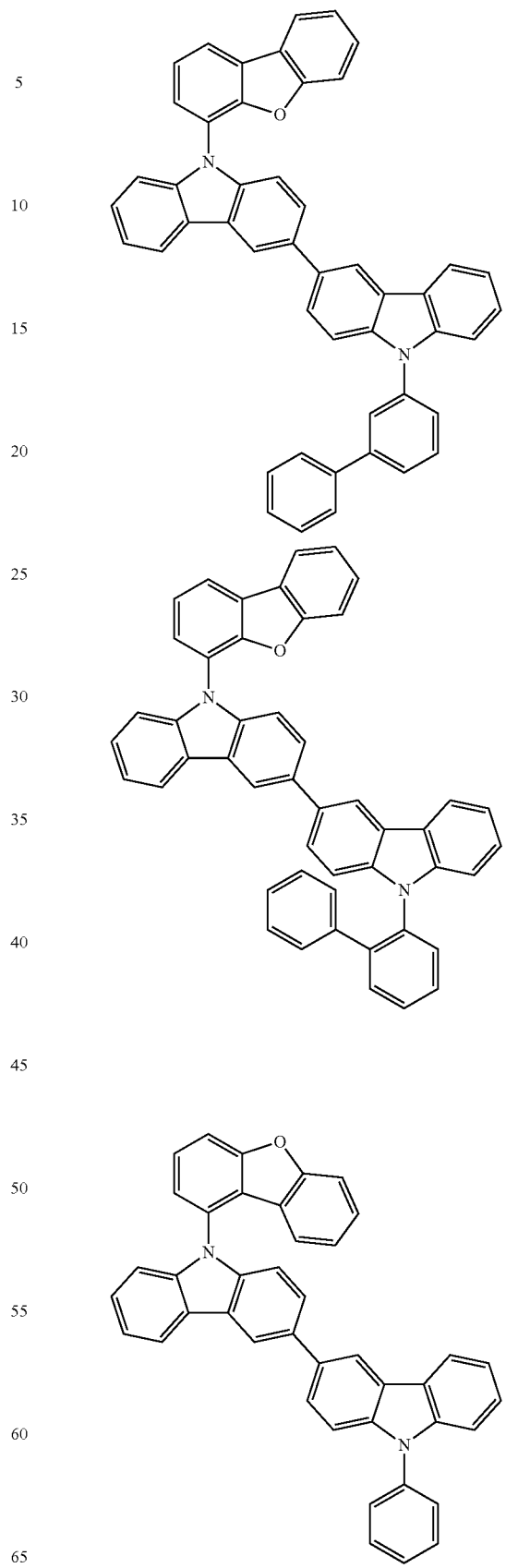

201
-continued
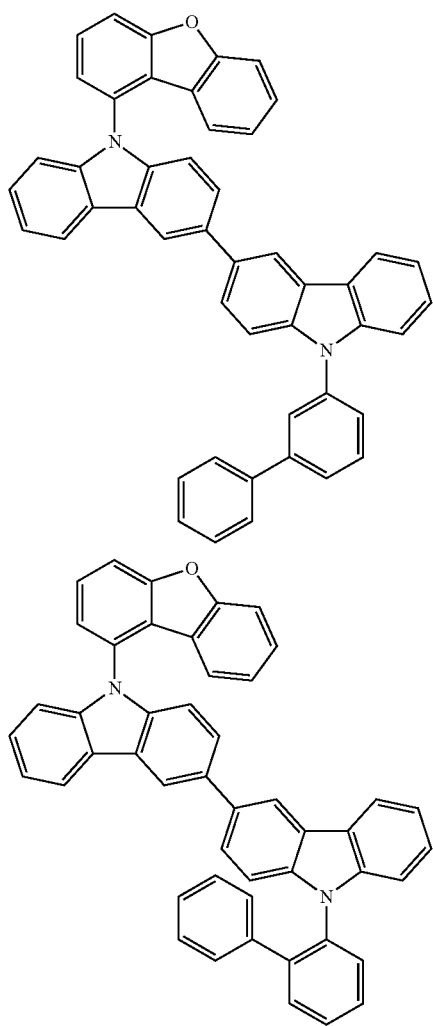
202
-continued
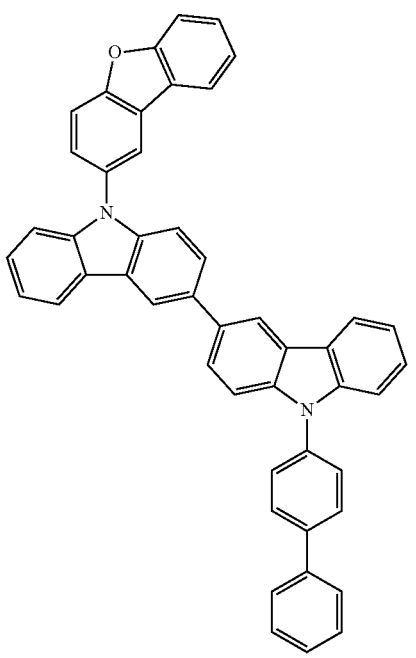
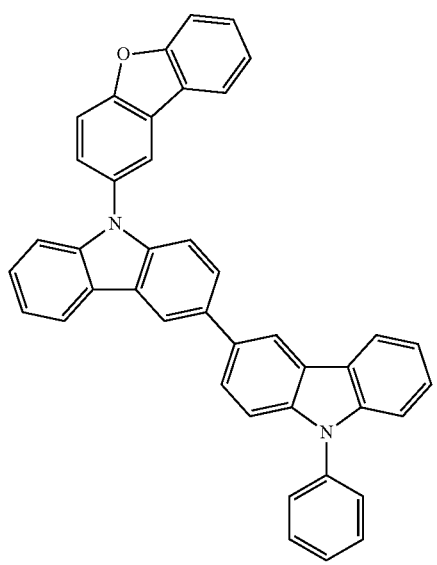
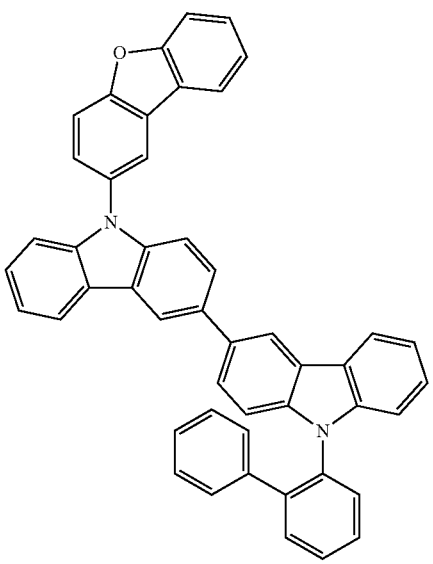

203
-continued
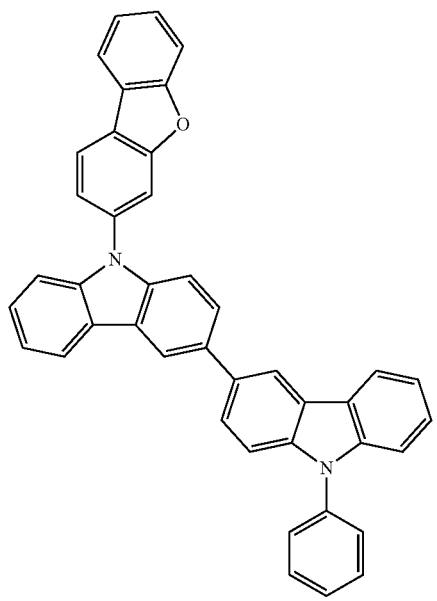
204
-continued
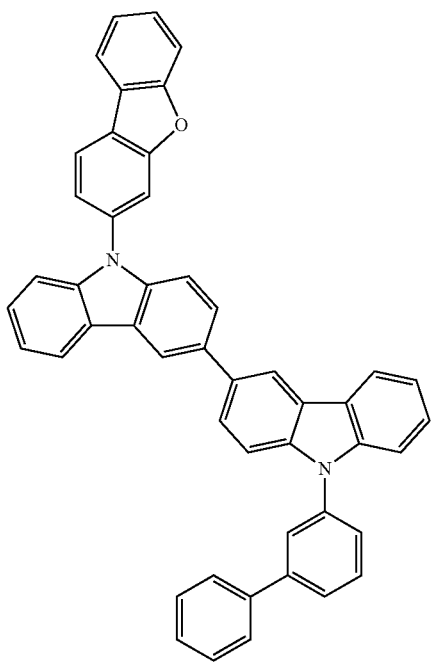
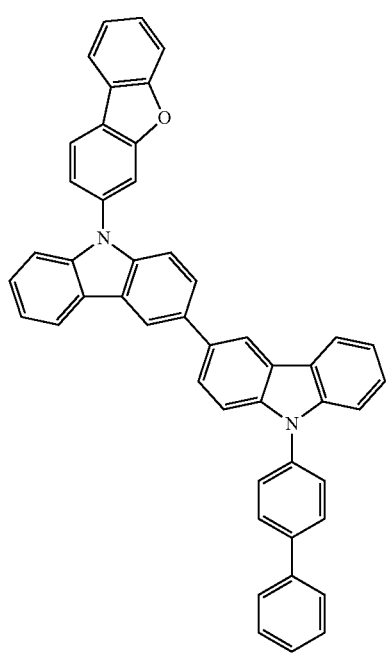
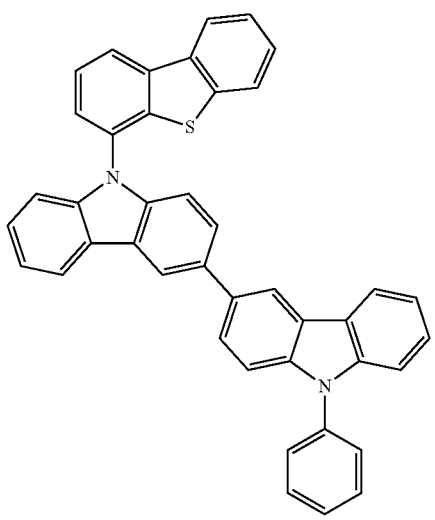

205
-continued
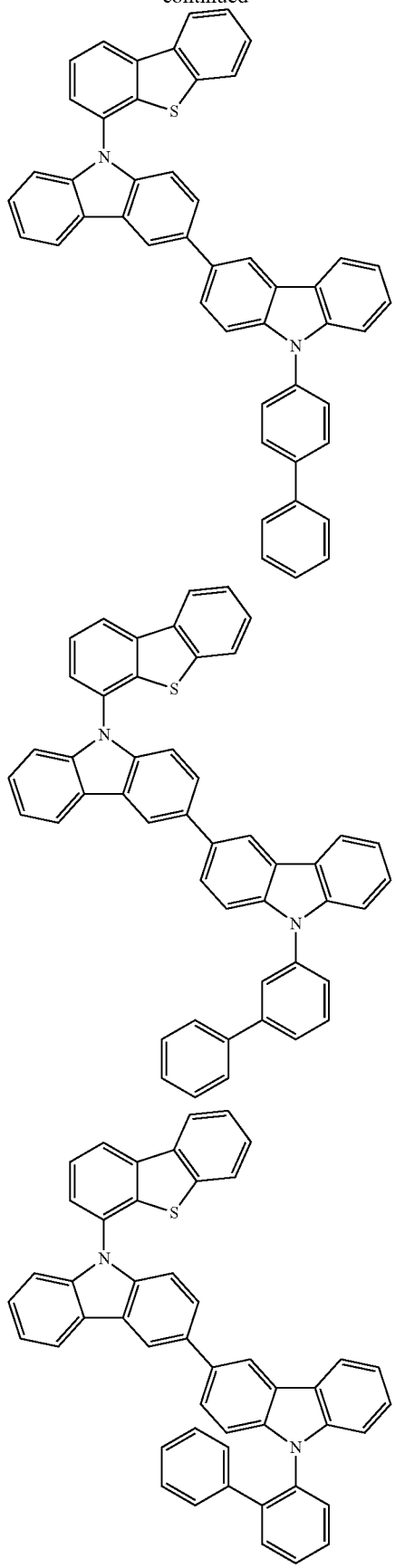
206
-continued
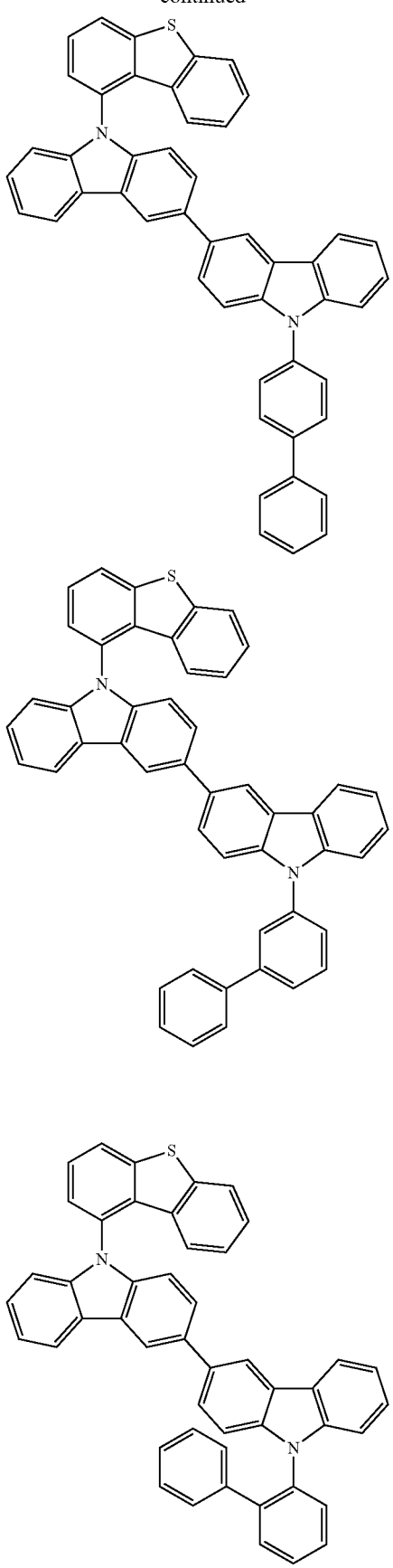

207
-continued
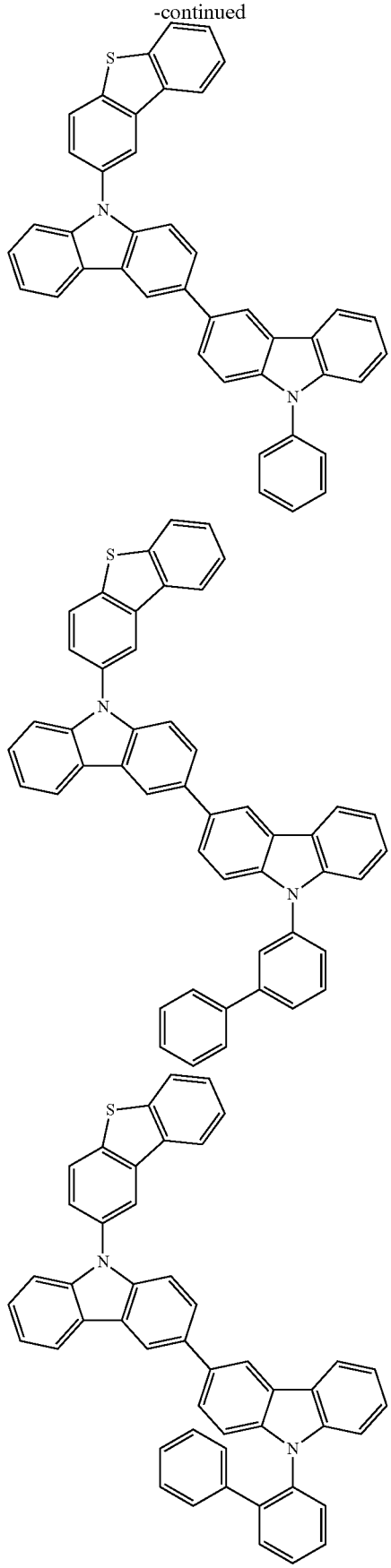
208
-continued

209
-continued
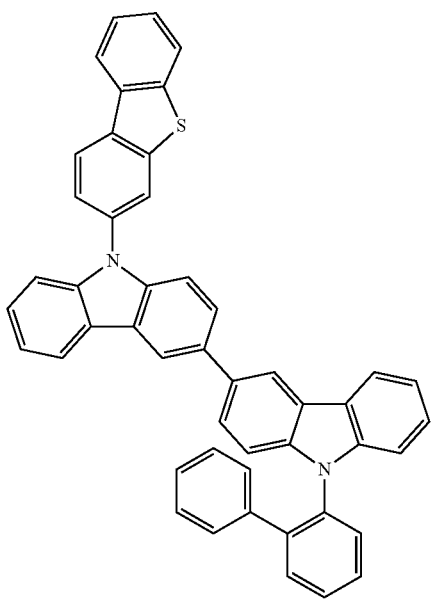
210
-continued
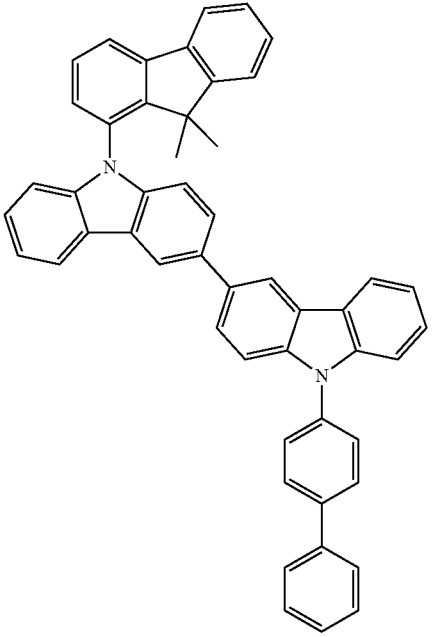
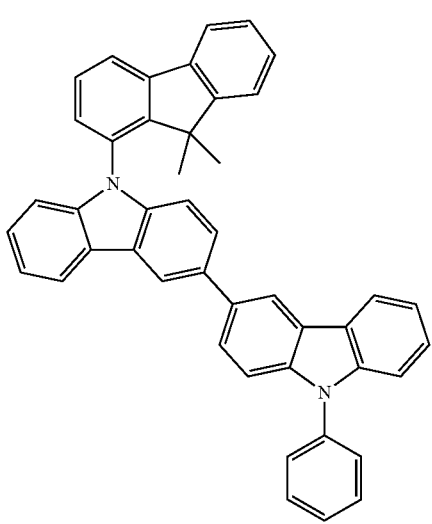

211
-continued
212
-continued
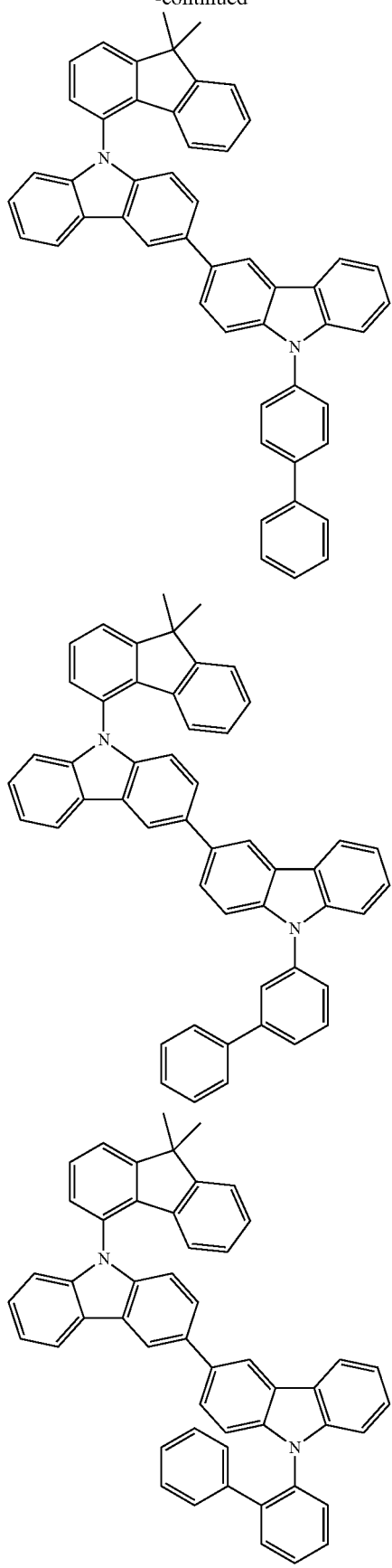
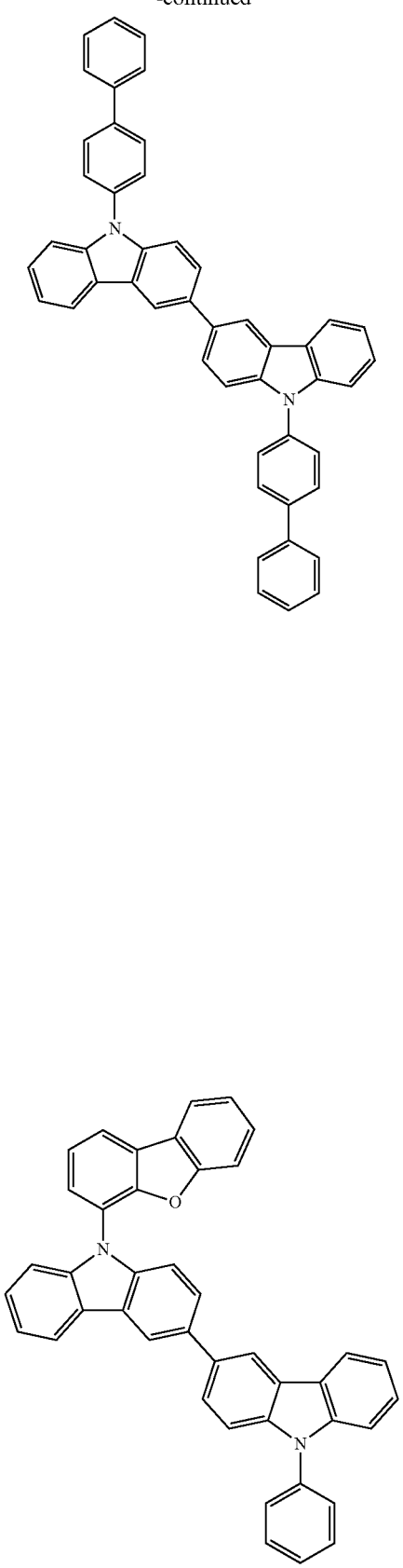

213
-continued
214
-continued
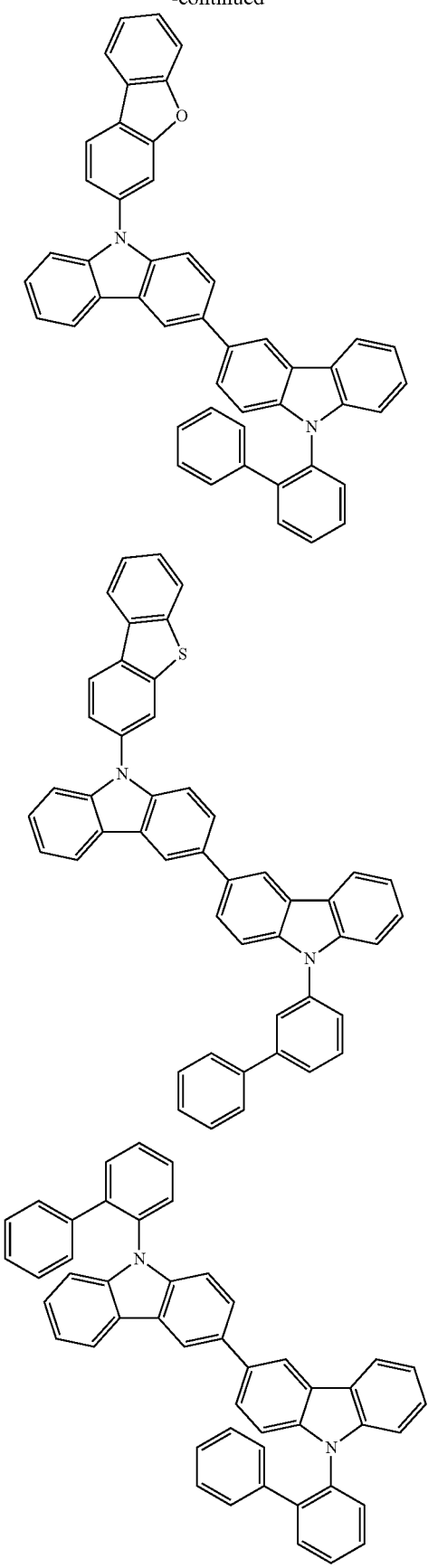

215
-continued
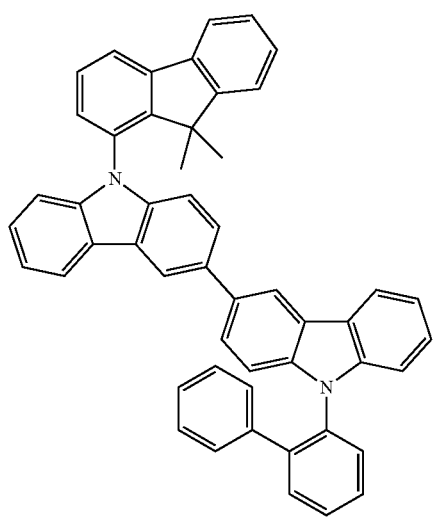
216
-continued
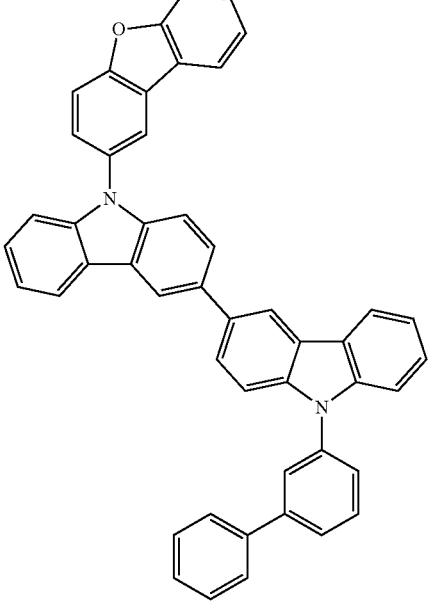
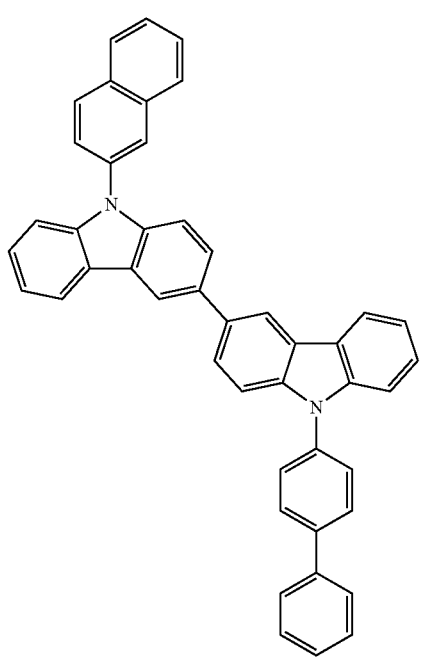
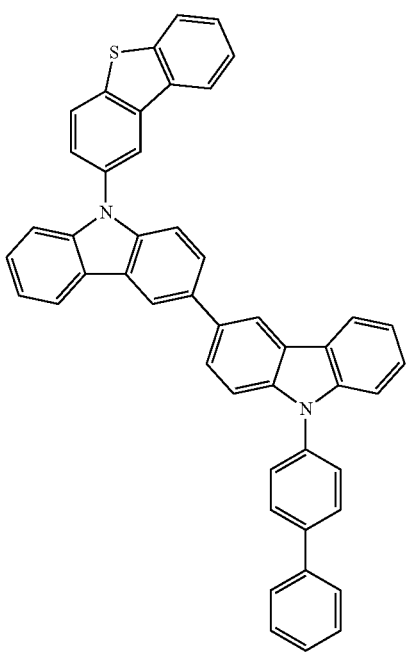

217
-continued
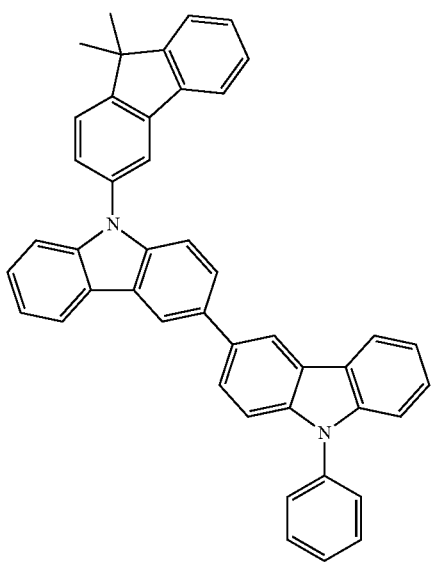
218
-continued
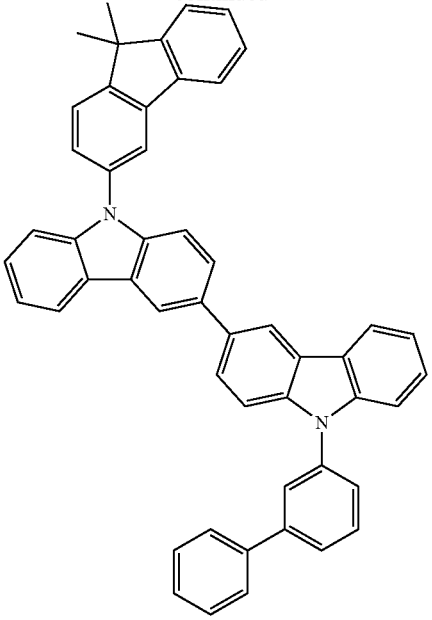
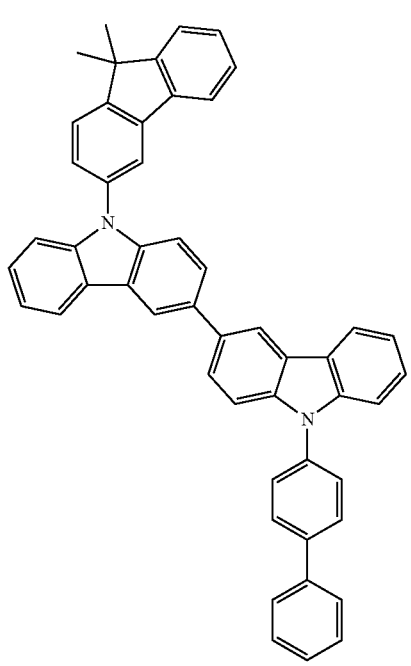
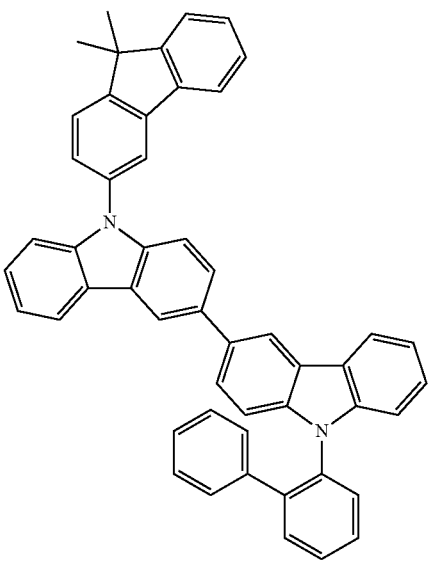

219
-continued
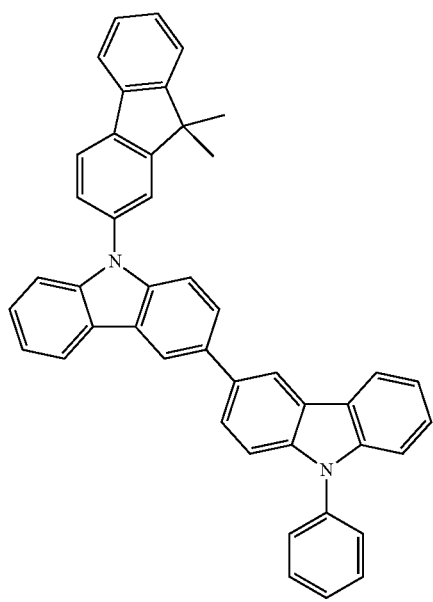
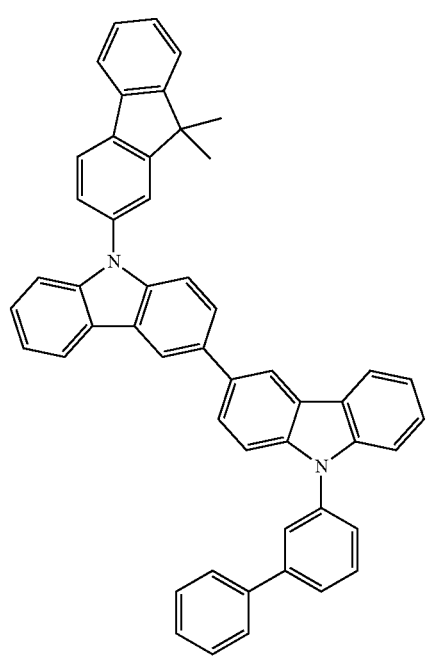
220
-continued
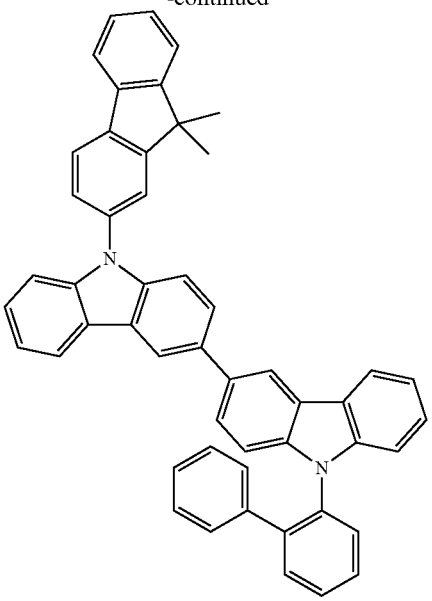
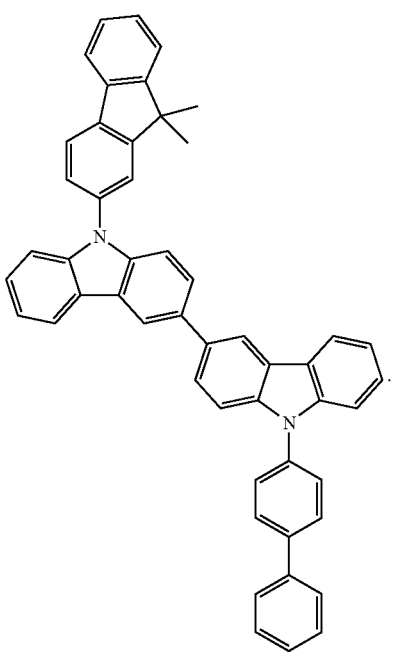
* * * * *